(12) United States Patent
Baker et al.

(10) Patent No.: US 10,248,758 B2
(45) Date of Patent: Apr. 2, 2019

(54) SELF-ASSEMBLING PROTEIN NANOSTRUCTURES

(71) Applicant: UNIVERSITY OF WASHINGTON THROUGH ITS CENTER FOR COMMERCIALIZATION, Seattle, WA (US)

(72) Inventors: David Baker, Seattle, WA (US); Neil King, Seattle, WA (US); Jacob Bale, Seattle, WA (US); William Sheffler, Seattle, WA (US)

(73) Assignee: University of Washington Through its Center for Commercialization, Seattle, WA (US)

( * ) Notice: Subject to any disclaimer, the term of this patent is extended or adjusted under 35 U.S.C. 154(b) by 763 days.

(21) Appl. No.: 14/759,308

(22) PCT Filed: Feb. 7, 2014

(86) PCT No.: PCT/US2014/015371
§ 371 (c)(1),
(2) Date: Jul. 6, 2015

(87) PCT Pub. No.: WO2014/124301
PCT Pub. Date: Aug. 14, 2014

(65) Prior Publication Data
US 2015/0356240 A1 Dec. 10, 2015

Related U.S. Application Data

(60) Provisional application No. 61/762,194, filed on Feb. 7, 2013.

(51) Int. Cl.
| | |
|---|---|
| *G06F 19/18* | (2011.01) |
| *C07K 14/00* | (2006.01) |
| *G01N 33/68* | (2006.01) |
| *G06F 19/16* | (2011.01) |
| *G06F 19/12* | (2011.01) |
| *C07K 14/195* | (2006.01) |
| *B82Y 5/00* | (2011.01) |

(52) U.S. Cl.
CPC .............. *G06F 19/18* (2013.01); *C07K 14/00* (2013.01); *C07K 14/195* (2013.01); *G01N 33/6845* (2013.01); *G06F 19/12* (2013.01); *G06F 19/16* (2013.01); *B82Y 5/00* (2013.01); *C07K 2319/735* (2013.01); *G01N 2570/00* (2013.01)

(58) Field of Classification Search
CPC .............................. G06F 19/18; C07K 14/00
See application file for complete search history.

(56) References Cited

U.S. PATENT DOCUMENTS

| | | | | |
|---|---|---|---|---|
| 8,586,056 B2 * | 11/2013 | Phogat | ................. | C07K 14/005 424/186.1 |
| 8,969,521 B2 * | 3/2015 | Baker | ..................... | G06F 19/16 435/252.33 |
| 2006/0075522 A1 * | 4/2006 | Cleveland | ............ | C07K 14/415 800/289 |
| 2007/0020624 A1 * | 1/2007 | Rubenfield | ............ | C07K 14/21 435/6.15 |
| 2007/0218547 A1 * | 9/2007 | Yeates | .................. | C07K 14/005 435/325 |
| 2011/0020311 A1 * | 1/2011 | Boucher | ............ | A61K 31/7056 424/94.5 |
| 2011/0020378 A1 * | 1/2011 | Burkhard | ............. | A61K 39/145 424/184.1 |
| 2011/0085939 A1 * | 4/2011 | Salemme | ................ | B82Y 30/00 422/68.1 |
| 2011/0200560 A1 | 8/2011 | Zhang | | |
| 2012/0015000 A1 * | 1/2012 | Lanar | ................... | A61K 39/015 424/400 |
| 2012/0059156 A1 * | 3/2012 | Salemme | ............ | B81C 1/00206 530/387.3 |
| 2012/0210459 A1 * | 8/2012 | Kerfeld | ................ | C07K 14/195 800/278 |
| 2015/0356240 A1 | 12/2015 | Baker et al. | | |

FOREIGN PATENT DOCUMENTS

| | | | | |
|---|---|---|---|---|
| WO | WO 2005/049641 | * | 6/2005 | ............. C07K 14/19 |
| WO | 2006033679 A2 | | 3/2006 | |
| WO | 2010019725 A2 | | 2/2010 | |
| WO | 2010035009 A1 | | 4/2010 | |
| WO | 2011019585 A1 | | 2/2011 | |
| WO | 2016138525 A1 | | 8/2011 | |
| WO | 2013056122 A1 | | 4/2013 | |
| WO | 2014124301 A1 | | 8/2014 | |

OTHER PUBLICATIONS

Henne et al., 2004, The genome sequence of the extreme thermophile Thermus Thermophilus, Nature Biotechnology, 22(5): 547-553.*
Ivens et al., 2005, The Genome of the Kinetoplastid Parasite, Leishmania major, Science, 309: 436-442.*
Smith, "XIMDISP—A visualization tool to aid structure determination from electron microscope images," Journal of Structural Biology, vol. 125, No. 2-3, pp. 223-228, 1999.
Stahelin, "Lipid binding domains: more than simple lipid effectors," Journal of Lipid Research, vol. 50, Suppl S299-S304, 2009.
Stranges, et al., "Computational design of a symmetric homodimer using β-strand assembly," Proceedings of the National Academy of Sciences USA, vol. 108, No. 51, pp. 20562-20567, 2011.
Sun, et al., "Cyclic GMP-AMP synthase is a cytosolic DNA sensor that activates the type I interferon pathway," Science, vol. 339, No. 6121, pp. 786-791, 2013.

(Continued)

*Primary Examiner* — Amber D Steele
(74) *Attorney, Agent, or Firm* — McDonnell Boehnen Hulbert & Berghoff LLP

(57) ABSTRACT

Synthetic nanostructures, proteins that are useful, for example, in making synthetic nanostructures, and methods for designing such synthetic nanostructures are disclosed herein.

22 Claims, 51 Drawing Sheets

Specification includes a Sequence Listing.

(56) References Cited

OTHER PUBLICATIONS

Théry, et al., "Isolation and Characterization of Exosomes from Cell and Culture Supernatants and Biological Fluids," Current Protocols in Cell Biology, Chapter 3, Unit 3.22, pp. 3.22.1-3.22.19, 2006.
Tobiume, et al., "Nef does not affect the efficiency of human immunodeficiency virus type 1 fusion with target cells," Journal of Virology, vol. 77, No. 19, pp. 10645-10650, 2003.
Tsai, et al., "Analysis of lattice-translocation disorder in the layered hexagonal structure of carboxysome shell protein CsoS1C," Acta Crystallographica, Section D: Biological Crystallography, vol. 65, Pt 9, pp. 980-988, 2009.
Tsvetkova, et al., "Cutting edge: an NK cell-independent role for Slamf4 in controlling humoral autoimmunity," Protein Cages, Methods in Molecular Biology, 1252:1-15, 2014.
Usami, et al., "SERINC3 and SERINC5 restrict HIV-1 infectivity and are counteracted by Nef," Nature, vol. 526, No. 7572, pp. 218-223, 2015.
Usui, et al., "Nanoscale elongating control of the self-assembled protein filament with the cysteine-introduced building blocks," Protein Science, vol. 18, No. 5, pp. 960-969, 2009.
Van Heel, et al., "A new generation of the IMAGIC image processing system," Journal of Structural Biology, vol. 116, No. 1, pp. 17-24, 1996.
Votteler, et al., "Virus budding the ESCRT pathway," Cell Host & Microbe, vol. 14, No. 3, pp. 232-241, 2013.
Wang, et al., "Expanding the genetic code of *Escherichia coli*," Science, vol. 292, No. 5516, pp. 498-500, 2001.
Whitehead, et al., "Optimization of Affinity, Specificity and Function of Designed Influenza Inhibitors Using Deep Sequencing," Nature Biotechnology, vol. 30, No. 6, pp. 543-548, 2012.
Winn, et al., "Macromolecular TLS refinement in REFMAC at moderate resolutions," Methods in Enzymology, vol. 374, pp. 300-321, 2003.
Wu, et al., "Cyclic GMP-AMP is an endogenous second messenger in innate immune signaling by cytosolic DNA," Science, vol. 339, No. 6121, pp. 826-830, 2013.
Yeates, et al., "Bacterial microcompartment organelles: protein shell structure and evolution," Annual Review of Biophysics, vol. 39, pp. 185-205, 2010.
Yee, et al., "Generation of high-titer pseudotyped retroviral vectors with very broad host range," Methods in Cell Biology, vol. 43, Pt A, pp. 99-112, 1994.
Zaccai, et al., "A de novo peptide hexamer with a mutable channel," Nature Chemical Biology, vol. 7, No. 12, pp. 935-941, 2011.
Zacharias, et al., "Partitioning of lipid-modified GFPs into membrane microdomains in live cells," Science, vol. 296, No. 5569, pp. 913-916, 2002.
Zhang, "Fabrication of novel biomaterials through molecular self-assembly," Nature Biotechnology, vol. 21, No. 10, pp. 1171-1178, 2003.
Zhao, et al., "A simple guide to biochemical approaches for analyzing lipid-protein interactions," Molecular Biology of the Cell, vol. 23, No. 15, pp. 2823-2830, 2012.
Zheng, et al., "From molecular to macroscopic via the rational design of a self-assembled 3D DNA crystal," Nature, vol. 461, No. 7260, pp. 74-77, 2009.
Zhou, et al., "Genetically encoded short peptide tags for orthogonal protein labeling by Sfp and AcpS phosphopantetheinyl transferases," ACS Chemical Biology, vol. 2, No. 5, pp. 337-346, 2007.
AfosrApan, "Computational design of self- and co-assembling protein nanomaterials with atomic level accuracy" available online at: https://community.apan.org/afosr/w/researchareas/7659.human-performance-and-biosystems.aspx, 2014.
Andersen, et al., "Self-assembly of a nanoscale DNA box with a controllable lid," Nature, vol. 459, No. 7243, pp. 73-76, 2009.
Apolonia, et al., "Promiscuous RNA binding ensures effective encapsidation of APOBEC3 proteins by HIV-1," PLoS Pathogens, vol. 11, No. 1, e1004609, 2015.

Bagby, et al., "[2]—Optimization of Protein Solubility and Stability for Protein Nuclear Magnetic Resonance," Methods in Enzymology, vol. 339, pp. 20-41, 2001.
Ballister, et al., "In vitro self-assembly of tailorable nanotubes from a simple protein building block," Proceedings of the National Academy of Sciences USA, vol. 105, No. 10, pp. 3733-3738, 2008.
Bieniasz, "Late budding domains and host proteins in enveloped virus release," Virology, vol. 344, No. 1, pp. 55-63, 2006.
Biswas, et al., "The human immunodeficiency virus type 1 ribosomal frameshifting site is an invariant sequence determinant and an important target for antiviral therapy," Journal of Virology, vol. 78, No. 4, pp. 2082-2087, 2004.
Blanc, et al., "Refinement of severely incomplete structures with maximum likelihood in BUSTER-TNT," Acta Crystallographica, Section D: Biological Crystallography, vol. 60, Pt 12, Pt 1, pp. 2210-2221, 2004.
Bondos, et al., "Detection and Prevention of Protein Aggregation Before, During, and After Purification," Analytical Biochemistry, vol. 316, No. 2, pp. 223-231, 2003.
Bridgeman, et al., "Viruses transfer the antiviral second messenger cGAMP between cells," Science, vol. 349, No. 6253, pp. 1228-1232, 2015.
Cavrois, et al., "A sensitive and specific enzyme-based-assay detecting HIV-1 virion fusion in primary T lymphocytes," Nature Biotechology, vol. 20, No. 11, pp. 1151-1154, 2002.
Chao, et al., "Isolating and Engineering Human Antibodies Using Yeast Surface Display," Nature Protocols, vol. 1, No. 2, pp. 755-768, 2016.
Chao et al., "Structural basis for the coevolution of a viral RNA-protein complex," Nature Structural & Molecular Biology, vol. 15, No. 1, pp. 103-105, 2008.
Colovos, et al., "Verification of protein structures: patterns of nonbonded atomic interactions," Protein Science, vol. 2, No. 9, pp. 1511-1519, 1993.
Cooper, et al., "Predicting protein structures with a multiplayer online game," Nature, vol. 466, No. 7307, pp. 756-760, 2010.
Crowley, et al., "Structural insight into the mechanisms of transport across the *Salmonella enterica* Pdu microcompartment shell," Journal of Biological Chemistry, vol. 285, No. 48, pp. 37838-37846, 2010.
Das, et al., "Simultaneous prediction of protein folding and docking at high resolution," Proceedings of the National Academy of Sciences USA, vol. 106, No. 45, pp. 18978-18983, 2009.
De Guzman, et al., "Structure of the HIV-1 nucleocapsid protein bound to the SL3 psi-RNA recognition element," Science, vol. 279, No. 5349, pp. 384-388, 1998.
DiMaio, et al., "Modeling symmetric macromolecular structures in Rosetta3," PLoS ONE, vol. 6, No. 6, e20450, pp. 1-13, 2011.
Douglas, et al., "Viruses: making friends with old foes," Science, vol. 312, No. 5775, pp. 873-875, 2006.
Emsley, et al., "Features and development of Coot," Acta Crystallographica, Section D: Biological Crystallography, vol. 66, Pt 4, pp. 486-501, 2010.
Fleishman, et al., "Community-wide assessment of protein-interface modeling suggests improvements to design methodology," Journal of Molecular Biology, vol. 414, No. 2, pp. 289-302, 2011.
Fleishman, et al., "Computational design of proteins targeting the conserved stem region of influenza hemagglutinin," Science, vol. 332, No. 6031, pp. 816-821, 2011.
Fleishman, et al., "Hotspot-centric de novo design of protein binders," Journal of Molecular Biology, vol. 413, No. 5, pp. 1047-1062, 2011.
Fleishman, et al., "Restricted sidechain plasticity in the structures of native proteins and complexes," Protein Science, vol. 20, No. 4, pp. 753-757, 2011.
Freed, et al., "Single amino acid changes in the human immunodeficiency virus type 1 matrix block virus particle production," Journal of Virology, vol. 68, No. 8, pp. 5311-5320, 1994.
Gentili, et al., "Transmission of innate immune signaling by packaging of cGAMP in viral particles," Science, vol. 349, No. 6253, pp. 1232-1236, 2015.
Golovanov, et al., "A Simple Method for Improving Protein Solubility and Long-Term Stability," Journal of the American Chemical Society, vol. 126, No. 29, pp. 8933-8939, 2004.

(56) References Cited

OTHER PUBLICATIONS

Gosser, et al., "Peptide-triggered conformational switch in HIV-1 RRE RNA complexes," Nature Structural Biology, vol. 8, No. 2, pp. 146-150, 2001.
Gray, et al., "Cutting Edge: cGAS is Required for Lethal Autoimmune Disease in the Trex1-Deficient Mouse Model of Aicardi-Goutiéres Syndrome," Journal of Immunology, vol. 195, No. 5, pp. 1939-1943, 2015.
Gribbon, et al., "MagicWand: a single, designed peptide that assembles to stable, ordered alpha-helical fibers," Biochemistry, vol. 47, No. 39, pp. 10365-10371, 2008.
Griffiths, et al., "Cloning, isolation and characterization of the Thermotoga maritima KDPG aldolase," Bioorganic & Medicinal Chemistry, vol. 10, No. 3, pp. 545-550, 2002.
Grigorieff, "FREALIGN: high-resolution refinement of single particle structures," Journal of Structural Biology, vol. 157, No. 1, pp. 117-125, 2007.
Grigoryan, et al., "Computational design of virus-like protein assemblies on carbon nanotube surfaces," Science, vol. 332, No. 6033, pp. 1071-1076, 2011.
Grueninger, et al., "Designed protein-protein association," Science, vol. 319, No. 5860, pp. 206-209, 2008.
Harbury, et al., "High-resolution protein design with backbone freedom," Science, vol. 282, No. 5393, pp. 1462-1467, 1998.
Huang, et al., "A de novo designed protein protein interface," Protein Science, vol. 16, No. 12, pp. 2770-2774, 2007.
Hurley, et al., "Membrane Budding and Scission by the ESCRT Machinery: It's All in the Neck," Nature Reviews Molecular Cell Biology, vol. 11, No. 8, pp. 556-566, 2010.
Ishikawa, et al., "STING is an endoplasmic reticulum adaptor that facilitates innate immune signalling," Nature, vol. 455, No. 7213, pp. 674-678, 2008.
Jacak, et al., "Computational Protein Design with Explicit Consideration of Surface Hydrophobic Patches," Proteins: Structure, Function, and Bioinformatics, vol. 80, No. 3, pp. 825-838, 2012.
Jäckel, et al., "Consensus Protein Design Without Phylogenetic Bias," Journal of Molecular Biology, vol. 399, No. 4, pp. 541-546, 2010.
Janin, et al., "Protein-protein interaction and quaternary structure," Quarterly Reviews of Biophysics, vol. 41, No. 2, pp. 133-180, 2008.
Jha, et al., "Computational design of a PAK1 binding protein," Journal of Molecular Biology, vol. 400, No. 2, pp. 257-270, 2010.
Julien, et al., "Crystal structure of a soluble cleaved HIV-1 envelope trimer," Science, vol. 342, No. 6165, pp. 1477-1483, 2013.
Kabsch, "XDS," Acta Crystallographica, Section D: Biological Crystallography, vol. 66, Pt 2, pp. 125-132, 2010.
Karanicolas, et al., "A de novo protein binding pair by computational design and directed evolution," Molecular Cell, vol. 42, No. 2, pp. 250-260, 2011.
King, et al., "Accurate design of co-assembling multi-component protein nanomaterials," Nature, vol. 510, No. 7503, pp. 103-108, 2014.
King, et al., "Computational design of self-assembling protein nanomaterials with atomic level accuracy," Science, vol. 336, No. 6085, pp. 1171-1174, 2012.
Koder, et al., "Design and engineering of an O(2) transport protein," Nature, vol. 458, No. 7236, pp. 305-309, 2009.
Kortemme, et al., "Computational redesign of protein-protein interaction specificity," Nature Structural & Molecular Biology, vol. 11, No. 4, pp. 371-379, 2004.
Kremer, et al., "Computer visualization of three-dimensional image data using IMOD," Journal of Structural Biology, vol. 116, No. 1, pp. 71-76, 1996.
Krissinel, et al., "Inference of macromolecular assemblies from crystalline state," Journal of Molecular Biology, vol. 372, No. 3, pp. 774-797, 2007.
Kuhlman, et al., "Native protein sequences are close to optimal for their structures," Proceedings of the National Academy of Sciences USA, vol. 97, No. 19, pp. 10383-10388, 2000.
Kumar, et al., "Crystal structure analysis of icosahedral lumazine synthase from *Salmonella typhimurium*, an antibacterial drug target," Acta Crystallographica, Section D: Biological Crystallography, vol. 67, Pt 2, pp. 131-139, 2011.
Lai, et al., "Principles for designing ordered protein assemblies," Trends in Cell Biology, vol. 22, No. 12, pp. 653-661, 2012.
Lai, et al., "Structure of a 16-nm Cage Designed by Using Protein Oligomers," Science, vol. 336, No. 6085, pp. 1129, 2012.
Lanci, et al., "Computational design of a protein crystal," Proceedings of the National Academy of Sciences USA, vol. 109, No. 19, pp. 7304-7309, 2012.
Laskowski, et al., "PROCHECK: a program to check the stereochemical quality of protein structures," Journal of Applied Crystallography, 26:283-291, 1993.
Lawrence, et al., "Shape complementarity at protein/protein interfaces," Journal of Molecular Biology, vol. 234, No. 4, pp. 946-950 1993.
Lemmon, "Membrane recognition by phospholipid-binding domains." Nature Reviews Molecular Cell Biology, vol. 9, No. 2, pp. 99-111, 2008.
Levy, et al., "3D complex: a structural classification of protein complexes," PLoS Computational Biology, vol. 2, No. 11, e155, pp. 1395-1406, 2006.
Lovejoy, et al., "Crystal structure of a synthetic triple-stranded alpha-helical bundle," Science, vol. 259, No. 5099, pp. 1288-1293, 1993.
Ludtke, et al., "EMAN: semiautomated software for high-resolution single-particle reconstructions," Journal of Structural Biology, vol. 128, No. 1, pp. 82-97, 1999.
Lüthy, et al., "Assessment of protein models with three-dimensional profiles," Nature, vol. 356, No. 6364, pp. 83-85, 1992.
Lyumkis, et al., "Cryo-EM structure of a fully glycosylated soluble cleaved HIV-1 envelope trimer," Science, vol. 342, No. 6165, pp. 1484-1490, 2013.
Mangeot, et al., "Protein transfer into human cells by VSV-G-induced nanovesicles," Molecular Therapy, vol. 19, No. 9, pp. 1656-1666, 2011.
McCoy, et al., "Phaser crystallographic software," Journal of Applied Crystallography, vol. 40, Pt 4, pp. 658-674, 2007.
McCullough, et al., "Membrane Fission Reactions of the Mammalian ESCRT Pathway," Annual Review of Biochemistry, vol. 82, pp. 663-692, 2013.
McDonald, et al., "No strings attached: the ESCRT machinery in viral budding and cytokinesis," Journal of Cell Science, vol. 122, Pt 13, pp. 2167-2177, 2009.
Mindell, et al., "Accurate determination of local defocus and specimen tilt in electron microscopy," Journal of Structural Biology, vol. 142, No. 3, pp. 334-347, 2003.
Murshudov, et al., "Refinement of macromolecular structures by the maximum-likelihood method," Acta Crystallographica, Section D: Biological Crystallography, vol. 53, Pt 3, pp. 240-255, 1997.
Nam, et al., "Molecular basis for interaction of let-7 microRNAs with Lin28," Cell, vol. 147, No. 5, pp. 1080-1091, 2011.
Ni, et al., "Crystal structure of the MS2 coat protein dimer: implication for RNA binding and virus assembly," Structure, vol. 3, No. 3, pp. 255-263, 1995.
Ohi, et al., "Negative staining and image classification—powerful tools in modern electron microscopy," Biological Procedures Online, vol. 6, pp. 23-34, 2004.
Olsen, "Gene transfer vectors derived from equine infectious anemia virus," Gene Therapy, vol. 5, No. 11, pp. 1481-1487, 1998.
Otwinowski, et al., "[20] Processing of X-ray diffraction data collected in oscillation mode," Methods in Enzymology, vol. 276, pp. 307-326, 1997.
Oubridge, et al., "Crystal structure at 1.92 a resolution of the RNA-binding domain of the U1A spliceosomal protein complexed with an RNA hairpin," Nature, vol. 372, No. 6505, pp. 432-438, 1994.
Padilla, et al., "Nanohedra: using symmetry to design self assembling protein cages, layers, crystals, and filaments," Proceedings of the National Academy of Sciences USA, vol. 98, No. 5, pp. 2217-2221, 2001.

(56) References Cited

OTHER PUBLICATIONS

Pancera, et al., "Structure and immune recognition of trimeric pre-fusion HIV-1 Env.," Nature, vol. 514, No. 7523, pp. 455-461, 2014.
Parent, et al., "Positionally independent and exchangeable late budding functions of the Rous Sarcoma Virus and Human Immunodeficiency Virus Gag proteins," Journal of Virology, vol. 69, No. 9, pp. 5455-5460, 1995.
Patterson, et al., "Characterization of a highly flexible self-assembling protein system designed to form nanocages," Protein Science, vol. 23, No. 2, pp. 190-199, 2014.
PCT/US2014/015371 International Search Report and Written Opinion, dated 2014.
PCT/US2016/020090, International Search Report and Written Opinion, 10 pages, dated 2016.
Pesarrodona, et al., "Intracellular targeting of CD44+ cells with self-assembling, protein only nanoparticles," International Journal of Pharmaceutics, vol. 473, No. 1-2, pp. 286-295, 2014.
Pettersen, et al., "UCSF Chimera—a visualization system for exploratory research and analysis," Journal of Computational Chemistry, vol. 25, No. 13, pp. 1605-1612, 2004.
Prodromou, et al, "Recursive PCR: a novel technique for total gene synthesis," Protein Engineering, vol. 5, No. 8, pp. 827-829, 1992.
Puglisi, et al., "Solution structure of a bovine immunodeficiency virus Tat-TAR peptide-RNA complex," Science, vol. 270, No. 5239, pp. 1200-1203, 1995.
Raman, et al., "Design of Peptide Nanoparticles Using Simple Protein Oligomerization Domains," The Open Nanomedicine Journal, vol. 2, pp. 15-26, 2009.
Resh, "Covalent lipid modifications of proteins," Current Biology, vol. 23, No. 10, pp. R431-R435, 2013.
Resh, "Fatty acylation of proteins: new insights into membrane targeting of myristoylated and palmitoylated proteins," Biochimica et Biophysica Acta, vol. 1451, No. 1, pp. 1-16, 1999.
Ringler, et al., "Self-assembly of proteins into designed networks," Science, vol. 302, No. 5642, pp. 106-109, 2003.
Rosa, et al., "HIV-1 Nef promotes infection by excluding SERINC5 from virion incorporation," Nature, vol. 526, No. 7572, pp. 212-217, 2015.
Rothemund, "Folding DNA to create nanoscale shapes and patterns," Nature, vol. 440, No. 7082, pp. 297-302, 2006.
Salgado, et al., "Controlling protein-protein interactions through metal coordination: assembly of a 16-helix bundle protein," Journal of the American Chemical Society, vol. 129, No. 44, pp. 13374-13375, 2007.
Salgado, et al., "Metal-directed protein self-assembly," Accounts of Chemical Research, vol. 43, No. 5, pp. 661-672, 2010.
Schrödinger, LLC, "The PyMOL Molecular Graphics System, Version 1.4," available online at: http://www.pymol.org, 2011.
Schuck, "Size-distribution analysis of macromolecules by sedimentation velocity ultracentrifugation and lamm equation modeling," Biophysical Journal, vol. 78, No. 3, pp. 1606-1619, 2000.
Seeman, "Nanomaterials based on DNA," Annual Review of Biochemistry, vol. 79, pp. 65-87, 2010.
Sheffler, et al., "RosettaHoles2: a volumetric packing measure for protein structure refinement and validation," Protein Science, vol. 19, No. 10, pp. 1991-1995, 2010.
Sinclair, et al., "Generation of protein lattices by fusing proteins with matching rotational symmetry," Nature Nanotechnology, vol. 6, No. 9, pp. 558-562, 2011.

* cited by examiner

T32-28A

| residue | amino acid | allowed amino acids | SASA |
|---|---|---|---|
| 1 | M | (1-3) Optional or any; (4) M | N/A |
| 2 | G | (1) Any; (2) Con; (3) Con; (4) G | 115.8 |
| 3 | E | (1) Any; (2) Con; (3) Con; (4) E | 76.7 |
| 4 | V | (1) Con; (2) Con; (3-4) V | 49.5 |
| 5 | P | (1) Any; (2) Con; (3) Con (4) P | 109.3 |
| 6 | I | (1) Con; (2) Con; (3-4) I | 22 |
| 7 | G | (1) Con; (2) Con; (3-4) G | 41.3 |
| 8 | D | (1) Any; (2) Con; (3) Con; (4) D | 76.8 |
| 9 | P | (1) Any; (2) Con; (3) Con; (4) P | 98.3 |
| 10 | K | (1) Con; (2) Con; (3-4) K | 46.2 |
| 11 | E | (1) Any; (2) Con; (3) Con; (4) E | 92.2 |
| 12 | L | (1) Any; (2) Con; (3) Con; (4) L | 67.8 |
| 13 | N | (1) Any; (2) Con; (3) Con; (4) N | 71.8 |
| 14 | G | (1) Con; (2) Con; (3-4) G | 22.8 |
| 15 | M | (1) Con; (2) Con; (3-4) M | 31.7 |
| 16 | E | (1) Con; (2) Con; (3-4) E | 40.7 |
| 17 | I | (1) Any; (2) Con; (3) Con; (4) I | 51.7 |
| 18 | A | (1) Con; (2) Con; (3-4) A | 34.5 |
| 19 | A | (1) Con; (2) Con; (3-4) A | 41.7 |
| 20 | V | (1) Con; (2) Con; (3-4) V | 35.3 |
| 21 | Y | (1) Con; (2) Con; (3-4) Y | 33.7 |
| 22 | L | (1) Con; (2) Con; (3-4) L | 27 |
| 23 | Q | (1) Any; (2) Con; (3) Con; (4) Q | 52.8 |
| 24 | P | (1) Con; (2) Con; (3-4) P | 35.7 |
| 25 | I | (1) Con; (2) Con; (3-4) I | 36 |
| 26 | E | (1) Any; (2) Con; (3) Con; (4) E | 51.5 |
| 27 | M | (1) Con; (2) Con; (3-4) M | 41.5 |
| 28 | E | (1) Any; (2) Con; (3) Con; (4) E | 57 |
| 29 | P | (1) Any; (2) Con; (3) Con; (4) P | 76 |
| 30 | R | (1) Any; (2) Con; (3) Con; (4) R | 96.5 |
| 31 | G | (1) Any; (2) Con; (3) Con; (4) G | 86.2 |
| 32 | I | (1) Any; (2) Con; (3) Con; (4) I | 88.2 |
| 33 | D | (1) Con; (2) Con; (3-4) D | 43 |
| 34 | L | (1) Con; (2) Con; (3-4) L | 46.8 |
| 35 | A | (1) Any; (2) Con; (3) Con; (4) A | 58.2 |
| 36 | A | (1) Con; (2) Con; (3-4) A | 45.8 |
| 37 | S | (1) Any; (2) Con; (3) Con; (4) S | 105.7 |
| 38 | L | (1) Any; (2) Con; (3) Con; (4) L | 57 |
| 39 | A | (1) Con; (2) Con; (3-4) A | 13.3 |

FIGURE 10A

| | | | |
|---|---|---|---|
| 40 | D | (1) Con; (2) Con; (3-4) D | 8.8 |
| 41 | I | (1) Con; (2) Con; (3-4) I | 24.3 |
| 42 | H | (1) Con; (2) Con; (3-4) H | 16.8 |
| 43 | L | (1) Any; (2) Con; (3) Con; (4) L | 58.5 |
| 44 | E | (1) Con; (2) Con; (3-4) E | 41.5 |
| 45 | A | (1) Con; (2) Con; (3-4) A | 41.7 |
| 46 | D | (1) Any; (2) Con; (3) Con; (4) D | 55.7 |
| 47 | I | (1) Con; (2) Con; (3-4) I | 40 |
| 48 | H | (1) Con; (2) Con; (3-4) H | 33.3 |
| 49 | A | (1) Con; (2) Con; (3-4) A | 12.5 |
| 50 | L | (1) Con; (2) Con; (3-4) L | 35.8 |
| 51 | K | (1) Any; (2) Con; (3) Con; (4) K | 82.8 |
| 52 | N | (1) Any; (2) Con; (3) Con; (4) N | 100.7 |
| 53 | N | (1) Con; (2) Con; (3-4) N | 19.5 |
| 54 | P | (1) Any; (2) Con; (3) Con; (4) P | 71.5 |
| 55 | N | (1) Con; (2) Con; (3-4) N | 46 |
| 56 | G | (1) Con; (2) Con; (3-4) G | 15.8 |
| 57 | F | (1) Con; (2) Con; (3-4) F | 33 |
| 58 | P | (1) Any; (2) Con; (3) Con; (4) P | 57.2 |
| 59 | E | (1) Any; (2) Con; (3) Con; (4) E | 74.8 |
| 60 | G | (1) Any; (2) Con; (3) Con; (4) G | 57.2 |
| 61 | F | (1) Con; (2) Con; (3-4) F | 21.5 |
| 62 | W | (1) Con; (2) Con; (3-4) W | 42.5 |
| 63 | M | (1) Any; (2) Con; (3) Con; (4) M | 54 |
| 64 | P | (1) Any; (2) Con; (3) Con; (4) P | 60.3 |
| 65 | Y | (1) Any; (2) Con; (3) Con; (4) Y | 51.2 |
| 66 | L | (1) Any; (2) Con; (3) Con; (4) L | 51.5 |
| 67 | T | (1) Con; (2) Con; (3-4) T | 46.8 |
| 68 | I | (1) Con; (2) Con; (3-4) I | 32 |
| 69 | A | (1-4) A | 39.7 |
| 70 | Y | (1-4) Y | 51.3 |
| 71 | A | (1-4) A | 9.8 |
| 72 | L | (1-4) L | 61.5 |
| 73 | A | (1-4) A | 3.3 |
| 74 | N | (1-4) N | 10.8 |
| 75 | A | (1-4) A | 19.7 |
| 76 | D | (1-4) D | 78.2 |
| 77 | T | (1-4) T | 60.3 |
| 78 | G | (1-4) G | 13.2 |
| 79 | A | (1-4) A | 29.5 |
| 80 | I | (1-4) I | 78.8 |
| 81 | K | (1-4) K | 68.2 |
| 82 | T | (1-4) T | 97 |
| 83 | G | (1-4) G | 38.5 |
| 84 | T | (1) Any; (2) Con; (3) Con; (4) T | 80.5 |
| 85 | L | (1) Con; (2) Con; (3-4) L | 32.8 |

FIGURE 10B

| | | | |
|---|---|---|---|
| 86 | M | (1) Con; (2) Con; (3-4) M | 44.3 |
| 87 | P | (1) Any; (2) Con; (3) Con; (4) P | 81.2 |
| 88 | M | (1) Con; (2) Con; (3-4) M | 32.3 |
| 89 | V | (1) Con; (2) Con; (3-4) V | 27.7 |
| 90 | A | (1) Con; (2) Con; (3-4) A | 23.8 |
| 91 | D | (1) Any; (2) Con; (3) Con; (4) D | 56.8 |
| 92 | D | (1) Any; (2) Con; (3) Con; (4) D | 103.8 |
| 93 | G | (1) Con; (2) Con; (3-4) G | 7.2 |
| 94 | P | (1) Any; (2) Con; (3) Con; (4) P | 58.5 |
| 95 | H | (1) Con; (2) Con; (3-4) H | 39.2 |
| 96 | Y | (1) Con; (2) Con; (3-4) Y | 23.8 |
| 97 | G | (1) Con; (2) Con; (3-4) G | 24.2 |
| 98 | A | (1) Con; (2) Con; (3-4) A | 31 |
| 99 | N | (1) Con; (2) Con; (3-4) N | 18.3 |
| 100 | I | (1) Con; (2) Con; (3-4) I | 46.7 |
| 101 | A | (1) Con; (2) Con; (3-4) A | 47.2 |
| 102 | M | (1) Con; (2) Con; (3-4) M | 31 |
| 103 | E | (1) Any; (2) Con; (3) Con; (4) E | 85.2 |
| 104 | K | (1) Any; (2) Con; (3) Con; (4) K | 63.5 |
| 105 | D | (1) Con; (2) Con; (3-4) D | 27.7 |
| 106 | K | (1) Any; (2) Con; (3) Con; (4) K | 114 |
| 107 | K | (1) Any; (2) Con; (3) Con; (4) K | 102.5 |
| 108 | G | (1) Con; (2) Con; (3-4) G | 32.5 |
| 109 | G | (1) Con; (2) Con; (3-4) G | 32.7 |
| 110 | F | (1) Con; (2) Con; (3-4) F | 40.8 |
| 111 | G | (1) Con; (2) Con; (3-4) G | 33.7 |
| 112 | V | (1) Any; (2) Con; (3) Con; (4) V | 87.8 |
| 113 | G | (1) Con; (2) Con; (3-4) G | 24.5 |
| 114 | T | (1-4) T | 55.3 |
| 115 | Y | (1-4) Y | 31.5 |
| 116 | A | (1-4) A | 5 |
| 117 | L | (1-4) L | 41.8 |
| 118 | T | (1-4) T | 6.3 |
| 119 | F | (1-4) F | 48.5 |
| 120 | L | (1-4) L | 27.8 |
| 121 | I | (1-4) I | 52 |
| 122 | S | (1) Con; (2) Con; (3-4) S | 35.2 |
| 123 | N | (1) Con; (2) Con; (3-4) N | 19.2 |
| 124 | P | (1) Con; (2) Con; (3-4) P | 47.8 |
| 125 | E | (1) Con; (2) Con; (3-4) E | 49.7 |
| 126 | K | (1) Any; (2) Con; (3) Con; (4) K | 87.5 |
| 127 | Q | (1) Any; (2) Con; (3) Con; (4) Q | 70 |
| 128 | G | (1) Con; (2) Con; (3-4) G | 50 |
| 129 | F | (1) Con; (2) Con; (3-4) F | 20.8 |
| 130 | G | (1) Con; (2) Con; (3-4) G | 15.2 |
| 131 | R | (1) Con; (2) Con; (3-4) R | 31 |
| 132 | H | (1) Con; (2) Con; (3-4) H | 12.8 |
| 133 | V | (1) Any; (2) Con; (3) Con; (4) V | 70.7 |

FIGURE 10C

| | | | |
|---|---|---|---|
| 134 | D | (1) Con; (2) Con; (3-4) D | 32.8 |
| 135 | E | (1) Any; (2) Con; (3) Con; (4) E | 117.7 |
| 136 | E | (1) Any; (2) Con; (3) Con; (4) E | 102.5 |
| 137 | T | (1) Con; (2) Con; (3-4) T | 43.5 |
| 138 | G | (1) Con; (2) Con; (3-4) G | 25.2 |
| 139 | V | (1) Con; (2) Con; (3-4) V | 34.2 |
| 140 | G | (1) Con; (2) Con; (3-4) G | 39 |
| 141 | K | (1) Any; (2) Con; (3) Con; (4) K | 95 |
| 142 | W | (1) Any; (2) Con; (3) Con; (4) W | 61.3 |
| 143 | F | (1) Con; (2) Con; (3-4) F | 47.5 |
| 144 | E | (1) Any; (2) Con; (3) Con; (4) E | 77 |
| 145 | P | (1-4) P | 106.5 |
| 146 | F | (1-4) F | 61 |
| 147 | V | (1-4) V | 62.5 |
| 148 | V | (1-4) V | 40.7 |
| 149 | T | (1-4) T | 60 |
| 150 | Y | (1-4) Y | 20.5 |
| 151 | F | (1-4) F | 69.3 |
| 152 | F | (1-4) F | 36 |
| 153 | K | (1) Any; (2) Con; (3) Con; (4) K | 84.2 |
| 154 | Y | (1) Con; (2) Con; (3-4) Y | 47.7 |
| 155 | T | (1) Any; (2) Con; (3) Con; (4) T | 105 |
| 156 | G | (1) Con; (2) Con; (3-4) G | 45.8 |
| 157 | T | (1) Any; (2) Con; (3) Con; (4) T | 70.7 |
| 158 | P | (1) Any; (2) Con; (3) Con; (4) P | 102 |
| 159 | K | (1) Any; (2) Con; (3) Con; (4) K | N/A |

(SEQ ID NOs: 1, 11, 21, and 31)

FIGURE 10D

| T32-28B residue | amino acid | allowed amino acids | SASA |
|---|---|---|---|
| 1 | M | (1-3) Optional/any; (4) M | N/A |
| 2 | S | (1) Any; (2-3) Con; (4) S | 121.5 |
| 3 | Q | (1-2) Con; (3-4) Q | 28.5 |
| 4 | A | (1-2) Con; (3-4) A | 10.8 |
| 5 | I | (1-2) Con; (3-4) I | 50.3 |
| 6 | G | (1-2) Con; (3-4) G | 12.2 |
| 7 | I | (1-2) Con; (3-4) I | 48.3 |
| 8 | L | (1-2) Con; (3-4) L | 50.7 |
| 9 | E | (1-2) Con; (3-4) E | 36 |
| 10 | L | (1-2) Con; (3-4) L | 16.5 |
| 11 | T | (1) Any; (2-3) Con; (4) T | 67.7 |
| 12 | S | (1-2) Con; (3-4) S | 13.2 |
| 13 | I | (1-2) Con; (3-4) I | 43.7 |
| 14 | A | (1-2) Con; (3-4) A | 4.3 |
| 15 | K | (1-2) Con; (3-4) K | 34.5 |
| 16 | G | (1-2) Con; (3-4) G | 20.7 |
| 17 | M | (1) Any; (2-3) Con; (4) M | 55.3 |
| 18 | E | (1-2) Con; (3-4) E | 34.5 |
| 19 | L | (1-2) Con; (3-4) L | 32.2 |
| 20 | G | (1-2) Con; (3-4) G | 28 |
| 21 | D | (1-2) Con; (3-4) D | 16 |
| 22 | A | (1) Any; (2-3) Con; (4) A | 57.5 |
| 23 | M | (1-2) Con; (3-4) M | 27.8 |
| 24 | L | (1-2) Con; (3-4) L | 37.2 |
| 25 | K | (1) Any; (2-3) Con; (4) K | 79.5 |
| 26 | S | (1) Any; (2-3) Con; (4) S | 56.7 |
| 27 | A | (1-2) Con; (3-4) A | 22.7 |
| 28 | N | (1) Any; (2-3) Con; (4) N | 93.5 |
| 29 | V | (1-2) Con; (3-4) V | 32 |
| 30 | D | (1) Any; (2-3) Con; (4) D | 63.7 |
| 31 | L | (1) Any; (2-3) Con; (4) L | 71.8 |
| 32 | L | (1-2) Con; (3-4) L | 28.3 |
| 33 | V | (1-2) Con; (3-4) V | 44.7 |
| 34 | S | (1) Any; (2-3) Con; (4) S | 84.7 |
| 35 | K | (1) Any; (2-3) Con; (4) K | 66.5 |
| 36 | T | (1) Any; (2-3) Con; (4) T | 78.2 |
| 37 | I | (1-2) Con; (3-4) I | 34.2 |
| 38 | S | (1) Any; (2-3) Con; (4) S | 100.2 |
| 39 | P | (1) Any; (2-3) Con; (4) P | 120.7 |
| 40 | G | (1-2) Con; (3-4) G | 25.2 |
| 41 | K | (1-2) Con; (3-4) K | 28.3 |
| 42 | F | (1-2) Con; (3-4) F | 16.8 |
| 43 | L | (1-2) Con; (3-4) L | 47.3 |
| 44 | L | (1-2) Con; (3-4) L | 43.2 |
| 45 | M | (1-2) Con; (3-4) M | 30.2 |

FIGURE 11A

| | | | |
|---|---|---|---|
| 46 | L | (1-2) Con; (3-4) L | 32 |
| 47 | G | (1-2) Con; (3-4) G | 18.5 |
| 48 | G | (1-2) Con; (3-4) G | 23.2 |
| 49 | D | (1) Any; (2-3) Con; (4) D | 58.5 |
| 50 | I | (1) Any; (2-3) Con; (4) I | 55.5 |
| 51 | G | (1) Any; (2-3) Con; (4) G | 54.7 |
| 52 | A | (1-2) Con; (3-4) A | 19.8 |
| 53 | I | (1-2) Con; (3-4) I | 11 |
| 54 | Q | (1) Any; (2-3) Con; (4) Q | 58.7 |
| 55 | Q | (1) Any; (2-3) Con; (4) Q | 51 |
| 56 | A | (1-2) Con; (3-4) A | 9.8 |
| 57 | I | (1-2) Con; (3-4) I | 37.5 |
| 58 | E | (1) Any; (2-3) Con; (4) E | 58.8 |
| 59 | T | (1-2) Con; (3-4) T | 43.7 |
| 60 | G | (1-2) Con; (3-4) G | 16.3 |
| 61 | T | (1) Any; (2-3) Con; (4) T | 57.8 |
| 62 | S | (1) Any; (2-3) Con; (4) S | 89.2 |
| 63 | Q | (1) Any; (2-3) Con; (4) Q | 82.3 |
| 64 | A | (1-2) Con; (3-4) A | 30 |
| 65 | G | (1) Any; (2-3) Con; (4) G | 57.8 |
| 66 | E | (1) Any; (2-3) Con; (4) E | 112.5 |
| 67 | M | (1-2) Con; (3-4) M | 22 |
| 68 | L | (1) Any; (2-3) Con; (4) L | 55.8 |
| 69 | V | (1) Any; (2-3) Con; (4) V | 73.3 |
| 70 | D | (1) Any; (2-3) Con; (4) D | 66.7 |
| 71 | S | (1) Any; (2-3) Con; (4) S | 79.8 |
| 72 | L | (1) Any; (2-3) Con; (4) L | 63.7 |
| 73 | V | (1) Any; (2-3) Con; (4) V | 88.3 |
| 74 | L | (1-2) Con; (3-4) L | 49.2 |
| 75 | A | (1) Any; (2-3) Con; (4) A | 77.7 |
| 76 | N | (1) Any; (2-3) Con; (4) N | 89.3 |
| 77 | I | (1-2) Con; (3-4) I | 20.7 |
| 78 | H | (1-2) Con; (3-4) H | 21.2 |
| 79 | P | (1) Any; (2-3) Con; (4) P | 97.7 |
| 80 | S | (1-2) Con; (3-4) S | 49.5 |
| 81 | V | (1-2) Con; (3-4) V | 34.8 |
| 82 | L | (1) Any; (2-3) Con; (4) L | 55.2 |
| 83 | P | (1) Any; (2-3) Con; (4) P | 74.5 |
| 84 | A | (1-2) Con; (3-4) A | 7 |
| 85 | I | (1) Any; (2-3) Con; (4) I | 60.3 |
| 86 | S | (1) Any; (2-3) Con; (4) S | 66.3 |
| 87 | G | (1-2) Con; (3-4) G | 33.7 |
| 88 | L | (1) Any; (2-3) Con; (4) L | 67.7 |
| 89 | N | (1) Any; (2-3) Con; (4) N | 55 |
| 90 | S | (1) Any; (2-3) Con; (4) S | 107.3 |
| 91 | V | (1) Any; (2-3) Con; (4) V | 56.3 |
| 92 | D | (1) Any; (2-3) Con; (4) D | 117.5 |
| 93 | K | (1) Any; (2-3) Con; (4) K | 52.8 |

FIGURE 11B

| | | | |
|---|---|---|---|
| 94 | R | (1) Any; (2-3) Con; (4) R | 76.3 |
| 95 | Q | (1) Any; (2-3) Con; (4) Q | 67.7 |
| 96 | A | (1-4) A | 6.7 |
| 97 | V | (1-2) Con; (3-4) V | 33.5 |
| 98 | G | (1-2) Con; (3-4) G | 10 |
| 99 | I | (1-2) Con; (3-4) I | 27 |
| 100 | V | (1-2) Con; (3-4) V | 18.7 |
| 101 | E | (1-2) Con; (3-4) E | 6.7 |
| 102 | T | (1-2) Con; (3-4) T | 4.8 |
| 103 | W | (1-2) Con; (3-4) W | 50.5 |
| 104 | S | (1-2) Con; (3-4) S | 26.7 |
| 105 | V | (1-2) Con; (3-4) V | 35 |
| 106 | A | (1) Any; (2-3) Con; (4) A | 79.3 |
| 107 | A | (1-2) Con; (3-4) A | 18.5 |
| 108 | C | (1-2) Con; (3-4) C | 8 |
| 109 | I | (1) Any; (2-3) Con; (4) I | 53.7 |
| 110 | S | (1) Any; (2-3) Con; (4) S | 58.7 |
| 111 | A | (1-2) Con; (3-4) A | 6.7 |
| 112 | A | (1-2) Con; (3-4) A | 24.8 |
| 113 | D | (1-2) Con; (3-4) D | 22.7 |
| 114 | L | (1-4) L | 40.2 |
| 115 | A | (1-4) A | 10.5 |
| 116 | V | (1-2) Con; (3-4) V | 31.5 |
| 117 | K | (1-4) K | 89 |
| 118 | G | (1-4) G | 32.3 |
| 119 | S | (1-4) S | 31.8 |
| 120 | N | (1-4) N | 96.5 |
| 121 | V | (1-2) Con; (3-4) V | 18 |
| 122 | T | (1) Any; (2-3) Con; (4) T | 60.7 |
| 123 | L | (1-2) Con; (3-4) L | 31.2 |
| 124 | V | (1-2) Con; (3-4) V | 12.8 |
| 125 | R | (1-2) Con; (3-4) R | 23.8 |
| 126 | V | (1-2) Con; (3-4) V | 45 |
| 127 | H | (1) Any; (2-3) Con; (4) H | 64.5 |
| 128 | M | (1) Any; (2-3) Con; (4) M | 62.8 |
| 129 | A | (1) Any; (2-3) Con; (4) A | 70.7 |
| 130 | F | (1) Any; (2-3) Con; (4) F | 58.5 |
| 131 | G | (1-2) Con; (3-4) G | 34 |
| 132 | I | (1) Any; (2-3) Con; (4) I | 71.5 |
| 133 | G | (1) Any; (2-3) Con; (4) G | 72 |
| 134 | G | (1-2) Con; (3-4) G | 19 |
| 135 | K | (1-2) Con; (3-4) K | 41.7 |
| 136 | C | (1-2) Con; (3-4) C | 5.3 |
| 137 | Y | (1-2) Con; (3-4) Y | 28.7 |
| 138 | M | (1-2) Con; (3-4) M | 23 |
| 139 | V | (1-2) Con; (3-4) V | 27.8 |
| 140 | V | (1-2) Con; (3-4) V | 22.5 |
| 141 | A | (1-2) Con; (3-4) A | 15.3 |
| 142 | G | (1-2) Con; (3-4) G | 14.2 |
| 143 | D | (1-4) D | 61.5 |
| 144 | V | (1-4) V | 45.2 |
| 145 | L | (1-4) L | 55.2 |

FIGURE 11C

| | | | |
|---|---|---|---|
| 146 | D | (1-4) D | 16.2 |
| 147 | V | (1-4) V | 5.2 |
| 148 | A | (1-4) A | 4.2 |
| 149 | A | (1-4) A | 13.7 |
| 150 | A | (1-4) A | 6.2 |
| 151 | V | (1-4) V | 16.8 |
| 152 | A | (1-4) A | 7.3 |
| 153 | T | (1-4) T | 7.5 |
| 154 | A | (1-4) A | 7.8 |
| 155 | S | (1-4) S | 36.8 |
| 156 | L | (1-4) L | 26.5 |
| 157 | A | (1-4) A | 40.2 |
| 158 | A | (1-2) Con; (3-4) A | 5 |
| 159 | G | (1-4) G | 44.5 |
| 160 | A | (1-4) A | 91.3 |
| 161 | K | (1) Any; (2-3) Con; (4) K | 81.3 |
| 162 | G | (1) Any; (2-3) Con; (4) G | 69 |
| 163 | L | (1-2) Con; (3-4) L | 18.2 |
| 164 | L | (1) Any; (2-3) Con; (4) L | 53 |
| 165 | V | (1) Any; (2-3) Con; (4) V | 65 |
| 166 | Y | (1-2) Con; (3-4) Y | 24.3 |
| 167 | A | (1-4) A | 61.7 |
| 168 | S | (1-4) S | 20.8 |
| 169 | I | (1-4) I | 30.7 |
| 170 | I | (1-4) I | 27.7 |
| 171 | P | (1-4) P | 56.7 |
| 172 | R | (1-4) R | 83.7 |
| 173 | P | (1-2) Con; (3-4) P | 29.2 |
| 174 | H | (1-2) Con; (3-4) H | 28.3 |
| 175 | E | (1) Any; (2-3) Con; (4) E | 92.2 |
| 176 | A | (1) Any; (2-3) Con; (4) A | 68.7 |
| 177 | M | (1-2) Con; (3-4) M | 32 |
| 178 | W | (1-2) Con; (3-4) W | 31.5 |
| 179 | R | (1) Any; (2-3) Con; (4) R | 60.5 |
| 180 | Q | (1) Any; (2-3) Con; (4) Q | 63 |
| 181 | M | (1) Any; (2-3) Con; (4) M | 66.3 |
| 182 | V | (1) Any; (2-3) Con; (4) V | 53 |
| 183 | E | (1) Any; (2-3) Con; (4) E | 120 |
| 184 | G | (1) Any; (2-3) Con; (4) G | N/A |

(SEQ ID NOs: 2, 12, 22, and 32)

FIGURE 11D

| T33-09A residue | | amino acid | allowed amino acids | SASA |
|---|---|---|---|---|
| | 1 | M | (1-3) Optional/any (4) M | 115.3 |
| | 2 | E | (1-2) Con; (3-4) E | 21.3 |
| | 3 | E | (1-2) Con; (3-4) E | 4.3 |
| | 4 | V | (1-2) Con; (3-4) V | 0.8 |
| | 5 | V | (1-2) Con; (3-4) V | 0 |
| | 6 | L | (1-2) Con; (3-4) L | 8.8 |
| | 7 | I | (1-2) Con; (3-4) I | 0 |
| | 8 | T | (1-2) Con; (3-4) T | 7.3 |
| | 9 | V | (1-2) Con; (3-4) V | 0 |
| | 10 | P | (1-2) Con; (3-4) P | 32.2 |
| | 11 | S | (1-2) Con; (3-4) S | 36.3 |
| | 12 | A | (1-4) A | 17.8 |
| | 13 | L | (1-4) L | 65.3 |
| | 14 | V | (1-4) V | 26 |
| | 15 | A | (1-4) A | 0 |
| | 16 | V | (1-4) V | 0.7 |
| | 17 | K | (1-4) K | 89.8 |
| | 18 | I | (1-2) Con; (3-4) I | 0.7 |
| | 19 | A | (1-2) Con; (3-4) A | 0 |
| | 20 | H | (1-4) H | 19.5 |
| | 21 | A | (1-2) Con; (3-4) A | 11.5 |
| | 22 | L | (1-2) Con; (3-4) L | 1.2 |
| | 23 | V | (1-2) Con; (3-4) V | 0 |
| | 24 | E | (1) Any; (2-3) Con; (4) E | 99.8 |
| | 25 | E | (1) Any; (2-3) Con; (4) E | 74.8 |
| | 26 | R | (1) Any; (2-3) Con; (4) R | 88.7 |
| | 27 | L | (1-2) Con; (3-4) L | 10.8 |
| | 28 | A | (1-2) Con; (3-4) A | 0 |
| | 29 | A | (1-2) Con; (3-4) A | 0 |
| | 30 | C | (1-2) Con; (3-4) C | 7.5 |
| | 31 | V | (1-2) Con; (3-4) V | 0 |
| | 32 | N | (1-2) Con; (3-4) N | 0.7 |
| | 33 | I | (1-4) I | 0 |
| | 34 | V | (1-2) Con; (3-4) V | 4.7 |
| | 35 | P | (1-4) P | 44.7 |
| | 36 | G | (1-4) G | 17 |
| | 37 | L | (1-4) L | 0.2 |
| | 38 | T | (1-4) T | 5 |
| | 39 | S | (1-2) Con; (3-4) S | 0 |
| | 40 | I | (1-4) I | 6.7 |
| | 41 | Y | (1) Any; (2-3) Con; (4) Y | 57.3 |
| | 42 | R | (1-2) Con; (3-4) R | 13.8 |
| | 43 | W | (1-4) W | 157 |
| | 44 | Q | (1) Any; (2-3) Con; (4) Q | 143.8 |
| | 45 | G | (1) Any; (2-3) Con; (4) G | 57 |
| | 46 | S | (1-4) S | 31 |
| | 47 | V | (1-4) V | 25.7 |
| | 48 | V | (1-4) V | 14.7 |
| | 49 | S | (1-4) S | 24.2 |
| | 50 | D | (1-2) Con; (3-4) D | 44.3 |
| | 51 | H | (1-4) H | 39.5 |
| | 52 | E | (1-2) Con; (3-4) E | 16.3 |

FIGURE 12A

| | | | |
|---|---|---|---|
| 53 | L | (1-4) L | 8.7 |
| 54 | L | (1-2) Con; (3-4) L | 9.7 |
| 55 | L | (1-2) Con; (3-4) L | 0 |
| 56 | L | (1-2) Con; (3-4) L | 11 |
| 57 | V | (1-2) Con; (3-4) V | 0 |
| 58 | K | (1-2) Con; (3-4) K | 0.3 |
| 59 | T | (1-2) Con; (3-4) T | 0 |
| 60 | T | (1-2) Con; (3-4) T | 9.2 |
| 61 | T | (1) Any; (2-3) Con; (4) T | 59.5 |
| 62 | H | (1) Any; (2-3) Con; (4) H | 117.2 |
| 63 | A | (1-2) Con; (3-4) A | 0 |
| 64 | F | (1-2) Con; (3-4) F | 2.3 |
| 65 | P | (1) Any; (2-3) Con; (4) P | 57.3 |
| 66 | K | (1) Any; (2-3) Con; (4) K | 90.8 |
| 67 | L | (1-2) Con; (3-4) L | 0 |
| 68 | K | (1-2) Con; (3-4) K | 21.7 |
| 69 | E | (1) Any; (2-3) Con; (4) E | 132.3 |
| 70 | R | (1) Any; (2-3) Con; (4) R | 77.8 |
| 71 | V | (1-2) Con; (3-4) V | 0.3 |
| 72 | K | (1) Any; (2-3) Con; (4) K | 80.5 |
| 73 | A | (1) Any; (2-3) Con; (4) A | 73.5 |
| 74 | L | (1-2) Con; (3-4) L | 43.8 |
| 75 | H | (1-2) Con; (3-4) H | 10.7 |
| 76 | P | (1) Any; (2-3) Con; (4) P | 73.5 |
| 77 | Y | (1) Any; (2-3) Con; (4) Y | 112.7 |
| 78 | T | (1) Any; (2-3) Con; (4) T | 131.5 |
| 79 | V | (1) Any; (2-3) Con; (4) V | 59.5 |
| 80 | P | (1-2) Con; (3-4) P | 2.5 |
| 81 | E | (1-2) Con; (3-4) E | 8.2 |
| 82 | I | (1-2) Con; (3-4) I | 0 |
| 83 | V | (1-2) Con; (3-4) V | 0 |
| 84 | A | (1-2) Con; (3-4) A | 0 |
| 85 | L | (1-2) Con; (3-4) L | 5.2 |
| 86 | P | (1-2) Con; (3-4) P | 36.8 |
| 87 | I | (1-2) Con; (3-4) I | 12.7 |
| 88 | A | (1) Any; (2-3) Con; (4) A | 61.7 |
| 89 | E | (1) Any; (2-3) Con; (4) E | 51 |
| 90 | G | (1-2) Con; (3-4) G | 5.2 |
| 91 | N | (1-2) Con; (3-4) N | 1.8 |
| 92 | R | (1) Any; (2-3) Con; (4) R | 179.5 |
| 93 | E | (1) Any; (2-3) Con; (4) E | 119.3 |
| 94 | Y | (1-2) Con; (3-4) Y | 12.3 |
| 95 | L | (1-2) Con; (3-4) L | 16.3 |
| 96 | D | (1) Any; (2-3) Con; (4) D | 73.8 |
| 97 | W | (1-2) Con; (3-4) W | 47.2 |
| 98 | L | (1-2) Con; (3-4) L | 0 |
| 99 | R | (1) Any; (2-3) Con; (4) R | 87 |
| 100 | E | (1) Any; (2-3) Con; (4) E | 120.5 |
| 101 | N | (1-2) Con; (3-4) N | 14.7 |
| 102 | T | (1-2) Con; (3-4) T | 21.7 |
| 103 | G | (1-2) Con; (3-4) G | 50.8 |

(SEQ ID NOs: 3, 13, 23, and 33)

FIGURE 12B

| T33-09B residue | amino acid | allowed amino acids | SASA |
|---|---|---|---|
| 1 | M | (1-3) Optional or any; (4) M | 68.5 |
| 2 | V | (1-2) Con; (3-4) V | 4.8 |
| 3 | R | (1-2) Con; (3-4) R | 20.7 |
| 4 | G | (1-2) Con; (3-4) G | 2.2 |
| 5 | I | (1-2) Con; (3-4) I | 1.2 |
| 6 | R | (1-2) Con; (3-4) R | 17.7 |
| 7 | G | (1-2) Con; (3-4) G | 0 |
| 8 | A | (1-2) Con; (3-4) A | 0 |
| 9 | I | (1-4) I | 0 |
| 10 | T | (1-2) Con; (3-4) T | 9.5 |
| 11 | V | (1-2) Con; (3-4) V | 8.3 |
| 12 | E | (1-4) E | 102.7 |
| 13 | E | (1-4) E | 32.5 |
| 14 | D | (1) Any; (2-3) Con; (4) D | 55 |
| 15 | T | (1-4) T | 34.7 |
| 16 | P | (1-4) P | 47.7 |
| 17 | A | (1-4) A | 2.7 |
| 18 | A | (1-4) A | 12.7 |
| 19 | I | (1-2) Con; (3-4) I | 0.5 |
| 20 | L | (1-4) L | 3.3 |
| 21 | A | (1-4) A | 6.5 |
| 22 | A | (1-4) A | 2.5 |
| 23 | T | (1-2) Con; (3-4) T | 0.2 |
| 24 | I | (1-4) I | 6 |
| 25 | E | (1-4) E | 11.3 |
| 26 | L | (1-2) Con; (3-4) L | 0 |
| 27 | L | (1-2) Con; (3-4) L | 6.8 |
| 28 | L | (1-4) L | 46.2 |
| 29 | K | (1-4) K | 50.2 |
| 30 | M | (1-2) Con; (3-4) M | 4 |
| 31 | L | (1-2) Con; (3-4) L | 19.2 |
| 32 | E | (1-4) E | 126.5 |
| 33 | A | (1-2) Con; (3-4) A | 49.2 |
| 34 | N | (1-2) Con; (3-4) N | 21.8 |
| 35 | G | (1) Any; (2-3) Con; (4) G | 52.2 |
| 36 | I | (1-2) Con; (3-4) I | 27 |
| 37 | Q | (1) Any; (2-3) Con; (4) Q | 172.8 |
| 38 | S | (1-2) Con; (3-4) S | 35.8 |
| 39 | Y | (1) Any; (2-3) Con; (4) Y | 63.3 |
| 40 | E | (1) Any; (2-3) Con; (4) E | 102.7 |
| 41 | E | (1-2) Con; (3-4) E | 45.7 |
| 42 | L | (1-2) Con; (3-4) L | 1.7 |
| 43 | A | (1-2) Con; (3-4) A | 0.7 |
| 44 | A | (1-2) Con; (3-4) A | 0 |
| 45 | V | (1-2) Con; (3-4) V | 1.5 |
| 46 | I | (1-2) Con; (3-4) I | 12.3 |

FIGURE 13A

| | | | |
|---|---|---|---|
| 47 | F | (1-2) Con; (3-4) F | 0 |
| 48 | T | (1-2) Con; (3-4) T | 1.7 |
| 49 | V | (1-2) Con; (3-4) V | 0.3 |
| 50 | T | (1-2) Con; (3-4) T | 13.5 |
| 51 | E | (1) Any; (2-3) Con; (4) E | 57.3 |
| 52 | D | (1) Any; (2-3) Con; (4) D | 100.5 |
| 53 | L | (1-2) Con; (3-4) L | 0.3 |
| 54 | T | (1-2) Con; (3-4) T | 35.2 |
| 55 | S | (1-2) Con; (3-4) S | 27.7 |
| 56 | A | (1-2) Con; (3-4) A | 7.5 |
| 57 | F | (1-2) Con; (3-4) F | 34.8 |
| 58 | P | (1-2) Con; (3-4) P | 0.2 |
| 59 | A | (1-2) Con; (3-4) A | 11.3 |
| 60 | E | (1-4) E | 54.8 |
| 61 | A | (1-4) A | 0 |
| 62 | A | (1-2) Con; (3-4) A | 0 |
| 63 | R | (1-2) Con; (3-4) R | 41.7 |
| 64 | L | (1-4) L | 32.5 |
| 65 | I | (1-4) I | 22.8 |
| 66 | G | (1-2) Con; (3-4) G | 40 |
| 67 | M | (1-2) Con; (3-4) M | 1.3 |
| 68 | H | (1-4) H | 68 |
| 69 | R | (1) Any; (2-3) Con; (4) R | 64.2 |
| 70 | V | (1-2) Con; (3-4) V | 3.5 |
| 71 | P | (1-2) Con; (3-4) P | 6.5 |
| 72 | L | (1-2) Con; (3-4) L | 5.2 |
| 73 | L | (1-2) Con; (3-4) L | 5.8 |
| 74 | S | (1-2) Con; (3-4) S | 5.5 |
| 75 | A | (1-2) Con; (3-4) A | 6.8 |
| 76 | R | (1-2) Con; (3-4) R | 16.7 |
| 77 | E | (1-2) Con; (3-4) E | 5.7 |
| 78 | V | (1-2) Con; (3-4) V | 2.5 |
| 79 | P | (1) Any; (2-3) Con; (4) P | 51.7 |
| 80 | V | (1-2) Con; (3-4) V | 17.3 |
| 81 | P | (1) Any; (2-3) Con; (4) P | 98.3 |
| 82 | G | (1) Any; (2-3) Con; (4) G | 84.5 |
| 83 | S | (1-2) Con; (3-4) S | 39.2 |
| 84 | L | (1-2) Con; (3-4) L | 22.7 |
| 85 | P | (1) Any; (2-3) Con; (4) P | 54 |
| 86 | R | (1) Any; (2-3) Con; (4) R | 65 |
| 87 | V | (1-2) Con; (3-4) V | 0.2 |
| 88 | I | (1-2) Con; (3-4) I | 0 |
| 89 | R | (1-2) Con; (3-4) R | 18.5 |
| 90 | V | (1-2) Con; (3-4) V | 0.3 |
| 91 | L | (1-2) Con; (3-4) L | 0 |
| 92 | A | (1-2) Con; (3-4) A | 6 |
| 93 | L | (1-2) Con; (3-4) L | 3.3 |
| 94 | W | (1-2) Con; (3-4) W | 9.8 |
| 95 | N | (1-2) Con; (3-4) N | 27.5 |
| 96 | T | (1-2) Con; (3-4) T | 21.5 |
| 97 | D | (1) Any; (2-3) Con; (4) D | 125.7 |
| 98 | T | (1-2) Con; (3-4) T | 27.7 |

FIGURE 13B

| | | | |
|---|---|---|---|
| 99 | P | (1) Any; (2-3) Con; (4) P | 66.7 |
| 100 | Q | (1-2) Con; (3-4) Q | 12.3 |
| 101 | D | (1) Any; (2-3) Con; (4) D | 87.2 |
| 102 | R | (1) Any; (2-3) Con; (4) R | 164.2 |
| 103 | V | (1-2) Con; (3-4) V | 2.3 |
| 104 | R | (1) Any; (2-3) Con; (4) R | 105.7 |
| 105 | H | (1-2) Con; (3-4) H | 32.5 |
| 106 | V | (1-2) Con; (3-4) V | 17.7 |
| 107 | Y | (1-2) Con; (3-4) Y | 28.2 |
| 108 | L | (1-2) Con; (3-4) L | 29 |
| 109 | N | (1-4) N | 79 |
| 110 | E | (1) Any; (2-3) Con; (4) E | 79.5 |
| 111 | A | (1-2) Con; (3-4) A | 0 |
| 112 | V | (1) Any; (2-3) Con; (4) V | 56.8 |
| 113 | R | (1) Any; (2-3) Con; (4) R | 146.8 |
| 114 | L | (1-2) Con; (3-4) L | 42.7 |
| 115 | R | (1-2) Con; (3-4) R | 18 |
| 116 | P | (1) Any; (2-3) Con; (4) P | 88.3 |
| 117 | D | (1) Any; (2-3) Con; (4) D | 69 |
| 118 | L | (1) Any; (2-3) Con; (4) L | 57.8 |
| 119 | E | (1) Any; (2-3) Con; (4) E | 123.7 |
| 120 | S | (1) Any; (2-3) Con; (4) S | 105.8 |
| 121 | A | (1) Any; (2-3) Con; (4) A | 161 |
| 122 | Q | (1) Any; (2-3) Con; (4) Q | N/A |

(SEQ ID NOs: 4, 14, 24, and 34)

FIGURE 13C

| T33-15A residue | amino acid | allowed amino acids | SASA |
|---|---|---|---|
| 1 | M | (1-3) Optional or any; (4) M | N/A |
| 2 | S | (1) Any; (2-3) Con; (4) S | N/A |
| 3 | K | (1) Any; (2-3) Con; (4) K | 116.5 |
| 4 | A | (1-2) Con; (3-4) A | 7.5 |
| 5 | K | (1-2) Con; (3-4) K | 16.3 |
| 6 | I | (1-2) Con; (3-4) I | 0 |
| 7 | G | (1-2) Con; (3-4) G | 0 |
| 8 | I | (1-2) Con; (3-4) I | 0 |
| 9 | V | (1-2) Con; (3-4) V | 0 |
| 10 | T | (1-2) Con; (3-4) T | 4.3 |
| 11 | V | (1-2) Con; (3-4) V | 5.7 |
| 12 | S | (1-2) Con; (3-4) S | 31.2 |
| 13 | D | (1-2) Con; (3-4) D | 50.5 |
| 14 | R | (1-2) Con; (3-4) R | 47.3 |
| 15 | A | (1-2) Con; (3-4) A | 18.8 |
| 16 | S | (1) Any; (2-3) Con; (4) S | 51.2 |
| 17 | A | (1) Any; (2-3) Con; (4) A | 81.5 |
| 18 | G | (1) Any; (2-3) Con; (4) G | 62.5 |
| 19 | I | (1) Any; (2-3) Con; (4) I | 89.2 |
| 20 | T | (1) Any; (2-3) Con; (4) T | 51.5 |
| 21 | A | (1) Any; (2-3) Con; (4) A | 85.2 |
| 22 | D | (1-2) Con; (3-4) D | 31 |
| 23 | I | (1-4) I | 81.3 |
| 24 | S | (1-2) Con; (3-4) S | 16.5 |
| 25 | G | (1-2) Con; (3-4) G | 0 |
| 26 | K | (1-4) K | 56.3 |
| 27 | A | (1-4) A | 2.5 |
| 28 | I | (1-2) Con; (3-4) I | 0 |
| 29 | I | (1-2) Con; (3-4) I | 39.8 |
| 30 | L | (1-4) L | 26.5 |
| 31 | A | (1-4) A | 0.7 |
| 32 | L | (1-2) Con; (3-4) L | 0 |
| 33 | N | (1-4) N | 79.5 |
| 34 | L | (1-4) L | 11.2 |
| 35 | Y | (1-4) Y | 0.2 |
| 36 | L | (1-2) Con; (3-4) L | 13.2 |
| 37 | T | (1) Any; (2-3) Con; (4) T | 92.7 |
| 38 | S | (1-2) Con; (3-4) S | 31.3 |
| 39 | E | (1) Any; (2-3) Con; (4) E | 74.5 |
| 40 | W | (1-2) Con; (3-4) W | 36.7 |
| 41 | E | (1-2) Con; (3-4) E | 43.3 |
| 42 | P | (1) Any; (2-3) Con; (4) P | 69.7 |
| 43 | I | (1-2) Con; (3-4) I | 37.3 |
| 44 | Y | (1) Any; (2-3) Con; (4) Y | 100.3 |
| 45 | Q | (1) Any; (2-3) Con; (4) Q | 87.2 |
| 46 | V | (1-2) Con; (3-4) V | 45 |
| 47 | I | (1-2) Con; (3-4) I | 4.7 |
| 48 | P | (1-2) Con; (3-4) P | 44.3 |
| 49 | D | (1-2) Con; (3-4) D | 16.7 |

FIGURE 14A

| | | | |
|---|---|---|---|
| 50 | E | (1-2) Con; (3-4) E | 27.7 |
| 51 | Q | (1) Any; (2-3) Con; (4) Q | 66.8 |
| 52 | D | (1) Any; (2-3) Con; (4) D | 71.5 |
| 53 | V | (1) Any; (2-3) Con; (4) V | 57.7 |
| 54 | I | (1-2) Con; (3-4) I | 0.2 |
| 55 | E | (1-2) Con; (3-4) E | 49.7 |
| 56 | T | (1) Any; (2-3) Con; (4) T | 92.2 |
| 57 | T | (1-2) Con; (3-4) T | 12.3 |
| 58 | L | (1-2) Con; (3-4) L | 0 |
| 59 | I | (1) Any; (2-3) Con; (4) I | 56.8 |
| 60 | K | (1-2) Con; (3-4) K | 43.8 |
| 61 | M | (1-2) Con; (3-4) M | 3.2 |
| 62 | A | (1-2) Con; (3-4) A | 0.7 |
| 63 | D | (1) Any; (2-3) Con; (4) D | 86.5 |
| 64 | E | (1) Any; (2-3) Con; (4) E | 85 |
| 65 | Q | (1) Any; (2-3) Con; (4) Q | 95.3 |
| 66 | D | (1) Any; (2-3) Con; (4) D | 86 |
| 67 | C | (1-2) Con; (3-4) C | 0.8 |
| 68 | C | (1-2) Con; (3-4) C | 9.8 |
| 69 | L | (1-2) Con; (3-4) L | 0.3 |
| 70 | I | (1-2) Con; (3-4) I | 0 |
| 71 | V | (1-2) Con; (3-4) V | 1.3 |
| 72 | T | (1-2) Con; (3-4) T | 0 |
| 73 | T | (1-2) Con; (3-4) T | 2.2 |
| 74 | G | (1-2) Con; (3-4) G | 5.7 |
| 75 | G | (1-2) Con; (3-4) G | 8.7 |
| 76 | T | (1-2) Con; (3-4) T | 8.5 |
| 77 | G | (1-2) Con; (3-4) G | 13.8 |
| 78 | P | (1-2) Con; (3-4) P | 6 |
| 79 | A | (1-2) Con; (3-4) A | 27.5 |
| 80 | K | (1) Any; (2-3) Con; (4) K | 86 |
| 81 | R | (1) Any; (2-3) Con; (4) R | 120.3 |
| 82 | D | (1-2) Con; (3-4) D | 28.8 |
| 83 | V | (1-2) Con; (3-4) V | 23 |
| 84 | T | (1-2) Con; (3-4) T | 0 |
| 85 | P | (1-2) Con; (3-4) P | 8.2 |
| 86 | E | (1-2) Con; (3-4) E | 46.3 |
| 87 | A | (1-2) Con; (3-4) A | 0 |
| 88 | T | (1-2) Con; (3-4) T | 0 |
| 89 | E | (1) Any; (2-3) Con; (4) E | 54.7 |
| 90 | A | (1) Any; (2-3) Con; (4) A | 63.5 |
| 91 | V | (1-2) Con; (3-4) V | 7 |
| 92 | C | (1-2) Con; (3-4) C | 18.2 |
| 93 | D | (1) Any; (2-3) Con; (4) D | 83.5 |
| 94 | R | (1-2) Con; (3-4) R | 11.3 |
| 95 | M | (1) Any; (2-3) Con; (4) M | 57.5 |
| 96 | M | (1-2) Con; (3-4) M | 0.3 |
| 97 | P | (1-2) Con; (3-4) P | 40.3 |
| 98 | G | (1-2) Con; (3-4) G | 2.5 |
| 99 | F | (1-2) Con; (3-4) F | 0 |
| 100 | G | (1-2) Con; (3-4) G | 0.7 |
| 101 | E | (1-2) Con; (3-4) E | 30.5 |
| 102 | L | (1-2) Con; (3-4) L | 35.2 |
| 103 | M | (1-2) Con; (3-4) M | 3.2 |
| 104 | R | (1-2) Con; (3-4) R | 9.8 |

FIGURE 14B

| | | | |
|---|---|---|---|
| 105 | A | (1) Any; (2-3) Con; (4) A | 59.5 |
| 106 | E | (1) Any; (2-3) Con; (4) E | 60.2 |
| 107 | S | (1-2) Con; (3-4) S | 43.8 |
| 108 | L | (1) Any; (2-3) Con; (4) L | 53.3 |
| 109 | K | (1) Any; (2-3) Con; (4) K | 98 |
| 110 | E | (1) Any; (2-3) Con; (4) E | 86.3 |
| 111 | V | (1-2) Con; (3-4) V | 36 |
| 112 | P | (1-2) Con; (3-4) P | 48.5 |
| 113 | T | (1-2) Con; (3-4) T | 31.3 |
| 114 | A | (1-2) Con; (3-4) A | 10.3 |
| 115 | I | (1-2) Con; (3-4) I | 1 |
| 116 | L | (1-2) Con; (3-4) L | 7.2 |
| 117 | S | (1-2) Con; (3-4) S | 21.3 |
| 118 | R | (1-2) Con; (3-4) R | 5.5 |
| 119 | Q | (1-2) Con; (3-4) Q | 6.2 |
| 120 | T | (1-2) Con; (3-4) T | 38 |
| 121 | A | (1-2) Con; (3-4) A | 0 |
| 122 | G | (1-2) Con; (3-4) G | 0 |
| 123 | L | (1-2) Con; (3-4) L | 0 |
| 124 | R | (1) Any; (2-3) Con; (4) R | 55.5 |
| 125 | G | (1-2) Con; (3-4) G | 48 |
| 126 | D | (1) Any; (2-3) Con; (4) D | 64.5 |
| 127 | S | (1-2) Con; (3-4) S | 0 |
| 128 | L | (1-2) Con; (3-4) L | 0.2 |
| 129 | I | (1-2) Con; (3-4) I | 0 |
| 130 | V | (1-2) Con; (3-4) V | 1.3 |
| 131 | N | (1-2) Con; (3-4) N | 0 |
| 132 | L | (1-2) Con; (3-4) L | 0 |
| 133 | P | (1-2) Con; (3-4) P | 20.8 |
| 134 | G | (1-2) Con; (3-4) G | 33.2 |
| 135 | D | (1) Any; (2-3) Con; (4) D | 80.2 |
| 136 | P | (1-2) Con; (3-4) P | 50.8 |
| 137 | A | (1-4) A | 30.8 |
| 138 | S | (1-4) S | 35.2 |
| 139 | I | (1-2) Con; (3-4) I | 2 |
| 140 | S | (1-4) S | 10.2 |
| 141 | D | (1-4) D | 48.5 |
| 142 | C | (1-2) Con; (3-4) C | 6.8 |
| 143 | L | (1-2) Con; (3-4) L | 1.7 |
| 144 | L | (1-4) L | 49.3 |
| 145 | A | (1-2) Con; (3-4) A | 30.3 |
| 146 | V | (1-2) Con; (3-4) V | 0 |
| 147 | F | (1-2) Con; (3-4) F | 0.2 |
| 148 | P | (1-2) Con; (3-4) P | 17.5 |
| 149 | A | (1-2) Con; (3-4) A | 0.8 |
| 150 | I | (1-2) Con; (3-4) I | 1 |
| 151 | P | (1-2) Con; (3-4) P | 0.2 |
| 152 | Y | (1) Any; (2-3) Con; (4) Y | 77 |
| 153 | C | (1-2) Con; (3-4) C | 0.2 |
| 154 | I | (1-2) Con; (3-4) I | 3.7 |
| 155 | D | (1-2) Con; (3-4) D | 42 |
| 156 | L | (1) Any; (2-3) Con; (4) L | 56.5 |
| 157 | M | (1-2) Con; (3-4) M | 19 |
| 158 | E | (1) Any; (2-3) Con; (4) E | 160.7 |

FIGURE 14C

| | | | |
|---|---|---|---|
| 159 | G | (1-2) Con; (3-4) G | 29.7 |
| 160 | P | (1-2) Con; (3-4) P | 47.3 |
| 161 | Y | (1) Any; (2-3) Con; (4) Y | 151.8 |
| 162 | L | (1-2) Con; (3-4) L | 2 |
| 163 | E | (1-2) Con; (3-4) E | 37 |
| 164 | C | (1-2) Con; (3-4) C | 32.2 |
| 165 | N | (1) Any; (2-3) Con; (4) N | 58.5 |
| 166 | E | (1) Any; (2-3) Con; (4) E | 80.3 |
| 167 | A | (1-4) A | 79.7 |
| 168 | M | (1-4) M | 22.8 |
| 169 | I | (1-2) Con; (3-4) I | 6.3 |
| 170 | K | (1) Any; (2-3) Con; (4) K | 71.2 |
| 171 | P | (1-2) Con; (3-4) P | 42.2 |
| 172 | F | (1-2) Con; (3-4) F | 42.8 |
| 173 | R | (1) Any; (2-3) Con; (4) R | 117.5 |
| 174 | P | (1) Any; (2-3) Con; (4) P | N/A |
| 175 | K | (1) Any; (2-3) Con; (4) K | N/A |
| 176 | A | (1) Any; (2-3) Con; (4) A | N/A |
| 177 | K | (1) Any; (2-3) Con; (4) K | N/A |

(SEQ ID NOs: 5, 15, 25, and 35)

FIGURE 14D

| T33-15B residue | | amino acid | allowed amino acids | SASA |
|---|---|---|---|---|
| | 1 | M | (1-3) Optional or any; (4) M | 75.7 |
| | 2 | V | (1-2) Con; (3-4) V | 5.8 |
| | 3 | R | (1-2) Con; (3-4) R | 19.5 |
| | 4 | G | (1-2) Con; (3-4) G | 2.2 |
| | 5 | I | (1-2) Con; (3-4) I | 2.7 |
| | 6 | R | (1-2) Con; (3-4) R | 23 |
| | 7 | G | (1-2) Con; (3-4) G | 0 |
| | 8 | A | (1-2) Con; (3-4) A | 0 |
| | 9 | I | (1-2) Con; (3-4) I | 11.8 |
| | 10 | T | (1-2) Con; (3-4) T | 16.2 |
| | 11 | V | (1-2) Con; (3-4) V | 8.3 |
| | 12 | N | (1-4) N | 81.3 |
| | 13 | S | (1-4) S | 24.5 |
| | 14 | D | (1) Any; (2-3) Con; (4) D | 54.3 |
| | 15 | T | (1-4) T | 22.8 |
| | 16 | P | (1-4) P | 30.7 |
| | 17 | T | (1-4) T | 1 |
| | 18 | S | (1-4) S | 7.8 |
| | 19 | I | (1-2) Con; (3-4) I | 0.7 |
| | 20 | I | (1-4) I | 12.8 |
| | 21 | I | (1-4) I | 12.8 |
| | 22 | A | (1-2) Con; (3-4) A | 7.8 |
| | 23 | T | (1-2) Con; (3-4) T | 0 |
| | 24 | I | (1-4) I | 1 |
| | 25 | L | (1-4) L | 30.2 |
| | 26 | L | (1-2) Con; (3-4) L | 0 |
| | 27 | L | (1-2) Con; (3-4) L | 7 |
| | 28 | E | (1-4) E | 76 |
| | 29 | K | (1-2) Con; (3-4) K | 47.5 |
| | 30 | M | (1-2) Con; (3-4) M | 6 |
| | 31 | L | (1-2) Con; (3-4) L | 26.5 |
| | 32 | E | (1) Any; (2-3) Con; (4) E | 77.5 |
| | 33 | A | (1) Any; (2-3) Con; (4) A | 53 |
| | 34 | N | (1-2) Con; (3-4) N | 24.3 |
| | 35 | G | (1) Any; (2-3) Con; (4) G | 59.2 |
| | 36 | I | (1-2) Con; (3-4) I | 25.5 |
| | 37 | Q | (1) Any; (2-3) Con; (4) Q | 95.8 |
| | 38 | S | (1-2) Con; (3-4) S | 42 |
| | 39 | Y | (1) Any; (2-3) Con; (4) Y | 64.5 |
| | 40 | E | (1-2) Con; (3-4) E | 48 |
| | 41 | E | (1) Any; (2-3) Con; (4) E | 53.2 |
| | 42 | L | (1-2) Con; (3-4) L | 2.5 |

FIGURE 15A

| | | | |
|---|---|---|---|
| 43 | A | (1-2) Con; (3-4) A | 1.2 |
| 44 | A | (1-2) Con; (3-4) A | 0 |
| 45 | V | (1-2) Con; (3-4) V | 1.5 |
| 46 | I | (1-2) Con; (3-4) I | 12.7 |
| 47 | F | (1-2) Con; (3-4) F | 0.2 |
| 48 | T | (1-2) Con; (3-4) T | 1.8 |
| 49 | V | (1-2) Con; (3-4) V | 3 |
| 50 | T | (1-2) Con; (3-4) T | 15.7 |
| 51 | E | (1) Any; (2-3) Con; (4) E | 93.5 |
| 52 | D | (1) Any; (2-3) Con; (4) D | 66.5 |
| 53 | L | (1-2) Con; (3-4) L | 2 |
| 54 | T | (1-2) Con; (3-4) T | 38 |
| 55 | S | (1-2) Con; (3-4) S | 32.8 |
| 56 | A | (1-2) Con; (3-4) A | 9 |
| 57 | F | (1) Any; (2-3) Con; (4) F | 55.3 |
| 58 | P | (1-2) Con; (3-4) P | 0.2 |
| 59 | A | (1-2) Con; (3-4) A | 23.2 |
| 60 | E | (1-2) Con; (3-4) E | 43.5 |
| 61 | A | (1-2) Con; (3-4) A | 0 |
| 62 | A | (1-2) Con; (3-4) A | 0.2 |
| 63 | R | (1-2) Con; (3-4) R | 40.5 |
| 64 | Q | (1-4) Q | 95.7 |
| 65 | I | (1-2) Con; (3-4) I | 33.5 |
| 66 | G | (1-2) Con; (3-4) G | 37.8 |
| 67 | M | (1-2) Con; (3-4) M | 3.7 |
| 68 | H | (1) Any; (2-3) Con; (4) H | 146 |
| 69 | R | (1-2) Con; (3-4) R | 42.3 |
| 70 | V | (1-2) Con; (3-4) V | 8.3 |
| 71 | P | (1-2) Con; (3-4) P | 5.5 |
| 72 | L | (1-2) Con; (3-4) L | 22.2 |
| 73 | L | (1-2) Con; (3-4) L | 7.7 |
| 74 | S | (1-2) Con; (3-4) S | 14.7 |
| 75 | A | (1-2) Con; (3-4) A | 7.2 |
| 76 | R | (1-2) Con; (3-4) R | 23.7 |
| 77 | E | (1-2) Con; (3-4) E | 4.8 |
| 78 | V | (1-2) Con; (3-4) V | 4 |
| 79 | P | (1) Any; (2-3) Con; (4) P | 65 |
| 80 | V | (1-2) Con; (3-4) V | 18.7 |
| 81 | P | (1) Any; (2-3) Con; (4) P | 98.3 |
| 82 | G | (1) Any; (2-3) Con; (4) G | 89.5 |
| 83 | S | (1-2) Con; (3-4) S | 35.7 |
| 84 | L | (1-2) Con; (3-4) L | 50.2 |
| 85 | P | (1) Any; (2-3) Con; (4) P | 57 |
| 86 | R | (1) Any; (2-3) Con; (4) R | 69 |
| 87 | V | (1-2) Con; (3-4) V | 0.2 |
| 88 | I | (1-2) Con; (3-4) I | 0 |
| 89 | R | (1-2) Con; (3-4) R | 32.2 |
| 90 | V | (1-2) Con; (3-4) V | 0.2 |
| 91 | L | (1-2) Con; (3-4) L | 0.2 |

FIGURE 15B

| | | | |
|---|---|---|---|
| 92 | A | (1-2) Con; (3-4) A | 7.3 |
| 93 | L | (1-2) Con; (3-4) L | 5.3 |
| 94 | W | (1-2) Con; (3-4) W | 13.8 |
| 95 | N | (1-2) Con; (3-4) N | 28 |
| 96 | T | (1-2) Con; (3-4) T | 23.2 |
| 97 | D | (1) Any; (2-3) Con; (4) D | 84 |
| 98 | T | (1-2) Con; (3-4) T | 30.2 |
| 99 | P | (1) Any; (2-3) Con; (4) P | 80.8 |
| 100 | Q | (1-2) Con; (3-4) Q | 23.3 |
| 101 | D | (1) Any; (2-3) Con; (4) D | 99.7 |
| 102 | R | (1) Any; (2-3) Con; (4) R | 54.5 |
| 103 | V | (1-2) Con; (3-4) V | 15.5 |
| 104 | R | (1) Any; (2-3) Con; (4) R | 51 |
| 105 | H | (1) Any; (2-3) Con; (4) H | 66.8 |
| 106 | V | (1-2) Con; (3-4) V | 12.7 |
| 107 | Y | (1) Any; (2-3) Con; (4) Y | 81.8 |
| 108 | L | (1-2) Con; (3-4) L | 47.2 |
| 109 | S | (1-4) S | 68.7 |
| 110 | E | (1-2) Con; (3-4) E | 47.8 |
| 111 | A | (1-2) Con; (3-4) A | 0 |
| 112 | V | (1) Any; (2-3) Con; (4) V | 92.3 |
| 113 | R | (1) Any; (2-3) Con; (4) R | 107.3 |
| 114 | L | (1) Any; (2-3) Con; (4) L | 91.2 |
| 115 | R | (1) Any; (2-3) Con; (4) R | N/A |
| 116 | P | (1) Any; (2-3) Con; (4) P | N/A |
| 117 | D | (1) Any; (2-3) Con; (4) D | N/A |
| 118 | L | (1) Any; (2-3) Con; (4) L | N/A |
| 119 | E | (1) Any; (2-3) Con; (4) E | N/A |
| 120 | S | (1) Any; (2-3) Con; (4) S | N/A |
| 121 | A | (1) Any; (2-3) Con; (4) A | N/A |
| 122 | Q | (1) Any; (2-3) Con; (4) Q | N/A |

(SEQ ID NOs: 6, 16, 26, and 36)

FIGURE 15C

| T33-21A residue | amino acid | allowed amino acids | SASA |
|---|---|---|---|
| 1 | M | (1-3) Optional/any; (4) M | N/A |
| 2 | R | (1) Any; (2-3) Con; (4) R | N/A |
| 3 | I | (1) Any; (2-3) Con; (4) I | N/A |
| 4 | T | (1) Any; (2-3) Con; (4) T | N/A |
| 5 | T | (1) Any; (2-3) Con; (4) T | N/A |
| 6 | K | (1) Any; (2-3) Con; (4) K | N/A |
| 7 | V | (1) Any; (2-3) Con; (4) V | N/A |
| 8 | G | (1) Any; (2-3) Con; (4) G | N/A |
| 9 | D | (1) Any; (2-3) Con; (4) D | N/A |
| 10 | K | (1) Any; (2-3) Con; (4) K | N/A |
| 11 | G | (1) Any; (2-3) Con; (4) G | N/A |
| 12 | S | (1) Any; (2-3) Con; (4) S | N/A |
| 13 | T | (1) Any; (2-3) Con; (4) T | N/A |
| 14 | R | (1) Any; (2-3) Con; (4) R | N/A |
| 15 | L | (1) Any; (2-3) Con; (4) L | N/A |
| 16 | F | (1) Any; (2-3) Con; (4) F | N/A |
| 17 | G | (1) Any; (2-3) Con; (4) G | N/A |
| 18 | G | (1) Any; (2-3) Con; (4) G | N/A |
| 19 | E | (1) Any; (2-3) Con; (4) E | N/A |
| 20 | E | (1) Any; (2-3) Con; (4) E | N/A |
| 21 | V | (1) Any; (2-3) Con; (4) V | N/A |
| 22 | W | (1) Any; (2-3) Con; (4) W | N/A |
| 23 | K | (1-4) K | 101.7 |
| 24 | D | (1) Any; (2-3) Con; (4) D | 71.8 |
| 25 | S | (1) Any; (2-3) Con; (4) S | 71.8 |
| 26 | P | (1-2) Con; (3-4) P | 41.2 |
| 27 | I | (1-2) Con; (3-4) I | 5.3 |
| 28 | I | (1) Any; (2-3) Con; (4) I | 75.7 |
| 29 | E | (1) Any; (2-3) Con; (4) E | 52.2 |
| 30 | A | (1-2) Con; (3-4) A | 0 |
| 31 | N | (1-2) Con; (3-4) N | 44 |
| 32 | G | (1-2) Con; (3-4) G | 11.7 |
| 33 | T | (1-2) Con; (3-4) T | 1.2 |
| 34 | L | (1-2) Con; (3-4) L | 0 |
| 35 | D | (1-2) Con; (3-4) D | 26.5 |
| 36 | E | (1-2) Con; (3-4) E | 1.3 |
| 37 | L | (1-2) Con; (3-4) L | 0 |
| 38 | T | (1-2) Con; (3-4) T | 7 |
| 39 | S | (1-2) Con; (3-4) S | 0.2 |
| 40 | F | (1-2) Con; (3-4) F | 8.8 |
| 41 | I | (1-2) Con; (3-4) I | 0 |
| 42 | G | (1-2) Con; (3-4) G | 0 |
| 43 | E | (1-2) Con; (3-4) E | 12.2 |
| 44 | A | (1-2) Con; (3-4) A | 1.3 |

FIGURE 16A

| | | | |
|---|---|---|---|
| 45 | K | (1-2) Con; (3-4) K | 4.3 |
| 46 | H | (1) Any; (2-3) Con; (4) H | 57.3 |
| 47 | Y | (1-2) Con; (3-4) Y | 45 |
| 48 | V | (1-2) Con; (3-4) V | 27 |
| 49 | D | (1) Any; (2-3) Con; (4) D | 88.8 |
| 50 | E | (1) Any; (2-3) Con; (4) E | 113.5 |
| 51 | E | (1) Any; (2-3) Con; (4) E | 82.8 |
| 52 | M | (1-2) Con; (3-4) M | 15 |
| 53 | K | (1) Any; (2-3) Con; (4) K | 72.2 |
| 54 | G | (1-2) Con; (3-4) G | 31 |
| 55 | I | (1-2) Con; (3-4) I | 14 |
| 56 | L | (1-2) Con; (3-4) L | 2 |
| 57 | E | (1-2) Con; (3-4) E | 47.3 |
| 58 | E | (1) Any; (2-3) Con; (4) E | 76.8 |
| 59 | I | (1-2) Con; (3-4) I | 0 |
| 60 | Q | (1-2) Con; (3-4) Q | 1.7 |
| 61 | N | (1-2) Con; (3-4) N | 35.3 |
| 62 | D | (1-2) Con; (3-4) D | 12 |
| 63 | I | (1-2) Con; (3-4) I | 0.3 |
| 64 | Y | (1) Any; (2-3) Con; (4) Y | 107.7 |
| 65 | K | (1-2) Con; (3-4) K | 45.2 |
| 66 | I | (1-2) Con; (3-4) I | 0 |
| 67 | M | (1-2) Con; (3-4) M | 37.3 |
| 68 | G | (1-2) Con; (3-4) G | 26.3 |
| 69 | E | (1-2) Con; (3-4) E | 29.8 |
| 70 | I | (1-2) Con; (3-4) I | 0.2 |
| 71 | G | (1-2) Con; (3-4) G | 45.5 |
| 72 | S | (1-2) Con; (3-4) S | 30.8 |
| 73 | K | (1) Any; (2-3) Con; (4) K | 64.5 |
| 74 | G | (1-2) Con; (3-4) G | 37.5 |
| 75 | K | (1) Any; (2-3) Con; (4) K | 89.2 |
| 76 | I | (1) Any; (2-3) Con; (4) I | 97.2 |
| 77 | E | (1) Any; (2-3) Con; (4) E | 157 |
| 78 | G | (1-2) Con; (3-4) G | 16.8 |
| 79 | I | (1-2) Con; (3-4) I | 19 |
| 80 | S | (1) Any; (2-3) Con; (4) S | 59.5 |
| 81 | E | (1-4) E | 48 |
| 82 | E | (1) Any; (2-3) Con; (4) E | 60.3 |
| 83 | R | (1) Any; (2-3) Con; (4) R | 51.2 |
| 84 | I | (1-4) I | 1 |
| 85 | A | (1-4) A | 24.8 |
| 86 | W | (1-2) Con; (3-4) W | 31.8 |
| 87 | L | (1-2) Con; (3-4) L | 0 |
| 88 | L | (1-4) L | 22.2 |
| 89 | K | (1) Any; (2-3) Con; (4) K | 103 |
| 90 | L | (1-2) Con; (3-4) L | 4.5 |
| 91 | I | (1-4) I | 12 |
| 92 | L | (1-4) L | 66 |

FIGURE 16B

| | | | | |
|---|---|---|---|---|
| 93 | R | (1) Any; (2-3) Con; (4) R | | 123.3 |
| 94 | Y | (1-2) Con; (3-4) Y | | 21.7 |
| 95 | M | (1-4) M | | 53.3 |
| 96 | E | (1) Any; (2-3) Con; (4) E | | 141 |
| 97 | M | (1) Any; (2-3) Con; (4) M | | 79 |
| 98 | V | (1-2) Con; (3-4) V | | 23.5 |
| 99 | N | (1) Any; (2-3) Con; (4) N | | 102 |
| 100 | L | (1) Any; (2-3) Con; (4) L | | 129.7 |
| 101 | K | (1) Any; (2-3) Con; (4) K | N/A | |
| 102 | S | (1) Any; (2-3) Con; (4) S | N/A | |
| 103 | F | (1) Any; (2-3) Con; (4) F | | 137.7 |
| 104 | V | (1) Any; (2-3) Con; (4) V | | 104.3 |
| 105 | L | (1-2) Con; (3-4) L | | 44.7 |
| 106 | P | (1-2) Con; (3-4) P | | 19.5 |
| 107 | G | (1-2) Con; (3-4) G | | 0.2 |
| 108 | G | (1-2) Con; (3-4) G | | 49.3 |
| 109 | T | (1-2) Con; (3-4) T | | 29.3 |
| 110 | L | (1-2) Con; (3-4) L | | 39.8 |
| 111 | E | (1) Any; (2-3) Con; (4) E | | 67.3 |
| 112 | S | (1-2) Con; (3-4) S | | 0 |
| 113 | A | (1-2) Con; (3-4) A | | 0 |
| 114 | K | (1-2) Con; (3-4) K | | 8.2 |
| 115 | L | (1-2) Con; (3-4) L | | 0.8 |
| 116 | D | (1-2) Con; (3-4) D | | 0.5 |
| 117 | V | (1-2) Con; (3-4) V | | 3.7 |
| 118 | C | (1-2) Con; (3-4) C | | 1.3 |
| 119 | R | (1-2) Con; (3-4) R | | 29 |
| 120 | T | (1-2) Con; (3-4) T | | 1.7 |
| 121 | I | (1-2) Con; (3-4) I | | 0 |
| 122 | A | (1-2) Con; (3-4) A | | 0 |
| 123 | R | (1) Any; (2-3) Con; (4) R | | 96.8 |
| 124 | R | (1-2) Con; (3-4) R | | 12.8 |
| 125 | A | (1-2) Con; (3-4) A | | 0 |
| 126 | L | (1-4) L | | 8.3 |
| 127 | R | (1-2) Con; (3-4) R | | 34.3 |
| 128 | K | (1-2) Con; (3-4) K | | 32.7 |
| 129 | V | (1-2) Con; (3-4) V | | 0 |
| 130 | L | (1-4) L | | 12.2 |
| 131 | T | (1) Any; (2-3) Con; (4) T | | 68.5 |
| 132 | V | (1-2) Con; (3-4) V | | 0.2 |
| 133 | T | (1-4) T | | 5.7 |
| 134 | R | (1-4) R | | 149.5 |
| 135 | E | (1) Any; (2-3) Con; (4) E | | 67.8 |
| 136 | F | (1) Any; (2-3) Con; (4) F | | 87.7 |
| 137 | G | (1-4) G | | 39.3 |
| 138 | I | (1-4) I | | 31.7 |
| 139 | G | (1-2) Con; (3-4) G | | 4.7 |
| 140 | A | (1-4) A | | 5.3 |

FIGURE 16C

| | | | |
|---|---|---|---|
| 141 | E | (1-4) E | 44.3 |
| 142 | A | (1-2) Con; (3-4) A | 0.2 |
| 143 | A | (1-4) A | 0 |
| 144 | A | (1-4) A | 0 |
| 145 | Y | (1-2) Con; (3-4) Y | 0 |
| 146 | L | (1-2) Con; (3-4) L | 0 |
| 147 | L | (1-4) L | 9.3 |
| 148 | A | (1-4) A | 1.7 |
| 149 | L | (1-2) Con; (3-4) L | 0 |
| 150 | S | (1-2) Con; (3-4) S | 2.2 |
| 151 | D | (1-4) D | 36.7 |
| 152 | L | (1-2) Con; (3-4) L | 0.3 |
| 153 | L | (1-2) Con; (3-4) L | 0.3 |
| 154 | F | (1) Any; (2-3) Con; (4) F | 82.3 |
| 155 | L | (1-2) Con; (3-4) L | 15.5 |
| 156 | L | (1-2) Con; (3-4) L | 1 |
| 157 | A | (1-2) Con; (3-4) A | 0 |
| 158 | R | (1-2) Con; (3-4) R | 19.5 |
| 159 | V | (1-2) Con; (3-4) V | 5.3 |
| 160 | I | (1-2) Con; (3-4) I | 25.7 |
| 161 | E | (1-2) Con; (3-4) E | 29.8 |
| 162 | I | (1) Any; (2-3) Con; (4) I | 82.2 |
| 163 | E | (1) Any; (2-3) Con; (4) E | 97 |
| 164 | K | (1) Any; (2-3) Con; (4) K | 76.5 |
| 165 | N | (1) Any; (2-3) Con; (4) N | 117.7 |
| 166 | K | (1) Any; (2-3) Con; (4) K | N/A |
| 167 | L | (1) Any; (2-3) Con; (4) L | N/A |
| 168 | K | (1) Any; (2-3) Con; (4) K | N/A |
| 169 | E | (1) Any; (2-3) Con; (4) E | N/A |
| 170 | V | (1) Any; (2-3) Con; (4) V | N/A |
| 171 | R | (1) Any; (2-3) Con; (4) R | N/A |
| 172 | S | (1) Any; (2-3) Con; (4) S | N/A |

(SEQ ID NOs: 7, 17, 27, and 37)

FIGURE 16D

| T33-21B residue | amino acid | allowed amino acids | SASA |
|---|---|---|---|
| 1 | M | (1-3) Optional/any (4) M | N/A |
| 2 | P | (1-2) Con; (3-4) P | 23.8 |
| 3 | H | (1-2) Con; (3-4) H | 6.7 |
| 4 | L | (1-2) Con; (3-4) L | 1.2 |
| 5 | V | (1-2) Con; (3-4) V | 23 |
| 6 | I | (1-2) Con; (3-4) I | 0.5 |
| 7 | E | (1-2) Con; (3-4) E | 25.2 |
| 8 | A | (1-2) Con; (3-4) A | 3.7 |
| 9 | T | (1-2) Con; (3-4) T | 2.5 |
| 10 | A | (1-2) Con; (3-4) A | 50.8 |
| 11 | N | (1-2) Con; (3-4) N | 47.8 |
| 12 | L | (1-2) Con; (3-4) L | 20.7 |
| 13 | R | (1) Any; (2-3) Con; (4) R | 136 |
| 14 | L | (1-2) Con; (3-4) L | 42.5 |
| 15 | E | (1) Any; (2-3) Con; (4) E | 130.8 |
| 16 | T | (1-2) Con; (3-4) T | 45.3 |
| 17 | S | (1) Any; (2-3) Con; (4) S | 63 |
| 18 | P | (1-2) Con; (3-4) P | 48.8 |
| 19 | G | (1-2) Con; (3-4) G | 13.7 |
| 20 | E | (1) Any; (2-3) Con; (4) E | 85.8 |
| 21 | L | (1-2) Con; (3-4) L | 0 |
| 22 | L | (1-2) Con; (3-4) L | 0.3 |
| 23 | E | (1-2) Con; (3-4) E | 35.8 |
| 24 | Q | (1) Any; (2-3) Con; (4) Q | 71 |
| 25 | A | (1-2) Con; (3-4) A | 0.3 |
| 26 | N | (1-2) Con; (3-4) N | 0 |
| 27 | K | (1-4) K | 55.7 |
| 28 | A | (1-4) A | 6.7 |
| 29 | L | (1-2) Con; (3-4) L | 0.7 |
| 30 | F | (1-4) F | 79 |
| 31 | A | (1-4) A | 20.8 |
| 32 | S | (1-4) S | 18.2 |
| 33 | G | (1) Any; (2-3) Con; (4) G | 65.5 |
| 34 | Q | (1-4) Q | 43.3 |
| 35 | F | (1-2) Con; (3-4) F | 14.8 |
| 36 | G | (1-2) Con; (3-4) G | 40.3 |
| 37 | E | (1-2) Con; (3-4) E | 44.2 |
| 38 | A | (1-2) Con; (3-4) A | 27.3 |
| 39 | D | (1) Any; (2-3) Con; (4) D | 72 |
| 40 | I | (1-2) Con; (3-4) I | 0.8 |
| 41 | K | (1-2) Con; (3-4) K | 10.7 |
| 42 | S | (1) Any; (2-3) Con; (4) S | N/A |
| 43 | R | (1) Any; (2-3) Con; (4) R | N/A |
| 44 | F | (1-2) Con; (3-4) F | 22.2 |
| 45 | V | (1-2) Con; (3-4) V | 38 |
| 46 | T | (1) Any; (2-3) Con; (4) T | 70 |
| 47 | L | (1-2) Con; (3-4) L | 7.5 |
| 48 | E | (1) Any; (2-3) Con; (4) E | 143.7 |

FIGURE 17A

| | | | |
|---|---|---|---|
| 49 | A | (1-2) Con; (3-4) A | 25.8 |
| 50 | Y | (1-2) Con; (3-4) Y | 43.3 |
| 51 | R | (1) Any; (2-3) Con; (4) R | 80 |
| 52 | Q | (1-2) Con; (3-4) Q | 17.8 |
| 53 | G | (1-2) Con; (3-4) G | 7.7 |
| 54 | T | (1) Any; (2-3) Con; (4) T | 70.2 |
| 55 | A | (1-2) Con; (3-4) A | 44.3 |
| 56 | A | (1) Any; (2-3) Con; (4) A | 113.8 |
| 57 | V | (1) Any; (2-3) Con; (4) V | 65.3 |
| 58 | E | (1) Any; (2-3) Con; (4) E | 52.5 |
| 59 | R | (1-2) Con; (3-4) R | 25.2 |
| 60 | A | (1-2) Con; (3-4) A | 0.7 |
| 61 | Y | (1-2) Con; (3-4) Y | 6.7 |
| 62 | L | (1-2) Con; (3-4) L | 0.5 |
| 63 | H | (1-2) Con; (3-4) H | 10 |
| 64 | A | (1-2) Con; (3-4) A | 0.5 |
| 65 | C | (1-2) Con; (3-4) C | 26.2 |
| 66 | L | (1-2) Con; (3-4) L | 0.3 |
| 67 | S | (1-2) Con; (3-4) S | 13 |
| 68 | I | (1-2) Con; (3-4) I | 0.5 |
| 69 | L | (1-2) Con; (3-4) L | 41.2 |
| 70 | D | (1) Any; (2-3) Con; (4) D | 54 |
| 71 | G | (1-4) G | 60.5 |
| 72 | R | (1) Any; (2-3) Con; (4) R | N/A |
| 73 | D | (1-4) D | 52.8 |
| 74 | I | (1-4) I | 9.8 |
| 75 | A | (1-4) A | 0 |
| 76 | T | (1-4) T | 7.5 |
| 77 | R | (1-2) Con; (3-4) R | 28 |
| 78 | T | (1-4) T | 0.8 |
| 79 | L | (1-4) L | 13 |
| 80 | L | (1-2) Con; (3-4) L | 2 |
| 81 | G | (1-2) Con; (3-4) G | 0 |
| 82 | A | (1-4) A | 3.8 |
| 83 | S | (1-4) S | N/A |
| 84 | L | (1-2) Con; (3-4) L | 2 |
| 85 | C | (1-4) C | 2.2 |
| 86 | A | (1-4) A | 16.5 |
| 87 | V | (1-2) Con; (3-4) V | 22.7 |
| 88 | L | (1-2) Con; (3-4) L | 1.7 |
| 89 | A | (1-2) Con; (3-4) A | 5 |
| 90 | E | (1) Any; (2-3) Con; (4) E | 93.3 |
| 91 | A | (1-2) Con; (3-4) A | 3.8 |
| 92 | V | (1-2) Con; (3-4) V | 11.8 |
| 93 | A | (1-2) Con; (3-4) A | 50 |
| 94 | G | (1-2) Con; (3-4) G | 12 |
| 95 | G | (1-2) Con; (3-4) G | 3.7 |
| 96 | G | (1-2) Con; (3-4) G | 38.5 |
| 97 | E | (1) Any; (2-3) Con; (4) E | 80.3 |
| 98 | E | (1) Any; (2-3) Con; (4) E | 91.8 |
| 99 | G | (1-2) Con; (3-4) G | 31 |
| 100 | V | (1-2) Con; (3-4) V | 1 |
| 101 | Q | (1-2) Con; (3-4) Q | 39.7 |

FIGURE 17B

| | | | |
|---|---|---|---|
| 102 | V | (1-2) Con; (3-4) V | 1.2 |
| 103 | S | (1-2) Con; (3-4) S | 3.2 |
| 104 | V | (1-2) Con; (3-4) V | 0 |
| 105 | E | (1-2) Con; (3-4) E | 4.5 |
| 106 | V | (1-2) Con; (3-4) V | 3.3 |
| 107 | R | (1-2) Con; (3-4) R | 34.8 |
| 108 | E | (1) Any; (2-3) Con; (4) E | 76 |
| 109 | M | (1-2) Con; (3-4) M | 3.5 |
| 110 | E | (1-2) Con; (3-4) E | 50.3 |
| 111 | R | (1) Any; (2-3) Con; (4) R | 109.7 |
| 112 | L | (1-4) L | 66 |
| 113 | S | (1-2) Con; (3-4) S | 0.5 |
| 114 | Y | (1-4) Y | 32.3 |
| 115 | A | (1-4) A | 3.5 |
| 116 | K | (1-4) K | 88.2 |
| 117 | R | (1-4) R | 91.8 |
| 118 | V | (1) Any; (2-3) Con; (4) V | 105.5 |
| 119 | V | (1) Any; (2-3) Con; (4) V | 68.7 |
| 120 | A | (1) Any; (2-3) Con; (4) A | N/A |
| 121 | R | (1) Any; (2-3) Con; (4) R | N/A |
| 122 | Q | (1) Any; (2-3) Con; (4) Q | N/A |
| 123 | R | (1) Any; (2-3) Con; (4) R | N/A |

(SEQ ID NOs: 8, 18, 28, and 38)

FIGURE 17C

| T33-28A residue | | amino acid | allowed amino acids | SASA |
|---|---|---|---|---|
| | 1 | M | (1-3) Optional/any; (4) M | N/A |
| | 2 | E | (1) Any; (2-3) Con; (4) E | N/A |
| | 3 | S | (1) Any; (2-3) Con; (4) S | 99 |
| | 4 | V | (1) Any; (2-3) Con; (4) V | 67.8 |
| | 5 | N | (1-2) Con; (3-4) N | 24.2 |
| | 6 | T | (1-2) Con; (3-4) T | 32.5 |
| | 7 | S | (1-2) Con; (3-4) S | 0.8 |
| | 8 | F | (1-2) Con; (3-4) F | 0.3 |
| | 9 | L | (1-2) Con; (3-4) L | 31.2 |
| | 10 | S | (1-2) Con; (3-4) S | 14.7 |
| | 11 | P | (1-2) Con; (3-4) P | 0 |
| | 12 | S | (1-2) Con; (3-4) S | 8.7 |
| | 13 | L | (1-2) Con; (3-4) L | 41.2 |
| | 14 | V | (1-2) Con; (3-4) V | 0 |
| | 15 | T | (1-2) Con; (3-4) T | 0 |
| | 16 | I | (1-2) Con; (3-4) I | 0 |
| | 17 | R | (1-2) Con; (3-4) R | 15.8 |
| | 18 | D | (1-2) Con; (3-4) D | 15.2 |
| | 19 | F | (1) Any; (2-3) Con; (4) F | 55.7 |
| | 20 | D | (1) Any; (2-3) Con; (4) D | 114.8 |
| | 21 | N | (1) Any; (2-3) Con; (4) N | 75.2 |
| | 22 | G | (1-2) Con; (3-4) G | 24.5 |
| | 23 | Q | (1-2) Con; (3-4) Q | 14.2 |
| | 24 | F | (1-2) Con; (3-4) F | 2 |
| | 25 | A | (1-2) Con; (3-4) A | 0.3 |
| | 26 | V | (1-2) Con; (3-4) V | 0 |
| | 27 | L | (1-2) Con; (3-4) L | 0.2 |
| | 28 | R | (1-2) Con; (3-4) R | 18.5 |
| | 29 | I | (1-2) Con; (3-4) I | 0.7 |
| | 30 | G | (1) Any; (2-3) Con; (4) G | 56.2 |
| | 31 | R | (1) Any; (2-3) Con; (4) R | 73.5 |
| | 32 | T | (1-2) Con; (3-4) T | 33.3 |
| | 33 | G | (1-2) Con; (3-4) G | 2 |
| | 34 | F | (1-2) Con; (3-4) F | 22.7 |
| | 35 | P | (1-2) Con; (3-4) P | 16.2 |
| | 36 | A | (1-2) Con; (3-4) A | 0.5 |
| | 37 | D | (1-2) Con; (3-4) D | 38.5 |
| | 38 | K | (1) Any; (2-3) Con; (4) K | 62.3 |
| | 39 | G | (1-2) Con; (3-4) G | 34.3 |
| | 40 | D | (1-2) Con; (3-4) D | 10.7 |
| | 41 | I | (1-2) Con; (3-4) I | 17.2 |
| | 42 | D | (1-2) Con; (3-4) D | 39.5 |
| | 43 | L | (1-2) Con; (3-4) L | 7.7 |
| | 44 | C | (1-2) Con; (3-4) C | 0.2 |
| | 45 | L | (1) Any; (2-3) Con; (4) L | 61.3 |
| | 46 | D | (1) Any; (2-3) Con; (4) D | 51.5 |
| | 47 | K | (1-2) Con; (3-4) K | 11.8 |
| | 48 | M | (1-2) Con; (3-4) M | 3.8 |
| | 49 | I | (1-4) I | 25.7 |

FIGURE 18A

| | | | |
|---|---|---|---|
| 50 | G | (1-4) G | 0.2 |
| 51 | V | (1-2) Con; (3-4) V | 1.2 |
| 52 | R | (1-4) R | 21.7 |
| 53 | A | (1-4) A | 0 |
| 54 | A | (1-4) A | 1.5 |
| 55 | Q | (1-2) Con; (3-4) Q | 25.2 |
| 56 | I | (1-4) I | 18.2 |
| 57 | F | (1-4) F | 29.3 |
| 58 | L | (1-2) Con; (3-4) L | 49.2 |
| 59 | G | (1-2) Con; (3-4) G | 19 |
| 60 | D | (1-4) D | 50.5 |
| 61 | D | (1-2) Con; (3-4) D | 30.8 |
| 62 | T | (1) Any; (2-3) Con; (4) T | 96.7 |
| 63 | E | (1) Any; (2-3) Con; (4) E | 55.2 |
| 64 | D | (1) Any; (2-3) Con; (4) D | 105.2 |
| 65 | G | (1) Any; (2-3) Con; (4) G | 76 |
| 66 | F | (1-2) Con; (3-4) F | 24.3 |
| 67 | K | (1) Any; (2-3) Con; (4) K | 100.3 |
| 68 | G | (1-2) Con; (3-4) G | 23.2 |
| 69 | P | (1-2) Con; (3-4) P | 38.5 |
| 70 | H | (1-2) Con; (3-4) H | 24.7 |
| 71 | I | (1-2) Con; (3-4) I | 8.8 |
| 72 | R | (1-2) Con; (3-4) R | 29.8 |
| 73 | I | (1-2) Con; (3-4) I | 6.5 |
| 74 | R | (1-2) Con; (3-4) R | 2.7 |
| 75 | C | (1-2) Con; (3-4) C | 2.7 |
| 76 | V | (1-2) Con; (3-4) V | 0.3 |
| 77 | D | (1-2) Con; (3-4) D | 43.5 |
| 78 | I | (1-2) Con; (3-4) I | 0.3 |
| 79 | D | (1) Any; (2-3) Con; (4) D | 64.2 |
| 80 | D | (1-2) Con; (3-4) D | 39.7 |
| 81 | K | (1-2) Con; (3-4) K | 34.8 |
| 82 | H | (1) Any; (2-3) Con; (4) H | 162 |
| 83 | T | (1) Any; (2-3) Con; (4) T | 91.8 |
| 84 | Y | (1) Any; (2-3) Con; (4) Y | 60.5 |
| 85 | N | (1-2) Con; (3-4) N | 48.5 |
| 86 | A | (1-2) Con; (3-4) A | 5.5 |
| 87 | M | (1) Any; (2-3) Con; (4) M | 64.2 |
| 88 | V | (1-2) Con; (3-4) V | 0.3 |
| 89 | Y | (1) Any; (2-3) Con; (4) Y | 57.2 |
| 90 | V | (1-2) Con; (3-4) V | 2.7 |
| 91 | D | (1-2) Con; (3-4) D | 17.2 |
| 92 | L | (1-2) Con; (3-4) L | 19.3 |
| 93 | I | (1-2) Con; (3-4) I | 17.5 |
| 94 | V | (1) Any; (2-3) Con; (4) V | 74.3 |
| 95 | G | (1) Any; (2-3) Con; (4) G | N/A |
| 96 | T | (1) Any; (2-3) Con; (4) T | N/A |
| 97 | G | (1) Any; (2-3) Con; (4) G | N/A |
| 98 | A | (1) Any; (2-3) Con; (4) A | N/A |
| 99 | S | (1) Any; (2-3) Con; (4) S | N/A |
| 100 | E | (1) Any; (2-3) Con; (4) E | 122.5 |
| 101 | V | (1) Any; (2-3) Con; (4) V | 84 |
| 102 | E | (1) Any; (2-3) Con; (4) E | 76 |

FIGURE 18B

| | | | |
|---|---|---|---|
| 103 | R | (1) Any; (2-3) Con; (4) R | 56.7 |
| 104 | E | (1) Any; (2-3) Con; (4) E | 64.2 |
| 105 | T | (1) Any; (2-3) Con; (4) T | 51.5 |
| 106 | A | (1-2) Con; (3-4) A | 26.8 |
| 107 | E | (1-2) Con; (3-4) E | 43.2 |
| 108 | E | (1-2) Con; (3-4) E | 49.3 |
| 109 | E | (1) Any; (2-3) Con; (4) E | 66.3 |
| 110 | A | (1-2) Con; (3-4) A | 16.7 |
| 111 | K | (1-2) Con; (3-4) K | 18.3 |
| 112 | L | (1-4) L | 83.5 |
| 113 | A | (1-4) A | 2 |
| 114 | L | (1-2) Con; (3-4) L | 0.5 |
| 115 | R | (1) Any; (2-3) Con; (4) R | 119.7 |
| 116 | V | (1-4) V | 11.7 |
| 117 | A | (1-4) A | 12.8 |
| 118 | L | (1-2) Con; (3-4) L | 10.2 |
| 119 | Q | (1-4) Q | 65.7 |
| 120 | V | (1-2) Con; (3-4) V | 28.2 |
| 121 | D | (1) Any; (2-3) Con; (4) D | 135.3 |
| 122 | I | (1-2) Con; (3-4) I | 43.7 |
| 123 | A | (1) Any; (2-3) Con; (4) A | 76.7 |
| 124 | D | (1-2) Con; (3-4) D | 20.2 |
| 125 | E | (1) Any; (2-3) Con; (4) E | 95.5 |
| 126 | H | (1) Any; (2-3) Con; (4) H | 74 |
| 127 | S | (1) Any; (2-3) Con; (4) S | 92 |
| 128 | C | (1-2) Con; (3-4) C | 1.5 |
| 129 | V | (1-2) Con; (3-4) V | 38.2 |
| 130 | T | (1-2) Con; (3-4) T | 7.2 |
| 131 | Q | (1-2) Con; (3-4) Q | 29 |
| 132 | F | (1-2) Con; (3-4) F | 38 |
| 133 | E | (1) Any; (2-3) Con; (4) E | 114.5 |
| 134 | M | (1) Any; (2-3) Con; (4) M | 62.5 |
| 135 | K | (1-2) Con; (3-4) K | 47.5 |
| 136 | L | (1) Any; (2-3) Con; (4) L | 99.8 |
| 137 | R | (1) Any; (2-3) Con; (4) R | 75.3 |
| 138 | E | (1) Any; (2-3) Con; (4) E | 88.3 |
| 139 | E | (1) Any; (2-3) Con; (4) E | 91 |
| 140 | L | (1) Any; (2-3) Con; (4) L | 61.7 |
| 141 | L | (1) Any; (2-3) Con; (4) L | 56.5 |
| 142 | S | (1) Any; (2-3) Con; (4) S | 105.3 |
| 143 | S | (1-2) Con; (3-4) S | 43.2 |
| 144 | D | (1-2) Con; (3-4) D | 44.5 |
| 145 | S | (1) Any; (2-3) Con; (4) S | 87.5 |
| 146 | F | (1-2) Con; (3-4) F | 27.8 |
| 147 | H | (1) Any; (2-3) Con; (4) H | 63 |
| 148 | P | (1-2) Con; (3-4) P | 26 |
| 149 | D | (1-2) Con; (3-4) D | 2.2 |
| 150 | K | (1-2) Con; (3-4) K | 15.2 |
| 151 | D | (1) Any; (2-3) Con; (4) D | 55.2 |
| 152 | E | (1) Any; (2-3) Con; (4) E | 72.3 |
| 153 | Y | (1-2) Con; (3-4) Y | 22.3 |
| 154 | Y | (1-2) Con; (3-4) Y | 0.8 |
| 155 | K | (1) Any; (2-3) Con; (4) K | 71.3 |
| 156 | D | (1) Any; (2-3) Con; (4) D | 128.3 |
| 157 | F | (1) Any; (2-3) Con; (4) F | 51.5 |
| 158 | L | (1) Any; (2-3) Con; (4) L | 88.3 |

(SEQ ID NOs: 9, 19, 29, and 39)     FIGURE 18C

| T33-28B residue | | amino acid | allowed amino acids | SASA | |
|---|---|---|---|---|---|
| | 1 | M | (1-3) Optional/any (4) M | | 60 |
| | 2 | P | (1-2) Con; (3-4) P | | 15.3 |
| | 3 | V | (1-2) Con; (3-4) V | | 3 |
| | 4 | I | (1-2) Con; (3-4) I | | 11.2 |
| | 5 | Q | (1-2) Con; (3-4) Q | | 9.3 |
| | 6 | T | (1-2) Con; (3-4) T | | 0.5 |
| | 7 | F | (1-2) Con; (3-4) F | | 7.8 |
| | 8 | V | (1-2) Con; (3-4) V | | 0.7 |
| | 9 | S | (1-2) Con; (3-4) S | | 31.2 |
| | 10 | T | (1-2) Con; (3-4) T | | 24.2 |
| | 11 | P | (1) Any; (2-3) Con; (4) P | | 96.3 |
| | 12 | L | (1-2) Con; (3-4) L | | 18.3 |
| | 13 | D | (1) Any; (2-3) Con; (4) D | | 68.3 |
| | 14 | H | (1) Any; (2-3) Con; (4) H | | 123 |
| | 15 | H | (1-4) H | | 70.8 |
| | 16 | K | (1) Any; (2-3) Con; (4) K | | 60 |
| | 17 | R | (1) Any; (2-3) Con; (4) R | | 64.5 |
| | 18 | L | (1-4) L | | 47.8 |
| | 19 | L | (1-4) L | | 37 |
| | 20 | L | (1-2) Con; (3-4) L | | 0 |
| | 21 | A | (1-2) Con; (3-4) A | | 0.5 |
| | 22 | I | (1-4) I | | 19.5 |
| | 23 | I | (1-4) I | | 0.7 |
| | 24 | Y | (1-2) Con; (3-4) Y | | 9.5 |
| | 25 | R | (1-4) R | | 29.8 |
| | 26 | I | (1-4) I | | 0 |
| | 27 | V | (1-4) V | | 10.2 |
| | 28 | T | (1-2) Con; (3-4) T | | 8.5 |
| | 29 | R | (1-4) R | | 30.8 |
| | 30 | V | (1-4) V | | 53.2 |
| | 31 | V | (1-4) V | | 28.3 |
| | 32 | L | (1-2) Con; (3-4) L | | 47.5 |
| | 33 | G | (1) Any; (2-3) Con; (4) G | | 64.7 |
| | 34 | K | (1-2) Con; (3-4) K | | 20.5 |
| | 35 | P | (1) Any; (2-3) Con; (4) P | | 80.5 |
| | 36 | E | (1-4) E | | 50.3 |
| | 37 | D | (1-2) Con; (3-4) D | | 32.5 |
| | 38 | L | (1-2) Con; (3-4) L | | 28 |
| | 39 | V | (1-2) Con; (3-4) V | | 3.3 |
| | 40 | M | (1-2) Con; (3-4) M | | 0.3 |
| | 41 | M | (1-2) Con; (3-4) M | | 0.8 |
| | 42 | T | (1-2) Con; (3-4) T | | 2.3 |
| | 43 | F | (1-2) Con; (3-4) F | | 4.8 |
| | 44 | H | (1-2) Con; (3-4) H | | 30.5 |
| | 45 | D | (1) Any; (2-3) Con; (4) D | | 53.3 |
| | 46 | S | (1) Any; (2-3) Con; (4) S | | 63.3 |
| | 47 | T | (1-2) Con; (3-4) T | | 12.2 |
| | 48 | P | (1-2) Con; (3-4) P | | 47.2 |
| | 49 | M | (1-2) Con; (3-4) M | | 10.8 |
| | 50 | H | (1-2) Con; (3-4) H | | 21.5 |
| | 51 | F | (1-2) Con; (3-4) F | | 4.8 |

FIGURE 19A

| | | | |
|---|---|---|---|
| 52 | F | (1-2) Con; (3-4) F | 50 |
| 53 | G | (1-2) Con; (3-4) G | 45 |
| 54 | S | (1-2) Con; (3-4) S | 22.8 |
| 55 | T | (1) Any; (2-3) Con; (4) T | 94.5 |
| 56 | D | (1) Any; (2-3) Con; (4) D | 80.2 |
| 57 | P | (1) Any; (2-3) Con; (4) P | 64.7 |
| 58 | V | (1-2) Con; (3-4) V | 0.2 |
| 59 | A | (1-2) Con; (3-4) A | 0.3 |
| 60 | C | (1-2) Con; (3-4) C | 1.5 |
| 61 | V | (1-2) Con; (3-4) V | 0.8 |
| 62 | R | (1-2) Con; (3-4) R | 9.2 |
| 63 | V | (1-2) Con; (3-4) V | 21.5 |
| 64 | E | (1-2) Con; (3-4) E | 5 |
| 65 | A | (1-2) Con; (3-4) A | 16.3 |
| 66 | L | (1) Any; (2-3) Con; (4) L | 56 |
| 67 | G | (1) Any; (2-3) Con; (4) G | 87.5 |
| 68 | G | (1-2) Con; (3-4) G | 30.5 |
| 69 | Y | (1) Any; (2-3) Con; (4) Y | 60 |
| 70 | G | (1-2) Con; (3-4) G | 17.2 |
| 71 | P | (1) Any; (2-3) Con; (4) P | 139.7 |
| 72 | S | (1) Any; (2-3) Con; (4) S | 74.7 |
| 73 | E | (1-2) Con; (3-4) E | 50 |
| 74 | P | (1-2) Con; (3-4) P | 4.5 |
| 75 | E | (1) Any; (2-3) Con; (4) E | 58.2 |
| 76 | K | (1-2) Con; (3-4) K | 36.8 |
| 77 | V | (1-2) Con; (3-4) V | 16.8 |
| 78 | T | (1-2) Con; (3-4) T | 0 |
| 79 | S | (1-2) Con; (3-4) S | 46.5 |
| 80 | I | (1-4) I | 27.5 |
| 81 | V | (1-2) Con; (3-4) V | 3.7 |
| 82 | T | (1-2) Con; (3-4) T | 5 |
| 83 | A | (1-4) A | 30.7 |
| 84 | A | (1-4) A | 0.7 |
| 85 | I | (1-2) Con; (3-4) I | 0.2 |
| 86 | T | (1-4) T | 45.7 |
| 87 | A | (1-4) A | 44.8 |
| 88 | V | (1-4) V | 19.3 |
| 89 | C | (1-2) Con; (3-4) C | 20.3 |
| 90 | G | (1) Any; (2-3) Con; (4) G | 55.5 |
| 91 | I | (1-2) Con; (3-4) I | 1 |
| 92 | V | (1) Any; (2-3) Con; (4) V | 68.7 |
| 93 | A | (1-2) Con; (3-4) A | 37.5 |
| 94 | D | (1) Any; (2-3) Con; (4) D | 77.3 |
| 95 | R | (1-2) Con; (3-4) R | 20 |
| 96 | I | (1-2) Con; (3-4) I | 0.2 |
| 97 | F | (1-2) Con; (3-4) F | 2 |
| 98 | V | (1-2) Con; (3-4) V | 0 |
| 99 | L | (1-2) Con; (3-4) L | 1 |
| 100 | Y | (1-2) Con; (3-4) Y | 1.5 |
| 101 | F | (1-2) Con; (3-4) F | 17.2 |
| 102 | S | (1) Any; (2-3) Con; (4) S | 57.7 |
| 103 | P | (1-2) Con; (3-4) P | 13.2 |
| 104 | L | (1) Any; (2-3) Con; (4) L | 80 |
| 105 | H | (1-2) Con; (3-4) H | 35.5 |

FIGURE 19B

| | | | |
|---|---|---|---|
| 106 | C | (1-2) Con; (3-4) C | 13.7 |
| 107 | G | (1-2) Con; (3-4) G | 0.3 |
| 108 | W | (1) Any; (2-3) Con; (4) W | 112.2 |
| 109 | N | (1-2) Con; (3-4) N | 49.2 |
| 110 | G | (1-2) Con; (3-4) G | 28.5 |
| 111 | T | (1) Any; (2-3) Con; (4) T | 54.2 |
| 112 | N | (1) Any; (2-3) Con; (4) N | 63.2 |
| 113 | F | (1) Any; (2-3) Con; (4) F | 140.3 |

(SEQ ID NOs: 10, 20, 30, and 40)

FIGURE 19C

SEQUENCE LISTING

<160> NUMBER OF SEQ ID NOS: 52

<210> SEQ ID NO 1
<211> LENGTH: 159
<212> TYPE: PRT
<213> ORGANISM: Artificial Sequence
<220> FEATURE:
<223> OTHER INFORMATION: Synthetic

<400> SEQUENCE: 1

```
Met Gly Glu Val Pro Ile Gly Asp Pro Lys Glu Leu Asn Gly Met Glu
1               5                   10                  15

Ile Ala Ala Val Tyr Leu Gln Pro Ile Glu Met Glu Pro Arg Gly Ile
                20                  25                  30

Asp Leu Ala Ala Ser Leu Ala Asp Ile His Leu Glu Ala Asp Ile His
            35                  40                  45

Ala Leu Lys Asn Asn Pro Asn Gly Phe Pro Glu Gly Phe Trp Met Pro
        50                  55                  60

Tyr Leu Thr Ile Ala Tyr Ala Leu Ala Asn Ala Asp Thr Gly Ala Ile
65                  70                  75                  80

Lys Thr Gly Thr Leu Met Pro Met Val Ala Asp Asp Gly Pro His Tyr
                85                  90                  95

Gly Ala Asn Ile Ala Met Glu Lys Asp Lys Lys Gly Gly Phe Gly Val
            100                 105                 110

Gly Thr Tyr Ala Leu Thr Phe Leu Ile Ser Asn Pro Glu Lys Gln Gly
        115                 120                 125

Phe Gly Arg His Val Asp Glu Glu Thr Gly Val Gly Lys Trp Phe Glu
    130                 135                 140

Pro Phe Val Val Thr Tyr Phe Phe Lys Tyr Thr Gly Thr Pro Lys
145                 150                 155
```

<210> SEQ ID NO 2
<211> LENGTH: 184
<212> TYPE: PRT
<213> ORGANISM: Artificial Sequence
<220> FEATURE:
<223> OTHER INFORMATION: Synthetic

<400> SEQUENCE: 2

```
Met Ser Gln Ala Ile Gly Ile Leu Glu Leu Thr Ser Ile Ala Lys Gly
1               5                   10                  15

Met Glu Leu Gly Asp Ala Met Leu Lys Ser Ala Asn Val Asp Leu Leu
                20                  25                  30

Val Ser Lys Thr Ile Ser Pro Gly Lys Phe Leu Leu Met Leu Gly Gly
            35                  40                  45

Asp Ile Gly Ala Ile Gln Gln Ala Ile Glu Thr Gly Thr Ser Gln Ala
        50                  55                  60

Gly Glu Met Leu Val Asp Ser Leu Val Leu Ala Asn Ile His Pro Ser
65                  70                  75                  80

Val Leu Pro Ala Ile Ser Gly Leu Asn Ser Val Asp Lys Arg Gln Ala
                85                  90                  95

Val Gly Ile Val Glu Thr Trp Ser Val Ala Ala Cys Ile Ser Ala Ala
            100                 105                 110

Asp Leu Ala Val Lys Gly Ser Asn Val Thr Leu Val Arg Val His Met
        115                 120                 125

Ala Phe Gly Ile Gly Gly Lys Cys Tyr Met Val Ala Gly Asp Val
    130                 135                 140
```

```
Leu Asp Val Ala Ala Val Ala Thr Ala Ser Leu Ala Gly Ala
145                 150                 155                 160

Lys Gly Leu Leu Val Tyr Ala Ser Ile Ile Pro Arg Pro His Glu Ala
                165                 170                 175

Met Trp Arg Gln Met Val Glu Gly
            180

<210> SEQ ID NO 3
<211> LENGTH: 103
<212> TYPE: PRT
<213> ORGANISM: Artificial Sequence
<220> FEATURE:
<223> OTHER INFORMATION: Synthetic

<400> SEQUENCE: 3

Met Glu Glu Val Val Leu Ile Thr Val Pro Ser Ala Leu Val Ala Val
1               5                   10                  15

Lys Ile Ala His Ala Leu Val Glu Glu Arg Leu Ala Ala Cys Val Asn
                20                  25                  30

Ile Val Pro Gly Leu Thr Ser Ile Tyr Arg Trp Gln Gly Ser Val Val
            35                  40                  45

Ser Asp His Glu Leu Leu Leu Val Lys Thr Thr Thr His Ala Phe
    50                  55                  60

Pro Lys Leu Lys Glu Arg Val Lys Ala Leu His Pro Tyr Thr Val Pro
65                  70                  75                  80

Glu Ile Val Ala Leu Pro Ile Ala Glu Gly Asn Arg Glu Tyr Leu Asp
                85                  90                  95

Trp Leu Arg Glu Asn Thr Gly
            100

<210> SEQ ID NO 4
<211> LENGTH: 122
<212> TYPE: PRT
<213> ORGANISM: Artificial Sequence
<220> FEATURE:
<223> OTHER INFORMATION: Synthetic

<400> SEQUENCE: 4

Met Val Arg Gly Ile Arg Gly Ala Ile Thr Val Glu Glu Asp Thr Pro
1               5                   10                  15

Ala Ala Ile Leu Ala Ala Thr Ile Glu Leu Leu Leu Lys Met Leu Glu
                20                  25                  30

Ala Asn Gly Ile Gln Ser Tyr Glu Glu Leu Ala Ala Val Ile Phe Thr
            35                  40                  45

Val Thr Glu Asp Leu Thr Ser Ala Phe Pro Ala Glu Ala Ala Arg Leu
50                  55                  60

Ile Gly Met His Arg Val Pro Leu Leu Ser Arg Glu Val Pro Val
65                  70                  75                  80

Pro Gly Ser Leu Pro Arg Val Ile Arg Val Leu Ala Leu Trp Asn Thr
                85                  90                  95

Asp Thr Pro Gln Asp Arg Val Arg His Val Tyr Leu Asn Glu Ala Val
            100                 105                 110

Arg Leu Arg Pro Asp Leu Glu Ser Ala Gln
        115                 120

<210> SEQ ID NO 5
<211> LENGTH: 177
<212> TYPE: PRT
<213> ORGANISM: Artificial Sequence
```

<220> FEATURE:
<223> OTHER INFORMATION: Synthetic

<400> SEQUENCE: 5

Met Ser Lys Ala Lys Ile Gly Ile Val Thr Val Ser Asp Arg Ala Ser
1               5                   10                  15

Ala Gly Ile Thr Ala Asp Ile Ser Gly Lys Ala Ile Ile Leu Ala Leu
            20                  25                  30

Asn Leu Tyr Leu Thr Ser Glu Trp Glu Pro Ile Tyr Gln Val Ile Pro
        35                  40                  45

Asp Glu Gln Asp Val Ile Glu Thr Thr Leu Ile Lys Met Ala Asp Glu
    50                  55                  60

Gln Asp Cys Cys Leu Ile Val Thr Thr Gly Thr Gly Pro Ala Lys
65                  70                  75                  80

Arg Asp Val Thr Pro Glu Ala Thr Glu Ala Val Cys Arg Met Met
                85                  90                  95

Pro Gly Phe Gly Glu Leu Met Arg Ala Glu Ser Leu Lys Glu Val Pro
            100                 105                 110

Thr Ala Ile Leu Ser Arg Gln Thr Ala Gly Leu Arg Gly Asp Ser Leu
        115                 120                 125

Ile Val Asn Leu Pro Gly Asp Pro Ala Ser Ile Ser Asp Cys Leu Leu
    130                 135                 140

Ala Val Phe Pro Ala Ile Pro Tyr Cys Ile Asp Leu Met Glu Gly Pro
145                 150                 155                 160

Tyr Leu Glu Cys Asn Glu Ala Met Ile Lys Pro Phe Arg Pro Lys Ala
                165                 170                 175

Lys

<210> SEQ ID NO 6
<211> LENGTH: 122
<212> TYPE: PRT
<213> ORGANISM: Artificial Sequence
<220> FEATURE:
<223> OTHER INFORMATION: Synthetic

<400> SEQUENCE: 6

Met Val Arg Gly Ile Arg Gly Ala Ile Thr Val Asn Ser Asp Thr Pro
1               5                   10                  15

Thr Ser Ile Ile Ile Ala Thr Ile Leu Leu Glu Lys Met Leu Glu
            20                  25                  30

Ala Asn Gly Ile Gln Ser Tyr Glu Glu Leu Ala Ala Val Ile Phe Thr
        35                  40                  45

Val Thr Glu Asp Leu Thr Ser Ala Phe Pro Ala Glu Ala Ala Arg Gln
    50                  55                  60

Ile Gly Met His Arg Val Pro Leu Leu Ser Arg Glu Val Pro Val
65                  70                  75                  80

Pro Gly Ser Leu Pro Arg Val Ile Arg Val Leu Ala Leu Trp Asn Thr
                85                  90                  95

Asp Thr Pro Gln Asp Arg Val Arg His Val Tyr Leu Ser Glu Ala Val
            100                 105                 110

Arg Leu Arg Pro Asp Leu Glu Ser Ala Gln
        115                 120

<210> SEQ ID NO 7
<211> LENGTH: 172
<212> TYPE: PRT
<213> ORGANISM: Artificial Sequence -continued

```
<220> FEATURE:
<223> OTHER INFORMATION: Synthetic

<400> SEQUENCE: 7

Met Arg Ile Thr Thr Lys Val Gly Asp Lys Gly Ser Thr Arg Leu Phe
1               5                   10                  15

Gly Gly Glu Glu Val Trp Lys Asp Ser Pro Ile Ile Glu Ala Asn Gly
            20                  25                  30

Thr Leu Asp Glu Leu Thr Ser Phe Ile Gly Glu Ala Lys His Tyr Val
        35                  40                  45

Asp Glu Glu Met Lys Gly Ile Leu Glu Glu Ile Gln Asn Asp Ile Tyr
    50                  55                  60

Lys Ile Met Gly Glu Ile Gly Ser Lys Gly Lys Ile Glu Gly Ile Ser
65                  70                  75                  80

Glu Glu Arg Ile Ala Trp Leu Leu Lys Leu Ile Leu Arg Tyr Met Glu
                85                  90                  95

Met Val Asn Leu Lys Ser Phe Val Leu Pro Gly Gly Thr Leu Glu Ser
            100                 105                 110

Ala Lys Leu Asp Val Cys Arg Thr Ile Ala Arg Arg Ala Leu Arg Lys
        115                 120                 125

Val Leu Thr Val Thr Arg Glu Phe Gly Ile Gly Ala Glu Ala Ala Ala
    130                 135                 140

Tyr Leu Ala Leu Ser Asp Leu Leu Phe Leu Leu Ala Arg Val Ile
145                 150                 155                 160

Glu Ile Glu Lys Asn Lys Leu Lys Glu Val Arg Ser
                165                 170

<210> SEQ ID NO 8
<211> LENGTH: 123
<212> TYPE: PRT
<213> ORGANISM: Artificial Sequence
<220> FEATURE:
<223> OTHER INFORMATION: Synthetic

<400> SEQUENCE: 8

Met Pro His Leu Val Ile Glu Ala Thr Ala Asn Leu Arg Leu Glu Thr
1               5                   10                  15

Ser Pro Gly Glu Leu Leu Glu Gln Ala Asn Lys Ala Leu Phe Ala Ser
            20                  25                  30

Gly Gln Phe Gly Glu Ala Asp Ile Lys Ser Arg Phe Val Thr Leu Glu
        35                  40                  45

Ala Tyr Arg Gln Gly Thr Ala Val Glu Arg Ala Tyr Leu His Ala
    50                  55                  60

Cys Leu Ser Ile Leu Asp Gly Arg Asp Ile Ala Thr Arg Thr Leu Leu
65                  70                  75                  80

Gly Ala Ser Leu Cys Ala Val Leu Ala Glu Val Ala Gly Gly Gly
                85                  90                  95

Glu Glu Gly Val Gln Val Ser Val Glu Val Arg Glu Met Glu Arg Leu
            100                 105                 110

Ser Tyr Ala Lys Arg Val Val Ala Arg Gln Arg
        115                 120

<210> SEQ ID NO 9
<211> LENGTH: 158
<212> TYPE: PRT
<213> ORGANISM: Artificial Sequence
<220> FEATURE:
<223> OTHER INFORMATION: Synthetic
```

<400> SEQUENCE: 9

Met Glu Ser Val Asn Thr Ser Phe Leu Ser Pro Ser Leu Val Thr Ile
1               5                   10                  15

Arg Asp Phe Asp Asn Gly Gln Phe Ala Val Leu Arg Ile Gly Arg Thr
            20                  25                  30

Gly Phe Pro Ala Asp Lys Gly Asp Ile Asp Leu Cys Leu Asp Lys Met
        35                  40                  45

Ile Gly Val Arg Ala Ala Gln Ile Phe Leu Gly Asp Asp Thr Glu Asp
50                  55                  60

Gly Phe Lys Gly Pro His Ile Arg Ile Arg Cys Val Asp Ile Asp Asp
65                  70                  75                  80

Lys His Thr Tyr Asn Ala Met Val Tyr Val Asp Leu Ile Val Gly Thr
                85                  90                  95

Gly Ala Ser Glu Val Glu Arg Glu Thr Ala Glu Glu Ala Lys Leu
            100                 105                 110

Ala Leu Arg Val Ala Leu Gln Val Asp Ile Ala Asp Glu His Ser Cys
        115                 120                 125

Val Thr Gln Phe Glu Met Lys Leu Arg Glu Glu Leu Leu Ser Ser Asp
130                 135                 140

Ser Phe His Pro Asp Lys Asp Glu Tyr Tyr Lys Asp Phe Leu
145                 150                 155

<210> SEQ ID NO 10
<211> LENGTH: 113
<212> TYPE: PRT
<213> ORGANISM: Artificial Sequence
<220> FEATURE:
<223> OTHER INFORMATION: Synthetic

<400> SEQUENCE: 10

Met Pro Val Ile Gln Thr Phe Val Ser Thr Pro Leu Asp His His Lys
1               5                   10                  15

Arg Leu Leu Leu Ala Ile Ile Tyr Arg Ile Val Thr Arg Val Val Leu
            20                  25                  30

Gly Lys Pro Glu Asp Leu Val Met Met Thr Phe His Asp Ser Thr Pro
        35                  40                  45

Met His Phe Phe Gly Ser Thr Asp Pro Val Ala Cys Val Arg Val Glu
50                  55                  60

Ala Leu Gly Gly Tyr Gly Pro Ser Glu Pro Glu Lys Val Thr Ser Ile
65                  70                  75                  80

Val Thr Ala Ala Ile Thr Ala Val Cys Gly Ile Val Ala Asp Arg Ile
                85                  90                  95

Phe Val Leu Tyr Phe Ser Pro Leu His Cys Gly Trp Asn Gly Thr Asn
            100                 105                 110

Phe

<210> SEQ ID NO 11
<211> LENGTH: 159
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE

```
<222> LOCATION: (2)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is A, C, G, P, M, V, I, L, Sme, or Sce
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(7)
<223> OTHER INFORMATION: Xaa is A, C, G, P, M, V, I, L, Sme, or Sce
<220> FEATURE:
<221> NAME/KEY: MISC_FEATURE
<222> LOCATION: (8)..(9)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is R, H, or K
<220> FEATURE:
<221> NAME/KEY: MISC_FEATURE
<222> LOCATION: (11)..(13)
<223> OTHER INFORMATION: Xaa is any amino acid
<220> FEATURE:
<221> NAME/KEY: MISC_FEATURE
<222> LOCATION: (14)..(15)
<223> OTHER INFORMATION: Xaa is A, C, G, P, M, V, I, L, Sme, or Sce
<220> FEATURE:
<221> NAME/KEY: MISC_FEATURE
<222> LOCATION: (16)..(16)
<223> OTHER INFORMATION: Xaa is D or E
<220> FEATURE:
<221> NAME/KEY: MISC_FEATURE
<222> LOCATION: (17)..(17)
<223> OTHER INFORMATION: Xaa is any amino acid
<220> FEATURE:
<221> NAME/KEY: MISC_FEATURE
<222> LOCATION: (18)..(20)
<223> OTHER INFORMATION: Xaa is A, C, G, P, M, V, I, L, Sme, or Sce
<220> FEATURE:
<221> NAME/KEY: MISC_FEATURE
<222> LOCATION: (21)..(21)
<223> OTHER INFORMATION: Xaa is F, W, or Y
<220> FEATURE:
<221> NAME/KEY: MISC_FEATURE
<222> LOCATION: (22)..(22)
<223> OTHER INFORMATION: Xaa is A, C, G, P, M, V, I, L, Sme, or Sce
<220> FEATURE:
<221> NAME/KEY: MISC_FEATURE
<222> LOCATION: (23)..(23)
<223> OTHER INFORMATION: Xaa is any amino acid
<220> FEATURE:
<221> NAME/KEY: MISC_FEATURE
<222> LOCATION: (24)..(25)
<223> OTHER INFORMATION: Xaa is A, C, G, P, M, V, I, L, Sme, or Sce
<220> FEATURE:
<221> NAME/KEY: MISC_FEATURE
<222> LOCATION: (26)..(26)
<223> OTHER INFORMATION: Xaa is any amino acid
<220> FEATURE:
<221> NAME/KEY: MISC_FEATURE
<222> LOCATION: (27)..(27)
<223> OTHER INFORMATION: Xaa is A, C, G, P, M, V, I, L, Sme, or Sce
<220> FEATURE:
<221> NAME/KEY: MISC_FEATURE
<222> LOCATION: (28)..(32)
<223> OTHER INFORMATION: Xaa is any amino acid
<220> FEATURE:
<221> NAME/KEY: MISC_FEATURE
<222> LOCATION: (33)..(33)
<223> OTHER INFORMATION: Xaa is D or E
<220> FEATURE:
<221> NAME/KEY: MISC_FEATURE
<222> LOCATION: (34)..(34)
<223> OTHER INFORMATION: Xaa is A, C, G, P, M, V, I, L, Sme, or Sce
<220> FEATURE:
```

```
<221> NAME/KEY: MISC_FEATURE
<222> LOCATION: (35)..(35)
<223> OTHER INFORMATION: Xaa is any amino acid
<220> FEATURE:
<221> NAME/KEY: MISC_FEATURE
<222> LOCATION: (36)..(36)
<223> OTHER INFORMATION: Xaa is A, C, G, P, M, V, I, L, Sme, or Sce
<220> FEATURE:
<221> NAME/KEY: MISC_FEATURE
<222> LOCATION: (37)..(38)
<223> OTHER INFORMATION: Xaa is any amino acid
<220> FEATURE:
<221> NAME/KEY: MISC_FEATURE
<222> LOCATION: (39)..(39)
<223> OTHER INFORMATION: Xaa is A, C, G, P, M, V, I, L, Sme, or Sce
<220> FEATURE:
<221> NAME/KEY: MISC_FEATURE
<222> LOCATION: (40)..(40)
<223> OTHER INFORMATION: Xaa is D or E
<220> FEATURE:
<221> NAME/KEY: MISC_FEATURE
<222> LOCATION: (41)..(41)
<223> OTHER INFORMATION: Xaa is A, C, G, P, M, V, I, L, Sme, or Sce
<220> FEATURE:
<221> NAME/KEY: MISC_FEATURE
<222> LOCATION: (42)..(42)
<223> OTHER INFORMATION: Xaa is R, H or K
<220> FEATURE:
<221> NAME/KEY: MISC_FEATURE
<222> LOCATION: (43)..(43)
<223> OTHER INFORMATION: Xaa is any amino acid
<220> FEATURE:
<221> NAME/KEY: MISC_FEATURE
<222> LOCATION: (44)..(44)
<223> OTHER INFORMATION: Xaa is D or E
<220> FEATURE:
<221> NAME/KEY: MISC_FEATURE
<222> LOCATION: (45)..(45)
<223> OTHER INFORMATION: Xaa is A, C, G, P, M, V, I, L, Sme, or Sce
<220> FEATURE:
<221> NAME/KEY: MISC_FEATURE
<222> LOCATION: (46)..(46)
<223> OTHER INFORMATION: Xaa is any amino acid
<220> FEATURE:
<221> NAME/KEY: MISC_FEATURE
<222> LOCATION: (47)..(47)
<223> OTHER INFORMATION: Xaa is A, C, G, P, M, V, I, L, Sme, or Sce
<220> FEATURE:
<221> NAME/KEY: MISC_FEATURE
<222> LOCATION: (48)..(48)
<223> OTHER INFORMATION: Xaa is R, H, or K
<220> FEATURE:
<221> NAME/KEY: MISC_FEATURE
<222> LOCATION: (49)..(50)
<223> OTHER INFORMATION: Xaa is A, C, G, P, M, V, I, L, Sme, or Sce
<220> FEATURE:
<221> NAME/KEY: MISC_FEATURE
<222> LOCATION: (51)..(52)
<223> OTHER INFORMATION: Xaa is any amino acid
<220> FEATURE:
<221> NAME/KEY: MISC_FEATURE
<222> LOCATION: (53)..(53)
<223> OTHER INFORMATION: Xaa is S, T, N, or Q
<220> FEATURE:
<221> NAME/KEY: MISC_FEATURE
<222> LOCATION: (54)..(54)
<223> OTHER INFORMATION: Xaa is any amino acid
<220> FEATURE:
<221> NAME/KEY: MISC_FEATURE
<222> LOCATION: (55)..(55)
<223> OTHER INFORMATION: Xaa is S, T, N, or Q
<220> FEATURE:
<221> NAME/KEY: MISC_FEATURE
<222> LOCATION: (56)..(56)
<223> OTHER INFORMATION: Xaa is A, C, G, P, M, V, I, L, Sme, or Sce
<220> FEATURE:
<221> NAME/KEY: MISC_FEATURE
<222> LOCATION: (57)..(57)
<223> OTHER INFORMATION: Xaa is F, W, or Y
```

```
<220> FEATURE:
<221> NAME/KEY: MISC_FEATURE
<222> LOCATION: (58)..(60)
<223> OTHER INFORMATION: Xaa is any amino acid
<220> FEATURE:
<221> NAME/KEY: MISC_FEATURE
<222> LOCATION: (61)..(62)
<223> OTHER INFORMATION: Xaa is F, W, or Y
<220> FEATURE:
<221> NAME/KEY: MISC_FEATURE
<222> LOCATION: (63)..(66)
<223> OTHER INFORMATION: Xaa is any amino acid
<220> FEATURE:
<221> NAME/KEY: MISC_FEATURE
<222> LOCATION: (66)..(66)
<223> OTHER INFORMATION: Xaa is A, C, G, P, M, V, I, L, Sme, or Sce
<220> FEATURE:
<221> NAME/KEY: MISC_FEATURE
<222> LOCATION: (67)..(67)
<223> OTHER INFORMATION: Xaa is S, T, N, or Q
<220> FEATURE:
<221> NAME/KEY: MISC_FEATURE
<222> LOCATION: (68)..(68)
<223> OTHER INFORMATION: Xaa is A, C, G, P, M, V, I, L, Sme, or Sce
<220> FEATURE:
<221> NAME/KEY: MISC_FEATURE
<222> LOCATION: (84)..(84)
<223> OTHER INFORMATION: Xaa is any amino acid
<220> FEATURE:
<221> NAME/KEY: MISC_FEATURE
<222> LOCATION: (85)..(86)
<223> OTHER INFORMATION: Xaa is A, C, G, P, M, V, I, L, Sme, or Sce
<220> FEATURE:
<221> NAME/KEY: MISC_FEATURE
<222> LOCATION: (87)..(87)
<223> OTHER INFORMATION: Xaa is any amino acid
<220> FEATURE:
<221> NAME/KEY: MISC_FEATURE
<222> LOCATION: (88)..(90)
<223> OTHER INFORMATION: Xaa is A, C, G, P, M, V, I, L, Sme, or Sce
<220> FEATURE:
<221> NAME/KEY: MISC_FEATURE
<222> LOCATION: (91)..(92)
<223> OTHER INFORMATION: Xaa is any amino acid
<220> FEATURE:
<221> NAME/KEY: MISC_FEATURE
<222> LOCATION: (93)..(93)
<223> OTHER INFORMATION: Xaa is A, C, G, P, M, V, I, L, Sme, or Sce
<220> FEATURE:
<221> NAME/KEY: MISC_FEATURE
<222> LOCATION: (94)..(94)
<223> OTHER INFORMATION: Xaa is any amino acid
<220> FEATURE:
<221> NAME/KEY: MISC_FEATURE
<222> LOCATION: (95)..(95)
<223> OTHER INFORMATION: Xaa is R, H, or K
<220> FEATURE:
<221> NAME/KEY: MISC_FEATURE
<222> LOCATION: (96)..(96)
<223> OTHER INFORMATION: Xaa is F, W, or Y
<220> FEATURE:
<221> NAME/KEY: MISC_FEATURE
<222> LOCATION: (97)..(98)
<223> OTHER INFORMATION: Xaa is A, C, G, P, M, V, I, L, Sme, or Sce
<220> FEATURE:
<221> NAME/KEY: MISC_FEATURE
<222> LOCATION: (99)..(99)
<223> OTHER INFORMATION: Xaa is S, T, N, or Q
<220> FEATURE:
<221> NAME/KEY: MISC_FEATURE
<222> LOCATION: (100)..(102)
<223> OTHER INFORMATION: Xaa is A, C, G, P, M, V, I, L, Sme, or Sce
<220> FEATURE:
<221> NAME/KEY: MISC_FEATURE
<222> LOCATION: (103)..(104)
<223> OTHER INFORMATION: Xaa is any amino acid
<220> FEATURE:
<221> NAME/KEY: MISC_FEATURE
<222> LOCATION: (105)..(105)
```

```
<223> OTHER INFORMATION: Xaa is D or E
<220> FEATURE:
<221> NAME/KEY: MISC_FEATURE
<222> LOCATION: (106)..(107)
<223> OTHER INFORMATION: Xaa is any amino acid
<220> FEATURE:
<221> NAME/KEY: MISC_FEATURE
<222> LOCATION: (108)..(109)
<223> OTHER INFORMATION: Xaa is A, C, G, P, M, V, I, L, Sme, or Sce
<220> FEATURE:
<221> NAME/KEY: MISC_FEATURE
<222> LOCATION: (110)..(110)
<223> OTHER INFORMATION: Xaa is F, W, or Y
<220> FEATURE:
<221> NAME/KEY: MISC_FEATURE
<222> LOCATION: (111)..(111)
<223> OTHER INFORMATION: Xaa is A, C, G, P, M, V, I, L, Sme, or Sce
<220> FEATURE:
<221> NAME/KEY: MISC_FEATURE
<222> LOCATION: (112)..(112)
<223> OTHER INFORMATION: Xaa is any amino acid
<220> FEATURE:
<221> NAME/KEY: MISC_FEATURE
<222> LOCATION: (113)..(113)
<223> OTHER INFORMATION: Xaa is A, C, G, P, M, V, I, L, Sme, or Sce
<220> FEATURE:
<221> NAME/KEY: MISC_FEATURE
<222> LOCATION: (122)..(123)
<223> OTHER INFORMATION: Xaa is S, T, N, or Q
<220> FEATURE:
<221> NAME/KEY: MISC_FEATURE
<222> LOCATION: (124)..(124)
<223> OTHER INFORMATION: Xaa is A, C, G, P, M, V, I, L, Sme, or Sce
<220> FEATURE:
<221> NAME/KEY: MISC_FEATURE
<222> LOCATION: (125)..(125)
<223> OTHER INFORMATION: Xaa is D or E
<220> FEATURE:
<221> NAME/KEY: MISC_FEATURE
<222> LOCATION: (126)..(127)
<223> OTHER INFORMATION: Xaa is any amino acid
<220> FEATURE:
<221> NAME/KEY: MISC_FEATURE
<222> LOCATION: (128)..(128)
<223> OTHER INFORMATION: Xaa is A, C, G, P, M, V, I, L, Sme, or Sce
<220> FEATURE:
<221> NAME/KEY: MISC_FEATURE
<222> LOCATION: (129)..(129)
<223> OTHER INFORMATION: Xaa is F, W, or Y
<220> FEATURE:
<221> NAME/KEY: MISC_FEATURE
<222> LOCATION: (130)..(130)
<223> OTHER INFORMATION: Xaa is A, C, G, P, M, V, I, L, Sme, or Sce
<220> FEATURE:
<221> NAME/KEY: MISC_FEATURE
<222> LOCATION: (131)..(132)
<223> OTHER INFORMATION: Xaa is R, H, or K
<220> FEATURE:
<221> NAME/KEY: MISC_FEATURE
<222> LOCATION: (133)..(133)
<223> OTHER INFORMATION: Xaa is any amino acid
<220> FEATURE:
<221> NAME/KEY: MISC_FEATURE
<222> LOCATION: (134)..(134)
<223> OTHER INFORMATION: Xaa is D or E
<220> FEATURE:
<221> NAME/KEY: MISC_FEATURE
<222> LOCATION: (135)..(136)
<223> OTHER INFORMATION: Xaa is any amino acid
<220> FEATURE:
<221> NAME/KEY: MISC_FEATURE
<222> LOCATION: (137)..(137)
<223> OTHER INFORMATION: Xaa is S, T, N, or Q
<220> FEATURE:
<221> NAME/KEY: MISC_FEATURE
<222> LOCATION: (138)..(140)
<223> OTHER INFORMATION: Xaa is A, C, G, P, M, V, I, L, Sme, or Sce
<220> FEATURE:
<221> NAME/KEY: MISC_FEATURE
```

```
<222> LOCATION: (141)..(142)
<223> OTHER INFORMATION: Xaa is any amino acid
<220> FEATURE:
<221> NAME/KEY: MISC_FEATURE
<222> LOCATION: (143)..(143)
<223> OTHER INFORMATION: Xaa is F, W, or Y
<220> FEATURE:
<221> NAME/KEY: MISC_FEATURE
<222> LOCATION: (144)..(144)
<223> OTHER INFORMATION: Xaa is any amino acid
<220> FEATURE:
<221> NAME/KEY: MISC_FEATURE
<222> LOCATION: (146)..(146)
<223> OTHER INFORMATION: Xaa is F, W, or Y
<220> FEATURE:
<221> NAME/KEY: MISC_FEATURE
<222> LOCATION: (153)..(153)
<223> OTHER INFORMATION: Xaa is any amino acid
<220> FEATURE:
<221> NAME/KEY: MISC_FEATURE
<222> LOCATION: (154)..(154)
<223> OTHER INFORMATION: Xaa is F, W, or Y
<220> FEATURE:
<221> NAME/KEY: MISC_FEATURE
<222> LOCATION: (155)..(155)
<223> OTHER INFORMATION: Xaa is any amino acid
<220> FEATURE:
<221> NAME/KEY: MISC_FEATURE
<222> LOCATION: (156)..(156)
<223> OTHER INFORMATION: Xaa is A, C, G, P, M, V, I, L, Sme, or Sce
<220> FEATURE:
<221> NAME/KEY: MISC_FEATURE
<222> LOCATION: (157)..(159)
<223> OTHER INFORMATION: Xaa is any amino acid

<400> SEQUENCE: 11

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Ala Tyr Ala Leu Ala Asn Ala Asp Thr Gly Ala Ile
65                  70                  75                  80

Lys Thr Gly Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Thr Tyr Ala Leu Thr Phe Leu Ile Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Pro Phe Val Val Thr Tyr Phe Phe Xaa Xaa Xaa Xaa Xaa Xaa Xaa
145                 150                 155

<210> SEQ ID NO 12
<211> LENGTH: 184
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or optionally absent
<220> FEATURE:
```

```
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is S, T, N, or Q
<220> FEATURE:
<221> NAME/KEY: MISC_FEATURE
<222> LOCATION: (4)..(8)
<223> OTHER INFORMATION: Xaa is A, C, G, P, M, V, I, L, Sce or Sme
<220> FEATURE:
<221> NAME/KEY: MISC_FEATURE
<222> LOCATION: (9)..(9)
<223> OTHER INFORMATION: Xaa is D or E
<220> FEATURE:
<221> NAME/KEY: MISC_FEATURE
<222> LOCATION: (10)..(10)
<223> OTHER INFORMATION: Xaa is A, C, G, P, M, V, I, L, Sce or Sme
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is S, T, N, or Q
<220> FEATURE:
<221> NAME/KEY: MISC_FEATURE
<222> LOCATION: (13)..(14)
<223> OTHER INFORMATION: Xaa is A, C, G, P, M, V, I, L, Sce or Sme
<220> FEATURE:
<221> NAME/KEY: MISC_FEATURE
<222> LOCATION: (15)..(15)
<223> OTHER INFORMATION: Xaa is R, H, or K
<220> FEATURE:
<221> NAME/KEY: MISC_FEATURE
<222> LOCATION: (16)..(16)
<223> OTHER INFORMATION: Xaa is A, C, G, P, M, V, I, L, Sce or Sme
<220> FEATURE:
<221> NAME/KEY: MISC_FEATURE
<222> LOCATION: (17)..(17)
<223> OTHER INFORMATION: Xaa is any amino acid
<220> FEATURE:
<221> NAME/KEY: MISC_FEATURE
<222> LOCATION: (18)..(18)
<223> OTHER INFORMATION: Xaa is D or E
<220> FEATURE:
<221> NAME/KEY: MISC_FEATURE
<222> LOCATION: (19)..(20)
<223> OTHER INFORMATION: Xaa is A, C, G, P, M, V, I, L, Sce or Sme
<220> FEATURE:
<221> NAME/KEY: MISC_FEATURE
<222> LOCATION: (21)..(21)
<223> OTHER INFORMATION: Xaa is D or E
<220> FEATURE:
<221> NAME/KEY: MISC_FEATURE
<222> LOCATION: (22)..(22)
<223> OTHER INFORMATION: Xaa is any amino acid
<220> FEATURE:
<221> NAME/KEY: MISC_FEATURE
<222> LOCATION: (23)..(24)
<223> OTHER INFORMATION: Xaa is A, C, G, P, M, V, I, L, Sce or Sme
<220> FEATURE:
<221> NAME/KEY: MISC_FEATURE
<222> LOCATION: (25)..(26)
<223> OTHER INFORMATION: Xaa is any amino acid
<220> FEATURE:
<221> NAME/KEY: MISC_FEATURE
<222> LOCATION: (27)..(27)
<223> OTHER INFORMATION: Xaa is A, C, G, P, M, V, I, L, Sce or Sme
<220> FEATURE:
<221> NAME/KEY: MISC_FEATURE
<222> LOCATION: (28)..(28)
<223> OTHER INFORMATION: Xaa is any amino acid
<220> FEATURE:
<221> NAME/KEY: MISC_FEATURE
<222> LOCATION: (29)..(29)
<223> OTHER INFORMATION: Xaa is A, C, G, P, M, V, I, L, Sce or Sme
```

```
<220> FEATURE:
<221> NAME/KEY: MISC_FEATURE
<222> LOCATION: (30)..(31)
<223> OTHER INFORMATION: Xaa is any amino acid
<220> FEATURE:
<221> NAME/KEY: MISC_FEATURE
<222> LOCATION: (32)..(33)
<223> OTHER INFORMATION: Xaa is A, C, G, P, M, V, I, L, Sce or Sme
<220> FEATURE:
<221> NAME/KEY: MISC_FEATURE
<222> LOCATION: (34)..(36)
<223> OTHER INFORMATION: Xaa is any amino acid
<220> FEATURE:
<221> NAME/KEY: MISC_FEATURE
<222> LOCATION: (35)..(35)
<223> OTHER INFORMATION: Xaa is R, H, or K
<220> FEATURE:
<221> NAME/KEY: MISC_FEATURE
<222> LOCATION: (37)..(37)
<223> OTHER INFORMATION: Xaa is A, C, G, P, M, V, I, L, Sce or Sme
<220> FEATURE:
<221> NAME/KEY: MISC_FEATURE
<222> LOCATION: (38)..(39)
<223> OTHER INFORMATION: Xaa is any amino acid
<220> FEATURE:
<221> NAME/KEY: MISC_FEATURE
<222> LOCATION: (40)..(40)
<223> OTHER INFORMATION: Xaa is A, C, G, P, M, V, I, L, Sce or Sme
<220> FEATURE:
<221> NAME/KEY: MISC_FEATURE
<222> LOCATION: (41)..(41)
<223> OTHER INFORMATION: Xaa is R, H, or K
<220> FEATURE:
<221> NAME/KEY: MISC_FEATURE
<222> LOCATION: (42)..(42)
<223> OTHER INFORMATION: Xaa is F, W, or Y
<220> FEATURE:
<221> NAME/KEY: MISC_FEATURE
<222> LOCATION: (43)..(48)
<223> OTHER INFORMATION: Xaa is A, C, G, P, M, V, I, L, Sce or Sme
<220> FEATURE:
<221> NAME/KEY: MISC_FEATURE
<222> LOCATION: (49)..(51)
<223> OTHER INFORMATION: Xaa is any amino acid
<220> FEATURE:
<221> NAME/KEY: MISC_FEATURE
<222> LOCATION: (52)..(53)
<223> OTHER INFORMATION: Xaa is A, C, G, P, M, V, I, L, Sce or Sme
<220> FEATURE:
<221> NAME/KEY: MISC_FEATURE
<222> LOCATION: (54)..(55)
<223> OTHER INFORMATION: Xaa is any amino acid
<220> FEATURE:
<221> NAME/KEY: MISC_FEATURE
<222> LOCATION: (56)..(57)
<223> OTHER INFORMATION: Xaa is A, C, G, P, M, V, I, L, Sce or Sme
<220> FEATURE:
<221> NAME/KEY: MISC_FEATURE
<222> LOCATION: (58)..(58)
<223> OTHER INFORMATION: Xaa is any amino acid
<220> FEATURE:
<221> NAME/KEY: MISC_FEATURE
<222> LOCATION: (59)..(59)
<223> OTHER INFORMATION: Xaa is S, T, N, or Q
<220> FEATURE:
<221> NAME/KEY: MISC_FEATURE
<222> LOCATION: (60)..(60)
<223> OTHER INFORMATION: Xaa is A, C, G, P, M, V, I, L, Sce or Sme
<220> FEATURE:
<221> NAME/KEY: MISC_FEATURE
<222> LOCATION: (61)..(63)
<223> OTHER INFORMATION: Xaa is any amino acid
<220> FEATURE:
<221> NAME/KEY: MISC_FEATURE
<222> LOCATION: (64)..(64)
<223> OTHER INFORMATION: Xaa is A, C, G, P, M, V, I, L, Sce or Sme
<220> FEATURE:
<221> NAME/KEY: MISC_FEATURE
<222> LOCATION: (65)..(66)
```

```
<223> OTHER INFORMATION: Xaa is any amino acid
<220> FEATURE:
<221> NAME/KEY: MISC_FEATURE
<222> LOCATION: (67)..(67)
<223> OTHER INFORMATION: Xaa is A, C, G, P, M, V, I, L, Sce or Sme
<220> FEATURE:
<221> NAME/KEY: MISC_FEATURE
<222> LOCATION: (68)..(73)
<223> OTHER INFORMATION: Xaa is any amino acid
<220> FEATURE:
<221> NAME/KEY: MISC_FEATURE
<222> LOCATION: (74)..(74)
<223> OTHER INFORMATION: Xaa is A, C, G, P, M, V, I, L, Sce or Sme
<220> FEATURE:
<221> NAME/KEY: MISC_FEATURE
<222> LOCATION: (75)..(76)
<223> OTHER INFORMATION: Xaa is any amino acid
<220> FEATURE:
<221> NAME/KEY: MISC_FEATURE
<222> LOCATION: (77)..(77)
<223> OTHER INFORMATION: Xaa is A, C, G, P, M, V, I, L, Sce or Sme
<220> FEATURE:
<221> NAME/KEY: MISC_FEATURE
<222> LOCATION: (78)..(78)
<223> OTHER INFORMATION: Xaa is R, H, or K
<220> FEATURE:
<221> NAME/KEY: MISC_FEATURE
<222> LOCATION: (79)..(79)
<223> OTHER INFORMATION: Xaa is any amino acid
<220> FEATURE:
<221> NAME/KEY: MISC_FEATURE
<222> LOCATION: (80)..(80)
<223> OTHER INFORMATION: Xaa is S, T, N, or Q
<220> FEATURE:
<221> NAME/KEY: MISC_FEATURE
<222> LOCATION: (81)..(81)
<223> OTHER INFORMATION: Xaa is A, C, G, P, M, V, I, L, Sce or Sme
<220> FEATURE:
<221> NAME/KEY: MISC_FEATURE
<222> LOCATION: (82)..(83)
<223> OTHER INFORMATION: Xaa is any amino acid
<220> FEATURE:
<221> NAME/KEY: MISC_FEATURE
<222> LOCATION: (84)..(84)
<223> OTHER INFORMATION: Xaa is A, C, G, P, M, V, I, L, Sce or Sme
<220> FEATURE:
<221> NAME/KEY: MISC_FEATURE
<222> LOCATION: (85)..(86)
<223> OTHER INFORMATION: Xaa is any amino acid
<220> FEATURE:
<221> NAME/KEY: MISC_FEATURE
<222> LOCATION: (87)..(87)
<223> OTHER INFORMATION: Xaa is A, C, G, P, M, V, I, L, Sce or Sme
<220> FEATURE:
<221> NAME/KEY: MISC_FEATURE
<222> LOCATION: (88)..(95)
<223> OTHER INFORMATION: Xaa is any amino acid
<220> FEATURE:
<221> NAME/KEY: MISC_FEATURE
<222> LOCATION: (97)..(97)
<223> OTHER INFORMATION: Xaa is A, C, G, P, M, V, I, L, Sce or Sme
<220> FEATURE:
<221> NAME/KEY: MISC_FEATURE
<222> LOCATION: (98)..(98)
<223> OTHER INFORMATION: Xaa is S, T, N, or Q
<220> FEATURE:
<221> NAME/KEY: MISC_FEATURE
<222> LOCATION: (99)..(100)
<223> OTHER INFORMATION: Xaa is A, C, G, P, M, V, I, L, Sce or Sme
<220> FEATURE:
<221> NAME/KEY: MISC_FEATURE
<222> LOCATION: (101)..(101)
<223> OTHER INFORMATION: Xaa is D or E
<220> FEATURE:
<221> NAME/KEY: MISC_FEATURE
<222> LOCATION: (102)..(102)
<223> OTHER INFORMATION: Xaa is S, T, N, or Q
<220> FEATURE:
<221> NAME/KEY: MISC_FEATURE
```

```
<222> LOCATION: (103)..(103)
<223> OTHER INFORMATION: Xaa is F, W, or Y
<220> FEATURE:
<221> NAME/KEY: MISC_FEATURE
<222> LOCATION: (104)..(104)
<223> OTHER INFORMATION: Xaa is S, T, N, or Q
<220> FEATURE:
<221> NAME/KEY: MISC_FEATURE
<222> LOCATION: (105)..(105)
<223> OTHER INFORMATION: Xaa is A, C, G, P, M, V, I, L, Sce or Sme
<220> FEATURE:
<221> NAME/KEY: MISC_FEATURE
<222> LOCATION: (106)..(106)
<223> OTHER INFORMATION: Xaa is any amino acid
<220> FEATURE:
<221> NAME/KEY: MISC_FEATURE
<222> LOCATION: (107)..(108)
<223> OTHER INFORMATION: Xaa is A, C, G, P, M, V, I, L, Sce or Sme
<220> FEATURE:
<221> NAME/KEY: MISC_FEATURE
<222> LOCATION: (109)..(110)
<223> OTHER INFORMATION: Xaa is any amino acid
<220> FEATURE:
<221> NAME/KEY: MISC_FEATURE
<222> LOCATION: (111)..(112)
<223> OTHER INFORMATION: Xaa is A, C, G, P, M, V, I, L, Sce or Sme
<220> FEATURE:
<221> NAME/KEY: MISC_FEATURE
<222> LOCATION: (112)..(112)
<223> OTHER INFORMATION: Xaa is any amino acid
<220> FEATURE:
<221> NAME/KEY: MISC_FEATURE
<222> LOCATION: (113)..(113)
<223> OTHER INFORMATION: Xaa is D or E
<220> FEATURE:
<221> NAME/KEY: MISC_FEATURE
<222> LOCATION: (116)..(116)
<223> OTHER INFORMATION: Xaa is A, C, G, P, M, V, I, L, Sce or Sme
<220> FEATURE:
<221> NAME/KEY: MISC_FEATURE
<222> LOCATION: (121)..(121)
<223> OTHER INFORMATION: Xaa is A, C, G, P, M, V, I, L, Sce or Sme
<220> FEATURE:
<221> NAME/KEY: MISC_FEATURE
<222> LOCATION: (122)..(122)
<223> OTHER INFORMATION: Xaa is any amino acid
<220> FEATURE:
<221> NAME/KEY: MISC_FEATURE
<222> LOCATION: (123)..(124)
<223> OTHER INFORMATION: Xaa is A, C, G, P, M, V, I, L, Sce or Sme
<220> FEATURE:
<221> NAME/KEY: MISC_FEATURE
<222> LOCATION: (125)..(125)
<223> OTHER INFORMATION: Xaa is R, H, or K
<220> FEATURE:
<221> NAME/KEY: MISC_FEATURE
<222> LOCATION: (126)..(126)
<223> OTHER INFORMATION: Xaa is A, C, G, P, M, V, I, L, Sce or Sme
<220> FEATURE:
<221> NAME/KEY: MISC_FEATURE
<222> LOCATION: (127)..(130)
<223> OTHER INFORMATION: Xaa is any amino acid
<220> FEATURE:
<221> NAME/KEY: MISC_FEATURE
<222> LOCATION: (131)..(131)
<223> OTHER INFORMATION: Xaa is A, C, G, P, M, V, I, L, Sce or Sme
<220> FEATURE:
<221> NAME/KEY: MISC_FEATURE
<222> LOCATION: (132)..(133)
<223> OTHER INFORMATION: Xaa is any amino acid
<220> FEATURE:
<221> NAME/KEY: MISC_FEATURE
<222> LOCATION: (134)..(134)
<223> OTHER INFORMATION: Xaa is A, C, G, P, M, V, I, L, Sce or Sme
<220> FEATURE:
<221> NAME/KEY: MISC_FEATURE
<222> LOCATION: (135)..(135)
<223> OTHER INFORMATION: Xaa is R, H, or K
<220> FEATURE:
```

```
<221> NAME/KEY: MISC_FEATURE
<222> LOCATION: (136)..(136)
<223> OTHER INFORMATION: Xaa is A, C, G, P, M, V, I, L, Sce or Sme
<220> FEATURE:
<221> NAME/KEY: MISC_FEATURE
<222> LOCATION: (137)..(137)
<223> OTHER INFORMATION: Xaa is F, W, or Y
<220> FEATURE:
<221> NAME/KEY: MISC_FEATURE
<222> LOCATION: (138)..(142)
<223> OTHER INFORMATION: Xaa is A, C, G, P, M, V, I, L, Sce or Sme
<220> FEATURE:
<221> NAME/KEY: MISC_FEATURE
<222> LOCATION: (158)..(158)
<223> OTHER INFORMATION: Xaa is A, C, G, P, M, V, I, L, Sce or Sme
<220> FEATURE:
<221> NAME/KEY: MISC_FEATURE
<222> LOCATION: (161)..(162)
<223> OTHER INFORMATION: Xaa is any amino acid
<220> FEATURE:
<221> NAME/KEY: MISC_FEATURE
<222> LOCATION: (163)..(163)
<223> OTHER INFORMATION: Xaa is A, C, G, P, M, V, I, L, Sce or Sme
<220> FEATURE:
<221> NAME/KEY: MISC_FEATURE
<222> LOCATION: (164)..(165)
<223> OTHER INFORMATION: Xaa is any amino acid
<220> FEATURE:
<221> NAME/KEY: MISC_FEATURE
<222> LOCATION: (166)..(166)
<223> OTHER INFORMATION: Xaa is F, W, or Y
<220> FEATURE:
<221> NAME/KEY: MISC_FEATURE
<222> LOCATION: (173)..(173)
<223> OTHER INFORMATION: Xaa is A, C, G, P, M, V, I, L, Sce or Sme
<220> FEATURE:
<221> NAME/KEY: MISC_FEATURE
<222> LOCATION: (174)..(174)
<223> OTHER INFORMATION: Xaa is R, H, or K
<220> FEATURE:
<221> NAME/KEY: MISC_FEATURE
<222> LOCATION: (175)..(176)
<223> OTHER INFORMATION: Xaa is any amino acid
<220> FEATURE:
<221> NAME/KEY: MISC_FEATURE
<222> LOCATION: (177)..(177)
<223> OTHER INFORMATION: Xaa is A, C, G, P, M, V, I, L, Sce or Sme
<220> FEATURE:
<221> NAME/KEY: MISC_FEATURE
<222> LOCATION: (178)..(178)
<223> OTHER INFORMATION: Xaa is F, W, or Y
<220> FEATURE:
<221> NAME/KEY: MISC_FEATURE
<222> LOCATION: (179)..(184)
<223> OTHER INFORMATION: Xaa is any amino acid

<400> SEQUENCE: 12

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Ala
                85                  90                  95

Xaa Xaa Xaa Xaa Xaa Xaa Xaa Xaa Xaa Xaa Xaa Xaa Xaa Xaa Xaa Xaa
            100                 105                 110
```

```
Xaa Leu Ala Xaa Lys Gly Ser Asn Xaa Xaa Xaa Xaa Xaa Xaa
        115                 120                 125

Xaa Xaa Xaa Xaa Xaa Xaa Xaa Xaa Xaa Xaa Xaa Xaa Xaa Asp Val
        130                 135                 140

Leu Asp Val Ala Ala Ala Val Ala Thr Ala Ser Leu Ala Xaa Gly Ala
145                 150                 155                 160

Xaa Xaa Xaa Xaa Xaa Xaa Ala Ser Ile Ile Pro Arg Xaa Xaa Xaa Xaa
                165                 170                 175

Xaa Xaa Xaa Xaa Xaa Xaa Xaa Xaa
            180

<210> SEQ ID NO 13
<211> LENGTH: 103
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or optionally absent
<220> FEATURE:
<221> NAME/KEY: MISC_FEATURE
<222> LOCATION: (2)..(3)
<223> OTHER INFORMATION: Xaa is D or E
<220> FEATURE:
<221> NAME/KEY: MISC_FEATURE
<222> LOCATION: (4)..(7)
<223> OTHER INFORMATION: Xaa is A, C, G, P, M, V, I, L, Sce or Sme
<220> FEATURE:
<221> NAME/KEY: MISC_FEATURE
<222> LOCATION: (8)..(8)
<223> OTHER INFORMATION: Xaa is S, T, N, or Q
<220> FEATURE:
<221> NAME/KEY: MISC_FEATURE
<222> LOCATION: (9)..(10)
<223> OTHER INFORMATION: Xaa is A, C, G, P, M, V, I, L, Sce or Sme
<220> FEATURE:
<221> NAME/KEY: MISC_FEATURE
<222> LOCATION: (11)..(11)
<223> OTHER INFORMATION: Xaa is S, T, N, or Q
<220> FEATURE:
<221> NAME/KEY: MISC_FEATURE
<222> LOCATION: (18)..(19)
<223> OTHER INFORMATION: Xaa is A, C, G, P, M, V, I, L, Sce or Sme
<220> FEATURE:
<221> NAME/KEY: MISC_FEATURE
<222> LOCATION: (21)..(23)
<223> OTHER INFORMATION: Xaa is A, C, G, P, M, V, I, L, Sce or Sme
<220> FEATURE:
<221> NAME/KEY: MISC_FEATURE
<222> LOCATION: (24)..(26)
<223> OTHER INFORMATION: Xaa is any amino acid
<220> FEATURE:
<221> NAME/KEY: MISC_FEATURE
<222> LOCATION: (27)..(31)
<223> OTHER INFORMATION: Xaa is A, C, G, P, M, V, I, L, Sce or Sme
<220> FEATURE:
<221> NAME/KEY: MISC_FEATURE
<222> LOCATION: (32)..(32)
<223> OTHER INFORMATION: Xaa is S, T, N, or Q
<220> FEATURE:
<221> NAME/KEY: MISC_FEATURE
<222> LOCATION: (34)..(34)
<223> OTHER INFORMATION: Xaa is A, C, G, P, M, V, I, L, Sce or Sme
<220> FEATURE:
<221> NAME/KEY: MISC_FEATURE
<222> LOCATION: (39)..(39)
<223> OTHER INFORMATION: Xaa is S, T, N, or Q
<220> FEATURE:
<221> NAME/KEY: MISC_FEATURE
<222> LOCATION: (41)..(41)
<223> OTHER INFORMATION: Xaa is any amino acid
<220> FEATURE:
```

```
<221> NAME/KEY: MISC_FEATURE
<222> LOCATION: (42)..(42)
<223> OTHER INFORMATION: Xaa is R, H or K
<220> FEATURE:
<221> NAME/KEY: MISC_FEATURE
<222> LOCATION: (44)..(45)
<223> OTHER INFORMATION: Xaa is any amino acid
<220> FEATURE:
<221> NAME/KEY: MISC_FEATURE
<222> LOCATION: (50)..(50)
<223> OTHER INFORMATION: Xaa is D or E
<220> FEATURE:
<221> NAME/KEY: MISC_FEATURE
<222> LOCATION: (52)..(52)
<223> OTHER INFORMATION: Xaa is D or E
<220> FEATURE:
<221> NAME/KEY: MISC_FEATURE
<222> LOCATION: (54)..(57)
<223> OTHER INFORMATION: Xaa is A, C, G, P, M, V, I, L, Sce or Sme
<220> FEATURE:
<221> NAME/KEY: MISC_FEATURE
<222> LOCATION: (58)..(58)
<223> OTHER INFORMATION: Xaa is R, H or K
<220> FEATURE:
<221> NAME/KEY: MISC_FEATURE
<222> LOCATION: (59)..(60)
<223> OTHER INFORMATION: Xaa is S, T, N, or Q
<220> FEATURE:
<221> NAME/KEY: MISC_FEATURE
<222> LOCATION: (61)..(62)
<223> OTHER INFORMATION: Xaa is any amino acid
<220> FEATURE:
<221> NAME/KEY: MISC_FEATURE
<222> LOCATION: (63)..(63)
<223> OTHER INFORMATION: Xaa is A, C, G, P, M, V, I, L, Sce or Sme
<220> FEATURE:
<221> NAME/KEY: MISC_FEATURE
<222> LOCATION: (64)..(64)
<223> OTHER INFORMATION: Xaa is F, W, or Y
<220> FEATURE:
<221> NAME/KEY: MISC_FEATURE
<222> LOCATION: (65)..(66)
<223> OTHER INFORMATION: Xaa is any amino acid
<220> FEATURE:
<221> NAME/KEY: MISC_FEATURE
<222> LOCATION: (67)..(67)
<223> OTHER INFORMATION: Xaa is A, C, G, P, M, V, I, L, Sce or Sme
<220> FEATURE:
<221> NAME/KEY: MISC_FEATURE
<222> LOCATION: (68)..(68)
<223> OTHER INFORMATION: Xaa is R, H or K
<220> FEATURE:
<221> NAME/KEY: MISC_FEATURE
<222> LOCATION: (69)..(70)
<223> OTHER INFORMATION: Xaa is any amino acid
<220> FEATURE:
<221> NAME/KEY: MISC_FEATURE
<222> LOCATION: (71)..(71)
<223> OTHER INFORMATION: Xaa is A, C, G, P, M, V, I, L, Sce or Sme
<220> FEATURE:
<221> NAME/KEY: MISC_FEATURE
<222> LOCATION: (72)..(73)
<223> OTHER INFORMATION: Xaa is any amino acid
<220> FEATURE:
<221> NAME/KEY: MISC_FEATURE
<222> LOCATION: (74)..(74)
<223> OTHER INFORMATION: Xaa is A, C, G, P, M, V, I, L, Sce or Sme
<220> FEATURE:
<221> NAME/KEY: MISC_FEATURE
<222> LOCATION: (75)..(75)
<223> OTHER INFORMATION: Xaa is R, H or K
<220> FEATURE:
<221> NAME/KEY: MISC_FEATURE
<222> LOCATION: (76)..(79)
<223> OTHER INFORMATION: Xaa is any amino acid
<220> FEATURE:
<221> NAME/KEY: MISC_FEATURE
<222> LOCATION: (80)..(80)
<223> OTHER INFORMATION: Xaa is A, C, G, P, M, V, I, L, Sce or Sme
```

```
<220> FEATURE:
<221> NAME/KEY: MISC_FEATURE
<222> LOCATION: (81)..(81)
<223> OTHER INFORMATION: Xaa is D or E
<220> FEATURE:
<221> NAME/KEY: MISC_FEATURE
<222> LOCATION: (82)..(87)
<223> OTHER INFORMATION: Xaa is A, C, G, P, M, V, I, L, Sce or Sme
<220> FEATURE:
<221> NAME/KEY: MISC_FEATURE
<222> LOCATION: (88)..(89)
<223> OTHER INFORMATION: Xaa is any amino acid
<220> FEATURE:
<221> NAME/KEY: MISC_FEATURE
<222> LOCATION: (90)..(90)
<223> OTHER INFORMATION: Xaa is A, C, G, P, M, V, I, L, Sce or Sme
<220> FEATURE:
<221> NAME/KEY: MISC_FEATURE
<222> LOCATION: (91)..(91)
<223> OTHER INFORMATION: Xaa is S, T, N, or Q
<220> FEATURE:
<221> NAME/KEY: MISC_FEATURE
<222> LOCATION: (92)..(93)
<223> OTHER INFORMATION: Xaa is any amino acid
<220> FEATURE:
<221> NAME/KEY: MISC_FEATURE
<222> LOCATION: (94)..(94)
<223> OTHER INFORMATION: Xaa is F, W, or Y
<220> FEATURE:
<221> NAME/KEY: MISC_FEATURE
<222> LOCATION: (95)..(95)
<223> OTHER INFORMATION: Xaa is A, C, G, P, M, V, I, L, Sce or Sme
<220> FEATURE:
<221> NAME/KEY: MISC_FEATURE
<222> LOCATION: (96)..(96)
<223> OTHER INFORMATION: Xaa is any amino acid
<220> FEATURE:
<221> NAME/KEY: MISC_FEATURE
<222> LOCATION: (97)..(97)
<223> OTHER INFORMATION: Xaa is F, W, or Y
<220> FEATURE:
<221> NAME/KEY: MISC_FEATURE
<222> LOCATION: (98)..(98)
<223> OTHER INFORMATION: Xaa is A, C, G, P, M, V, I, L, Sce or Sme
<220> FEATURE:
<221> NAME/KEY: MISC_FEATURE
<222> LOCATION: (99)..(100)
<223> OTHER INFORMATION: Xaa is any amino acid
<220> FEATURE:
<221> NAME/KEY: MISC_FEATURE
<222> LOCATION: (101)..(102)
<223> OTHER INFORMATION: Xaa is S, T, N, or Q
<220> FEATURE:
<221> NAME/KEY: MISC_FEATURE
<222> LOCATION: (103)..(103)
<223> OTHER INFORMATION: Xaa is A, C, G, P, M, V, I, L, Sce or Sme

<400> SEQUENCE: 13

Xaa Xaa Xaa Xaa Xaa Xaa Xaa Xaa Xaa Xaa Xaa Ala Leu Val Ala Val
1               5                   10                  15

Lys Xaa Xaa His Xaa Xaa Xaa Xaa Xaa Xaa Xaa Xaa Xaa Xaa Xaa Xaa
            20                  25                  30

Ile Xaa Pro Gly Leu Thr Xaa Ile Xaa Xaa Trp Xaa Xaa Ser Val Val
        35                  40                  45

Ser Xaa His Xaa Leu Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa
                100
```

```
<210> SEQ ID NO 14
<211> LENGTH: 122
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (2)..(2)
<223> OTHER INFORMATION: Xaa is A, C, G, P, M, V, I, L, Sce, or Sme
<220> FEATURE:
<221> NAME/KEY: MISC_FEATURE
<222> LOCATION: (3)..(3)
<223> OTHER INFORMATION: Xaa is R, H, or K
<220> FEATURE:
<221> NAME/KEY: MISC_FEATURE
<222> LOCATION: (4)..(5)
<223> OTHER INFORMATION: Xaa is A, C, G, P, M, V, I, L, Sce, or Sme
<220> FEATURE:
<221> NAME/KEY: MISC_FEATURE
<222> LOCATION: (6)..(6)
<223> OTHER INFORMATION: Xaa is R, H, or K
<220> FEATURE:
<221> NAME/KEY: MISC_FEATURE
<222> LOCATION: (7)..(8)
<223> OTHER INFORMATION: Xaa is A, C, G, P, M, V, I, L, Sce, or Sme
<220> FEATURE:
<221> NAME/KEY: MISC_FEATURE
<222> LOCATION: (10)..(10)
<223> OTHER INFORMATION: Xaa is S, T, N, or Q
<220> FEATURE:
<221> NAME/KEY: MISC_FEATURE
<222> LOCATION: (11)..(11)
<223> OTHER INFORMATION: Xaa is A, C, G, P, M, V, I, L, Sce, or Sme
<220> FEATURE:
<221> NAME/KEY: MISC_FEATURE
<222> LOCATION: (14)..(14)
<223> OTHER INFORMATION: Xaa is any amino acid
<220> FEATURE:
<221> NAME/KEY: MISC_FEATURE
<222> LOCATION: (19)..(19)
<223> OTHER INFORMATION: Xaa is A, C, G, P, M, V, I, L, Sce, or Sme
<220> FEATURE:
<221> NAME/KEY: MISC_FEATURE
<222> LOCATION: (23)..(23)
<223> OTHER INFORMATION: Xaa is S, T, N, or Q
<220> FEATURE:
<221> NAME/KEY: MISC_FEATURE
<222> LOCATION: (26)..(27)
<223> OTHER INFORMATION: Xaa is A, C, G, P, M, V, I, L, Sce, or Sme
<220> FEATURE:
<221> NAME/KEY: MISC_FEATURE
<222> LOCATION: (30)..(31)
<223> OTHER INFORMATION: Xaa is A, C, G, P, M, V, I, L, Sce, or Sme
<220> FEATURE:
<221> NAME/KEY: MISC_FEATURE
<222> LOCATION: (33)..(33)
<223> OTHER INFORMATION: Xaa is A, C, G, P, M, V, I, L, Sce, or Sme
<220> FEATURE:
<221> NAME/KEY: MISC_FEATURE
<222> LOCATION: (34)..(34)
<223> OTHER INFORMATION: Xaa is S, T, N, or Q
<220> FEATURE:
<221> NAME/KEY: MISC_FEATURE
<222> LOCATION: (35)..(35)
<223> OTHER INFORMATION: Xaa is any amino acid
<220> FEATURE:
<221> NAME/KEY: MISC_FEATURE
<222> LOCATION: (36)..(36)
<223> OTHER INFORMATION: Xaa is A, C, G, P, M, V, I, L, Sce, or Sme
<220> FEATURE:
<221> NAME/KEY: MISC_FEATURE
<222> LOCATION: (37)..(37)
```

```
<223> OTHER INFORMATION: Xaa is any amino acid
<220> FEATURE:
<221> NAME/KEY: MISC_FEATURE
<222> LOCATION: (38)..(38)
<223> OTHER INFORMATION: Xaa is S, T, N, or Q
<220> FEATURE:
<221> NAME/KEY: MISC_FEATURE
<222> LOCATION: (39)..(40)
<223> OTHER INFORMATION: Xaa is any amino acid
<220> FEATURE:
<221> NAME/KEY: MISC_FEATURE
<222> LOCATION: (41)..(41)
<223> OTHER INFORMATION: Xaa is D or E
<220> FEATURE:
<221> NAME/KEY: MISC_FEATURE
<222> LOCATION: (42)..(46)
<223> OTHER INFORMATION: Xaa is A, C, G, P, M, V, I, L, Sce, or Sme
<220> FEATURE:
<221> NAME/KEY: MISC_FEATURE
<222> LOCATION: (47)..(122)
<223> OTHER INFORMATION: Xaa is F, W, or Y
<220> FEATURE:
<221> NAME/KEY: MISC_FEATURE
<222> LOCATION: (48)..(48)
<223> OTHER INFORMATION: Xaa is S, T, N, or Q
<220> FEATURE:
<221> NAME/KEY: MISC_FEATURE
<222> LOCATION: (49)..(49)
<223> OTHER INFORMATION: Xaa is A, C, G, P, M, V, I, L, Sce, or Sme
<220> FEATURE:
<221> NAME/KEY: MISC_FEATURE
<222> LOCATION: (50)..(50)
<223> OTHER INFORMATION: Xaa is S, T, N, or Q
<220> FEATURE:
<221> NAME/KEY: MISC_FEATURE
<222> LOCATION: (51)..(52)
<223> OTHER INFORMATION: Xaa is any amino acid
<220> FEATURE:
<221> NAME/KEY: MISC_FEATURE
<222> LOCATION: (53)..(53)
<223> OTHER INFORMATION: Xaa is A, C, G, P, M, V, I, L, Sce, or Sme
<220> FEATURE:
<221> NAME/KEY: MISC_FEATURE
<222> LOCATION: (54)..(55)
<223> OTHER INFORMATION: Xaa is S, T, N, or Q
<220> FEATURE:
<221> NAME/KEY: MISC_FEATURE
<222> LOCATION: (56)..(56)
<223> OTHER INFORMATION: Xaa is A, C, G, P, M, V, I, L, Sce, or Sme
<220> FEATURE:
<221> NAME/KEY: MISC_FEATURE
<222> LOCATION: (57)..(57)
<223> OTHER INFORMATION: Xaa is F, W, or Y
<220> FEATURE:
<221> NAME/KEY: MISC_FEATURE
<222> LOCATION: (58)..(59)
<223> OTHER INFORMATION: Xaa is A, C, G, P, M, V, I, L, Sce, or Sme
<220> FEATURE:
<221> NAME/KEY: MISC_FEATURE
<222> LOCATION: (62)..(62)
<223> OTHER INFORMATION: Xaa is A, C, G, P, M, V, I, L, Sce, or Sme
<220> FEATURE:
<221> NAME/KEY: MISC_FEATURE
<222> LOCATION: (63)..(63)
<223> OTHER INFORMATION: Xaa is R, H, or K
<220> FEATURE:
<221> NAME/KEY: MISC_FEATURE
<222> LOCATION: (66)..(67)
<223> OTHER INFORMATION: Xaa is A, C, G, P, M, V, I, L, Sce, or Sme
<220> FEATURE:
<221> NAME/KEY: MISC_FEATURE
<222> LOCATION: (69)..(69)
<223> OTHER INFORMATION: Xaa is any amino acid
<220> FEATURE:
<221> NAME/KEY: MISC_FEATURE
<222> LOCATION: (70)..(73)
<223> OTHER INFORMATION: Xaa is A, C, G, P, M, V, I, L, Sce, or Sme
<220> FEATURE:
<221> NAME/KEY: MISC_FEATURE
```

```
<222> LOCATION: (74)..(74)
<223> OTHER INFORMATION: Xaa is S, T, N, or Q
<220> FEATURE:
<221> NAME/KEY: MISC_FEATURE
<222> LOCATION: (75)..(75)
<223> OTHER INFORMATION: Xaa is A, C, G, P, M, V, I, L, Sce, or Sme
<220> FEATURE:
<221> NAME/KEY: MISC_FEATURE
<222> LOCATION: (76)..(76)
<223> OTHER INFORMATION: Xaa is R, H, or K
<220> FEATURE:
<221> NAME/KEY: MISC_FEATURE
<222> LOCATION: (77)..(77)
<223> OTHER INFORMATION: Xaa is D or E
<220> FEATURE:
<221> NAME/KEY: MISC_FEATURE
<222> LOCATION: (78)..(78)
<223> OTHER INFORMATION: Xaa is A, C, G, P, M, V, I, L, Sce, or Sme
<220> FEATURE:
<221> NAME/KEY: MISC_FEATURE
<222> LOCATION: (79)..(79)
<223> OTHER INFORMATION: Xaa is any amino acid
<220> FEATURE:
<221> NAME/KEY: MISC_FEATURE
<222> LOCATION: (80)..(80)
<223> OTHER INFORMATION: Xaa is A, C, G, P, M, V, I, L, Sce, or Sme
<220> FEATURE:
<221> NAME/KEY: MISC_FEATURE
<222> LOCATION: (81)..(82)
<223> OTHER INFORMATION: Xaa is any amino acid
<220> FEATURE:
<221> NAME/KEY: MISC_FEATURE
<222> LOCATION: (83)..(83)
<223> OTHER INFORMATION: Xaa is S, T, N, or Q
<220> FEATURE:
<221> NAME/KEY: MISC_FEATURE
<222> LOCATION: (84)..(84)
<223> OTHER INFORMATION: Xaa is A, C, G, P, M, V, I, L, Sce, or Sme
<220> FEATURE:
<221> NAME/KEY: MISC_FEATURE
<222> LOCATION: (85)..(86)
<223> OTHER INFORMATION: Xaa is any amino acid
<220> FEATURE:
<221> NAME/KEY: MISC_FEATURE
<222> LOCATION: (87)..(88)
<223> OTHER INFORMATION: Xaa is A, C, G, P, M, V, I, L, Sce, or Sme
<220> FEATURE:
<221> NAME/KEY: MISC_FEATURE
<222> LOCATION: (89)..(89)
<223> OTHER INFORMATION: Xaa is R, H, or K
<220> FEATURE:
<221> NAME/KEY: MISC_FEATURE
<222> LOCATION: (90)..(93)
<223> OTHER INFORMATION: Xaa is A, C, G, P, M, V, I, L, Sce, or Sme
<220> FEATURE:
<221> NAME/KEY: MISC_FEATURE
<222> LOCATION: (94)..(94)
<223> OTHER INFORMATION: Xaa is F, W, or Y
<220> FEATURE:
<221> NAME/KEY: MISC_FEATURE
<222> LOCATION: (95)..(96)
<223> OTHER INFORMATION: Xaa is S, T, N, or Q
<220> FEATURE:
<221> NAME/KEY: MISC_FEATURE
<222> LOCATION: (97)..(97)
<223> OTHER INFORMATION: Xaa is any amino acid
<220> FEATURE:
<221> NAME/KEY: MISC_FEATURE
<222> LOCATION: (98)..(98)
<223> OTHER INFORMATION: Xaa is S, T, N, or Q
<220> FEATURE:
<221> NAME/KEY: MISC_FEATURE
<222> LOCATION: (99)..(99)
<223> OTHER INFORMATION: Xaa is any amino acid
<220> FEATURE:
<221> NAME/KEY: MISC_FEATURE
<222> LOCATION: (100)..(100)
<223> OTHER INFORMATION: Xaa is S, T, N, or Q
<220> FEATURE:
```

```
<221> NAME/KEY: MISC_FEATURE
<222> LOCATION: (101)..(102)
<223> OTHER INFORMATION: Xaa is any amino acid
<220> FEATURE:
<221> NAME/KEY: MISC_FEATURE
<222> LOCATION: (103)..(103)
<223> OTHER INFORMATION: Xaa is A, C, G, P, M, V, I, L, Sce, or Sme
<220> FEATURE:
<221> NAME/KEY: MISC_FEATURE
<222> LOCATION: (104)..(104)
<223> OTHER INFORMATION: Xaa is any amino acid
<220> FEATURE:
<221> NAME/KEY: MISC_FEATURE
<222> LOCATION: (105)..(105)
<223> OTHER INFORMATION: Xaa is R, H, or K
<220> FEATURE:
<221> NAME/KEY: MISC_FEATURE
<222> LOCATION: (106)..(106)
<223> OTHER INFORMATION: Xaa is A, C, G, P, M, V, I, L, Sce, or Sme
<220> FEATURE:
<221> NAME/KEY: MISC_FEATURE
<222> LOCATION: (107)..(107)
<223> OTHER INFORMATION: Xaa is F, W, or Y
<220> FEATURE:
<221> NAME/KEY: MISC_FEATURE
<222> LOCATION: (108)..(108)
<223> OTHER INFORMATION: Xaa is A, C, G, P, M, V, I, L, Sce, or Sme
<220> FEATURE:
<221> NAME/KEY: MISC_FEATURE
<222> LOCATION: (110)..(110)
<223> OTHER INFORMATION: Xaa is any amino acid
<220> FEATURE:
<221> NAME/KEY: MISC_FEATURE
<222> LOCATION: (111)..(111)
<223> OTHER INFORMATION: Xaa is A, C, G, P, M, V, I, L, Sce, or Sme
<220> FEATURE:
<221> NAME/KEY: MISC_FEATURE
<222> LOCATION: (112)..(113)
<223> OTHER INFORMATION: Xaa is any amino acid
<220> FEATURE:
<221> NAME/KEY: MISC_FEATURE
<222> LOCATION: (114)..(114)
<223> OTHER INFORMATION: Xaa is A, C, G, P, M, V, I, L, Sce, or Sme
<220> FEATURE:
<221> NAME/KEY: MISC_FEATURE
<222> LOCATION: (115)..(115)
<223> OTHER INFORMATION: Xaa is R, H, or K
<220> FEATURE:
<221> NAME/KEY: MISC_FEATURE
<222> LOCATION: (116)..(122)
<223> OTHER INFORMATION: Xaa is any amino acid

<400> SEQUENCE: 14

Xaa Xaa Xaa Xaa Xaa Xaa Xaa Xaa Ile Xaa Xaa Glu Glu Xaa Thr Pro
1               5                   10                  15

Ala Ala Xaa Leu Ala Ala Xaa Ile Glu Xaa Xaa Leu Lys Xaa Xaa Glu
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Glu Ala Xaa Xaa Leu
    50                  55                  60

Ile Xaa Xaa His Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Asn Xaa Xaa Xaa
            100                 105                 110

Xaa Xaa Xaa Xaa Xaa Xaa Xaa Xaa Xaa Xaa
        115                 120
```

```
<210> SEQ ID NO 15
<211> LENGTH: 177
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is A, C, G, P, M, V, I, L, Sce or Sme
<220> FEATURE:
<221> NAME/KEY: MISC_FEATURE
<222> LOCATION: (5)..(5)
<223> OTHER INFORMATION: Xaa is R, H, or K
<220> FEATURE:
<221> NAME/KEY: MISC_FEATURE
<222> LOCATION: (6)..(9)
<223> OTHER INFORMATION: Xaa is A, C, G, P, M, V, I, L, Sce or Sme
<220> FEATURE:
<221> NAME/KEY: MISC_FEATURE
<222> LOCATION: (10)..(10)
<223> OTHER INFORMATION: Xaa is S, T, N or Q
<220> FEATURE:
<221> NAME/KEY: MISC_FEATURE
<222> LOCATION: (11)..(11)
<223> OTHER INFORMATION: Xaa is A, C, G, P, M, V, I, L, Sce or Sme
<220> FEATURE:
<221> NAME/KEY: MISC_FEATURE
<222> LOCATION: (12)..(12)
<223> OTHER INFORMATION: Xaa is S, T, N or Q
<220> FEATURE:
<221> NAME/KEY: MISC_FEATURE
<222> LOCATION: (13)..(13)
<223> OTHER INFORMATION: Xaa is D or E
<220> FEATURE:
<221> NAME/KEY: MISC_FEATURE
<222> LOCATION: (14)..(14)
<223> OTHER INFORMATION: Xaa is R, H, or K
<220> FEATURE:
<221> NAME/KEY: MISC_FEATURE
<222> LOCATION: (15)..(15)
<223> OTHER INFORMATION: Xaa is A, C, G, P, M, V, I, L, Sce or Sme
<220> FEATURE:
<221> NAME/KEY: MISC_FEATURE
<222> LOCATION: (16)..(21)
<223> OTHER INFORMATION: Xaa is any amino acid
<220> FEATURE:
<221> NAME/KEY: MISC_FEATURE
<222> LOCATION: (22)..(22)
<223> OTHER INFORMATION: Xaa is D or E
<220> FEATURE:
<221> NAME/KEY: MISC_FEATURE
<222> LOCATION: (24)..(24)
<223> OTHER INFORMATION: Xaa is S, T, N or Q
<220> FEATURE:
<221> NAME/KEY: MISC_FEATURE
<222> LOCATION: (25)..(25)
<223> OTHER INFORMATION: Xaa is A, C, G, P, M, V, I, L, Sce or Sme
<220> FEATURE:
<221> NAME/KEY: MISC_FEATURE
<222> LOCATION: (28)..(29)
<223> OTHER INFORMATION: Xaa is A, C, G, P, M, V, I, L, Sce or Sme
<220> FEATURE:
<221> NAME/KEY: MISC_FEATURE
<222> LOCATION: (32)..(32)
<223> OTHER INFORMATION: Xaa is A, C, G, P, M, V, I, L, Sce or Sme
<220> FEATURE:
<221> NAME/KEY: MISC_FEATURE
<222> LOCATION: (36)..(36)
<223> OTHER INFORMATION: Xaa is A, C, G, P, M, V, I, L, Sce or Sme
<220> FEATURE:
```

```
<221> NAME/KEY: MISC_FEATURE
<222> LOCATION: (37)..(37)
<223> OTHER INFORMATION: Xaa is any amino acid
<220> FEATURE:
<221> NAME/KEY: MISC_FEATURE
<222> LOCATION: (38)..(38)
<223> OTHER INFORMATION: Xaa is S, T, N or Q
<220> FEATURE:
<221> NAME/KEY: MISC_FEATURE
<222> LOCATION: (39)..(39)
<223> OTHER INFORMATION: Xaa is any amino acid
<220> FEATURE:
<221> NAME/KEY: MISC_FEATURE
<222> LOCATION: (40)..(40)
<223> OTHER INFORMATION: Xaa is F, W, or Y
<220> FEATURE:
<221> NAME/KEY: MISC_FEATURE
<222> LOCATION: (41)..(41)
<223> OTHER INFORMATION: Xaa is D or E
<220> FEATURE:
<221> NAME/KEY: MISC_FEATURE
<222> LOCATION: (42)..(42)
<223> OTHER INFORMATION: Xaa is any amino acid
<220> FEATURE:
<221> NAME/KEY: MISC_FEATURE
<222> LOCATION: (43)..(43)
<223> OTHER INFORMATION: Xaa is A, C, G, P, M, V, I, L, Sce or Sme
<220> FEATURE:
<221> NAME/KEY: MISC_FEATURE
<222> LOCATION: (44)..(45)
<223> OTHER INFORMATION: Xaa is any amino acid
<220> FEATURE:
<221> NAME/KEY: MISC_FEATURE
<222> LOCATION: (46)..(48)
<223> OTHER INFORMATION: Xaa is A, C, G, P, M, V, I, L, Sce or Sme
<220> FEATURE:
<221> NAME/KEY: MISC_FEATURE
<222> LOCATION: (49)..(50)
<223> OTHER INFORMATION: Xaa is D or E
<220> FEATURE:
<221> NAME/KEY: MISC_FEATURE
<222> LOCATION: (51)..(53)
<223> OTHER INFORMATION: Xaa is any amino acid
<220> FEATURE:
<221> NAME/KEY: MISC_FEATURE
<222> LOCATION: (54)..(54)
<223> OTHER INFORMATION: Xaa is A, C, G, P, M, V, I, L, Sce or Sme
<220> FEATURE:
<221> NAME/KEY: MISC_FEATURE
<222> LOCATION: (55)..(55)
<223> OTHER INFORMATION: Xaa is D or E
<220> FEATURE:
<221> NAME/KEY: MISC_FEATURE
<222> LOCATION: (56)..(56)
<223> OTHER INFORMATION: Xaa is any amino acid
<220> FEATURE:
<221> NAME/KEY: MISC_FEATURE
<222> LOCATION: (57)..(57)
<223> OTHER INFORMATION: Xaa is S, T, N or Q
<220> FEATURE:
<221> NAME/KEY: MISC_FEATURE
<222> LOCATION: (58)..(58)
<223> OTHER INFORMATION: Xaa is A, C, G, P, M, V, I, L, Sce or Sme
<220> FEATURE:
<221> NAME/KEY: MISC_FEATURE
<222> LOCATION: (59)..(59)
<223> OTHER INFORMATION: Xaa is any amino acid
<220> FEATURE:
<221> NAME/KEY: MISC_FEATURE
<222> LOCATION: (60)..(60)
<223> OTHER INFORMATION: Xaa is R, H, or K
<220> FEATURE:
<221> NAME/KEY: MISC_FEATURE
<222> LOCATION: (61)..(62)
<223> OTHER INFORMATION: Xaa is A, C, G, P, M, V, I, L, Sce or Sme
<220> FEATURE:
<221> NAME/KEY: MISC_FEATURE
<222> LOCATION: (63)..(66)
<223> OTHER INFORMATION: Xaa is any amino acid
```

```
<220> FEATURE:
<221> NAME/KEY: MISC_FEATURE
<222> LOCATION: (67)..(71)
<223> OTHER INFORMATION: Xaa is A, C, G, P, M, V, I, L, Sce or Sme
<220> FEATURE:
<221> NAME/KEY: MISC_FEATURE
<222> LOCATION: (72)..(73)
<223> OTHER INFORMATION: Xaa is S, T, N or Q
<220> FEATURE:
<221> NAME/KEY: MISC_FEATURE
<222> LOCATION: (74)..(75)
<223> OTHER INFORMATION: Xaa is A, C, G, P, M, V, I, L, Sce or Sme
<220> FEATURE:
<221> NAME/KEY: MISC_FEATURE
<222> LOCATION: (76)..(76)
<223> OTHER INFORMATION: Xaa is S, T, N or Q
<220> FEATURE:
<221> NAME/KEY: MISC_FEATURE
<222> LOCATION: (77)..(79)
<223> OTHER INFORMATION: Xaa is A, C, G, P, M, V, I, L, Sce or Sme
<220> FEATURE:
<221> NAME/KEY: MISC_FEATURE
<222> LOCATION: (80)..(81)
<223> OTHER INFORMATION: Xaa is any amino acid
<220> FEATURE:
<221> NAME/KEY: MISC_FEATURE
<222> LOCATION: (82)..(82)
<223> OTHER INFORMATION: Xaa is D or E
<220> FEATURE:
<221> NAME/KEY: MISC_FEATURE
<222> LOCATION: (83)..(83)
<223> OTHER INFORMATION: Xaa is A, C, G, P, M, V, I, L, Sce or Sme
<220> FEATURE:
<221> NAME/KEY: MISC_FEATURE
<222> LOCATION: (84)..(84)
<223> OTHER INFORMATION: Xaa is S, T, N or Q
<220> FEATURE:
<221> NAME/KEY: MISC_FEATURE
<222> LOCATION: (85)..(85)
<223> OTHER INFORMATION: Xaa is A, C, G, P, M, V, I, L, Sce or Sme
<220> FEATURE:
<221> NAME/KEY: MISC_FEATURE
<222> LOCATION: (86)..(86)
<223> OTHER INFORMATION: Xaa is D or E
<220> FEATURE:
<221> NAME/KEY: MISC_FEATURE
<222> LOCATION: (87)..(87)
<223> OTHER INFORMATION: Xaa is A, C, G, P, M, V, I, L, Sce or Sme
<220> FEATURE:
<221> NAME/KEY: MISC_FEATURE
<222> LOCATION: (88)..(88)
<223> OTHER INFORMATION: Xaa is S, T, N or Q
<220> FEATURE:
<221> NAME/KEY: MISC_FEATURE
<222> LOCATION: (89)..(90)
<223> OTHER INFORMATION: Xaa is any amino acid
<220> FEATURE:
<221> NAME/KEY: MISC_FEATURE
<222> LOCATION: (91)..(92)
<223> OTHER INFORMATION: Xaa is A, C, G, P, M, V, I, L, Sce or Sme
<220> FEATURE:
<221> NAME/KEY: MISC_FEATURE
<222> LOCATION: (93)..(93)
<223> OTHER INFORMATION: Xaa is any amino acid
<220> FEATURE:
<221> NAME/KEY: MISC_FEATURE
<222> LOCATION: (94)..(94)
<223> OTHER INFORMATION: Xaa is R, H, or K
<220> FEATURE:
<221> NAME/KEY: MISC_FEATURE
<222> LOCATION: (95)..(95)
<223> OTHER INFORMATION: Xaa is any amino acid
<220> FEATURE:
<221> NAME/KEY: MISC_FEATURE
<222> LOCATION: (96)..(98)
<223> OTHER INFORMATION: Xaa is A, C, G, P, M, V, I, L, Sce or Sme
<220> FEATURE:
<221> NAME/KEY: MISC_FEATURE
<222> LOCATION: (99)..(99)
```

```
<223> OTHER INFORMATION: Xaa is F, W, or Y
<220> FEATURE:
<221> NAME/KEY: MISC_FEATURE
<222> LOCATION: (100)..(100)
<223> OTHER INFORMATION: Xaa is A, C, G, P, M, V, I, L, Sce or Sme
<220> FEATURE:
<221> NAME/KEY: MISC_FEATURE
<222> LOCATION: (101)..(101)
<223> OTHER INFORMATION: Xaa is D or E
<220> FEATURE:
<221> NAME/KEY: MISC_FEATURE
<222> LOCATION: (102)..(103)
<223> OTHER INFORMATION: Xaa is A, C, G, P, M, V, I, L, Sce or Sme
<220> FEATURE:
<221> NAME/KEY: MISC_FEATURE
<222> LOCATION: (104)..(104)
<223> OTHER INFORMATION: Xaa is R, H, or K
<220> FEATURE:
<221> NAME/KEY: MISC_FEATURE
<222> LOCATION: (105)..(106)
<223> OTHER INFORMATION: Xaa is any amino acid
<220> FEATURE:
<221> NAME/KEY: MISC_FEATURE
<222> LOCATION: (107)..(107)
<223> OTHER INFORMATION: Xaa is S, T, N or Q
<220> FEATURE:
<221> NAME/KEY: MISC_FEATURE
<222> LOCATION: (108)..(110)
<223> OTHER INFORMATION: Xaa is any amino acid
<220> FEATURE:
<221> NAME/KEY: MISC_FEATURE
<222> LOCATION: (111)..(112)
<223> OTHER INFORMATION: Xaa is A, C, G, P, M, V, I, L, Sce or Sme
<220> FEATURE:
<221> NAME/KEY: MISC_FEATURE
<222> LOCATION: (113)..(113)
<223> OTHER INFORMATION: Xaa is S, T, N or Q
<220> FEATURE:
<221> NAME/KEY: MISC_FEATURE
<222> LOCATION: (114)..(116)
<223> OTHER INFORMATION: Xaa is A, C, G, P, M, V, I, L, Sce or Sme
<220> FEATURE:
<221> NAME/KEY: MISC_FEATURE
<222> LOCATION: (117)..(117)
<223> OTHER INFORMATION: Xaa is S, T, N or Q
<220> FEATURE:
<221> NAME/KEY: MISC_FEATURE
<222> LOCATION: (118)..(118)
<223> OTHER INFORMATION: Xaa is R, H, or K
<220> FEATURE:
<221> NAME/KEY: MISC_FEATURE
<222> LOCATION: (119)..(120)
<223> OTHER INFORMATION: Xaa is S, T, N or Q
<220> FEATURE:
<221> NAME/KEY: MISC_FEATURE
<222> LOCATION: (121)..(123)
<223> OTHER INFORMATION: Xaa is A, C, G, P, M, V, I, L, Sce or Sme
<220> FEATURE:
<221> NAME/KEY: MISC_FEATURE
<222> LOCATION: (124)..(124)
<223> OTHER INFORMATION: Xaa is any amino acid
<220> FEATURE:
<221> NAME/KEY: MISC_FEATURE
<222> LOCATION: (125)..(125)
<223> OTHER INFORMATION: Xaa is A, C, G, P, M, V, I, L, Sce or Sme
<220> FEATURE:
<221> NAME/KEY: MISC_FEATURE
<222> LOCATION: (126)..(126)
<223> OTHER INFORMATION: Xaa is any amino acid
<220> FEATURE:
<221> NAME/KEY: MISC_FEATURE
<222> LOCATION: (127)..(127)
<223> OTHER INFORMATION: Xaa is S, T, N or Q
<220> FEATURE:
<221> NAME/KEY: MISC_FEATURE
<222> LOCATION: (128)..(130)
<223> OTHER INFORMATION: Xaa is A, C, G, P, M, V, I, L, Sce or Sme
<220> FEATURE:
<221> NAME/KEY: MISC_FEATURE
```

```
<222> LOCATION: (131)..(131)
<223> OTHER INFORMATION: Xaa is S, T, N or Q
<220> FEATURE:
<221> NAME/KEY: MISC_FEATURE
<222> LOCATION: (132)..(134)
<223> OTHER INFORMATION: Xaa is A, C, G, P, M, V, I, L, Sce or Sme
<220> FEATURE:
<221> NAME/KEY: MISC_FEATURE
<222> LOCATION: (135)..(135)
<223> OTHER INFORMATION: Xaa is any amino acid
<220> FEATURE:
<221> NAME/KEY: MISC_FEATURE
<222> LOCATION: (136)..(136)
<223> OTHER INFORMATION: Xaa is A, C, G, P, M, V, I, L, Sce or Sme
<220> FEATURE:
<221> NAME/KEY: MISC_FEATURE
<222> LOCATION: (139)..(139)
<223> OTHER INFORMATION: Xaa is A, C, G, P, M, V, I, L, Sce or Sme
<220> FEATURE:
<221> NAME/KEY: MISC_FEATURE
<222> LOCATION: (142)..(143)
<223> OTHER INFORMATION: Xaa is A, C, G, P, M, V, I, L, Sce or Sme
<220> FEATURE:
<221> NAME/KEY: MISC_FEATURE
<222> LOCATION: (145)..(146)
<223> OTHER INFORMATION: Xaa is A, C, G, P, M, V, I, L, Sce or Sme
<220> FEATURE:
<221> NAME/KEY: MISC_FEATURE
<222> LOCATION: (147)..(147)
<223> OTHER INFORMATION: Xaa is F, W, or Y
<220> FEATURE:
<221> NAME/KEY: MISC_FEATURE
<222> LOCATION: (148)..(151)
<223> OTHER INFORMATION: Xaa is A, C, G, P, M, V, I, L, Sce or Sme
<220> FEATURE:
<221> NAME/KEY: MISC_FEATURE
<222> LOCATION: (152)..(152)
<223> OTHER INFORMATION: Xaa is any amino acid
<220> FEATURE:
<221> NAME/KEY: MISC_FEATURE
<222> LOCATION: (153)..(154)
<223> OTHER INFORMATION: Xaa is A, C, G, P, M, V, I, L, Sce or Sme
<220> FEATURE:
<221> NAME/KEY: MISC_FEATURE
<222> LOCATION: (155)..(155)
<223> OTHER INFORMATION: Xaa is D or E
<220> FEATURE:
<221> NAME/KEY: MISC_FEATURE
<222> LOCATION: (156)..(156)
<223> OTHER INFORMATION: Xaa is any amino acid
<220> FEATURE:
<221> NAME/KEY: MISC_FEATURE
<222> LOCATION: (157)..(157)
<223> OTHER INFORMATION: Xaa is A, C, G, P, M, V, I, L, Sce or Sme
<220> FEATURE:
<221> NAME/KEY: MISC_FEATURE
<222> LOCATION: (158)..(158)
<223> OTHER INFORMATION: Xaa is any amino acid
<220> FEATURE:
<221> NAME/KEY: MISC_FEATURE
<222> LOCATION: (159)..(160)
<223> OTHER INFORMATION: Xaa is A, C, G, P, M, V, I, L, Sce or Sme
<220> FEATURE:
<221> NAME/KEY: MISC_FEATURE
<222> LOCATION: (161)..(161)
<223> OTHER INFORMATION: Xaa is any amino acid
<220> FEATURE:
<221> NAME/KEY: MISC_FEATURE
<222> LOCATION: (162)..(162)
<223> OTHER INFORMATION: Xaa is A, C, G, P, M, V, I, L, Sce or Sme
<220> FEATURE:
<221> NAME/KEY: MISC_FEATURE
<222> LOCATION: (163)..(163)
<223> OTHER INFORMATION: Xaa is D or E
<220> FEATURE:
<221> NAME/KEY: MISC_FEATURE
<222> LOCATION: (164)..(164)
<223> OTHER INFORMATION: Xaa is A, C, G, P, M, V, I, L, Sce or Sme
<220> FEATURE:
```

```
<221> NAME/KEY: MISC_FEATURE
<222> LOCATION: (165)..(166)
<223> OTHER INFORMATION: Xaa is any amino acid
<220> FEATURE:
<221> NAME/KEY: MISC_FEATURE
<222> LOCATION: (169)..(169)
<223> OTHER INFORMATION: Xaa is A, C, G, P, M, V, I, L, Sce or Sme
<220> FEATURE:
<221> NAME/KEY: MISC_FEATURE
<222> LOCATION: (170)..(170)
<223> OTHER INFORMATION: Xaa is any amino acid
<220> FEATURE:
<221> NAME/KEY: MISC_FEATURE
<222> LOCATION: (171)..(171)
<223> OTHER INFORMATION: Xaa is A, C, G, P, M, V, I, L, Sce or Sme
<220> FEATURE:
<221> NAME/KEY: MISC_FEATURE
<222> LOCATION: (172)..(172)
<223> OTHER INFORMATION: Xaa is F, W, or Y
<220> FEATURE:
<221> NAME/KEY: MISC_FEATURE
<222> LOCATION: (173)..(177)
<223> OTHER INFORMATION: Xaa is any amino acid

<400> SEQUENCE: 15

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Ile Xaa Xaa Lys Ala Xaa Xaa Leu Ala Xaa
                20                  25                  30

Asn Leu Tyr Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Ala Ser Xaa Ser Asp Xaa Xaa Leu
130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Ala Met Xaa Xaa Xaa Xaa Xaa Xaa Xaa Xaa
                165                 170                 175

Xaa

<210> SEQ ID NO 16
<211> LENGTH: 122
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (2)..(2)
<223> OTHER INFORMATION: Xaa is A, C, G, P, M, V, I, L, Sce, or Sme
<220> FEATURE:
<221> NAME/KEY: MISC_FEATURE
<222> LOCATION: (3)..(3)
```

```
<223> OTHER INFORMATION: Xaa is R, H, or K
<220> FEATURE:
<221> NAME/KEY: MISC_FEATURE
<222> LOCATION: (4)..(5)
<223> OTHER INFORMATION: Xaa is A, C, G, P, M, V, I, L, Sce, or Sme
<220> FEATURE:
<221> NAME/KEY: MISC_FEATURE
<222> LOCATION: (6)..(6)
<223> OTHER INFORMATION: Xaa is R, H, or K
<220> FEATURE:
<221> NAME/KEY: MISC_FEATURE
<222> LOCATION: (7)..(9)
<223> OTHER INFORMATION: Xaa is A, C, G, P, M, V, I, L, Sce, or Sme
<220> FEATURE:
<221> NAME/KEY: MISC_FEATURE
<222> LOCATION: (10)..(10)
<223> OTHER INFORMATION: Xaa is S, T, N, or Q
<220> FEATURE:
<221> NAME/KEY: MISC_FEATURE
<222> LOCATION: (11)..(11)
<223> OTHER INFORMATION: Xaa is A, C, G, P, M, V, I, L, Sce, or Sme
<220> FEATURE:
<221> NAME/KEY: MISC_FEATURE
<222> LOCATION: (14)..(14)
<223> OTHER INFORMATION: Xaa is any amino acid
<220> FEATURE:
<221> NAME/KEY: MISC_FEATURE
<222> LOCATION: (19)..(19)
<223> OTHER INFORMATION: Xaa is A, C, G, P, M, V, I, L, Sce, or Sme
<220> FEATURE:
<221> NAME/KEY: MISC_FEATURE
<222> LOCATION: (22)..(22)
<223> OTHER INFORMATION: Xaa is A, C, G, P, M, V, I, L, Sce, or Sme
<220> FEATURE:
<221> NAME/KEY: MISC_FEATURE
<222> LOCATION: (23)..(23)
<223> OTHER INFORMATION: Xaa is S, T, N, or Q
<220> FEATURE:
<221> NAME/KEY: MISC_FEATURE
<222> LOCATION: (26)..(27)
<223> OTHER INFORMATION: Xaa is A, C, G, P, M, V, I, L, Sce, or Sme
<220> FEATURE:
<221> NAME/KEY: MISC_FEATURE
<222> LOCATION: (29)..(29)
<223> OTHER INFORMATION: Xaa is R, H, or K
<220> FEATURE:
<221> NAME/KEY: MISC_FEATURE
<222> LOCATION: (30)..(31)
<223> OTHER INFORMATION: Xaa is A, C, G, P, M, V, I, L, Sce, or Sme
<220> FEATURE:
<221> NAME/KEY: MISC_FEATURE
<222> LOCATION: (32)..(33)
<223> OTHER INFORMATION: Xaa is any amino acid
<220> FEATURE:
<221> NAME/KEY: MISC_FEATURE
<222> LOCATION: (34)..(34)
<223> OTHER INFORMATION: Xaa is S, T, N, or Q
<220> FEATURE:
<221> NAME/KEY: MISC_FEATURE
<222> LOCATION: (35)..(35)
<223> OTHER INFORMATION: Xaa is any amino acid
<220> FEATURE:
<221> NAME/KEY: MISC_FEATURE
<222> LOCATION: (36)..(36)
<223> OTHER INFORMATION: Xaa is A, C, G, P, M, V, I, L, Sce, or Sme
<220> FEATURE:
<221> NAME/KEY: MISC_FEATURE
<222> LOCATION: (37)..(37)
<223> OTHER INFORMATION: Xaa is any amino acid
<220> FEATURE:
<221> NAME/KEY: MISC_FEATURE
<222> LOCATION: (38)..(38)
<223> OTHER INFORMATION: Xaa is S, T, N, or Q
<220> FEATURE:
<221> NAME/KEY: MISC_FEATURE
<222> LOCATION: (39)..(39)
<223> OTHER INFORMATION: Xaa is any amino acid
<220> FEATURE:
<221> NAME/KEY: MISC_FEATURE
```

```
<222> LOCATION: (40)..(40)
<223> OTHER INFORMATION: Xaa is D or E
<220> FEATURE:
<221> NAME/KEY: MISC_FEATURE
<222> LOCATION: (41)..(41)
<223> OTHER INFORMATION: Xaa is any amino acid
<220> FEATURE:
<221> NAME/KEY: MISC_FEATURE
<222> LOCATION: (42)..(46)
<223> OTHER INFORMATION: Xaa is A, C, G, P, M, V, I, L, Sce, or Sme
<220> FEATURE:
<221> NAME/KEY: MISC_FEATURE
<222> LOCATION: (47)..(47)
<223> OTHER INFORMATION: Xaa is F, W, or Y
<220> FEATURE:
<221> NAME/KEY: MISC_FEATURE
<222> LOCATION: (48)..(48)
<223> OTHER INFORMATION: Xaa is S, T, N, or Q
<220> FEATURE:
<221> NAME/KEY: MISC_FEATURE
<222> LOCATION: (49)..(49)
<223> OTHER INFORMATION: Xaa is A, C, G, P, M, V, I, L, Sce, or Sme
<220> FEATURE:
<221> NAME/KEY: MISC_FEATURE
<222> LOCATION: (50)..(50)
<223> OTHER INFORMATION: Xaa is S, T, N, or Q
<220> FEATURE:
<221> NAME/KEY: MISC_FEATURE
<222> LOCATION: (51)..(52)
<223> OTHER INFORMATION: Xaa is any amino acid
<220> FEATURE:
<221> NAME/KEY: MISC_FEATURE
<222> LOCATION: (53)..(53)
<223> OTHER INFORMATION: Xaa is A, C, G, P, M, V, I, L, Sce, or Sme
<220> FEATURE:
<221> NAME/KEY: MISC_FEATURE
<222> LOCATION: (54)..(55)
<223> OTHER INFORMATION: Xaa is S, T, N, or Q
<220> FEATURE:
<221> NAME/KEY: MISC_FEATURE
<222> LOCATION: (56)..(56)
<223> OTHER INFORMATION: Xaa is A, C, G, P, M, V, I, L, Sce, or Sme
<220> FEATURE:
<221> NAME/KEY: MISC_FEATURE
<222> LOCATION: (57)..(57)
<223> OTHER INFORMATION: Xaa is any amino acid
<220> FEATURE:
<221> NAME/KEY: MISC_FEATURE
<222> LOCATION: (58)..(59)
<223> OTHER INFORMATION: Xaa is A, C, G, P, M, V, I, L, Sce, or Sme
<220> FEATURE:
<221> NAME/KEY: MISC_FEATURE
<222> LOCATION: (60)..(60)
<223> OTHER INFORMATION: Xaa is D or E
<220> FEATURE:
<221> NAME/KEY: MISC_FEATURE
<222> LOCATION: (61)..(62)
<223> OTHER INFORMATION: Xaa is A, C, G, P, M, V, I, L, Sce, or Sme
<220> FEATURE:
<221> NAME/KEY: MISC_FEATURE
<222> LOCATION: (63)..(63)
<223> OTHER INFORMATION: Xaa is R, H, or K
<220> FEATURE:
<221> NAME/KEY: MISC_FEATURE
<222> LOCATION: (65)..(67)
<223> OTHER INFORMATION: Xaa is A, C, G, P, M, V, I, L, Sce, or Sme
<220> FEATURE:
<221> NAME/KEY: MISC_FEATURE
<222> LOCATION: (68)..(68)
<223> OTHER INFORMATION: Xaa is any amino acid
<220> FEATURE:
<221> NAME/KEY: MISC_FEATURE
<222> LOCATION: (69)..(69)
<223> OTHER INFORMATION: Xaa is R, H, or K
<220> FEATURE:
<221> NAME/KEY: MISC_FEATURE
<222> LOCATION: (70)..(73)
<223> OTHER INFORMATION: Xaa is A, C, G, P, M, V, I, L, Sce, or Sme
<220> FEATURE:
```

```
<221> NAME/KEY: MISC_FEATURE
<222> LOCATION: (74)..(74)
<223> OTHER INFORMATION: Xaa is S, T, N, or Q
<220> FEATURE:
<221> NAME/KEY: MISC_FEATURE
<222> LOCATION: (75)..(75)
<223> OTHER INFORMATION: Xaa is A, C, G, P, M, V, I, L, Sce, or Sme
<220> FEATURE:
<221> NAME/KEY: MISC_FEATURE
<222> LOCATION: (76)..(76)
<223> OTHER INFORMATION: Xaa is R, H, or K
<220> FEATURE:
<221> NAME/KEY: MISC_FEATURE
<222> LOCATION: (77)..(77)
<223> OTHER INFORMATION: Xaa is D or E
<220> FEATURE:
<221> NAME/KEY: MISC_FEATURE
<222> LOCATION: (78)..(78)
<223> OTHER INFORMATION: Xaa is A, C, G, P, M, V, I, L, Sce, or Sme
<220> FEATURE:
<221> NAME/KEY: MISC_FEATURE
<222> LOCATION: (79)..(79)
<223> OTHER INFORMATION: Xaa is any amino acid
<220> FEATURE:
<221> NAME/KEY: MISC_FEATURE
<222> LOCATION: (80)..(80)
<223> OTHER INFORMATION: Xaa is A, C, G, P, M, V, I, L, Sce, or Sme
<220> FEATURE:
<221> NAME/KEY: MISC_FEATURE
<222> LOCATION: (81)..(82)
<223> OTHER INFORMATION: Xaa is any amino acid
<220> FEATURE:
<221> NAME/KEY: MISC_FEATURE
<222> LOCATION: (83)..(83)
<223> OTHER INFORMATION: Xaa is S, T, N, or Q
<220> FEATURE:
<221> NAME/KEY: MISC_FEATURE
<222> LOCATION: (84)..(84)
<223> OTHER INFORMATION: Xaa is A, C, G, P, M, V, I, L, Sce, or Sme
<220> FEATURE:
<221> NAME/KEY: MISC_FEATURE
<222> LOCATION: (85)..(86)
<223> OTHER INFORMATION: Xaa is any amino acid
<220> FEATURE:
<221> NAME/KEY: MISC_FEATURE
<222> LOCATION: (87)..(88)
<223> OTHER INFORMATION: Xaa is A, C, G, P, M, V, I, L, Sce, or Sme
<220> FEATURE:
<221> NAME/KEY: MISC_FEATURE
<222> LOCATION: (89)..(89)
<223> OTHER INFORMATION: Xaa is R, H, or K
<220> FEATURE:
<221> NAME/KEY: MISC_FEATURE
<222> LOCATION: (90)..(93)
<223> OTHER INFORMATION: Xaa is A, C, G, P, M, V, I, L, Sce, or Sme
<220> FEATURE:
<221> NAME/KEY: MISC_FEATURE
<222> LOCATION: (94)..(94)
<223> OTHER INFORMATION: Xaa is F, W, or Y
<220> FEATURE:
<221> NAME/KEY: MISC_FEATURE
<222> LOCATION: (95)..(96)
<223> OTHER INFORMATION: Xaa is S, T, N, or Q
<220> FEATURE:
<221> NAME/KEY: MISC_FEATURE
<222> LOCATION: (97)..(97)
<223> OTHER INFORMATION: Xaa is any amino acid
<220> FEATURE:
<221> NAME/KEY: MISC_FEATURE
<222> LOCATION: (98)..(98)
<223> OTHER INFORMATION: Xaa is S, T, N, or Q
<220> FEATURE:
<221> NAME/KEY: MISC_FEATURE
<222> LOCATION: (99)..(99)
<223> OTHER INFORMATION: Xaa is any amino acid
<220> FEATURE:
<221> NAME/KEY: MISC_FEATURE
<222> LOCATION: (100)..(100)
<223> OTHER INFORMATION: Xaa is S, T, N, or Q
```

```
<220> FEATURE:
<221> NAME/KEY: MISC_FEATURE
<222> LOCATION: (101)..(102)
<223> OTHER INFORMATION: Xaa is any amino acid
<220> FEATURE:
<221> NAME/KEY: MISC_FEATURE
<222> LOCATION: (103)..(103)
<223> OTHER INFORMATION: Xaa is A, C, G, P, M, V, I, L, Sce, or Sme
<220> FEATURE:
<221> NAME/KEY: MISC_FEATURE
<222> LOCATION: (104)..(105)
<223> OTHER INFORMATION: Xaa is any amino acid
<220> FEATURE:
<221> NAME/KEY: MISC_FEATURE
<222> LOCATION: (106)..(106)
<223> OTHER INFORMATION: Xaa is A, C, G, P, M, V, I, L, Sce, or Sme
<220> FEATURE:
<221> NAME/KEY: MISC_FEATURE
<222> LOCATION: (107)..(107)
<223> OTHER INFORMATION: Xaa is any amino acid
<220> FEATURE:
<221> NAME/KEY: MISC_FEATURE
<222> LOCATION: (108)..(108)
<223> OTHER INFORMATION: Xaa is A, C, G, P, M, V, I, L, Sce, or Sme
<220> FEATURE:
<221> NAME/KEY: MISC_FEATURE
<222> LOCATION: (110)..(110)
<223> OTHER INFORMATION: Xaa is D or E
<220> FEATURE:
<221> NAME/KEY: MISC_FEATURE
<222> LOCATION: (111)..(111)
<223> OTHER INFORMATION: Xaa is A, C, G, P, M, V, I, L, Sce, or Sme
<220> FEATURE:
<221> NAME/KEY: MISC_FEATURE
<222> LOCATION: (112)..(122)
<223> OTHER INFORMATION: Xaa is any amino acid

<400> SEQUENCE: 16

Xaa Xaa Xaa Xaa Xaa Xaa Xaa Xaa Xaa Xaa Xaa Asn Ser Xaa Thr Pro
1               5                   10                  15

Thr Asp Xaa Ile Ile Xaa Xaa Ile Leu Xaa Xaa Glu Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Gln
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Ser Xaa Xaa Xaa
            100                 105                 110

Xaa Xaa Xaa Xaa Xaa Xaa Xaa Xaa Xaa Xaa
        115                 120

<210> SEQ ID NO 17
<211> LENGTH: 172
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or optionally absent
<220> FEATURE:
<221> NAME/KEY: MISC_FEATURE
<222> LOCATION: (2)..(22)
<223> OTHER INFORMATION: Xaa is any amino acid
<220> FEATURE:
```

```
<221> NAME/KEY: MISC_FEATURE
<222> LOCATION: (24)..(25)
<223> OTHER INFORMATION: Xaa is any amino acid
<220> FEATURE:
<221> NAME/KEY: MISC_FEATURE
<222> LOCATION: (26)..(27)
<223> OTHER INFORMATION: Xaa is A, C, G, P, M, V, I, L, Sce or Sme
<220> FEATURE:
<221> NAME/KEY: MISC_FEATURE
<222> LOCATION: (28)..(29)
<223> OTHER INFORMATION: Xaa is any amino acid
<220> FEATURE:
<221> NAME/KEY: MISC_FEATURE
<222> LOCATION: (30)..(30)
<223> OTHER INFORMATION: Xaa is A, C, G, P, M, V, I, L, Sce or Sme
<220> FEATURE:
<221> NAME/KEY: MISC_FEATURE
<222> LOCATION: (31)..(31)
<223> OTHER INFORMATION: Xaa is S, T, N, or Q
<220> FEATURE:
<221> NAME/KEY: MISC_FEATURE
<222> LOCATION: (32)..(32)
<223> OTHER INFORMATION: Xaa is A, C, G, P, M, V, I, L, Sce or Sme
<220> FEATURE:
<221> NAME/KEY: MISC_FEATURE
<222> LOCATION: (33)..(33)
<223> OTHER INFORMATION: Xaa is S, T, N, or Q
<220> FEATURE:
<221> NAME/KEY: MISC_FEATURE
<222> LOCATION: (34)..(34)
<223> OTHER INFORMATION: Xaa is A, C, G, P, M, V, I, L, Sce or Sme
<220> FEATURE:
<221> NAME/KEY: MISC_FEATURE
<222> LOCATION: (35)..(36)
<223> OTHER INFORMATION: Xaa is D or E
<220> FEATURE:
<221> NAME/KEY: MISC_FEATURE
<222> LOCATION: (37)..(37)
<223> OTHER INFORMATION: Xaa is A, C, G, P, M, V, I, L, Sce or Sme
<220> FEATURE:
<221> NAME/KEY: MISC_FEATURE
<222> LOCATION: (38)..(39)
<223> OTHER INFORMATION: Xaa is S, T, N, or Q
<220> FEATURE:
<221> NAME/KEY: MISC_FEATURE
<222> LOCATION: (40)..(40)
<223> OTHER INFORMATION: Xaa is F, W, or Y
<220> FEATURE:
<221> NAME/KEY: MISC_FEATURE
<222> LOCATION: (41)..(42)
<223> OTHER INFORMATION: Xaa is A, C, G, P, M, V, I, L, Sce or Sme
<220> FEATURE:
<221> NAME/KEY: MISC_FEATURE
<222> LOCATION: (43)..(43)
<223> OTHER INFORMATION: Xaa is D or E
<220> FEATURE:
<221> NAME/KEY: MISC_FEATURE
<222> LOCATION: (44)..(44)
<223> OTHER INFORMATION: Xaa is A, C, G, P, M, V, I, L, Sce or Sme
<220> FEATURE:
<221> NAME/KEY: MISC_FEATURE
<222> LOCATION: (45)..(45)
<223> OTHER INFORMATION: Xaa is R, H, or K
<220> FEATURE:
<221> NAME/KEY: MISC_FEATURE
<222> LOCATION: (46)..(46)
<223> OTHER INFORMATION: Xaa is any amino acid
<220> FEATURE:
<221> NAME/KEY: MISC_FEATURE
<222> LOCATION: (47)..(47)
<223> OTHER INFORMATION: Xaa is F, W, or Y
<220> FEATURE:
<221> NAME/KEY: MISC_FEATURE
<222> LOCATION: (48)..(48)
<223> OTHER INFORMATION: Xaa is A, C, G, P, M, V, I, L, Sce or Sme
<220> FEATURE:
<221> NAME/KEY: MISC_FEATURE
<222> LOCATION: (49)..(51)
<223> OTHER INFORMATION: Xaa is any amino acid
```

```
<220> FEATURE:
<221> NAME/KEY: MISC_FEATURE
<222> LOCATION: (52)..(52)
<223> OTHER INFORMATION: Xaa is A, C, G, P, M, V, I, L, Sce or Sme
<220> FEATURE:
<221> NAME/KEY: MISC_FEATURE
<222> LOCATION: (53)..(53)
<223> OTHER INFORMATION: Xaa is any amino acid
<220> FEATURE:
<221> NAME/KEY: MISC_FEATURE
<222> LOCATION: (54)..(56)
<223> OTHER INFORMATION: Xaa is A, C, G, P, M, V, I, L, Sce or Sme
<220> FEATURE:
<221> NAME/KEY: MISC_FEATURE
<222> LOCATION: (57)..(57)
<223> OTHER INFORMATION: Xaa is D or E
<220> FEATURE:
<221> NAME/KEY: MISC_FEATURE
<222> LOCATION: (58)..(58)
<223> OTHER INFORMATION: Xaa is any amino acid
<220> FEATURE:
<221> NAME/KEY: MISC_FEATURE
<222> LOCATION: (59)..(59)
<223> OTHER INFORMATION: Xaa is A, C, G, P, M, V, I, L, Sce or Sme
<220> FEATURE:
<221> NAME/KEY: MISC_FEATURE
<222> LOCATION: (60)..(61)
<223> OTHER INFORMATION: Xaa is S, T, N, or Q
<220> FEATURE:
<221> NAME/KEY: MISC_FEATURE
<222> LOCATION: (62)..(62)
<223> OTHER INFORMATION: Xaa is D or E
<220> FEATURE:
<221> NAME/KEY: MISC_FEATURE
<222> LOCATION: (63)..(63)
<223> OTHER INFORMATION: Xaa is A, C, G, P, M, V, I, L, Sce or Sme
<220> FEATURE:
<221> NAME/KEY: MISC_FEATURE
<222> LOCATION: (64)..(64)
<223> OTHER INFORMATION: Xaa is any amino acid
<220> FEATURE:
<221> NAME/KEY: MISC_FEATURE
<222> LOCATION: (65)..(65)
<223> OTHER INFORMATION: Xaa is R, H, or K
<220> FEATURE:
<221> NAME/KEY: MISC_FEATURE
<222> LOCATION: (66)..(68)
<223> OTHER INFORMATION: Xaa is A, C, G, P, M, V, I, L, Sce or Sme
<220> FEATURE:
<221> NAME/KEY: MISC_FEATURE
<222> LOCATION: (69)..(69)
<223> OTHER INFORMATION: Xaa is D or E
<220> FEATURE:
<221> NAME/KEY: MISC_FEATURE
<222> LOCATION: (70)..(71)
<223> OTHER INFORMATION: Xaa is A, C, G, P, M, V, I, L, Sce or Sme
<220> FEATURE:
<221> NAME/KEY: MISC_FEATURE
<222> LOCATION: (72)..(72)
<223> OTHER INFORMATION: Xaa is S, T, N, or Q
<220> FEATURE:
<221> NAME/KEY: MISC_FEATURE
<222> LOCATION: (73)..(73)
<223> OTHER INFORMATION: Xaa is any amino acid
<220> FEATURE:
<221> NAME/KEY: MISC_FEATURE
<222> LOCATION: (74)..(74)
<223> OTHER INFORMATION: Xaa is A, C, G, P, M, V, I, L, Sce or Sme
<220> FEATURE:
<221> NAME/KEY: MISC_FEATURE
<222> LOCATION: (75)..(77)
<223> OTHER INFORMATION: Xaa is any amino acid
<220> FEATURE:
<221> NAME/KEY: MISC_FEATURE
<222> LOCATION: (78)..(79)
<223> OTHER INFORMATION: Xaa is A, C, G, P, M, V, I, L, Sce or Sme
<220> FEATURE:
<221> NAME/KEY: MISC_FEATURE
<222> LOCATION: (80)..(80)
```

```
<223> OTHER INFORMATION: Xaa is any amino acid
<220> FEATURE:
<221> NAME/KEY: MISC_FEATURE
<222> LOCATION: (82)..(83)
<223> OTHER INFORMATION: Xaa is any amino acid
<220> FEATURE:
<221> NAME/KEY: MISC_FEATURE
<222> LOCATION: (86)..(86)
<223> OTHER INFORMATION: Xaa is F, W, or Y
<220> FEATURE:
<221> NAME/KEY: MISC_FEATURE
<222> LOCATION: (87)..(87)
<223> OTHER INFORMATION: Xaa is A, C, G, P, M, V, I, L, Sce or Sme
<220> FEATURE:
<221> NAME/KEY: MISC_FEATURE
<222> LOCATION: (89)..(89)
<223> OTHER INFORMATION: Xaa is any amino acid
<220> FEATURE:
<221> NAME/KEY: MISC_FEATURE
<222> LOCATION: (90)..(90)
<223> OTHER INFORMATION: Xaa is A, C, G, P, M, V, I, L, Sce or Sme
<220> FEATURE:
<221> NAME/KEY: MISC_FEATURE
<222> LOCATION: (93)..(93)
<223> OTHER INFORMATION: Xaa is any amino acid
<220> FEATURE:
<221> NAME/KEY: MISC_FEATURE
<222> LOCATION: (94)..(94)
<223> OTHER INFORMATION: Xaa is F, W, or Y
<220> FEATURE:
<221> NAME/KEY: MISC_FEATURE
<222> LOCATION: (96)..(97)
<223> OTHER INFORMATION: Xaa is any amino acid
<220> FEATURE:
<221> NAME/KEY: MISC_FEATURE
<222> LOCATION: (98)..(98)
<223> OTHER INFORMATION: Xaa is A, C, G, P, M, V, I, L, Sce or Sme
<220> FEATURE:
<221> NAME/KEY: MISC_FEATURE
<222> LOCATION: (99)..(104)
<223> OTHER INFORMATION: Xaa is any amino acid
<220> FEATURE:
<221> NAME/KEY: MISC_FEATURE
<222> LOCATION: (105)..(108)
<223> OTHER INFORMATION: Xaa is A, C, G, P, M, V, I, L, Sce or Sme
<220> FEATURE:
<221> NAME/KEY: MISC_FEATURE
<222> LOCATION: (109)..(109)
<223> OTHER INFORMATION: Xaa is S, T, N, or Q
<220> FEATURE:
<221> NAME/KEY: MISC_FEATURE
<222> LOCATION: (110)..(110)
<223> OTHER INFORMATION: Xaa is A, C, G, P, M, V, I, L, Sce or Sme
<220> FEATURE:
<221> NAME/KEY: MISC_FEATURE
<222> LOCATION: (111)..(111)
<223> OTHER INFORMATION: Xaa is any amino acid
<220> FEATURE:
<221> NAME/KEY: MISC_FEATURE
<222> LOCATION: (112)..(112)
<223> OTHER INFORMATION: Xaa is S, T, N, or Q
<220> FEATURE:
<221> NAME/KEY: MISC_FEATURE
<222> LOCATION: (113)..(113)
<223> OTHER INFORMATION: Xaa is A, C, G, P, M, V, I, L, Sce or Sme
<220> FEATURE:
<221> NAME/KEY: MISC_FEATURE
<222> LOCATION: (114)..(114)
<223> OTHER INFORMATION: Xaa is R, H, or K
<220> FEATURE:
<221> NAME/KEY: MISC_FEATURE
<222> LOCATION: (115)..(115)
<223> OTHER INFORMATION: Xaa is A, C, G, P, M, V, I, L, Sce or Sme
<220> FEATURE:
<221> NAME/KEY: MISC_FEATURE
<222> LOCATION: (116)..(116)
<223> OTHER INFORMATION: Xaa is D or E
<220> FEATURE:
<221> NAME/KEY: MISC_FEATURE
```

```
<222> LOCATION: (117)..(118)
<223> OTHER INFORMATION: Xaa is A, C, G, P, M, V, I, L, Sce or Sme
<220> FEATURE:
<221> NAME/KEY: MISC_FEATURE
<222> LOCATION: (119)..(119)
<223> OTHER INFORMATION: Xaa is R, H, or K
<220> FEATURE:
<221> NAME/KEY: MISC_FEATURE
<222> LOCATION: (120)..(120)
<223> OTHER INFORMATION: Xaa is S, T, N, or Q
<220> FEATURE:
<221> NAME/KEY: MISC_FEATURE
<222> LOCATION: (121)..(122)
<223> OTHER INFORMATION: Xaa is A, C, G, P, M, V, I, L, Sce or Sme
<220> FEATURE:
<221> NAME/KEY: MISC_FEATURE
<222> LOCATION: (123)..(123)
<223> OTHER INFORMATION: Xaa is any amino acid
<220> FEATURE:
<221> NAME/KEY: MISC_FEATURE
<222> LOCATION: (124)..(124)
<223> OTHER INFORMATION: Xaa is R, H, or K
<220> FEATURE:
<221> NAME/KEY: MISC_FEATURE
<222> LOCATION: (125)..(125)
<223> OTHER INFORMATION: Xaa is A, C, G, P, M, V, I, L, Sce or Sme
<220> FEATURE:
<221> NAME/KEY: MISC_FEATURE
<222> LOCATION: (127)..(128)
<223> OTHER INFORMATION: Xaa is R, H, or K
<220> FEATURE:
<221> NAME/KEY: MISC_FEATURE
<222> LOCATION: (129)..(129)
<223> OTHER INFORMATION: Xaa is A, C, G, P, M, V, I, L, Sce or Sme
<220> FEATURE:
<221> NAME/KEY: MISC_FEATURE
<222> LOCATION: (131)..(131)
<223> OTHER INFORMATION: Xaa is any amino acid
<220> FEATURE:
<221> NAME/KEY: MISC_FEATURE
<222> LOCATION: (132)..(132)
<223> OTHER INFORMATION: Xaa is A, C, G, P, M, V, I, L, Sce or Sme
<220> FEATURE:
<221> NAME/KEY: MISC_FEATURE
<222> LOCATION: (135)..(136)
<223> OTHER INFORMATION: Xaa is any amino acid
<220> FEATURE:
<221> NAME/KEY: MISC_FEATURE
<222> LOCATION: (139)..(139)
<223> OTHER INFORMATION: Xaa is A, C, G, P, M, V, I, L, Sce or Sme
<220> FEATURE:
<221> NAME/KEY: MISC_FEATURE
<222> LOCATION: (142)..(142)
<223> OTHER INFORMATION: Xaa is A, C, G, P, M, V, I, L, Sce or Sme
<220> FEATURE:
<221> NAME/KEY: MISC_FEATURE
<222> LOCATION: (145)..(145)
<223> OTHER INFORMATION: Xaa is F, W, or Y
<220> FEATURE:
<221> NAME/KEY: MISC_FEATURE
<222> LOCATION: (146)..(146)
<223> OTHER INFORMATION: Xaa is A, C, G, P, M, V, I, L, Sce or Sme
<220> FEATURE:
<221> NAME/KEY: MISC_FEATURE
<222> LOCATION: (149)..(149)
<223> OTHER INFORMATION: Xaa is A, C, G, P, M, V, I, L, Sce or Sme
<220> FEATURE:
<221> NAME/KEY: MISC_FEATURE
<222> LOCATION: (150)..(150)
<223> OTHER INFORMATION: Xaa is S, T, N, or Q
<220> FEATURE:
<221> NAME/KEY: MISC_FEATURE
<222> LOCATION: (152)..(153)
<223> OTHER INFORMATION: Xaa is A, C, G, P, M, V, I, L, Sce or Sme
<220> FEATURE:
<221> NAME/KEY: MISC_FEATURE
<222> LOCATION: (154)..(154)
<223> OTHER INFORMATION: Xaa is any amino acid
<220> FEATURE:
```

```
<221> NAME/KEY: MISC_FEATURE
<222> LOCATION: (155)..(157)
<223> OTHER INFORMATION: Xaa is A, C, G, P, M, V, I, L, Sce or Sme
<220> FEATURE:
<221> NAME/KEY: MISC_FEATURE
<222> LOCATION: (158)..(158)
<223> OTHER INFORMATION: Xaa is R, H, or K
<220> FEATURE:
<221> NAME/KEY: MISC_FEATURE
<222> LOCATION: (159)..(160)
<223> OTHER INFORMATION: Xaa is A, C, G, P, M, V, I, L, Sce or Sme
<220> FEATURE:
<221> NAME/KEY: MISC_FEATURE
<222> LOCATION: (161)..(161)
<223> OTHER INFORMATION: Xaa is D or E
<220> FEATURE:
<221> NAME/KEY: MISC_FEATURE
<222> LOCATION: (162)..(172)
<223> OTHER INFORMATION: Xaa is any amino acid

<400> SEQUENCE: 17

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Lys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Glu Xaa Xaa Ile Ala Xaa Xaa Leu Xaa Xaa Ile Leu Xaa Xaa Met Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Leu Xaa Xaa
        115                 120                 125

Xaa Leu Xaa Xaa Thr Arg Xaa Xaa Gly Ile Xaa Ala Glu Xaa Ala Ala
130                 135                 140

Xaa Xaa Leu Ala Xaa Xaa Asp Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa
            165                 170

<210> SEQ ID NO 18
<211> LENGTH: 123
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa ia any amino acid or is optionally absent
<220> FEATURE:
<221> NAME/KEY: MISC_FEATURE
<222> LOCATION: (2)..(2)
<223> OTHER INFORMATION: Xaa is A, C, G, P, M, V, I, L, Sce or Sme
<220> FEATURE:
<221> NAME/KEY: MISC_FEATURE
<222> LOCATION: (3)..(3)
<223> OTHER INFORMATION: Xaa is R, H, or K
<220> FEATURE:
<221> NAME/KEY: MISC_FEATURE
<222> LOCATION: (4)..(6)
<223> OTHER INFORMATION: Xaa is A, C, G, P, M, V, I, L, Sce or Sme
<220> FEATURE:
```

```
<221> NAME/KEY: MISC_FEATURE
<222> LOCATION: (7)..(7)
<223> OTHER INFORMATION: Xaa is D or E
<220> FEATURE:
<221> NAME/KEY: MISC_FEATURE
<222> LOCATION: (8)..(8)
<223> OTHER INFORMATION: Xaa is A, C, G, P, M, V, I, L, Sce or Sme
<220> FEATURE:
<221> NAME/KEY: MISC_FEATURE
<222> LOCATION: (9)..(9)
<223> OTHER INFORMATION: Xaa is S, T, N or Q
<220> FEATURE:
<221> NAME/KEY: MISC_FEATURE
<222> LOCATION: (10)..(10)
<223> OTHER INFORMATION: Xaa is A, C, G, P, M, V, I, L, Sce or Sme
<220> FEATURE:
<221> NAME/KEY: MISC_FEATURE
<222> LOCATION: (11)..(11)
<223> OTHER INFORMATION: Xaa is S, T, N or Q
<220> FEATURE:
<221> NAME/KEY: MISC_FEATURE
<222> LOCATION: (12)..(12)
<223> OTHER INFORMATION: Xaa is A, C, G, P, M, V, I, L, Sce or Sme
<220> FEATURE:
<221> NAME/KEY: MISC_FEATURE
<222> LOCATION: (13)..(13)
<223> OTHER INFORMATION: Xaa ia any amino acid
<220> FEATURE:
<221> NAME/KEY: MISC_FEATURE
<222> LOCATION: (14)..(14)
<223> OTHER INFORMATION: Xaa is A, C, G, P, M, V, I, L, Sce or Sme
<220> FEATURE:
<221> NAME/KEY: MISC_FEATURE
<222> LOCATION: (15)..(15)
<223> OTHER INFORMATION: Xaa ia any amino acid
<220> FEATURE:
<221> NAME/KEY: MISC_FEATURE
<222> LOCATION: (16)..(16)
<223> OTHER INFORMATION: Xaa is S, T, N or Q
<220> FEATURE:
<221> NAME/KEY: MISC_FEATURE
<222> LOCATION: (17)..(17)
<223> OTHER INFORMATION: Xaa ia any amino acid
<220> FEATURE:
<221> NAME/KEY: MISC_FEATURE
<222> LOCATION: (18)..(19)
<223> OTHER INFORMATION: Xaa is A, C, G, P, M, V, I, L, Sce or Sme
<220> FEATURE:
<221> NAME/KEY: MISC_FEATURE
<222> LOCATION: (20)..(20)
<223> OTHER INFORMATION: Xaa ia any amino acid
<220> FEATURE:
<221> NAME/KEY: MISC_FEATURE
<222> LOCATION: (21)..(22)
<223> OTHER INFORMATION: Xaa is A, C, G, P, M, V, I, L, Sce or Sme
<220> FEATURE:
<221> NAME/KEY: MISC_FEATURE
<222> LOCATION: (23)..(23)
<223> OTHER INFORMATION: Xaa is D or E
<220> FEATURE:
<221> NAME/KEY: MISC_FEATURE
<222> LOCATION: (24)..(24)
<223> OTHER INFORMATION: Xaa ia any amino acid
<220> FEATURE:
<221> NAME/KEY: MISC_FEATURE
<222> LOCATION: (25)..(25)
<223> OTHER INFORMATION: Xaa is A, C, G, P, M, V, I, L, Sce or Sme
<220> FEATURE:
<221> NAME/KEY: MISC_FEATURE
<222> LOCATION: (26)..(26)
<223> OTHER INFORMATION: Xaa is S, T, N or Q
<220> FEATURE:
<221> NAME/KEY: MISC_FEATURE
<222> LOCATION: (29)..(29)
<223> OTHER INFORMATION: Xaa is A, C, G, P, M, V, I, L, Sce or Sme
<220> FEATURE:
<221> NAME/KEY: MISC_FEATURE
<222> LOCATION: (33)..(33)
<223> OTHER INFORMATION: Xaa ia any amino acid
```

-continued

```
<220> FEATURE:
<221> NAME/KEY: MISC_FEATURE
<222> LOCATION: (35)..(35)
<223> OTHER INFORMATION: Xaa is F, W, or Y
<220> FEATURE:
<221> NAME/KEY: MISC_FEATURE
<222> LOCATION: (36)..(36)
<223> OTHER INFORMATION: Xaa is A, C, G, P, M, V, I, L, Sce or Sme
<220> FEATURE:
<221> NAME/KEY: MISC_FEATURE
<222> LOCATION: (37)..(37)
<223> OTHER INFORMATION: Xaa is D or E
<220> FEATURE:
<221> NAME/KEY: MISC_FEATURE
<222> LOCATION: (38)..(38)
<223> OTHER INFORMATION: Xaa is A, C, G, P, M, V, I, L, Sce or Sme
<220> FEATURE:
<221> NAME/KEY: MISC_FEATURE
<222> LOCATION: (39)..(39)
<223> OTHER INFORMATION: Xaa ia any amino acid
<220> FEATURE:
<221> NAME/KEY: MISC_FEATURE
<222> LOCATION: (40)..(40)
<223> OTHER INFORMATION: Xaa is A, C, G, P, M, V, I, L, Sce or Sme
<220> FEATURE:
<221> NAME/KEY: MISC_FEATURE
<222> LOCATION: (41)..(41)
<223> OTHER INFORMATION: Xaa is R, H, or K
<220> FEATURE:
<221> NAME/KEY: MISC_FEATURE
<222> LOCATION: (42)..(43)
<223> OTHER INFORMATION: Xaa ia any amino acid
<220> FEATURE:
<221> NAME/KEY: MISC_FEATURE
<222> LOCATION: (44)..(44)
<223> OTHER INFORMATION: Xaa is F, W, or Y
<220> FEATURE:
<221> NAME/KEY: MISC_FEATURE
<222> LOCATION: (45)..(45)
<223> OTHER INFORMATION: Xaa is A, C, G, P, M, V, I, L, Sce or Sme
<220> FEATURE:
<221> NAME/KEY: MISC_FEATURE
<222> LOCATION: (46)..(46)
<223> OTHER INFORMATION: Xaa ia any amino acid
<220> FEATURE:
<221> NAME/KEY: MISC_FEATURE
<222> LOCATION: (47)..(47)
<223> OTHER INFORMATION: Xaa is A, C, G, P, M, V, I, L, Sce or Sme
<220> FEATURE:
<221> NAME/KEY: MISC_FEATURE
<222> LOCATION: (48)..(48)
<223> OTHER INFORMATION: Xaa ia any amino acid
<220> FEATURE:
<221> NAME/KEY: MISC_FEATURE
<222> LOCATION: (49)..(49)
<223> OTHER INFORMATION: Xaa is A, C, G, P, M, V, I, L, Sce or Sme
<220> FEATURE:
<221> NAME/KEY: MISC_FEATURE
<222> LOCATION: (50)..(50)
<223> OTHER INFORMATION: Xaa is F, W, or Y
<220> FEATURE:
<221> NAME/KEY: MISC_FEATURE
<222> LOCATION: (51)..(51)
<223> OTHER INFORMATION: Xaa ia any amino acid
<220> FEATURE:
<221> NAME/KEY: MISC_FEATURE
<222> LOCATION: (52)..(52)
<223> OTHER INFORMATION: Xaa is S, T, N or Q
<220> FEATURE:
<221> NAME/KEY: MISC_FEATURE
<222> LOCATION: (53)..(53)
<223> OTHER INFORMATION: Xaa is A, C, G, P, M, V, I, L, Sce or Sme
<220> FEATURE:
<221> NAME/KEY: MISC_FEATURE
<222> LOCATION: (54)..(54)
<223> OTHER INFORMATION: Xaa ia any amino acid
<220> FEATURE:
<221> NAME/KEY: MISC_FEATURE
<222> LOCATION: (55)..(55)
```

-continued

```
<223> OTHER INFORMATION: Xaa is A, C, G, P, M, V, I, L, Sce or Sme
<220> FEATURE:
<221> NAME/KEY: MISC_FEATURE
<222> LOCATION: (56)..(58)
<223> OTHER INFORMATION: Xaa ia any amino acid
<220> FEATURE:
<221> NAME/KEY: MISC_FEATURE
<222> LOCATION: (59)..(59)
<223> OTHER INFORMATION: Xaa is R, H, or K
<220> FEATURE:
<221> NAME/KEY: MISC_FEATURE
<222> LOCATION: (60)..(60)
<223> OTHER INFORMATION: Xaa ia any amino acid
<220> FEATURE:
<221> NAME/KEY: MISC_FEATURE
<222> LOCATION: (61)..(61)
<223> OTHER INFORMATION: Xaa is F, W, or Y
<220> FEATURE:
<221> NAME/KEY: MISC_FEATURE
<222> LOCATION: (62)..(62)
<223> OTHER INFORMATION: Xaa ia any amino acid
<220> FEATURE:
<221> NAME/KEY: MISC_FEATURE
<222> LOCATION: (63)..(63)
<223> OTHER INFORMATION: Xaa is R, H, or K
<220> FEATURE:
<221> NAME/KEY: MISC_FEATURE
<222> LOCATION: (64)..(66)
<223> OTHER INFORMATION: Xaa ia any amino acid
<220> FEATURE:
<221> NAME/KEY: MISC_FEATURE
<222> LOCATION: (67)..(67)
<223> OTHER INFORMATION: Xaa is S, T, N or Q
<220> FEATURE:
<221> NAME/KEY: MISC_FEATURE
<222> LOCATION: (68)..(69)
<223> OTHER INFORMATION: Xaa ia any amino acid
<220> FEATURE:
<221> NAME/KEY: MISC_FEATURE
<222> LOCATION: (70)..(70)
<223> OTHER INFORMATION: Xaa ia any amino acid
<220> FEATURE:
<221> NAME/KEY: MISC_FEATURE
<222> LOCATION: (72)..(72)
<223> OTHER INFORMATION: Xaa ia any amino acid
<220> FEATURE:
<221> NAME/KEY: MISC_FEATURE
<222> LOCATION: (77)..(77)
<223> OTHER INFORMATION: Xaa is R, H, or K
<220> FEATURE:
<221> NAME/KEY: MISC_FEATURE
<222> LOCATION: (80)..(81)
<223> OTHER INFORMATION: Xaa ia any amino acid
<220> FEATURE:
<221> NAME/KEY: MISC_FEATURE
<222> LOCATION: (84)..(84)
<223> OTHER INFORMATION: Xaa ia any amino acid
<220> FEATURE:
<221> NAME/KEY: MISC_FEATURE
<222> LOCATION: (87)..(89)
<223> OTHER INFORMATION: Xaa ia any amino acid
<220> FEATURE:
<221> NAME/KEY: MISC_FEATURE
<222> LOCATION: (90)..(90)
<223> OTHER INFORMATION: Xaa ia any amino acid
<220> FEATURE:
<221> NAME/KEY: MISC_FEATURE
<222> LOCATION: (91)..(96)
<223> OTHER INFORMATION: Xaa ia any amino acid
<220> FEATURE:
<221> NAME/KEY: MISC_FEATURE
<222> LOCATION: (97)..(98)
<223> OTHER INFORMATION: Xaa ia any amino acid
<220> FEATURE:
<221> NAME/KEY: MISC_FEATURE
<222> LOCATION: (99)..(100)
<223> OTHER INFORMATION: Xaa ia any amino acid
<220> FEATURE:
<221> NAME/KEY: MISC_FEATURE
```

<222> LOCATION: (101)..(101)
<223> OTHER INFORMATION: Xaa is S, T, N or Q
<220> FEATURE:
<221> NAME/KEY: MISC_FEATURE
<222> LOCATION: (102)..(102)
<223> OTHER INFORMATION: Xaa ia any amino acid
<220> FEATURE:
<221> NAME/KEY: MISC_FEATURE
<222> LOCATION: (103)..(103)
<223> OTHER INFORMATION: Xaa is S, T, N or Q
<220> FEATURE:
<221> NAME/KEY: MISC_FEATURE
<222> LOCATION: (104)..(104)
<223> OTHER INFORMATION: Xaa ia any amino acid
<220> FEATURE:
<221> NAME/KEY: MISC_FEATURE
<222> LOCATION: (105)..(105)
<223> OTHER INFORMATION: Xaa is D or E
<220> FEATURE:
<221> NAME/KEY: MISC_FEATURE
<222> LOCATION: (106)..(106)
<223> OTHER INFORMATION: Xaa ia any amino acid
<220> FEATURE:
<221> NAME/KEY: MISC_FEATURE
<222> LOCATION: (107)..(107)
<223> OTHER INFORMATION: Xaa is R, H, or K
<220> FEATURE:
<221> NAME/KEY: MISC_FEATURE
<222> LOCATION: (108)..(108)
<223> OTHER INFORMATION: Xaa ia any amino acid
<220> FEATURE:
<221> NAME/KEY: MISC_FEATURE
<222> LOCATION: (109)..(109)
<223> OTHER INFORMATION: Xaa ia any amino acid
<220> FEATURE:
<221> NAME/KEY: MISC_FEATURE
<222> LOCATION: (110)..(110)
<223> OTHER INFORMATION: Xaa is D or E
<220> FEATURE:
<221> NAME/KEY: MISC_FEATURE
<222> LOCATION: (111)..(111)
<223> OTHER INFORMATION: Xaa ia any amino acid
<220> FEATURE:
<221> NAME/KEY: MISC_FEATURE
<222> LOCATION: (113)..(113)
<223> OTHER INFORMATION: Xaa is S, T, N or Q
<220> FEATURE:
<221> NAME/KEY: MISC_FEATURE
<222> LOCATION: (118)..(123)
<223> OTHER INFORMATION: Xaa ia any amino acid

<400> SEQUENCE: 18

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Lys Ala Xaa Phe Ala Ser
                20                  25                  30

Xaa Gln Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Gly Xaa Asp Ile Ala Thr Xaa Thr Leu Xaa
65                  70                  75                  80

Xaa Ala Ser Xaa Cys Ala Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Leu
        100                 105                 110

Xaa Tyr Ala Lys Arg Xaa Xaa Xaa Xaa Xaa Xaa
    115                 120

<210> SEQ ID NO 19

```
<211> LENGTH: 158
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (2)..(4)
<223> OTHER INFORMATION: Xaa is any amino acid
<220> FEATURE:
<221> NAME/KEY: MISC_FEATURE
<222> LOCATION: (5)..(7)
<223> OTHER INFORMATION: Xaa is S, T, N or Q
<220> FEATURE:
<221> NAME/KEY: MISC_FEATURE
<222> LOCATION: (8)..(8)
<223> OTHER INFORMATION: Xaa is F, W, or Y
<220> FEATURE:
<221> NAME/KEY: MISC_FEATURE
<222> LOCATION: (9)..(9)
<223> OTHER INFORMATION: Xaa is A, C, G, P, M, V, I, L, Sce or Sme
<220> FEATURE:
<221> NAME/KEY: MISC_FEATURE
<222> LOCATION: (10)..(10)
<223> OTHER INFORMATION: Xaa is S, T, N or Q
<220> FEATURE:
<221> NAME/KEY: MISC_FEATURE
<222> LOCATION: (11)..(11)
<223> OTHER INFORMATION: Xaa is A, C, G, P, M, V, I, L, Sce or Sme
<220> FEATURE:
<221> NAME/KEY: MISC_FEATURE
<222> LOCATION: (12)..(12)
<223> OTHER INFORMATION: Xaa is S, T, N or Q
<220> FEATURE:
<221> NAME/KEY: MISC_FEATURE
<222> LOCATION: (13)..(14)
<223> OTHER INFORMATION: Xaa is A, C, G, P, M, V, I, L, Sce or Sme
<220> FEATURE:
<221> NAME/KEY: MISC_FEATURE
<222> LOCATION: (15)..(15)
<223> OTHER INFORMATION: Xaa is S, T, N or Q
<220> FEATURE:
<221> NAME/KEY: MISC_FEATURE
<222> LOCATION: (16)..(16)
<223> OTHER INFORMATION: Xaa is A, C, G, P, M, V, I, L, Sce or Sme
<220> FEATURE:
<221> NAME/KEY: MISC_FEATURE
<222> LOCATION: (17)..(17)
<223> OTHER INFORMATION: Xaa is R, H, or K
<220> FEATURE:
<221> NAME/KEY: MISC_FEATURE
<222> LOCATION: (18)..(18)
<223> OTHER INFORMATION: Xaa is D or E
<220> FEATURE:
<221> NAME/KEY: MISC_FEATURE
<222> LOCATION: (19)..(21)
<223> OTHER INFORMATION: Xaa is any amino acid
<220> FEATURE:
<221> NAME/KEY: MISC_FEATURE
<222> LOCATION: (22)..(22)
<223> OTHER INFORMATION: Xaa is A, C, G, P, M, V, I, L, Sce or Sme
<220> FEATURE:
<221> NAME/KEY: MISC_FEATURE
<222> LOCATION: (23)..(23)
<223> OTHER INFORMATION: Xaa is S, T, N or Q
<220> FEATURE:
<221> NAME/KEY: MISC_FEATURE
<222> LOCATION: (24)..(24)
<223> OTHER INFORMATION: Xaa is F, W, or Y
<220> FEATURE:
<221> NAME/KEY: MISC_FEATURE
<222> LOCATION: (25)..(27)
<223> OTHER INFORMATION: Xaa is A, C, G, P, M, V, I, L, Sce or Sme
<220> FEATURE:
<221> NAME/KEY: MISC_FEATURE
```

```
<222> LOCATION: (28)..(28)
<223> OTHER INFORMATION: Xaa is R, H, or K
<220> FEATURE:
<221> NAME/KEY: MISC_FEATURE
<222> LOCATION: (29)..(29)
<223> OTHER INFORMATION: Xaa is A, C, G, P, M, V, I, L, Sce or Sme
<220> FEATURE:
<221> NAME/KEY: MISC_FEATURE
<222> LOCATION: (30)..(31)
<223> OTHER INFORMATION: Xaa is any amino acid
<220> FEATURE:
<221> NAME/KEY: MISC_FEATURE
<222> LOCATION: (32)..(32)
<223> OTHER INFORMATION: Xaa is S, T, N or Q
<220> FEATURE:
<221> NAME/KEY: MISC_FEATURE
<222> LOCATION: (33)..(33)
<223> OTHER INFORMATION: Xaa is A, C, G, P, M, V, I, L, Sce or Sme
<220> FEATURE:
<221> NAME/KEY: MISC_FEATURE
<222> LOCATION: (34)..(34)
<223> OTHER INFORMATION: Xaa is F, W, or Y
<220> FEATURE:
<221> NAME/KEY: MISC_FEATURE
<222> LOCATION: (35)..(36)
<223> OTHER INFORMATION: Xaa is A, C, G, P, M, V, I, L, Sce or Sme
<220> FEATURE:
<221> NAME/KEY: MISC_FEATURE
<222> LOCATION: (37)..(37)
<223> OTHER INFORMATION: Xaa is D or E
<220> FEATURE:
<221> NAME/KEY: MISC_FEATURE
<222> LOCATION: (38)..(38)
<223> OTHER INFORMATION: Xaa is any amino acid
<220> FEATURE:
<221> NAME/KEY: MISC_FEATURE
<222> LOCATION: (39)..(39)
<223> OTHER INFORMATION: Xaa is A, C, G, P, M, V, I, L, Sce or Sme
<220> FEATURE:
<221> NAME/KEY: MISC_FEATURE
<222> LOCATION: (40)..(40)
<223> OTHER INFORMATION: Xaa is D or E
<220> FEATURE:
<221> NAME/KEY: MISC_FEATURE
<222> LOCATION: (41)..(41)
<223> OTHER INFORMATION: Xaa is A, C, G, P, M, V, I, L, Sce or Sme
<220> FEATURE:
<221> NAME/KEY: MISC_FEATURE
<222> LOCATION: (42)..(42)
<223> OTHER INFORMATION: Xaa is D or E
<220> FEATURE:
<221> NAME/KEY: MISC_FEATURE
<222> LOCATION: (43)..(44)
<223> OTHER INFORMATION: Xaa is A, C, G, P, M, V, I, L, Sce or Sme
<220> FEATURE:
<221> NAME/KEY: MISC_FEATURE
<222> LOCATION: (45)..(46)
<223> OTHER INFORMATION: Xaa is any amino acid
<220> FEATURE:
<221> NAME/KEY: MISC_FEATURE
<222> LOCATION: (47)..(47)
<223> OTHER INFORMATION: Xaa is R, H, or K
<220> FEATURE:
<221> NAME/KEY: MISC_FEATURE
<222> LOCATION: (48)..(48)
<223> OTHER INFORMATION: Xaa is A, C, G, P, M, V, I, L, Sce or Sme
<220> FEATURE:
<221> NAME/KEY: MISC_FEATURE
<222> LOCATION: (51)..(51)
<223> OTHER INFORMATION: Xaa is A, C, G, P, M, V, I, L, Sce or Sme
<220> FEATURE:
<221> NAME/KEY: MISC_FEATURE
<222> LOCATION: (55)..(55)
<223> OTHER INFORMATION: Xaa is S, T, N or Q
<220> FEATURE:
<221> NAME/KEY: MISC_FEATURE
<222> LOCATION: (58)..(59)
<223> OTHER INFORMATION: Xaa is A, C, G, P, M, V, I, L, Sce or Sme
<220> FEATURE:
```

```
<221> NAME/KEY: MISC_FEATURE
<222> LOCATION: (61)..(61)
<223> OTHER INFORMATION: Xaa is D or E
<220> FEATURE:
<221> NAME/KEY: MISC_FEATURE
<222> LOCATION: (62)..(65)
<223> OTHER INFORMATION: Xaa is any amino acid
<220> FEATURE:
<221> NAME/KEY: MISC_FEATURE
<222> LOCATION: (66)..(66)
<223> OTHER INFORMATION: Xaa is F, W, or Y
<220> FEATURE:
<221> NAME/KEY: MISC_FEATURE
<222> LOCATION: (67)..(67)
<223> OTHER INFORMATION: Xaa is any amino acid
<220> FEATURE:
<221> NAME/KEY: MISC_FEATURE
<222> LOCATION: (68)..(69)
<223> OTHER INFORMATION: Xaa is A, C, G, P, M, V, I, L, Sce or Sme
<220> FEATURE:
<221> NAME/KEY: MISC_FEATURE
<222> LOCATION: (70)..(70)
<223> OTHER INFORMATION: Xaa is R, H, or K
<220> FEATURE:
<221> NAME/KEY: MISC_FEATURE
<222> LOCATION: (71)..(71)
<223> OTHER INFORMATION: Xaa is A, C, G, P, M, V, I, L, Sce or Sme
<220> FEATURE:
<221> NAME/KEY: MISC_FEATURE
<222> LOCATION: (72)..(72)
<223> OTHER INFORMATION: Xaa is R, H, or K
<220> FEATURE:
<221> NAME/KEY: MISC_FEATURE
<222> LOCATION: (73)..(73)
<223> OTHER INFORMATION: Xaa is A, C, G, P, M, V, I, L, Sce or Sme
<220> FEATURE:
<221> NAME/KEY: MISC_FEATURE
<222> LOCATION: (74)..(74)
<223> OTHER INFORMATION: Xaa is R, H, or K
<220> FEATURE:
<221> NAME/KEY: MISC_FEATURE
<222> LOCATION: (75)..(76)
<223> OTHER INFORMATION: Xaa is A, C, G, P, M, V, I, L, Sce or Sme
<220> FEATURE:
<221> NAME/KEY: MISC_FEATURE
<222> LOCATION: (77)..(77)
<223> OTHER INFORMATION: Xaa is D or E
<220> FEATURE:
<221> NAME/KEY: MISC_FEATURE
<222> LOCATION: (78)..(78)
<223> OTHER INFORMATION: Xaa is A, C, G, P, M, V, I, L, Sce or Sme
<220> FEATURE:
<221> NAME/KEY: MISC_FEATURE
<222> LOCATION: (79)..(79)
<223> OTHER INFORMATION: Xaa is any amino acid
<220> FEATURE:
<221> NAME/KEY: MISC_FEATURE
<222> LOCATION: (80)..(80)
<223> OTHER INFORMATION: Xaa is D or E
<220> FEATURE:
<221> NAME/KEY: MISC_FEATURE
<222> LOCATION: (81)..(81)
<223> OTHER INFORMATION: Xaa is R, H, or K
<220> FEATURE:
<221> NAME/KEY: MISC_FEATURE
<222> LOCATION: (82)..(84)
<223> OTHER INFORMATION: Xaa is any amino acid
<220> FEATURE:
<221> NAME/KEY: MISC_FEATURE
<222> LOCATION: (85)..(85)
<223> OTHER INFORMATION: Xaa is S, T, N or Q
<220> FEATURE:
<221> NAME/KEY: MISC_FEATURE
<222> LOCATION: (86)..(86)
<223> OTHER INFORMATION: Xaa is A, C, G, P, M, V, I, L, Sce or Sme
<220> FEATURE:
<221> NAME/KEY: MISC_FEATURE
<222> LOCATION: (87)..(87)
<223> OTHER INFORMATION: Xaa is any amino acid
```

-continued

```
<220> FEATURE:
<221> NAME/KEY: MISC_FEATURE
<222> LOCATION: (88)..(88)
<223> OTHER INFORMATION: Xaa is A, C, G, P, M, V, I, L, Sce or Sme
<220> FEATURE:
<221> NAME/KEY: MISC_FEATURE
<222> LOCATION: (89)..(89)
<223> OTHER INFORMATION: Xaa is any amino acid
<220> FEATURE:
<221> NAME/KEY: MISC_FEATURE
<222> LOCATION: (90)..(90)
<223> OTHER INFORMATION: Xaa is A, C, G, P, M, V, I, L, Sce or Sme
<220> FEATURE:
<221> NAME/KEY: MISC_FEATURE
<222> LOCATION: (91)..(91)
<223> OTHER INFORMATION: Xaa is D or E
<220> FEATURE:
<221> NAME/KEY: MISC_FEATURE
<222> LOCATION: (92)..(93)
<223> OTHER INFORMATION: Xaa is A, C, G, P, M, V, I, L, Sce or Sme
<220> FEATURE:
<221> NAME/KEY: MISC_FEATURE
<222> LOCATION: (94)..(105)
<223> OTHER INFORMATION: Xaa is any amino acid
<220> FEATURE:
<221> NAME/KEY: MISC_FEATURE
<222> LOCATION: (106)..(106)
<223> OTHER INFORMATION: Xaa is A, C, G, P, M, V, I, L, Sce or Sme
<220> FEATURE:
<221> NAME/KEY: MISC_FEATURE
<222> LOCATION: (107)..(108)
<223> OTHER INFORMATION: Xaa is D or E
<220> FEATURE:
<221> NAME/KEY: MISC_FEATURE
<222> LOCATION: (109)..(109)
<223> OTHER INFORMATION: Xaa is any amino acid
<220> FEATURE:
<221> NAME/KEY: MISC_FEATURE
<222> LOCATION: (110)..(110)
<223> OTHER INFORMATION: Xaa is A, C, G, P, M, V, I, L, Sce or Sme
<220> FEATURE:
<221> NAME/KEY: MISC_FEATURE
<222> LOCATION: (111)..(111)
<223> OTHER INFORMATION: Xaa is R, H, or K
<220> FEATURE:
<221> NAME/KEY: MISC_FEATURE
<222> LOCATION: (114)..(114)
<223> OTHER INFORMATION: Xaa is A, C, G, P, M, V, I, L, Sce or Sme
<220> FEATURE:
<221> NAME/KEY: MISC_FEATURE
<222> LOCATION: (115)..(115)
<223> OTHER INFORMATION: Xaa is any amino acid
<220> FEATURE:
<221> NAME/KEY: MISC_FEATURE
<222> LOCATION: (118)..(118)
<223> OTHER INFORMATION: Xaa is A, C, G, P, M, V, I, L, Sce or Sme
<220> FEATURE:
<221> NAME/KEY: MISC_FEATURE
<222> LOCATION: (120)..(120)
<223> OTHER INFORMATION: Xaa is A, C, G, P, M, V, I, L, Sce or Sme
<220> FEATURE:
<221> NAME/KEY: MISC_FEATURE
<222> LOCATION: (121)..(121)
<223> OTHER INFORMATION: Xaa is any amino acid
<220> FEATURE:
<221> NAME/KEY: MISC_FEATURE
<222> LOCATION: (122)..(122)
<223> OTHER INFORMATION: Xaa is A, C, G, P, M, V, I, L, Sce or Sme
<220> FEATURE:
<221> NAME/KEY: MISC_FEATURE
<222> LOCATION: (123)..(123)
<223> OTHER INFORMATION: Xaa is any amino acid
<220> FEATURE:
<221> NAME/KEY: MISC_FEATURE
<222> LOCATION: (124)..(124)
<223> OTHER INFORMATION: Xaa is D or E
<220> FEATURE:
<221> NAME/KEY: MISC_FEATURE
<222> LOCATION: (125)..(127)
```

```
<223> OTHER INFORMATION: Xaa is any amino acid
<220> FEATURE:
<221> NAME/KEY: MISC_FEATURE
<222> LOCATION: (128)..(129)
<223> OTHER INFORMATION: Xaa is A, C, G, P, M, V, I, L, Sce or Sme
<220> FEATURE:
<221> NAME/KEY: MISC_FEATURE
<222> LOCATION: (130)..(131)
<223> OTHER INFORMATION: Xaa is S, T, N or Q
<220> FEATURE:
<221> NAME/KEY: MISC_FEATURE
<222> LOCATION: (132)..(132)
<223> OTHER INFORMATION: Xaa is F, W, or Y
<220> FEATURE:
<221> NAME/KEY: MISC_FEATURE
<222> LOCATION: (133)..(134)
<223> OTHER INFORMATION: Xaa is any amino acid
<220> FEATURE:
<221> NAME/KEY: MISC_FEATURE
<222> LOCATION: (135)..(135)
<223> OTHER INFORMATION: Xaa is R, H, or K
<220> FEATURE:
<221> NAME/KEY: MISC_FEATURE
<222> LOCATION: (136)..(142)
<223> OTHER INFORMATION: Xaa is any amino acid
<220> FEATURE:
<221> NAME/KEY: MISC_FEATURE
<222> LOCATION: (143)..(143)
<223> OTHER INFORMATION: Xaa is S, T, N or Q
<220> FEATURE:
<221> NAME/KEY: MISC_FEATURE
<222> LOCATION: (144)..(144)
<223> OTHER INFORMATION: Xaa is D or E
<220> FEATURE:
<221> NAME/KEY: MISC_FEATURE
<222> LOCATION: (145)..(145)
<223> OTHER INFORMATION: Xaa is any amino acid
<220> FEATURE:
<221> NAME/KEY: MISC_FEATURE
<222> LOCATION: (146)..(146)
<223> OTHER INFORMATION: Xaa is F, W, or Y
<220> FEATURE:
<221> NAME/KEY: MISC_FEATURE
<222> LOCATION: (147)..(147)
<223> OTHER INFORMATION: Xaa is any amino acid
<220> FEATURE:
<221> NAME/KEY: MISC_FEATURE
<222> LOCATION: (148)..(148)
<223> OTHER INFORMATION: Xaa is A, C, G, P, M, V, I, L, Sce or Sme
<220> FEATURE:
<221> NAME/KEY: MISC_FEATURE
<222> LOCATION: (149)..(149)
<223> OTHER INFORMATION: Xaa is D or E
<220> FEATURE:
<221> NAME/KEY: MISC_FEATURE
<222> LOCATION: (150)..(150)
<223> OTHER INFORMATION: Xaa is R, H, or K
<220> FEATURE:
<221> NAME/KEY: MISC_FEATURE
<222> LOCATION: (151)..(152)
<223> OTHER INFORMATION: Xaa is any amino acid
<220> FEATURE:
<221> NAME/KEY: MISC_FEATURE
<222> LOCATION: (153)..(154)
<223> OTHER INFORMATION: Xaa is F, W, or Y
<220> FEATURE:
<221> NAME/KEY: MISC_FEATURE
<222> LOCATION: (155)..(158)
<223> OTHER INFORMATION: Xaa is any amino acid

<400> SEQUENCE: 19

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
```

```
              35                  40                  45
Ile Gly Xaa Arg Ala Ala Xaa Ile Phe Xaa Xaa Asp Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
             85                  90                  95

Xaa Xaa Xaa Xaa Xaa Xaa Xaa Xaa Xaa Xaa Xaa Xaa Xaa Xaa Xaa Leu
            100                 105                 110

Ala Xaa Xaa Val Ala Xaa Gln Xaa Xaa Xaa Xaa Xaa Xaa Xaa Xaa Xaa
           115                 120                 125

Xaa Xaa Xaa Xaa Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Xaa Xaa Xaa Xaa
145                 150                 155

<210> SEQ ID NO 20
<211> LENGTH: 113
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (2)..(4)
<223> OTHER INFORMATION: Xaa is A, C, G, P, M, V, I, L, Sce, Sme
<220> FEATURE:
<221> NAME/KEY: MISC_FEATURE
<222> LOCATION: (5)..(6)
<223> OTHER INFORMATION: Xaa is S, T, N, or Q
<220> FEATURE:
<221> NAME/KEY: MISC_FEATURE
<222> LOCATION: (7)..(7)
<223> OTHER INFORMATION: Xaa is F, W, or Y
<220> FEATURE:
<221> NAME/KEY: MISC_FEATURE
<222> LOCATION: (8)..(8)
<223> OTHER INFORMATION: Xaa is A, C, G, P, M, V, I, L, Sce, Sme
<220> FEATURE:
<221> NAME/KEY: MISC_FEATURE
<222> LOCATION: (9)..(10)
<223> OTHER INFORMATION: Xaa is S, T, N, or Q
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is A, C, G, P, M, V, I, L, Sce, Sme
<220> FEATURE:
<221> NAME/KEY: MISC_FEATURE
<222> LOCATION: (13)..(14)
<223> OTHER INFORMATION: Xaa is any amino acid
<220> FEATURE:
<221> NAME/KEY: MISC_FEATURE
<222> LOCATION: (16)..(17)
<223> OTHER INFORMATION: Xaa is any amino acid
<220> FEATURE:
<221> NAME/KEY: MISC_FEATURE
<222> LOCATION: (20)..(21)
<223> OTHER INFORMATION: Xaa is A, C, G, P, M, V, I, L, Sce, Sme
<220> FEATURE:
<221> NAME/KEY: MISC_FEATURE
<222> LOCATION: (24)..(24)
<223> OTHER INFORMATION: Xaa is F, W, or Y
<220> FEATURE:
```

```
<221> NAME/KEY: MISC_FEATURE
<222> LOCATION: (28)..(28)
<223> OTHER INFORMATION: Xaa is S, T, N, or Q
<220> FEATURE:
<221> NAME/KEY: MISC_FEATURE
<222> LOCATION: (32)..(32)
<223> OTHER INFORMATION: Xaa is A, C, G, P, M, V, I, L, Sce, Sme
<220> FEATURE:
<221> NAME/KEY: MISC_FEATURE
<222> LOCATION: (33)..(33)
<223> OTHER INFORMATION: Xaa is any amino acid
<220> FEATURE:
<221> NAME/KEY: MISC_FEATURE
<222> LOCATION: (34)..(34)
<223> OTHER INFORMATION: Xaa is R, H, or K
<220> FEATURE:
<221> NAME/KEY: MISC_FEATURE
<222> LOCATION: (35)..(35)
<223> OTHER INFORMATION: Xaa is any amino acid
<220> FEATURE:
<221> NAME/KEY: MISC_FEATURE
<222> LOCATION: (37)..(37)
<223> OTHER INFORMATION: Xaa is D or E
<220> FEATURE:
<221> NAME/KEY: MISC_FEATURE
<222> LOCATION: (38)..(41)
<223> OTHER INFORMATION: Xaa is A, C, G, P, M, V, I, L, Sce, Sme
<220> FEATURE:
<221> NAME/KEY: MISC_FEATURE
<222> LOCATION: (42)..(42)
<223> OTHER INFORMATION: Xaa is S, T, N, or Q
<220> FEATURE:
<221> NAME/KEY: MISC_FEATURE
<222> LOCATION: (43)..(43)
<223> OTHER INFORMATION: Xaa is F, W, or Y
<220> FEATURE:
<221> NAME/KEY: MISC_FEATURE
<222> LOCATION: (44)..(44)
<223> OTHER INFORMATION: Xaa is R, H, or K
<220> FEATURE:
<221> NAME/KEY: MISC_FEATURE
<222> LOCATION: (45)..(46)
<223> OTHER INFORMATION: Xaa is any amino acid
<220> FEATURE:
<221> NAME/KEY: MISC_FEATURE
<222> LOCATION: (47)..(47)
<223> OTHER INFORMATION: Xaa is S, T, N, or Q
<220> FEATURE:
<221> NAME/KEY: MISC_FEATURE
<222> LOCATION: (48)..(49)
<223> OTHER INFORMATION: Xaa is A, C, G, P, M, V, I, L, Sce, Sme
<220> FEATURE:
<221> NAME/KEY: MISC_FEATURE
<222> LOCATION: (50)..(50)
<223> OTHER INFORMATION: Xaa is R, H, or K
<220> FEATURE:
<221> NAME/KEY: MISC_FEATURE
<222> LOCATION: (51)..(52)
<223> OTHER INFORMATION: Xaa is F, W, or Y
<220> FEATURE:
<221> NAME/KEY: MISC_FEATURE
<222> LOCATION: (53)..(53)
<223> OTHER INFORMATION: Xaa is A, C, G, P, M, V, I, L, Sce, Sme
<220> FEATURE:
<221> NAME/KEY: MISC_FEATURE
<222> LOCATION: (54)..(54)
<223> OTHER INFORMATION: Xaa is S, T, N, or Q
<220> FEATURE:
<221> NAME/KEY: MISC_FEATURE
<222> LOCATION: (55)..(57)
<223> OTHER INFORMATION: Xaa is any amino acid
<220> FEATURE:
<221> NAME/KEY: MISC_FEATURE
<222> LOCATION: (58)..(61)
<223> OTHER INFORMATION: Xaa is A, C, G, P, M, V, I, L, Sce, Sme
<220> FEATURE:
<221> NAME/KEY: MISC_FEATURE
<222> LOCATION: (62)..(62)
<223> OTHER INFORMATION: Xaa is R, H, or K
```

-continued

```
<220> FEATURE:
<221> NAME/KEY: MISC_FEATURE
<222> LOCATION: (63)..(63)
<223> OTHER INFORMATION: Xaa is A, C, G, P, M, V, I, L, Sce, Sme
<220> FEATURE:
<221> NAME/KEY: MISC_FEATURE
<222> LOCATION: (64)..(64)
<223> OTHER INFORMATION: Xaa is D or E
<220> FEATURE:
<221> NAME/KEY: MISC_FEATURE
<222> LOCATION: (65)..(65)
<223> OTHER INFORMATION: Xaa is A, C, G, P, M, V, I, L, Sce, Sme
<220> FEATURE:
<221> NAME/KEY: MISC_FEATURE
<222> LOCATION: (66)..(67)
<223> OTHER INFORMATION: Xaa is any amino acid
<220> FEATURE:
<221> NAME/KEY: MISC_FEATURE
<222> LOCATION: (68)..(68)
<223> OTHER INFORMATION: Xaa is A, C, G, P, M, V, I, L, Sce, Sme
<220> FEATURE:
<221> NAME/KEY: MISC_FEATURE
<222> LOCATION: (69)..(69)
<223> OTHER INFORMATION: Xaa is any amino acid
<220> FEATURE:
<221> NAME/KEY: MISC_FEATURE
<222> LOCATION: (70)..(70)
<223> OTHER INFORMATION: Xaa is A, C, G, P, M, V, I, L, Sce, Sme
<220> FEATURE:
<221> NAME/KEY: MISC_FEATURE
<222> LOCATION: (71)..(72)
<223> OTHER INFORMATION: Xaa is any amino acid
<220> FEATURE:
<221> NAME/KEY: MISC_FEATURE
<222> LOCATION: (73)..(73)
<223> OTHER INFORMATION: Xaa is D or E
<220> FEATURE:
<221> NAME/KEY: MISC_FEATURE
<222> LOCATION: (74)..(74)
<223> OTHER INFORMATION: Xaa is A, C, G, P, M, V, I, L, Sce, Sme
<220> FEATURE:
<221> NAME/KEY: MISC_FEATURE
<222> LOCATION: (75)..(75)
<223> OTHER INFORMATION: Xaa is any amino acid
<220> FEATURE:
<221> NAME/KEY: MISC_FEATURE
<222> LOCATION: (76)..(76)
<223> OTHER INFORMATION: Xaa is R, H, or K
<220> FEATURE:
<221> NAME/KEY: MISC_FEATURE
<222> LOCATION: (77)..(77)
<223> OTHER INFORMATION: Xaa is A, C, G, P, M, V, I, L, Sce, Sme
<220> FEATURE:
<221> NAME/KEY: MISC_FEATURE
<222> LOCATION: (78)..(79)
<223> OTHER INFORMATION: Xaa is S, T, N, or Q
<220> FEATURE:
<221> NAME/KEY: MISC_FEATURE
<222> LOCATION: (81)..(81)
<223> OTHER INFORMATION: Xaa is A, C, G, P, M, V, I, L, Sce, Sme
<220> FEATURE:
<221> NAME/KEY: MISC_FEATURE
<222> LOCATION: (82)..(82)
<223> OTHER INFORMATION: Xaa is S, T, N, or Q
<220> FEATURE:
<221> NAME/KEY: MISC_FEATURE
<222> LOCATION: (85)..(85)
<223> OTHER INFORMATION: Xaa is A, C, G, P, M, V, I, L, Sce, Sme
<220> FEATURE:
<221> NAME/KEY: MISC_FEATURE
<222> LOCATION: (89)..(89)
<223> OTHER INFORMATION: Xaa is A, C, G, P, M, V, I, L, Sce, Sme
<220> FEATURE:
<221> NAME/KEY: MISC_FEATURE
<222> LOCATION: (90)..(90)
<223> OTHER INFORMATION: Xaa is any amino acid
<220> FEATURE:
<221> NAME/KEY: MISC_FEATURE
<222> LOCATION: (91)..(91)
```

```
<223> OTHER INFORMATION: Xaa is A, C, G, P, M, V, I, L, Sce, Sme
<220> FEATURE:
<221> NAME/KEY: MISC_FEATURE
<222> LOCATION: (92)..(92)
<223> OTHER INFORMATION: Xaa is any amino acid
<220> FEATURE:
<221> NAME/KEY: MISC_FEATURE
<222> LOCATION: (93)..(93)
<223> OTHER INFORMATION: Xaa is A, C, G, P, M, V, I, L, Sce, Sme
<220> FEATURE:
<221> NAME/KEY: MISC_FEATURE
<222> LOCATION: (94)..(94)
<223> OTHER INFORMATION: Xaa is any amino acid
<220> FEATURE:
<221> NAME/KEY: MISC_FEATURE
<222> LOCATION: (95)..(95)
<223> OTHER INFORMATION: Xaa is R, H, or K
<220> FEATURE:
<221> NAME/KEY: MISC_FEATURE
<222> LOCATION: (96)..(96)
<223> OTHER INFORMATION: Xaa is A, C, G, P, M, V, I, L, Sce, Sme
<220> FEATURE:
<221> NAME/KEY: MISC_FEATURE
<222> LOCATION: (97)..(97)
<223> OTHER INFORMATION: Xaa is F, W, or Y
<220> FEATURE:
<221> NAME/KEY: MISC_FEATURE
<222> LOCATION: (98)..(99)
<223> OTHER INFORMATION: Xaa is A, C, G, P, M, V, I, L, Sce, Sme
<220> FEATURE:
<221> NAME/KEY: MISC_FEATURE
<222> LOCATION: (100)..(101)
<223> OTHER INFORMATION: Xaa is F, W, or Y
<220> FEATURE:
<221> NAME/KEY: MISC_FEATURE
<222> LOCATION: (102)..(102)
<223> OTHER INFORMATION: Xaa is any amino acid
<220> FEATURE:
<221> NAME/KEY: MISC_FEATURE
<222> LOCATION: (103)..(103)
<223> OTHER INFORMATION: Xaa is A, C, G, P, M, V, I, L, Sce, Sme
<220> FEATURE:
<221> NAME/KEY: MISC_FEATURE
<222> LOCATION: (104)..(104)
<223> OTHER INFORMATION: Xaa is any amino acid
<220> FEATURE:
<221> NAME/KEY: MISC_FEATURE
<222> LOCATION: (105)..(105)
<223> OTHER INFORMATION: Xaa is R, H, or K
<220> FEATURE:
<221> NAME/KEY: MISC_FEATURE
<222> LOCATION: (106)..(107)
<223> OTHER INFORMATION: Xaa is A, C, G, P, M, V, I, L, Sce, Sme
<220> FEATURE:
<221> NAME/KEY: MISC_FEATURE
<222> LOCATION: (108)..(108)
<223> OTHER INFORMATION: Xaa is any amino acid
<220> FEATURE:
<221> NAME/KEY: MISC_FEATURE
<222> LOCATION: (109)..(109)
<223> OTHER INFORMATION: Xaa is S, T, N, or Q
<220> FEATURE:
<221> NAME/KEY: MISC_FEATURE
<222> LOCATION: (110)..(110)
<223> OTHER INFORMATION: Xaa is A, C, G, P, M, V, I, L, Sce, Sme
<220> FEATURE:
<221> NAME/KEY: MISC_FEATURE
<222> LOCATION: (111)..(113)
<223> OTHER INFORMATION: Xaa is any amino acid

<400> SEQUENCE: 20

Xaa Xaa Xaa Xaa Xaa Xaa Xaa Xaa Xaa Xaa Xaa Xaa Xaa His Xaa
1               5                   10                  15

Xaa Leu Leu Xaa Xaa Ile Ile Xaa Arg Ile Val Xaa Arg Val Val Xaa
            20                  25                  30

Xaa Xaa Xaa Glu Xaa Xaa Xaa Xaa Xaa Xaa Xaa Xaa Xaa Xaa Xaa
```

```
              35                  40                  45
Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Ile
65                  70                  75                  80

Xaa Xaa Ala Ala Xaa Thr Ala Val Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa

<210> SEQ ID NO 21
<211> LENGTH: 159
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or optionally absent
<220> FEATURE:
<221> NAME/KEY: MISC_FEATURE
<222> LOCATION: (2)..(2)
<223> OTHER INFORMATION: Xaa is A, C, G, P, M, V, I, L, Sme, or Sce
<220> FEATURE:
<221> NAME/KEY: MISC_FEATURE
<222> LOCATION: (3)..(3)
<223> OTHER INFORMATION: Xaa is D or E
<220> FEATURE:
<221> NAME/KEY: MISC_FEATURE
<222> LOCATION: (4)..(7)
<223> OTHER INFORMATION: Xaa is A, C, G, P, M, V, I, L, Sme, or Sce
<220> FEATURE:
<221> NAME/KEY: MISC_FEATURE
<222> LOCATION: (8)..(8)
<223> OTHER INFORMATION: Xaa is D or E
<220> FEATURE:
<221> NAME/KEY: MISC_FEATURE
<222> LOCATION: (9)..(9)
<223> OTHER INFORMATION: Xaa is A, C, G, P, M, V, I, L, Sme, or Sce
<220> FEATURE:
<221> NAME/KEY: MISC_FEATURE
<222> LOCATION: (10)..(10)
<223> OTHER INFORMATION: Xaa is R, H or K
<220> FEATURE:
<221> NAME/KEY: MISC_FEATURE
<222> LOCATION: (11)..(11)
<223> OTHER INFORMATION: Xaa is D or E
<220> FEATURE:
<221> NAME/KEY: MISC_FEATURE
<222> LOCATION: (12)..(12)
<223> OTHER INFORMATION: Xaa is A, C, G, P, M, V, I, L, Sme, or Sce
<220> FEATURE:
<221> NAME/KEY: MISC_FEATURE
<222> LOCATION: (13)..(13)
<223> OTHER INFORMATION: Xaa is S, T, N, or Q
<220> FEATURE:
<221> NAME/KEY: MISC_FEATURE
<222> LOCATION: (14)..(15)
<223> OTHER INFORMATION: Xaa is A, C, G, P, M, V, I, L, Sme, or Sce
<220> FEATURE:
<221> NAME/KEY: MISC_FEATURE
<222> LOCATION: (16)..(16)
<223> OTHER INFORMATION: Xaa is D or E
<220> FEATURE:
<221> NAME/KEY: MISC_FEATURE
<222> LOCATION: (17)..(20)
<223> OTHER INFORMATION: Xaa is A, C, G, P, M, V, I, L, Sme, or Sce
<220> FEATURE:
<221> NAME/KEY: MISC_FEATURE
<222> LOCATION: (21)..(21)
<223> OTHER INFORMATION: Xaa is F, W or Y
```

```
<220> FEATURE:
<221> NAME/KEY: MISC_FEATURE
<222> LOCATION: (22)..(22)
<223> OTHER INFORMATION: Xaa is A, C, G, P, M, V, I, L, Sme, or Sce
<220> FEATURE:
<221> NAME/KEY: MISC_FEATURE
<222> LOCATION: (23)..(23)
<223> OTHER INFORMATION: Xaa is S, T, N, or Q
<220> FEATURE:
<221> NAME/KEY: MISC_FEATURE
<222> LOCATION: (24)..(25)
<223> OTHER INFORMATION: Xaa is A, C, G, P, M, V, I, L, Sme, or Sce
<220> FEATURE:
<221> NAME/KEY: MISC_FEATURE
<222> LOCATION: (26)..(26)
<223> OTHER INFORMATION: Xaa is D or E
<220> FEATURE:
<221> NAME/KEY: MISC_FEATURE
<222> LOCATION: (27)..(27)
<223> OTHER INFORMATION: Xaa is A, C, G, P, M, V, I, L, Sme, or Sce
<220> FEATURE:
<221> NAME/KEY: MISC_FEATURE
<222> LOCATION: (28)..(28)
<223> OTHER INFORMATION: Xaa is D or E
<220> FEATURE:
<221> NAME/KEY: MISC_FEATURE
<222> LOCATION: (29)..(29)
<223> OTHER INFORMATION: Xaa is A, C, G, P, M, V, I, L, Sme, or Sce
<220> FEATURE:
<221> NAME/KEY: MISC_FEATURE
<222> LOCATION: (30)..(30)
<223> OTHER INFORMATION: Xaa is R, H or K
<220> FEATURE:
<221> NAME/KEY: MISC_FEATURE
<222> LOCATION: (31)..(32)
<223> OTHER INFORMATION: Xaa is A, C, G, P, M, V, I, L, Sme, or Sce
<220> FEATURE:
<221> NAME/KEY: MISC_FEATURE
<222> LOCATION: (33)..(33)
<223> OTHER INFORMATION: Xaa is D or E
<220> FEATURE:
<221> NAME/KEY: MISC_FEATURE
<222> LOCATION: (34)..(36)
<223> OTHER INFORMATION: Xaa is A, C, G, P, M, V, I, L, Sme, or Sce
<220> FEATURE:
<221> NAME/KEY: MISC_FEATURE
<222> LOCATION: (37)..(37)
<223> OTHER INFORMATION: Xaa is S, T, N, or Q
<220> FEATURE:
<221> NAME/KEY: MISC_FEATURE
<222> LOCATION: (38)..(39)
<223> OTHER INFORMATION: Xaa is A, C, G, P, M, V, I, L, Sme, or Sce
<220> FEATURE:
<221> NAME/KEY: MISC_FEATURE
<222> LOCATION: (40)..(40)
<223> OTHER INFORMATION: Xaa is D or E
<220> FEATURE:
<221> NAME/KEY: MISC_FEATURE
<222> LOCATION: (41)..(41)
<223> OTHER INFORMATION: Xaa is A, C, G, P, M, V, I, L, Sme, or Sce
<220> FEATURE:
<221> NAME/KEY: MISC_FEATURE
<222> LOCATION: (42)..(42)
<223> OTHER INFORMATION: Xaa is R, H or K
<220> FEATURE:
<221> NAME/KEY: MISC_FEATURE
<222> LOCATION: (43)..(43)
<223> OTHER INFORMATION: Xaa is A, C, G, P, M, V, I, L, Sme, or Sce
<220> FEATURE:
<221> NAME/KEY: MISC_FEATURE
<222> LOCATION: (44)..(44)
<223> OTHER INFORMATION: Xaa is D or E
<220> FEATURE:
<221> NAME/KEY: MISC_FEATURE
<222> LOCATION: (45)..(45)
<223> OTHER INFORMATION: Xaa is A, C, G, P, M, V, I, L, Sme, or Sce
<220> FEATURE:
<221> NAME/KEY: MISC_FEATURE
<222> LOCATION: (46)..(46)
```

```
<223> OTHER INFORMATION: Xaa is D or E
<220> FEATURE:
<221> NAME/KEY: MISC_FEATURE
<222> LOCATION: (47)..(47)
<223> OTHER INFORMATION: Xaa is A, C, G, P, M, V, I, L, Sme, or Sce
<220> FEATURE:
<221> NAME/KEY: MISC_FEATURE
<222> LOCATION: (48)..(48)
<223> OTHER INFORMATION: Xaa is R, H or K
<220> FEATURE:
<221> NAME/KEY: MISC_FEATURE
<222> LOCATION: (49)..(50)
<223> OTHER INFORMATION: Xaa is A, C, G, P, M, V, I, L, Sme, or Sce
<220> FEATURE:
<221> NAME/KEY: MISC_FEATURE
<222> LOCATION: (51)..(51)
<223> OTHER INFORMATION: Xaa is R, H or K
<220> FEATURE:
<221> NAME/KEY: MISC_FEATURE
<222> LOCATION: (52)..(53)
<223> OTHER INFORMATION: Xaa is S, T, N, or Q
<220> FEATURE:
<221> NAME/KEY: MISC_FEATURE
<222> LOCATION: (54)..(54)
<223> OTHER INFORMATION: Xaa is A, C, G, P, M, V, I, L, Sme, or Sce
<220> FEATURE:
<221> NAME/KEY: MISC_FEATURE
<222> LOCATION: (55)..(55)
<223> OTHER INFORMATION: Xaa is S, T, N, or Q
<220> FEATURE:
<221> NAME/KEY: MISC_FEATURE
<222> LOCATION: (56)..(56)
<223> OTHER INFORMATION: Xaa is A, C, G, P, M, V, I, L, Sme, or Sce
<220> FEATURE:
<221> NAME/KEY: MISC_FEATURE
<222> LOCATION: (57)..(57)
<223> OTHER INFORMATION: Xaa is F, W or Y
<220> FEATURE:
<221> NAME/KEY: MISC_FEATURE
<222> LOCATION: (58)..(58)
<223> OTHER INFORMATION: Xaa is A, C, G, P, M, V, I, L, Sme, or Sce
<220> FEATURE:
<221> NAME/KEY: MISC_FEATURE
<222> LOCATION: (59)..(59)
<223> OTHER INFORMATION: Xaa is D or E
<220> FEATURE:
<221> NAME/KEY: MISC_FEATURE
<222> LOCATION: (60)..(60)
<223> OTHER INFORMATION: Xaa is A, C, G, P, M, V, I, L, Sme, or Sce
<220> FEATURE:
<221> NAME/KEY: MISC_FEATURE
<222> LOCATION: (61)..(62)
<223> OTHER INFORMATION: Xaa is F, W or Y
<220> FEATURE:
<221> NAME/KEY: MISC_FEATURE
<222> LOCATION: (63)..(64)
<223> OTHER INFORMATION: Xaa is A, C, G, P, M, V, I, L, Sme, or Sce
<220> FEATURE:
<221> NAME/KEY: MISC_FEATURE
<222> LOCATION: (65)..(65)
<223> OTHER INFORMATION: Xaa is F, W or Y
<220> FEATURE:
<221> NAME/KEY: MISC_FEATURE
<222> LOCATION: (66)..(66)
<223> OTHER INFORMATION: Xaa is A, C, G, P, M, V, I, L, Sme, or Sce
<220> FEATURE:
<221> NAME/KEY: MISC_FEATURE
<222> LOCATION: (67)..(67)
<223> OTHER INFORMATION: Xaa is S, T, N, or Q
<220> FEATURE:
<221> NAME/KEY: MISC_FEATURE
<222> LOCATION: (68)..(68)
<223> OTHER INFORMATION: Xaa is A, C, G, P, M, V, I, L, Sme, or Sce
<220> FEATURE:
<221> NAME/KEY: MISC_FEATURE
<222> LOCATION: (84)..(84)
<223> OTHER INFORMATION: Xaa is S, T, N, or Q
<220> FEATURE:
<221> NAME/KEY: MISC_FEATURE
```

-continued

```
<222> LOCATION: (85)..(90)
<223> OTHER INFORMATION: Xaa is A, C, G, P, M, V, I, L, Sme, or Sce
<220> FEATURE:
<221> NAME/KEY: MISC_FEATURE
<222> LOCATION: (91)..(92)
<223> OTHER INFORMATION: Xaa is D or E
<220> FEATURE:
<221> NAME/KEY: MISC_FEATURE
<222> LOCATION: (93)..(94)
<223> OTHER INFORMATION: Xaa is A, C, G, P, M, V, I, L, Sme, or Sce
<220> FEATURE:
<221> NAME/KEY: MISC_FEATURE
<222> LOCATION: (95)..(95)
<223> OTHER INFORMATION: Xaa is R, H or K
<220> FEATURE:
<221> NAME/KEY: MISC_FEATURE
<222> LOCATION: (96)..(96)
<223> OTHER INFORMATION: Xaa is F, W or Y
<220> FEATURE:
<221> NAME/KEY: MISC_FEATURE
<222> LOCATION: (97)..(98)
<223> OTHER INFORMATION: Xaa is A, C, G, P, M, V, I, L, Sme, or Sce
<220> FEATURE:
<221> NAME/KEY: MISC_FEATURE
<222> LOCATION: (99)..(99)
<223> OTHER INFORMATION: Xaa is S, T, N, or Q
<220> FEATURE:
<221> NAME/KEY: MISC_FEATURE
<222> LOCATION: (100)..(102)
<223> OTHER INFORMATION: Xaa is A, C, G, P, M, V, I, L, Sme, or Sce
<220> FEATURE:
<221> NAME/KEY: MISC_FEATURE
<222> LOCATION: (103)..(103)
<223> OTHER INFORMATION: Xaa is D or E
<220> FEATURE:
<221> NAME/KEY: MISC_FEATURE
<222> LOCATION: (104)..(104)
<223> OTHER INFORMATION: Xaa is R, H or K
<220> FEATURE:
<221> NAME/KEY: MISC_FEATURE
<222> LOCATION: (105)..(105)
<223> OTHER INFORMATION: Xaa is D or E
<220> FEATURE:
<221> NAME/KEY: MISC_FEATURE
<222> LOCATION: (106)..(107)
<223> OTHER INFORMATION: Xaa is R, H or K
<220> FEATURE:
<221> NAME/KEY: MISC_FEATURE
<222> LOCATION: (108)..(109)
<223> OTHER INFORMATION: Xaa is A, C, G, P, M, V, I, L, Sme, or Sce
<220> FEATURE:
<221> NAME/KEY: MISC_FEATURE
<222> LOCATION: (110)..(110)
<223> OTHER INFORMATION: Xaa is F, W or Y
<220> FEATURE:
<221> NAME/KEY: MISC_FEATURE
<222> LOCATION: (111)..(113)
<223> OTHER INFORMATION: Xaa is A, C, G, P, M, V, I, L, Sme, or Sce
<220> FEATURE:
<221> NAME/KEY: MISC_FEATURE
<222> LOCATION: (122)..(123)
<223> OTHER INFORMATION: Xaa is S, T, N, or Q
<220> FEATURE:
<221> NAME/KEY: MISC_FEATURE
<222> LOCATION: (124)..(124)
<223> OTHER INFORMATION: Xaa is A, C, G, P, M, V, I, L, Sme, or Sce
<220> FEATURE:
<221> NAME/KEY: MISC_FEATURE
<222> LOCATION: (125)..(125)
<223> OTHER INFORMATION: Xaa is D or E
<220> FEATURE:
<221> NAME/KEY: MISC_FEATURE
<222> LOCATION: (126)..(126)
<223> OTHER INFORMATION: Xaa is R, H or K
<220> FEATURE:
<221> NAME/KEY: MISC_FEATURE
<222> LOCATION: (127)..(127)
<223> OTHER INFORMATION: Xaa is S, T, N, or Q
<220> FEATURE:
```

```
<221> NAME/KEY: MISC_FEATURE
<222> LOCATION: (128)..(128)
<223> OTHER INFORMATION: Xaa is A, C, G, P, M, V, I, L, Sme, or Sce
<220> FEATURE:
<221> NAME/KEY: MISC_FEATURE
<222> LOCATION: (129)..(129)
<223> OTHER INFORMATION: Xaa is F, W or Y
<220> FEATURE:
<221> NAME/KEY: MISC_FEATURE
<222> LOCATION: (130)..(130)
<223> OTHER INFORMATION: Xaa is A, C, G, P, M, V, I, L, Sme, or Sce
<220> FEATURE:
<221> NAME/KEY: MISC_FEATURE
<222> LOCATION: (131)..(132)
<223> OTHER INFORMATION: Xaa is R, H or K
<220> FEATURE:
<221> NAME/KEY: MISC_FEATURE
<222> LOCATION: (133)..(133)
<223> OTHER INFORMATION: Xaa is A, C, G, P, M, V, I, L, Sme, or Sce
<220> FEATURE:
<221> NAME/KEY: MISC_FEATURE
<222> LOCATION: (134)..(136)
<223> OTHER INFORMATION: Xaa is D or E
<220> FEATURE:
<221> NAME/KEY: MISC_FEATURE
<222> LOCATION: (137)..(137)
<223> OTHER INFORMATION: Xaa is S, T, N, or Q
<220> FEATURE:
<221> NAME/KEY: MISC_FEATURE
<222> LOCATION: (138)..(140)
<223> OTHER INFORMATION: Xaa is A, C, G, P, M, V, I, L, Sme, or Sce
<220> FEATURE:
<221> NAME/KEY: MISC_FEATURE
<222> LOCATION: (141)..(141)
<223> OTHER INFORMATION: Xaa is R, H or K
<220> FEATURE:
<221> NAME/KEY: MISC_FEATURE
<222> LOCATION: (142)..(143)
<223> OTHER INFORMATION: Xaa is F, W or Y
<220> FEATURE:
<221> NAME/KEY: MISC_FEATURE
<222> LOCATION: (144)..(144)
<223> OTHER INFORMATION: Xaa is D or E
<220> FEATURE:
<221> NAME/KEY: MISC_FEATURE
<222> LOCATION: (153)..(153)
<223> OTHER INFORMATION: Xaa is R, H or K
<220> FEATURE:
<221> NAME/KEY: MISC_FEATURE
<222> LOCATION: (154)..(154)
<223> OTHER INFORMATION: Xaa is F, W or Y
<220> FEATURE:
<221> NAME/KEY: MISC_FEATURE
<222> LOCATION: (155)..(155)
<223> OTHER INFORMATION: Xaa is S, T, N, or Q
<220> FEATURE:
<221> NAME/KEY: MISC_FEATURE
<222> LOCATION: (156)..(156)
<223> OTHER INFORMATION: Xaa is A, C, G, P, M, V, I, L, Sme, or Sce
<220> FEATURE:
<221> NAME/KEY: MISC_FEATURE
<222> LOCATION: (157)..(157)
<223> OTHER INFORMATION: Xaa is S, T, N, or Q
<220> FEATURE:
<221> NAME/KEY: MISC_FEATURE
<222> LOCATION: (158)..(158)
<223> OTHER INFORMATION: Xaa is A, C, G, P, M, V, I, L, Sme, or Sce
<220> FEATURE:
<221> NAME/KEY: MISC_FEATURE
<222> LOCATION: (159)..(159)
<223> OTHER INFORMATION: Xaa is R, H or K

<400> SEQUENCE: 21

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
        20                  25                  30
```

```
Xaa Xaa Xaa Xaa Xaa Xaa Xaa Xaa Xaa Xaa Xaa Xaa Xaa Xaa Xaa
    35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Ala Tyr Ala Leu Ala Asn Asp Thr Gly Ala Ile
65                  70                  75                  80

Lys Thr Gly Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
        100                 105                 110

Xaa Thr Tyr Ala Leu Thr Phe Leu Ile Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
        130                 135                 140

Pro Phe Val Val Thr Tyr Phe Phe Xaa Xaa Xaa Xaa Xaa Xaa Xaa
145                 150                 155

<210> SEQ ID NO 22
<211> LENGTH: 184
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is any amino acid or is optionally absent
<220> FEATURE:
<221> NAME/KEY: MISC_FEATURE
<222> LOCATION: (2)..(3)
<223> OTHER INFORMATION: X is S, T, N or Q
<220> FEATURE:
<221> NAME/KEY: MISC_FEATURE
<222> LOCATION: (4)..(8)
<223> OTHER INFORMATION: X is A, C, G, P, M, V, I, L, Sce or Sme
<220> FEATURE:
<221> NAME/KEY: MISC_FEATURE
<222> LOCATION: (9)..(9)
<223> OTHER INFORMATION: X is D or E
<220> FEATURE:
<221> NAME/KEY: MISC_FEATURE
<222> LOCATION: (10)..(10)
<223> OTHER INFORMATION: X is A, C, G, P, M, V, I, L, Sce or Sme
<220> FEATURE:
<221> NAME/KEY: MISC_FEATURE
<222> LOCATION: (11)..(12)
<223> OTHER INFORMATION: X is S, T, N or Q
<220> FEATURE:
<221> NAME/KEY: MISC_FEATURE
<222> LOCATION: (13)..(14)
<223> OTHER INFORMATION: X is A, C, G, P, M, V, I, L, Sce or Sme
<220> FEATURE:
<221> NAME/KEY: MISC_FEATURE
<222> LOCATION: (15)..(15)
<223> OTHER INFORMATION: X is R, H, or K
<220> FEATURE:
<221> NAME/KEY: MISC_FEATURE
<222> LOCATION: (16)..(17)
<223> OTHER INFORMATION: X is A, C, G, P, M, V, I, L, Sce or Sme
<220> FEATURE:
<221> NAME/KEY: MISC_FEATURE
<222> LOCATION: (18)..(18)
<223> OTHER INFORMATION: X is D or E
<220> FEATURE:
<221> NAME/KEY: MISC_FEATURE
<222> LOCATION: (19)..(20)
<223> OTHER INFORMATION: X is A, C, G, P, M, V, I, L, Sce or Sme
<220> FEATURE:
<221> NAME/KEY: MISC_FEATURE
<222> LOCATION: (21)..(21)
```

-continued

```
<223> OTHER INFORMATION: X is D or E
<220> FEATURE:
<221> NAME/KEY: MISC_FEATURE
<222> LOCATION: (22)..(24)
<223> OTHER INFORMATION: X is A, C, G, P, M, V, I, L, Sce or Sme
<220> FEATURE:
<221> NAME/KEY: MISC_FEATURE
<222> LOCATION: (25)..(25)
<223> OTHER INFORMATION: X is R, H, or K
<220> FEATURE:
<221> NAME/KEY: MISC_FEATURE
<222> LOCATION: (26)..(26)
<223> OTHER INFORMATION: X is S, T, N or Q
<220> FEATURE:
<221> NAME/KEY: MISC_FEATURE
<222> LOCATION: (27)..(27)
<223> OTHER INFORMATION: X is A, C, G, P, M, V, I, L, Sce or Sme
<220> FEATURE:
<221> NAME/KEY: MISC_FEATURE
<222> LOCATION: (28)..(28)
<223> OTHER INFORMATION: X is S, T, N or Q
<220> FEATURE:
<221> NAME/KEY: MISC_FEATURE
<222> LOCATION: (29)..(29)
<223> OTHER INFORMATION: X is A, C, G, P, M, V, I, L, Sce or Sme
<220> FEATURE:
<221> NAME/KEY: MISC_FEATURE
<222> LOCATION: (30)..(30)
<223> OTHER INFORMATION: X is D or E
<220> FEATURE:
<221> NAME/KEY: MISC_FEATURE
<222> LOCATION: (31)..(33)
<223> OTHER INFORMATION: X is A, C, G, P, M, V, I, L, Sce or Sme
<220> FEATURE:
<221> NAME/KEY: MISC_FEATURE
<222> LOCATION: (34)..(34)
<223> OTHER INFORMATION: X is S, T, N or Q
<220> FEATURE:
<221> NAME/KEY: MISC_FEATURE
<222> LOCATION: (35)..(35)
<223> OTHER INFORMATION: X is R, H, or K
<220> FEATURE:
<221> NAME/KEY: MISC_FEATURE
<222> LOCATION: (36)..(36)
<223> OTHER INFORMATION: X is S, T, N or Q
<220> FEATURE:
<221> NAME/KEY: MISC_FEATURE
<222> LOCATION: (37)..(37)
<223> OTHER INFORMATION: X is A, C, G, P, M, V, I, L, Sce or Sme
<220> FEATURE:
<221> NAME/KEY: MISC_FEATURE
<222> LOCATION: (38)..(38)
<223> OTHER INFORMATION: X is S, T, N or Q
<220> FEATURE:
<221> NAME/KEY: MISC_FEATURE
<222> LOCATION: (39)..(40)
<223> OTHER INFORMATION: X is A, C, G, P, M, V, I, L, Sce or Sme
<220> FEATURE:
<221> NAME/KEY: MISC_FEATURE
<222> LOCATION: (41)..(41)
<223> OTHER INFORMATION: X is R, H, or K
<220> FEATURE:
<221> NAME/KEY: MISC_FEATURE
<222> LOCATION: (42)..(42)
<223> OTHER INFORMATION: X is F, W, or Y
<220> FEATURE:
<221> NAME/KEY: MISC_FEATURE
<222> LOCATION: (43)..(48)
<223> OTHER INFORMATION: X is A, C, G, P, M, V, I, L, Sce or Sme
<220> FEATURE:
<221> NAME/KEY: MISC_FEATURE
<222> LOCATION: (49)..(49)
<223> OTHER INFORMATION: X is D or E
<220> FEATURE:
<221> NAME/KEY: MISC_FEATURE
<222> LOCATION: (50)..(53)
<223> OTHER INFORMATION: X is A, C, G, P, M, V, I, L, Sce or Sme
<220> FEATURE:
<221> NAME/KEY: MISC_FEATURE
```

```
<222> LOCATION: (54)..(55)
<223> OTHER INFORMATION: X is S, T, N or Q
<220> FEATURE:
<221> NAME/KEY: MISC_FEATURE
<222> LOCATION: (56)..(57)
<223> OTHER INFORMATION: X is A, C, G, P, M, V, I, L, Sce or Sme
<220> FEATURE:
<221> NAME/KEY: MISC_FEATURE
<222> LOCATION: (58)..(58)
<223> OTHER INFORMATION: X is D or E
<220> FEATURE:
<221> NAME/KEY: MISC_FEATURE
<222> LOCATION: (59)..(59)
<223> OTHER INFORMATION: X is S, T, N or Q
<220> FEATURE:
<221> NAME/KEY: MISC_FEATURE
<222> LOCATION: (60)..(60)
<223> OTHER INFORMATION: X is A, C, G, P, M, V, I, L, Sce or Sme
<220> FEATURE:
<221> NAME/KEY: MISC_FEATURE
<222> LOCATION: (61)..(63)
<223> OTHER INFORMATION: X is S, T, N or Q
<220> FEATURE:
<221> NAME/KEY: MISC_FEATURE
<222> LOCATION: (64)..(65)
<223> OTHER INFORMATION: X is A, C, G, P, M, V, I, L, Sce or Sme
<220> FEATURE:
<221> NAME/KEY: MISC_FEATURE
<222> LOCATION: (66)..(66)
<223> OTHER INFORMATION: X is D or E
<220> FEATURE:
<221> NAME/KEY: MISC_FEATURE
<222> LOCATION: (67)..(69)
<223> OTHER INFORMATION: X is A, C, G, P, M, V, I, L, Sce or Sme
<220> FEATURE:
<221> NAME/KEY: MISC_FEATURE
<222> LOCATION: (70)..(70)
<223> OTHER INFORMATION: X is D or E
<220> FEATURE:
<221> NAME/KEY: MISC_FEATURE
<222> LOCATION: (71)..(71)
<223> OTHER INFORMATION: X is S, T, N or Q
<220> FEATURE:
<221> NAME/KEY: MISC_FEATURE
<222> LOCATION: (72)..(75)
<223> OTHER INFORMATION: X is A, C, G, P, M, V, I, L, Sce or Sme
<220> FEATURE:
<221> NAME/KEY: MISC_FEATURE
<222> LOCATION: (76)..(76)
<223> OTHER INFORMATION: X is S, T, N or Q
<220> FEATURE:
<221> NAME/KEY: MISC_FEATURE
<222> LOCATION: (77)..(77)
<223> OTHER INFORMATION: X is A, C, G, P, M, V, I, L, Sce or Sme
<220> FEATURE:
<221> NAME/KEY: MISC_FEATURE
<222> LOCATION: (78)..(78)
<223> OTHER INFORMATION: X is R, H, or K
<220> FEATURE:
<221> NAME/KEY: MISC_FEATURE
<222> LOCATION: (79)..(79)
<223> OTHER INFORMATION: X is A, C, G, P, M, V, I, L, Sce or Sme
<220> FEATURE:
<221> NAME/KEY: MISC_FEATURE
<222> LOCATION: (80)..(80)
<223> OTHER INFORMATION: X is S, T, N or Q
<220> FEATURE:
<221> NAME/KEY: MISC_FEATURE
<222> LOCATION: (81)..(85)
<223> OTHER INFORMATION: X is A, C, G, P, M, V, I, L, Sce or Sme
<220> FEATURE:
<221> NAME/KEY: MISC_FEATURE
<222> LOCATION: (86)..(86)
<223> OTHER INFORMATION: X is S, T, N or Q
<220> FEATURE:
<221> NAME/KEY: MISC_FEATURE
<222> LOCATION: (87)..(88)
<223> OTHER INFORMATION: X is A, C, G, P, M, V, I, L, Sce or Sme
<220> FEATURE:
```

```
<221> NAME/KEY: MISC_FEATURE
<222> LOCATION: (89)..(90)
<223> OTHER INFORMATION: X is S, T, N or Q
<220> FEATURE:
<221> NAME/KEY: MISC_FEATURE
<222> LOCATION: (91)..(91)
<223> OTHER INFORMATION: X is A, C, G, P, M, V, I, L, Sce or Sme
<220> FEATURE:
<221> NAME/KEY: MISC_FEATURE
<222> LOCATION: (92)..(92)
<223> OTHER INFORMATION: X is D or E
<220> FEATURE:
<221> NAME/KEY: MISC_FEATURE
<222> LOCATION: (93)..(94)
<223> OTHER INFORMATION: X is R, H, or K
<220> FEATURE:
<221> NAME/KEY: MISC_FEATURE
<222> LOCATION: (95)..(95)
<223> OTHER INFORMATION: X is S, T, N or Q
<220> FEATURE:
<221> NAME/KEY: MISC_FEATURE
<222> LOCATION: (97)..(97)
<223> OTHER INFORMATION: X is A, C, G, P, M, V, I, L, Sce or Sme
<220> FEATURE:
<221> NAME/KEY: MISC_FEATURE
<222> LOCATION: (98)..(98)
<223> OTHER INFORMATION: X is S, T, N or Q
<220> FEATURE:
<221> NAME/KEY: MISC_FEATURE
<222> LOCATION: (99)..(100)
<223> OTHER INFORMATION: X is A, C, G, P, M, V, I, L, Sce or Sme
<220> FEATURE:
<221> NAME/KEY: MISC_FEATURE
<222> LOCATION: (101)..(101)
<223> OTHER INFORMATION: X is D or E
<220> FEATURE:
<221> NAME/KEY: MISC_FEATURE
<222> LOCATION: (102)..(102)
<223> OTHER INFORMATION: X is S, T, N or Q
<220> FEATURE:
<221> NAME/KEY: MISC_FEATURE
<222> LOCATION: (103)..(103)
<223> OTHER INFORMATION: X is F, W, or Y
<220> FEATURE:
<221> NAME/KEY: MISC_FEATURE
<222> LOCATION: (104)..(104)
<223> OTHER INFORMATION: X is S, T, N or Q
<220> FEATURE:
<221> NAME/KEY: MISC_FEATURE
<222> LOCATION: (105)..(109)
<223> OTHER INFORMATION: X is A, C, G, P, M, V, I, L, Sce or Sme
<220> FEATURE:
<221> NAME/KEY: MISC_FEATURE
<222> LOCATION: (110)..(110)
<223> OTHER INFORMATION: X is S, T, N or Q
<220> FEATURE:
<221> NAME/KEY: MISC_FEATURE
<222> LOCATION: (111)..(112)
<223> OTHER INFORMATION: X is A, C, G, P, M, V, I, L, Sce or Sme
<220> FEATURE:
<221> NAME/KEY: MISC_FEATURE
<222> LOCATION: (113)..(113)
<223> OTHER INFORMATION: X is D or E
<220> FEATURE:
<221> NAME/KEY: MISC_FEATURE
<222> LOCATION: (116)..(116)
<223> OTHER INFORMATION: X is A, C, G, P, M, V, I, L, Sce or Sme
<220> FEATURE:
<221> NAME/KEY: MISC_FEATURE
<222> LOCATION: (121)..(121)
<223> OTHER INFORMATION: X is A, C, G, P, M, V, I, L, Sce or Sme
<220> FEATURE:
<221> NAME/KEY: MISC_FEATURE
<222> LOCATION: (122)..(122)
<223> OTHER INFORMATION: X is S, T, N or Q
<220> FEATURE:
<221> NAME/KEY: MISC_FEATURE
<222> LOCATION: (123)..(124)
<223> OTHER INFORMATION: X is A, C, G, P, M, V, I, L, Sce or Sme
```

```
<220> FEATURE:
<221> NAME/KEY: MISC_FEATURE
<222> LOCATION: (125)..(125)
<223> OTHER INFORMATION: X is R, H, or K
<220> FEATURE:
<221> NAME/KEY: MISC_FEATURE
<222> LOCATION: (126)..(126)
<223> OTHER INFORMATION: X is A, C, G, P, M, V, I, L, Sce or Sme
<220> FEATURE:
<221> NAME/KEY: MISC_FEATURE
<222> LOCATION: (127)..(127)
<223> OTHER INFORMATION: X is R, H, or K
<220> FEATURE:
<221> NAME/KEY: MISC_FEATURE
<222> LOCATION: (128)..(129)
<223> OTHER INFORMATION: X is A, C, G, P, M, V, I, L, Sce or Sme
<220> FEATURE:
<221> NAME/KEY: MISC_FEATURE
<222> LOCATION: (130)..(130)
<223> OTHER INFORMATION: X is F, W, or Y
<220> FEATURE:
<221> NAME/KEY: MISC_FEATURE
<222> LOCATION: (131)..(134)
<223> OTHER INFORMATION: X is A, C, G, P, M, V, I, L, Sce or Sme
<220> FEATURE:
<221> NAME/KEY: MISC_FEATURE
<222> LOCATION: (135)..(135)
<223> OTHER INFORMATION: X is R, H, or K
<220> FEATURE:
<221> NAME/KEY: MISC_FEATURE
<222> LOCATION: (136)..(136)
<223> OTHER INFORMATION: X is A, C, G, P, M, V, I, L, Sce or Sme
<220> FEATURE:
<221> NAME/KEY: MISC_FEATURE
<222> LOCATION: (137)..(137)
<223> OTHER INFORMATION: X is F, W, or Y
<220> FEATURE:
<221> NAME/KEY: MISC_FEATURE
<222> LOCATION: (138)..(142)
<223> OTHER INFORMATION: X is A, C, G, P, M, V, I, L, Sce or Sme
<220> FEATURE:
<221> NAME/KEY: MISC_FEATURE
<222> LOCATION: (158)..(158)
<223> OTHER INFORMATION: X is A, C, G, P, M, V, I, L, Sce or Sme
<220> FEATURE:
<221> NAME/KEY: MISC_FEATURE
<222> LOCATION: (161)..(161)
<223> OTHER INFORMATION: X is R, H, or K
<220> FEATURE:
<221> NAME/KEY: MISC_FEATURE
<222> LOCATION: (162)..(165)
<223> OTHER INFORMATION: X is A, C, G, P, M, V, I, L, Sce or Sme
<220> FEATURE:
<221> NAME/KEY: MISC_FEATURE
<222> LOCATION: (166)..(166)
<223> OTHER INFORMATION: X is F, W, or Y
<220> FEATURE:
<221> NAME/KEY: MISC_FEATURE
<222> LOCATION: (173)..(173)
<223> OTHER INFORMATION: X is A, C, G, P, M, V, I, L, Sce or Sme
<220> FEATURE:
<221> NAME/KEY: MISC_FEATURE
<222> LOCATION: (174)..(174)
<223> OTHER INFORMATION: X is R, H, or K
<220> FEATURE:
<221> NAME/KEY: MISC_FEATURE
<222> LOCATION: (175)..(175)
<223> OTHER INFORMATION: X is D or E
<220> FEATURE:
<221> NAME/KEY: MISC_FEATURE
<222> LOCATION: (176)..(177)
<223> OTHER INFORMATION: X is A, C, G, P, M, V, I, L, Sce or Sme
<220> FEATURE:
<221> NAME/KEY: MISC_FEATURE
<222> LOCATION: (178)..(178)
<223> OTHER INFORMATION: X is F, W, or Y
<220> FEATURE:
<221> NAME/KEY: MISC_FEATURE
<222> LOCATION: (179)..(179)
```

<223> OTHER INFORMATION: X is R, H, or K
<220> FEATURE:
<221> NAME/KEY: MISC_FEATURE
<222> LOCATION: (180)..(180)
<223> OTHER INFORMATION: X is S, T, N or Q
<220> FEATURE:
<221> NAME/KEY: MISC_FEATURE
<222> LOCATION: (181)..(182)
<223> OTHER INFORMATION: X is A, C, G, P, M, V, I, L, Sce or Sme
<220> FEATURE:
<221> NAME/KEY: MISC_FEATURE
<222> LOCATION: (183)..(183)
<223> OTHER INFORMATION: X is D or E
<220> FEATURE:
<221> NAME/KEY: MISC_FEATURE
<222> LOCATION: (184)..(184)
<223> OTHER INFORMATION: X is A, C, G, P, M, V, I, L, Sce or Sme

<400> SEQUENCE: 22

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Ala
            85                  90                  95

Xaa Xaa Xaa Xaa Xaa Xaa Xaa Xaa Xaa Xaa Xaa Xaa Xaa Xaa Xaa
        100                 105                 110

Xaa Leu Ala Xaa Lys Gly Ser Asn Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Asp Val
130                 135                 140

Leu Asp Val Ala Ala Ala Val Ala Thr Ala Ser Leu Ala Xaa Gly Ala
145                 150                 155                 160

Xaa Xaa Xaa Xaa Xaa Xaa Ala Ser Ile Ile Pro Arg Xaa Xaa Xaa Xaa
            165                 170                 175

Xaa Xaa Xaa Xaa Xaa Xaa Xaa Xaa
            180
```

<210> SEQ ID NO 23
<211> LENGTH: 103
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is any amino acid or is optionally absent
<220> FEATURE:
<221> NAME/KEY: MISC_FEATURE
<222> LOCATION: (2)..(3)
<223> OTHER INFORMATION: X is D or E
<220> FEATURE:
<221> NAME/KEY: MISC_FEATURE
<222> LOCATION: (4)..(7)
<223> OTHER INFORMATION: X is A, C, G, P, M, V, I, L, Sce or Sme
<220> FEATURE:
<221> NAME/KEY: MISC_FEATURE
<222> LOCATION: (8)..(8)
<223> OTHER INFORMATION: X is S, T, N, or Q -continued

```
<220> FEATURE:
<221> NAME/KEY: MISC_FEATURE
<222> LOCATION: (9)..(10)
<223> OTHER INFORMATION: X is A, C, G, P, M, V, I, L, Sce or Sme
<220> FEATURE:
<221> NAME/KEY: MISC_FEATURE
<222> LOCATION: (11)..(11)
<223> OTHER INFORMATION: X is S, T, N, or Q
<220> FEATURE:
<221> NAME/KEY: MISC_FEATURE
<222> LOCATION: (18)..(19)
<223> OTHER INFORMATION: X is A, C, G, P, M, V, I, L, Sce or Sme
<220> FEATURE:
<221> NAME/KEY: MISC_FEATURE
<222> LOCATION: (21)..(23)
<223> OTHER INFORMATION: X is A, C, G, P, M, V, I, L, Sce or Sme
<220> FEATURE:
<221> NAME/KEY: MISC_FEATURE
<222> LOCATION: (24)..(25)
<223> OTHER INFORMATION: X is D or E
<220> FEATURE:
<221> NAME/KEY: MISC_FEATURE
<222> LOCATION: (26)..(26)
<223> OTHER INFORMATION: X is R, H, or K
<220> FEATURE:
<221> NAME/KEY: MISC_FEATURE
<222> LOCATION: (27)..(31)
<223> OTHER INFORMATION: X is A, C, G, P, M, V, I, L, Sce or Sme
<220> FEATURE:
<221> NAME/KEY: MISC_FEATURE
<222> LOCATION: (32)..(32)
<223> OTHER INFORMATION: X is S, T, N, or Q
<220> FEATURE:
<221> NAME/KEY: MISC_FEATURE
<222> LOCATION: (34)..(34)
<223> OTHER INFORMATION: X is A, C, G, P, M, V, I, L, Sce or Sme
<220> FEATURE:
<221> NAME/KEY: MISC_FEATURE
<222> LOCATION: (39)..(39)
<223> OTHER INFORMATION: X is S, T, N, or Q
<220> FEATURE:
<221> NAME/KEY: MISC_FEATURE
<222> LOCATION: (41)..(41)
<223> OTHER INFORMATION: X is F, W, or Y
<220> FEATURE:
<221> NAME/KEY: MISC_FEATURE
<222> LOCATION: (42)..(42)
<223> OTHER INFORMATION: X is R, H, or K
<220> FEATURE:
<221> NAME/KEY: MISC_FEATURE
<222> LOCATION: (44)..(44)
<223> OTHER INFORMATION: X is S, T, N, or Q
<220> FEATURE:
<221> NAME/KEY: MISC_FEATURE
<222> LOCATION: (45)..(45)
<223> OTHER INFORMATION: X is A, C, G, P, M, V, I, L, Sce or Sme
<220> FEATURE:
<221> NAME/KEY: MISC_FEATURE
<222> LOCATION: (50)..(50)
<223> OTHER INFORMATION: X is D or E
<220> FEATURE:
<221> NAME/KEY: MISC_FEATURE
<222> LOCATION: (52)..(52)
<223> OTHER INFORMATION: X is D or E
<220> FEATURE:
<221> NAME/KEY: MISC_FEATURE
<222> LOCATION: (54)..(57)
<223> OTHER INFORMATION: X is A, C, G, P, M, V, I, L, Sce or Sme
<220> FEATURE:
<221> NAME/KEY: MISC_FEATURE
<222> LOCATION: (58)..(58)
<223> OTHER INFORMATION: X is R, H, or K
<220> FEATURE:
<221> NAME/KEY: MISC_FEATURE
<222> LOCATION: (59)..(61)
<223> OTHER INFORMATION: X is S, T, N, or Q
<220> FEATURE:
<221> NAME/KEY: MISC_FEATURE
<222> LOCATION: (62)..(62)
```

```
<223> OTHER INFORMATION: X is R, H, or K
<220> FEATURE:
<221> NAME/KEY: MISC_FEATURE
<222> LOCATION: (63)..(63)
<223> OTHER INFORMATION: X is A, C, G, P, M, V, I, L, Sce or Sme
<220> FEATURE:
<221> NAME/KEY: MISC_FEATURE
<222> LOCATION: (64)..(64)
<223> OTHER INFORMATION: X is F, W, or Y
<220> FEATURE:
<221> NAME/KEY: MISC_FEATURE
<222> LOCATION: (65)..(65)
<223> OTHER INFORMATION: X is A, C, G, P, M, V, I, L, Sce or Sme
<220> FEATURE:
<221> NAME/KEY: MISC_FEATURE
<222> LOCATION: (66)..(66)
<223> OTHER INFORMATION: X is R, H, or K
<220> FEATURE:
<221> NAME/KEY: MISC_FEATURE
<222> LOCATION: (67)..(67)
<223> OTHER INFORMATION: X is A, C, G, P, M, V, I, L, Sce or Sme
<220> FEATURE:
<221> NAME/KEY: MISC_FEATURE
<222> LOCATION: (68)..(68)
<223> OTHER INFORMATION: X is R, H, or K
<220> FEATURE:
<221> NAME/KEY: MISC_FEATURE
<222> LOCATION: (69)..(69)
<223> OTHER INFORMATION: X is D or E
<220> FEATURE:
<221> NAME/KEY: MISC_FEATURE
<222> LOCATION: (70)..(70)
<223> OTHER INFORMATION: X is R, H, or K
<220> FEATURE:
<221> NAME/KEY: MISC_FEATURE
<222> LOCATION: (71)..(71)
<223> OTHER INFORMATION: X is A, C, G, P, M, V, I, L, Sce or Sme
<220> FEATURE:
<221> NAME/KEY: MISC_FEATURE
<222> LOCATION: (72)..(72)
<223> OTHER INFORMATION: X is R, H, or K
<220> FEATURE:
<221> NAME/KEY: MISC_FEATURE
<222> LOCATION: (73)..(74)
<223> OTHER INFORMATION: X is A, C, G, P, M, V, I, L, Sce or Sme
<220> FEATURE:
<221> NAME/KEY: MISC_FEATURE
<222> LOCATION: (75)..(75)
<223> OTHER INFORMATION: X is R, H, or K
<220> FEATURE:
<221> NAME/KEY: MISC_FEATURE
<222> LOCATION: (76)..(76)
<223> OTHER INFORMATION: X is A, C, G, P, M, V, I, L, Sce or Sme
<220> FEATURE:
<221> NAME/KEY: MISC_FEATURE
<222> LOCATION: (77)..(77)
<223> OTHER INFORMATION: X is F, W, or Y
<220> FEATURE:
<221> NAME/KEY: MISC_FEATURE
<222> LOCATION: (78)..(78)
<223> OTHER INFORMATION: X is S, T, N, or Q
<220> FEATURE:
<221> NAME/KEY: MISC_FEATURE
<222> LOCATION: (79)..(80)
<223> OTHER INFORMATION: X is A, C, G, P, M, V, I, L, Sce or Sme
<220> FEATURE:
<221> NAME/KEY: MISC_FEATURE
<222> LOCATION: (81)..(81)
<223> OTHER INFORMATION: X is D or E
<220> FEATURE:
<221> NAME/KEY: MISC_FEATURE
<222> LOCATION: (82)..(88)
<223> OTHER INFORMATION: X is A, C, G, P, M, V, I, L, Sce or Sme
<220> FEATURE:
<221> NAME/KEY: MISC_FEATURE
<222> LOCATION: (89)..(89)
<223> OTHER INFORMATION: X is D or E
<220> FEATURE:
<221> NAME/KEY: MISC_FEATURE
```

```
<222> LOCATION: (90)..(90)
<223> OTHER INFORMATION: X is A, C, G, P, M, V, I, L, Sce or Sme
<220> FEATURE:
<221> NAME/KEY: MISC_FEATURE
<222> LOCATION: (91)..(91)
<223> OTHER INFORMATION: X is S, T, N, or Q
<220> FEATURE:
<221> NAME/KEY: MISC_FEATURE
<222> LOCATION: (92)..(92)
<223> OTHER INFORMATION: X is R, H, or K
<220> FEATURE:
<221> NAME/KEY: MISC_FEATURE
<222> LOCATION: (93)..(93)
<223> OTHER INFORMATION: X is D or E
<220> FEATURE:
<221> NAME/KEY: MISC_FEATURE
<222> LOCATION: (94)..(94)
<223> OTHER INFORMATION: X is F, W, or Y
<220> FEATURE:
<221> NAME/KEY: MISC_FEATURE
<222> LOCATION: (95)..(95)
<223> OTHER INFORMATION: X is A, C, G, P, M, V, I, L, Sce or Sme
<220> FEATURE:
<221> NAME/KEY: MISC_FEATURE
<222> LOCATION: (96)..(96)
<223> OTHER INFORMATION: X is D or E
<220> FEATURE:
<221> NAME/KEY: MISC_FEATURE
<222> LOCATION: (97)..(97)
<223> OTHER INFORMATION: X is F, W, or Y
<220> FEATURE:
<221> NAME/KEY: MISC_FEATURE
<222> LOCATION: (98)..(98)
<223> OTHER INFORMATION: X is A, C, G, P, M, V, I, L, Sce or Sme
<220> FEATURE:
<221> NAME/KEY: MISC_FEATURE
<222> LOCATION: (99)..(99)
<223> OTHER INFORMATION: X is R, H, or K
<220> FEATURE:
<221> NAME/KEY: MISC_FEATURE
<222> LOCATION: (100)..(100)
<223> OTHER INFORMATION: X is D or E
<220> FEATURE:
<221> NAME/KEY: MISC_FEATURE
<222> LOCATION: (101)..(102)
<223> OTHER INFORMATION: X is S, T, N, or Q
<220> FEATURE:
<221> NAME/KEY: MISC_FEATURE
<222> LOCATION: (103)..(103)
<223> OTHER INFORMATION: X is A, C, G, P, M, V, I, L, Sce or Sme

<400> SEQUENCE: 23

Xaa Xaa Xaa Xaa Xaa Xaa Xaa Xaa Xaa Xaa Xaa Ala Leu Val Ala Val
1               5                   10                  15

Lys Xaa Xaa His Xaa Xaa Xaa Xaa Xaa Xaa Xaa Xaa Xaa Xaa Xaa Xaa
            20                  25                  30

Ile Xaa Pro Gly Leu Thr Xaa Ile Xaa Xaa Trp Xaa Xaa Ser Val Val
        35                  40                  45

Ser Xaa His Xaa Leu Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa
            100

<210> SEQ ID NO 24
<211> LENGTH: 122
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (2)..(2)
<223> OTHER INFORMATION: Xaa is A, C, G, P, M, V, I, L, Sce, or Sme
<220> FEATURE:
<221> NAME/KEY: MISC_FEATURE
<222> LOCATION: (3)..(3)
<223> OTHER INFORMATION: Xaa is R, H or K
<220> FEATURE:
<221> NAME/KEY: MISC_FEATURE
<222> LOCATION: (4)..(5)
<223> OTHER INFORMATION: Xaa is A, C, G, P, M, V, I, L, Sce, or Sme
<220> FEATURE:
<221> NAME/KEY: MISC_FEATURE
<222> LOCATION: (6)..(6)
<223> OTHER INFORMATION: Xaa is R, H or K
<220> FEATURE:
<221> NAME/KEY: MISC_FEATURE
<222> LOCATION: (7)..(8)
<223> OTHER INFORMATION: Xaa is A, C, G, P, M, V, I, L, Sce, or Sme
<220> FEATURE:
<221> NAME/KEY: MISC_FEATURE
<222> LOCATION: (10)..(119)
<223> OTHER INFORMATION: Xaa is S, T, N, or Q
<220> FEATURE:
<221> NAME/KEY: MISC_FEATURE
<222> LOCATION: (11)..(11)
<223> OTHER INFORMATION: Xaa is A, C, G, P, M, V, I, L, Sce, or Sme
<220> FEATURE:
<221> NAME/KEY: MISC_FEATURE
<222> LOCATION: (14)..(14)
<223> OTHER INFORMATION: Xaa is D or E
<220> FEATURE:
<221> NAME/KEY: MISC_FEATURE
<222> LOCATION: (19)..(19)
<223> OTHER INFORMATION: Xaa is A, C, G, P, M, V, I, L, Sce, or Sme
<220> FEATURE:
<221> NAME/KEY: MISC_FEATURE
<222> LOCATION: (23)..(23)
<223> OTHER INFORMATION: Xaa is S, T, N, or Q
<220> FEATURE:
<221> NAME/KEY: MISC_FEATURE
<222> LOCATION: (26)..(27)
<223> OTHER INFORMATION: Xaa is A, C, G, P, M, V, I, L, Sce, or Sme
<220> FEATURE:
<221> NAME/KEY: MISC_FEATURE
<222> LOCATION: (30)..(31)
<223> OTHER INFORMATION: Xaa is A, C, G, P, M, V, I, L, Sce, or Sme
<220> FEATURE:
<221> NAME/KEY: MISC_FEATURE
<222> LOCATION: (33)..(33)
<223> OTHER INFORMATION: Xaa is A, C, G, P, M, V, I, L, Sce, or Sme
<220> FEATURE:
<221> NAME/KEY: MISC_FEATURE
<222> LOCATION: (34)..(34)
<223> OTHER INFORMATION: Xaa is S, T, N, or Q
<220> FEATURE:
<221> NAME/KEY: MISC_FEATURE
<222> LOCATION: (35)..(36)
<223> OTHER INFORMATION: Xaa is A, C, G, P, M, V, I, L, Sce, or Sme
<220> FEATURE:
<221> NAME/KEY: MISC_FEATURE
<222> LOCATION: (37)..(38)
<223> OTHER INFORMATION: Xaa is S, T, N, or Q
<220> FEATURE:
<221> NAME/KEY: MISC_FEATURE
<222> LOCATION: (39)..(39)
<223> OTHER INFORMATION: Xaa is F, W, or Y
<220> FEATURE:
<221> NAME/KEY: MISC_FEATURE
<222> LOCATION: (40)..(41)
<223> OTHER INFORMATION: Xaa is D or E
<220> FEATURE:
```

-continued

```
<221> NAME/KEY: MISC_FEATURE
<222> LOCATION: (42)..(46)
<223> OTHER INFORMATION: Xaa is A, C, G, P, M, V, I, L, Sce, or Sme
<220> FEATURE:
<221> NAME/KEY: MISC_FEATURE
<222> LOCATION: (47)..(47)
<223> OTHER INFORMATION: Xaa is F, W, or Y
<220> FEATURE:
<221> NAME/KEY: MISC_FEATURE
<222> LOCATION: (48)..(48)
<223> OTHER INFORMATION: Xaa is S, T, N, or Q
<220> FEATURE:
<221> NAME/KEY: MISC_FEATURE
<222> LOCATION: (49)..(49)
<223> OTHER INFORMATION: Xaa is A, C, G, P, M, V, I, L, Sce, or Sme
<220> FEATURE:
<221> NAME/KEY: MISC_FEATURE
<222> LOCATION: (50)..(50)
<223> OTHER INFORMATION: Xaa is S, T, N, or Q
<220> FEATURE:
<221> NAME/KEY: MISC_FEATURE
<222> LOCATION: (51)..(52)
<223> OTHER INFORMATION: Xaa is D or E
<220> FEATURE:
<221> NAME/KEY: MISC_FEATURE
<222> LOCATION: (53)..(53)
<223> OTHER INFORMATION: Xaa is A, C, G, P, M, V, I, L, Sce, or Sme
<220> FEATURE:
<221> NAME/KEY: MISC_FEATURE
<222> LOCATION: (54)..(55)
<223> OTHER INFORMATION: Xaa is S, T, N, or Q
<220> FEATURE:
<221> NAME/KEY: MISC_FEATURE
<222> LOCATION: (56)..(56)
<223> OTHER INFORMATION: Xaa is A, C, G, P, M, V, I, L, Sce, or Sme
<220> FEATURE:
<221> NAME/KEY: MISC_FEATURE
<222> LOCATION: (57)..(57)
<223> OTHER INFORMATION: Xaa is F, W, or Y
<220> FEATURE:
<221> NAME/KEY: MISC_FEATURE
<222> LOCATION: (58)..(59)
<223> OTHER INFORMATION: Xaa is A, C, G, P, M, V, I, L, Sce, or Sme
<220> FEATURE:
<221> NAME/KEY: MISC_FEATURE
<222> LOCATION: (62)..(62)
<223> OTHER INFORMATION: Xaa is A, C, G, P, M, V, I, L, Sce, or Sme
<220> FEATURE:
<221> NAME/KEY: MISC_FEATURE
<222> LOCATION: (63)..(63)
<223> OTHER INFORMATION: Xaa is R, H or K
<220> FEATURE:
<221> NAME/KEY: MISC_FEATURE
<222> LOCATION: (66)..(67)
<223> OTHER INFORMATION: Xaa is A, C, G, P, M, V, I, L, Sce, or Sme
<220> FEATURE:
<221> NAME/KEY: MISC_FEATURE
<222> LOCATION: (69)..(69)
<223> OTHER INFORMATION: Xaa is R, H or K
<220> FEATURE:
<221> NAME/KEY: MISC_FEATURE
<222> LOCATION: (70)..(73)
<223> OTHER INFORMATION: Xaa is A, C, G, P, M, V, I, L, Sce, or Sme
<220> FEATURE:
<221> NAME/KEY: MISC_FEATURE
<222> LOCATION: (74)..(74)
<223> OTHER INFORMATION: Xaa is S, T, N, or Q
<220> FEATURE:
<221> NAME/KEY: MISC_FEATURE
<222> LOCATION: (75)..(75)
<223> OTHER INFORMATION: Xaa is A, C, G, P, M, V, I, L, Sce, or Sme
<220> FEATURE:
<221> NAME/KEY: MISC_FEATURE
<222> LOCATION: (76)..(76)
<223> OTHER INFORMATION: Xaa is R, H or K
<220> FEATURE:
<221> NAME/KEY: MISC_FEATURE
<222> LOCATION: (77)..(77)
<223> OTHER INFORMATION: Xaa is D or E
```

```
<220> FEATURE:
<221> NAME/KEY: MISC_FEATURE
<222> LOCATION: (78)..(82)
<223> OTHER INFORMATION: Xaa is A, C, G, P, M, V, I, L, Sce, or Sme
<220> FEATURE:
<221> NAME/KEY: MISC_FEATURE
<222> LOCATION: (83)..(83)
<223> OTHER INFORMATION: Xaa is S, T, N, or Q
<220> FEATURE:
<221> NAME/KEY: MISC_FEATURE
<222> LOCATION: (84)..(85)
<223> OTHER INFORMATION: Xaa is A, C, G, P, M, V, I, L, Sce, or Sme
<220> FEATURE:
<221> NAME/KEY: MISC_FEATURE
<222> LOCATION: (86)..(86)
<223> OTHER INFORMATION: Xaa is R, H or K
<220> FEATURE:
<221> NAME/KEY: MISC_FEATURE
<222> LOCATION: (87)..(88)
<223> OTHER INFORMATION: Xaa is A, C, G, P, M, V, I, L, Sce, or Sme
<220> FEATURE:
<221> NAME/KEY: MISC_FEATURE
<222> LOCATION: (89)..(89)
<223> OTHER INFORMATION: Xaa is R, H or K
<220> FEATURE:
<221> NAME/KEY: MISC_FEATURE
<222> LOCATION: (90)..(93)
<223> OTHER INFORMATION: Xaa is A, C, G, P, M, V, I, L, Sce, or Sme
<220> FEATURE:
<221> NAME/KEY: MISC_FEATURE
<222> LOCATION: (94)..(94)
<223> OTHER INFORMATION: Xaa is F, W, or Y
<220> FEATURE:
<221> NAME/KEY: MISC_FEATURE
<222> LOCATION: (95)..(96)
<223> OTHER INFORMATION: Xaa is S, T, N, or Q
<220> FEATURE:
<221> NAME/KEY: MISC_FEATURE
<222> LOCATION: (97)..(97)
<223> OTHER INFORMATION: Xaa is D or E
<220> FEATURE:
<221> NAME/KEY: MISC_FEATURE
<222> LOCATION: (98)..(98)
<223> OTHER INFORMATION: Xaa is S, T, N, or Q
<220> FEATURE:
<221> NAME/KEY: MISC_FEATURE
<222> LOCATION: (99)..(99)
<223> OTHER INFORMATION: Xaa is A, C, G, P, M, V, I, L, Sce, or Sme
<220> FEATURE:
<221> NAME/KEY: MISC_FEATURE
<222> LOCATION: (100)..(100)
<223> OTHER INFORMATION: Xaa is S, T, N, or Q
<220> FEATURE:
<221> NAME/KEY: MISC_FEATURE
<222> LOCATION: (101)..(101)
<223> OTHER INFORMATION: Xaa is D or E
<220> FEATURE:
<221> NAME/KEY: MISC_FEATURE
<222> LOCATION: (102)..(102)
<223> OTHER INFORMATION: Xaa is R, H or K
<220> FEATURE:
<221> NAME/KEY: MISC_FEATURE
<222> LOCATION: (103)..(103)
<223> OTHER INFORMATION: Xaa is A, C, G, P, M, V, I, L, Sce, or Sme
<220> FEATURE:
<221> NAME/KEY: MISC_FEATURE
<222> LOCATION: (104)..(105)
<223> OTHER INFORMATION: Xaa is R, H or K
<220> FEATURE:
<221> NAME/KEY: MISC_FEATURE
<222> LOCATION: (106)..(106)
<223> OTHER INFORMATION: Xaa is A, C, G, P, M, V, I, L, Sce, or Sme
<220> FEATURE:
<221> NAME/KEY: MISC_FEATURE
<222> LOCATION: (107)..(107)
<223> OTHER INFORMATION: Xaa is F, W, or Y
<220> FEATURE:
<221> NAME/KEY: MISC_FEATURE
<222> LOCATION: (108)..(108)
```

```
<223> OTHER INFORMATION: Xaa is A, C, G, P, M, V, I, L, Sce, or Sme
<220> FEATURE:
<221> NAME/KEY: MISC_FEATURE
<222> LOCATION: (110)..(110)
<223> OTHER INFORMATION: Xaa is D or E
<220> FEATURE:
<221> NAME/KEY: MISC_FEATURE
<222> LOCATION: (111)..(112)
<223> OTHER INFORMATION: Xaa is A, C, G, P, M, V, I, L, Sce, or Sme
<220> FEATURE:
<221> NAME/KEY: MISC_FEATURE
<222> LOCATION: (113)..(113)
<223> OTHER INFORMATION: Xaa is R, H or K
<220> FEATURE:
<221> NAME/KEY: MISC_FEATURE
<222> LOCATION: (114)..(114)
<223> OTHER INFORMATION: Xaa is A, C, G, P, M, V, I, L, Sce, or Sme
<220> FEATURE:
<221> NAME/KEY: MISC_FEATURE
<222> LOCATION: (115)..(115)
<223> OTHER INFORMATION: Xaa is R, H or K
<220> FEATURE:
<221> NAME/KEY: MISC_FEATURE
<222> LOCATION: (116)..(116)
<223> OTHER INFORMATION: Xaa is A, C, G, P, M, V, I, L, Sce, or Sme
<220> FEATURE:
<221> NAME/KEY: MISC_FEATURE
<222> LOCATION: (117)..(117)
<223> OTHER INFORMATION: Xaa is D or E
<220> FEATURE:
<221> NAME/KEY: MISC_FEATURE
<222> LOCATION: (118)..(118)
<223> OTHER INFORMATION: Xaa is A, C, G, P, M, V, I, L, Sce, or Sme
<220> FEATURE:
<221> NAME/KEY: MISC_FEATURE
<222> LOCATION: (119)..(119)
<223> OTHER INFORMATION: Xaa is D or E
<220> FEATURE:
<221> NAME/KEY: MISC_FEATURE
<222> LOCATION: (120)..(120)
<223> OTHER INFORMATION: Xaa is S, T, N, or Q
<220> FEATURE:
<221> NAME/KEY: MISC_FEATURE
<222> LOCATION: (121)..(121)
<223> OTHER INFORMATION: Xaa is A, C, G, P, M, V, I, L, Sce, or Sme
<220> FEATURE:
<221> NAME/KEY: MISC_FEATURE
<222> LOCATION: (122)..(122)
<223> OTHER INFORMATION: Xaa is S, T, N, or Q

<400> SEQUENCE: 24

Xaa Xaa Xaa Xaa Xaa Xaa Xaa Xaa Ile Xaa Xaa Glu Glu Xaa Thr Pro
 1               5                   10                  15

Ala Ala Xaa Leu Ala Ala Xaa Ile Glu Xaa Xaa Leu Lys Xaa Xaa Glu
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Glu Ala Xaa Xaa Leu
    50                  55                  60

Ile Xaa Xaa His Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Asn Xaa Xaa Xaa
            100                 105                 110

Xaa Xaa Xaa Xaa Xaa Xaa Xaa Xaa Xaa Xaa
            115                 120

<210> SEQ ID NO 25
<211> LENGTH: 177
```

```
-continued

<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (2)..(2)
<223> OTHER INFORMATION: Xaa is S, T, N or Q
<220> FEATURE:
<221> NAME/KEY: MISC_FEATURE
<222> LOCATION: (3)..(3)
<223> OTHER INFORMATION: Xaa is R, H, or K
<220> FEATURE:
<221> NAME/KEY: MISC_FEATURE
<222> LOCATION: (4)..(4)
<223> OTHER INFORMATION: Xaa is A, C, G, P, M, V, I, L, Sce, or Sme
<220> FEATURE:
<221> NAME/KEY: MISC_FEATURE
<222> LOCATION: (5)..(5)
<223> OTHER INFORMATION: Xaa is R, H, or K
<220> FEATURE:
<221> NAME/KEY: MISC_FEATURE
<222> LOCATION: (6)..(9)
<223> OTHER INFORMATION: Xaa is A, C, G, P, M, V, I, L, Sce, or Sme
<220> FEATURE:
<221> NAME/KEY: MISC_FEATURE
<222> LOCATION: (10)..(10)
<223> OTHER INFORMATION: Xaa is S, T, N or Q
<220> FEATURE:
<221> NAME/KEY: MISC_FEATURE
<222> LOCATION: (11)..(11)
<223> OTHER INFORMATION: Xaa is A, C, G, P, M, V, I, L, Sce, or Sme
<220> FEATURE:
<221> NAME/KEY: MISC_FEATURE
<222> LOCATION: (12)..(12)
<223> OTHER INFORMATION: Xaa is S, T, N or Q
<220> FEATURE:
<221> NAME/KEY: MISC_FEATURE
<222> LOCATION: (13)..(13)
<223> OTHER INFORMATION: Xaa is D or E
<220> FEATURE:
<221> NAME/KEY: MISC_FEATURE
<222> LOCATION: (14)..(14)
<223> OTHER INFORMATION: Xaa is R, H, or K
<220> FEATURE:
<221> NAME/KEY: MISC_FEATURE
<222> LOCATION: (15)..(15)
<223> OTHER INFORMATION: Xaa is A, C, G, P, M, V, I, L, Sce, or Sme
<220> FEATURE:
<221> NAME/KEY: MISC_FEATURE
<222> LOCATION: (16)..(16)
<223> OTHER INFORMATION: Xaa is S, T, N or Q
<220> FEATURE:
<221> NAME/KEY: MISC_FEATURE
<222> LOCATION: (17)..(19)
<223> OTHER INFORMATION: Xaa is A, C, G, P, M, V, I, L, Sce, or Sme
<220> FEATURE:
<221> NAME/KEY: MISC_FEATURE
<222> LOCATION: (20)..(20)
<223> OTHER INFORMATION: Xaa is S, T, N or Q
<220> FEATURE:
<221> NAME/KEY: MISC_FEATURE
<222> LOCATION: (21)..(21)
<223> OTHER INFORMATION: Xaa is A, C, G, P, M, V, I, L, Sce, or Sme
<220> FEATURE:
<221> NAME/KEY: MISC_FEATURE
<222> LOCATION: (22)..(22)
<223> OTHER INFORMATION: Xaa is D or E
<220> FEATURE:
<221> NAME/KEY: MISC_FEATURE
<222> LOCATION: (24)..(24)
<223> OTHER INFORMATION: Xaa is S, T, N or Q
<220> FEATURE:
<221> NAME/KEY: MISC_FEATURE
<222> LOCATION: (25)..(25)
```

```
<223> OTHER INFORMATION: Xaa is A, C, G, P, M, V, I, L, Sce, or Sme
<220> FEATURE:
<221> NAME/KEY: MISC_FEATURE
<222> LOCATION: (28)..(29)
<223> OTHER INFORMATION: Xaa is A, C, G, P, M, V, I, L, Sce, or Sme
<220> FEATURE:
<221> NAME/KEY: MISC_FEATURE
<222> LOCATION: (32)..(32)
<223> OTHER INFORMATION: Xaa is A, C, G, P, M, V, I, L, Sce, or Sme
<220> FEATURE:
<221> NAME/KEY: MISC_FEATURE
<222> LOCATION: (36)..(36)
<223> OTHER INFORMATION: Xaa is A, C, G, P, M, V, I, L, Sce, or Sme
<220> FEATURE:
<221> NAME/KEY: MISC_FEATURE
<222> LOCATION: (37)..(38)
<223> OTHER INFORMATION: Xaa is S, T, N or Q
<220> FEATURE:
<221> NAME/KEY: MISC_FEATURE
<222> LOCATION: (39)..(39)
<223> OTHER INFORMATION: Xaa is D or E
<220> FEATURE:
<221> NAME/KEY: MISC_FEATURE
<222> LOCATION: (40)..(40)
<223> OTHER INFORMATION: Xaa is F, W, or Y
<220> FEATURE:
<221> NAME/KEY: MISC_FEATURE
<222> LOCATION: (41)..(41)
<223> OTHER INFORMATION: Xaa is D or E
<220> FEATURE:
<221> NAME/KEY: MISC_FEATURE
<222> LOCATION: (42)..(43)
<223> OTHER INFORMATION: Xaa is A, C, G, P, M, V, I, L, Sce, or Sme
<220> FEATURE:
<221> NAME/KEY: MISC_FEATURE
<222> LOCATION: (44)..(44)
<223> OTHER INFORMATION: Xaa is F, W, or Y
<220> FEATURE:
<221> NAME/KEY: MISC_FEATURE
<222> LOCATION: (45)..(45)
<223> OTHER INFORMATION: Xaa is S, T, N or Q
<220> FEATURE:
<221> NAME/KEY: MISC_FEATURE
<222> LOCATION: (46)..(48)
<223> OTHER INFORMATION: Xaa is A, C, G, P, M, V, I, L, Sce, or Sme
<220> FEATURE:
<221> NAME/KEY: MISC_FEATURE
<222> LOCATION: (49)..(50)
<223> OTHER INFORMATION: Xaa is D or E
<220> FEATURE:
<221> NAME/KEY: MISC_FEATURE
<222> LOCATION: (51)..(51)
<223> OTHER INFORMATION: Xaa is S, T, N or Q
<220> FEATURE:
<221> NAME/KEY: MISC_FEATURE
<222> LOCATION: (52)..(52)
<223> OTHER INFORMATION: Xaa is D or E
<220> FEATURE:
<221> NAME/KEY: MISC_FEATURE
<222> LOCATION: (53)..(54)
<223> OTHER INFORMATION: Xaa is A, C, G, P, M, V, I, L, Sce, or Sme
<220> FEATURE:
<221> NAME/KEY: MISC_FEATURE
<222> LOCATION: (55)..(55)
<223> OTHER INFORMATION: Xaa is D or E
<220> FEATURE:
<221> NAME/KEY: MISC_FEATURE
<222> LOCATION: (56)..(57)
<223> OTHER INFORMATION: Xaa is S, T, N or Q
<220> FEATURE:
<221> NAME/KEY: MISC_FEATURE
<222> LOCATION: (58)..(59)
<223> OTHER INFORMATION: Xaa is A, C, G, P, M, V, I, L, Sce, or Sme
<220> FEATURE:
<221> NAME/KEY: MISC_FEATURE
<222> LOCATION: (60)..(60)
<223> OTHER INFORMATION: Xaa is R, H, or K
<220> FEATURE:
<221> NAME/KEY: MISC_FEATURE
```

```
<222> LOCATION: (61)..(62)
<223> OTHER INFORMATION: Xaa is A, C, G, P, M, V, I, L, Sce, or Sme
<220> FEATURE:
<221> NAME/KEY: MISC_FEATURE
<222> LOCATION: (63)..(64)
<223> OTHER INFORMATION: Xaa is D or E
<220> FEATURE:
<221> NAME/KEY: MISC_FEATURE
<222> LOCATION: (65)..(65)
<223> OTHER INFORMATION: Xaa is S, T, N or Q
<220> FEATURE:
<221> NAME/KEY: MISC_FEATURE
<222> LOCATION: (66)..(66)
<223> OTHER INFORMATION: Xaa is D or E
<220> FEATURE:
<221> NAME/KEY: MISC_FEATURE
<222> LOCATION: (67)..(71)
<223> OTHER INFORMATION: Xaa is A, C, G, P, M, V, I, L, Sce, or Sme
<220> FEATURE:
<221> NAME/KEY: MISC_FEATURE
<222> LOCATION: (72)..(73)
<223> OTHER INFORMATION: Xaa is S, T, N or Q
<220> FEATURE:
<221> NAME/KEY: MISC_FEATURE
<222> LOCATION: (74)..(75)
<223> OTHER INFORMATION: Xaa is A, C, G, P, M, V, I, L, Sce, or Sme
<220> FEATURE:
<221> NAME/KEY: MISC_FEATURE
<222> LOCATION: (76)..(76)
<223> OTHER INFORMATION: Xaa is S, T, N or Q
<220> FEATURE:
<221> NAME/KEY: MISC_FEATURE
<222> LOCATION: (77)..(79)
<223> OTHER INFORMATION: Xaa is A, C, G, P, M, V, I, L, Sce, or Sme
<220> FEATURE:
<221> NAME/KEY: MISC_FEATURE
<222> LOCATION: (80)..(81)
<223> OTHER INFORMATION: Xaa is R, H, or K
<220> FEATURE:
<221> NAME/KEY: MISC_FEATURE
<222> LOCATION: (82)..(82)
<223> OTHER INFORMATION: Xaa is D or E
<220> FEATURE:
<221> NAME/KEY: MISC_FEATURE
<222> LOCATION: (83)..(83)
<223> OTHER INFORMATION: Xaa is A, C, G, P, M, V, I, L, Sce, or Sme
<220> FEATURE:
<221> NAME/KEY: MISC_FEATURE
<222> LOCATION: (84)..(84)
<223> OTHER INFORMATION: Xaa is S, T, N or Q
<220> FEATURE:
<221> NAME/KEY: MISC_FEATURE
<222> LOCATION: (85)..(85)
<223> OTHER INFORMATION: Xaa is A, C, G, P, M, V, I, L, Sce, or Sme
<220> FEATURE:
<221> NAME/KEY: MISC_FEATURE
<222> LOCATION: (86)..(86)
<223> OTHER INFORMATION: Xaa is D or E
<220> FEATURE:
<221> NAME/KEY: MISC_FEATURE
<222> LOCATION: (87)..(87)
<223> OTHER INFORMATION: Xaa is A, C, G, P, M, V, I, L, Sce, or Sme
<220> FEATURE:
<221> NAME/KEY: MISC_FEATURE
<222> LOCATION: (88)..(88)
<223> OTHER INFORMATION: Xaa is S, T, N or Q
<220> FEATURE:
<221> NAME/KEY: MISC_FEATURE
<222> LOCATION: (89)..(89)
<223> OTHER INFORMATION: Xaa is D or E
<220> FEATURE:
<221> NAME/KEY: MISC_FEATURE
<222> LOCATION: (90)..(92)
<223> OTHER INFORMATION: Xaa is A, C, G, P, M, V, I, L, Sce, or Sme
<220> FEATURE:
<221> NAME/KEY: MISC_FEATURE
<222> LOCATION: (93)..(93)
<223> OTHER INFORMATION: Xaa is D or E
<220> FEATURE:
```

```
<221> NAME/KEY: MISC_FEATURE
<222> LOCATION: (94)..(94)
<223> OTHER INFORMATION: Xaa is R, H, or K
<220> FEATURE:
<221> NAME/KEY: MISC_FEATURE
<222> LOCATION: (95)..(98)
<223> OTHER INFORMATION: Xaa is A, C, G, P, M, V, I, L, Sce, or Sme
<220> FEATURE:
<221> NAME/KEY: MISC_FEATURE
<222> LOCATION: (99)..(99)
<223> OTHER INFORMATION: Xaa is F, W, or Y
<220> FEATURE:
<221> NAME/KEY: MISC_FEATURE
<222> LOCATION: (100)..(100)
<223> OTHER INFORMATION: Xaa is A, C, G, P, M, V, I, L, Sce, or Sme
<220> FEATURE:
<221> NAME/KEY: MISC_FEATURE
<222> LOCATION: (101)..(101)
<223> OTHER INFORMATION: Xaa is D or E
<220> FEATURE:
<221> NAME/KEY: MISC_FEATURE
<222> LOCATION: (102)..(103)
<223> OTHER INFORMATION: Xaa is A, C, G, P, M, V, I, L, Sce, or Sme
<220> FEATURE:
<221> NAME/KEY: MISC_FEATURE
<222> LOCATION: (104)..(104)
<223> OTHER INFORMATION: Xaa is R, H, or K
<220> FEATURE:
<221> NAME/KEY: MISC_FEATURE
<222> LOCATION: (105)..(105)
<223> OTHER INFORMATION: Xaa is A, C, G, P, M, V, I, L, Sce, or Sme
<220> FEATURE:
<221> NAME/KEY: MISC_FEATURE
<222> LOCATION: (106)..(106)
<223> OTHER INFORMATION: Xaa is D or E
<220> FEATURE:
<221> NAME/KEY: MISC_FEATURE
<222> LOCATION: (107)..(107)
<223> OTHER INFORMATION: Xaa is S, T, N or Q
<220> FEATURE:
<221> NAME/KEY: MISC_FEATURE
<222> LOCATION: (108)..(108)
<223> OTHER INFORMATION: Xaa is A, C, G, P, M, V, I, L, Sce, or Sme
<220> FEATURE:
<221> NAME/KEY: MISC_FEATURE
<222> LOCATION: (109)..(109)
<223> OTHER INFORMATION: Xaa is R, H, or K
<220> FEATURE:
<221> NAME/KEY: MISC_FEATURE
<222> LOCATION: (110)..(110)
<223> OTHER INFORMATION: Xaa is D or E
<220> FEATURE:
<221> NAME/KEY: MISC_FEATURE
<222> LOCATION: (111)..(112)
<223> OTHER INFORMATION: Xaa is A, C, G, P, M, V, I, L, Sce, or Sme
<220> FEATURE:
<221> NAME/KEY: MISC_FEATURE
<222> LOCATION: (113)..(113)
<223> OTHER INFORMATION: Xaa is S, T, N or Q
<220> FEATURE:
<221> NAME/KEY: MISC_FEATURE
<222> LOCATION: (114)..(116)
<223> OTHER INFORMATION: Xaa is A, C, G, P, M, V, I, L, Sce, or Sme
<220> FEATURE:
<221> NAME/KEY: MISC_FEATURE
<222> LOCATION: (117)..(117)
<223> OTHER INFORMATION: Xaa is S, T, N or Q
<220> FEATURE:
<221> NAME/KEY: MISC_FEATURE
<222> LOCATION: (118)..(118)
<223> OTHER INFORMATION: Xaa is R, H, or K
<220> FEATURE:
<221> NAME/KEY: MISC_FEATURE
<222> LOCATION: (119)..(120)
<223> OTHER INFORMATION: Xaa is S, T, N or Q
<220> FEATURE:
<221> NAME/KEY: MISC_FEATURE
<222> LOCATION: (121)..(123)
<223> OTHER INFORMATION: Xaa is A, C, G, P, M, V, I, L, Sce, or Sme
```

```
<220> FEATURE:
<221> NAME/KEY: MISC_FEATURE
<222> LOCATION: (124)..(124)
<223> OTHER INFORMATION: Xaa is R, H, or K
<220> FEATURE:
<221> NAME/KEY: MISC_FEATURE
<222> LOCATION: (125)..(125)
<223> OTHER INFORMATION: Xaa is A, C, G, P, M, V, I, L, Sce, or Sme
<220> FEATURE:
<221> NAME/KEY: MISC_FEATURE
<222> LOCATION: (126)..(126)
<223> OTHER INFORMATION: Xaa is D or E
<220> FEATURE:
<221> NAME/KEY: MISC_FEATURE
<222> LOCATION: (127)..(127)
<223> OTHER INFORMATION: Xaa is S, T, N or Q
<220> FEATURE:
<221> NAME/KEY: MISC_FEATURE
<222> LOCATION: (128)..(130)
<223> OTHER INFORMATION: Xaa is A, C, G, P, M, V, I, L, Sce, or Sme
<220> FEATURE:
<221> NAME/KEY: MISC_FEATURE
<222> LOCATION: (131)..(131)
<223> OTHER INFORMATION: Xaa is S, T, N or Q
<220> FEATURE:
<221> NAME/KEY: MISC_FEATURE
<222> LOCATION: (132)..(134)
<223> OTHER INFORMATION: Xaa is A, C, G, P, M, V, I, L, Sce, or Sme
<220> FEATURE:
<221> NAME/KEY: MISC_FEATURE
<222> LOCATION: (135)..(135)
<223> OTHER INFORMATION: Xaa is D or E
<220> FEATURE:
<221> NAME/KEY: MISC_FEATURE
<222> LOCATION: (136)..(136)
<223> OTHER INFORMATION: Xaa is A, C, G, P, M, V, I, L, Sce, or Sme
<220> FEATURE:
<221> NAME/KEY: MISC_FEATURE
<222> LOCATION: (139)..(139)
<223> OTHER INFORMATION: Xaa is A, C, G, P, M, V, I, L, Sce, or Sme
<220> FEATURE:
<221> NAME/KEY: MISC_FEATURE
<222> LOCATION: (142)..(143)
<223> OTHER INFORMATION: Xaa is A, C, G, P, M, V, I, L, Sce, or Sme
<220> FEATURE:
<221> NAME/KEY: MISC_FEATURE
<222> LOCATION: (145)..(146)
<223> OTHER INFORMATION: Xaa is A, C, G, P, M, V, I, L, Sce, or Sme
<220> FEATURE:
<221> NAME/KEY: MISC_FEATURE
<222> LOCATION: (147)..(147)
<223> OTHER INFORMATION: Xaa is F, W, or Y
<220> FEATURE:
<221> NAME/KEY: MISC_FEATURE
<222> LOCATION: (148)..(151)
<223> OTHER INFORMATION: Xaa is A, C, G, P, M, V, I, L, Sce, or Sme
<220> FEATURE:
<221> NAME/KEY: MISC_FEATURE
<222> LOCATION: (152)..(152)
<223> OTHER INFORMATION: Xaa is F, W, or Y
<220> FEATURE:
<221> NAME/KEY: MISC_FEATURE
<222> LOCATION: (153)..(154)
<223> OTHER INFORMATION: Xaa is A, C, G, P, M, V, I, L, Sce, or Sme
<220> FEATURE:
<221> NAME/KEY: MISC_FEATURE
<222> LOCATION: (155)..(155)
<223> OTHER INFORMATION: Xaa is D or E
<220> FEATURE:
<221> NAME/KEY: MISC_FEATURE
<222> LOCATION: (156)..(157)
<223> OTHER INFORMATION: Xaa is A, C, G, P, M, V, I, L, Sce, or Sme
<220> FEATURE:
<221> NAME/KEY: MISC_FEATURE
<222> LOCATION: (158)..(158)
<223> OTHER INFORMATION: Xaa is D or E
<220> FEATURE:
<221> NAME/KEY: MISC_FEATURE
<222> LOCATION: (159)..(160)
```

```
<223> OTHER INFORMATION: Xaa is A, C, G, P, M, V, I, L, Sce, or Sme
<220> FEATURE:
<221> NAME/KEY: MISC_FEATURE
<222> LOCATION: (161)..(161)
<223> OTHER INFORMATION: Xaa is F, W, or Y
<220> FEATURE:
<221> NAME/KEY: MISC_FEATURE
<222> LOCATION: (162)..(162)
<223> OTHER INFORMATION: Xaa is A, C, G, P, M, V, I, L, Sce, or Sme
<220> FEATURE:
<221> NAME/KEY: MISC_FEATURE
<222> LOCATION: (163)..(163)
<223> OTHER INFORMATION: Xaa is D or E
<220> FEATURE:
<221> NAME/KEY: MISC_FEATURE
<222> LOCATION: (164)..(164)
<223> OTHER INFORMATION: Xaa is A, C, G, P, M, V, I, L, Sce, or Sme
<220> FEATURE:
<221> NAME/KEY: MISC_FEATURE
<222> LOCATION: (165)..(165)
<223> OTHER INFORMATION: Xaa is S, T, N or Q
<220> FEATURE:
<221> NAME/KEY: MISC_FEATURE
<222> LOCATION: (166)..(166)
<223> OTHER INFORMATION: Xaa is D or E
<220> FEATURE:
<221> NAME/KEY: MISC_FEATURE
<222> LOCATION: (169)..(169)
<223> OTHER INFORMATION: Xaa is A, C, G, P, M, V, I, L, Sce, or Sme
<220> FEATURE:
<221> NAME/KEY: MISC_FEATURE
<222> LOCATION: (170)..(170)
<223> OTHER INFORMATION: Xaa is R, H, or K
<220> FEATURE:
<221> NAME/KEY: MISC_FEATURE
<222> LOCATION: (171)..(171)
<223> OTHER INFORMATION: Xaa is A, C, G, P, M, V, I, L, Sce, or Sme
<220> FEATURE:
<221> NAME/KEY: MISC_FEATURE
<222> LOCATION: (172)..(172)
<223> OTHER INFORMATION: Xaa is F, W, or Y
<220> FEATURE:
<221> NAME/KEY: MISC_FEATURE
<222> LOCATION: (173)..(173)
<223> OTHER INFORMATION: Xaa is R, H, or K
<220> FEATURE:
<221> NAME/KEY: MISC_FEATURE
<222> LOCATION: (174)..(174)
<223> OTHER INFORMATION: Xaa is A, C, G, P, M, V, I, L, Sce, or Sme
<220> FEATURE:
<221> NAME/KEY: MISC_FEATURE
<222> LOCATION: (175)..(175)
<223> OTHER INFORMATION: Xaa is R, H, or K
<220> FEATURE:
<221> NAME/KEY: MISC_FEATURE
<222> LOCATION: (176)..(176)
<223> OTHER INFORMATION: Xaa is A, C, G, P, M, V, I, L, Sce, or Sme
<220> FEATURE:
<221> NAME/KEY: MISC_FEATURE
<222> LOCATION: (177)..(177)
<223> OTHER INFORMATION: Xaa is R, H, or K

<400> SEQUENCE: 25

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Ile Xaa Xaa Lys Ala Xaa Xaa Leu Ala Xaa
             20                  25                  30

Asn Leu Tyr Xaa Xaa Xaa Xaa Xaa Xaa Xaa Xaa Xaa Xaa Xaa Xaa Xaa
             35                  40                  45

Xaa Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
65                  70                  75                  80
```

```
Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Ala Ser Xaa Ser Asp Xaa Xaa Leu
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Ala Met Xaa Xaa Xaa Xaa Xaa Xaa Xaa
            165                 170                 175

Xaa

<210> SEQ ID NO 26
<211> LENGTH: 122
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or optionally absent
<220> FEATURE:
<221> NAME/KEY: MISC_FEATURE
<222> LOCATION: (2)..(2)
<223> OTHER INFORMATION: Xaa is A, C, G, P, M, V, I, L, Sce, or Sme
<220> FEATURE:
<221> NAME/KEY: MISC_FEATURE
<222> LOCATION: (3)..(3)
<223> OTHER INFORMATION: Xaa is R, H, or K
<220> FEATURE:
<221> NAME/KEY: MISC_FEATURE
<222> LOCATION: (4)..(5)
<223> OTHER INFORMATION: Xaa is A, C, G, P, M, V, I, L, Sce, or Sme
<220> FEATURE:
<221> NAME/KEY: MISC_FEATURE
<222> LOCATION: (6)..(6)
<223> OTHER INFORMATION: Xaa is R, H, or K
<220> FEATURE:
<221> NAME/KEY: MISC_FEATURE
<222> LOCATION: (7)..(9)
<223> OTHER INFORMATION: Xaa is A, C, G, P, M, V, I, L, Sce, or Sme
<220> FEATURE:
<221> NAME/KEY: MISC_FEATURE
<222> LOCATION: (10)..(10)
<223> OTHER INFORMATION: Xaa is S, T, N or Q
<220> FEATURE:
<221> NAME/KEY: MISC_FEATURE
<222> LOCATION: (11)..(11)
<223> OTHER INFORMATION: Xaa is A, C, G, P, M, V, I, L, Sce, or Sme
<220> FEATURE:
<221> NAME/KEY: MISC_FEATURE
<222> LOCATION: (14)..(14)
<223> OTHER INFORMATION: Xaa is D or E
<220> FEATURE:
<221> NAME/KEY: MISC_FEATURE
<222> LOCATION: (19)..(19)
<223> OTHER INFORMATION: Xaa is A, C, G, P, M, V, I, L, Sce, or Sme
<220> FEATURE:
<221> NAME/KEY: MISC_FEATURE
<222> LOCATION: (22)..(22)
<223> OTHER INFORMATION: Xaa is A, C, G, P, M, V, I, L, Sce, or Sme
<220> FEATURE:
<221> NAME/KEY: MISC_FEATURE
<222> LOCATION: (23)..(23)
<223> OTHER INFORMATION: Xaa is S, T, N or Q
<220> FEATURE:
<221> NAME/KEY: MISC_FEATURE
<222> LOCATION: (26)..(27)
<223> OTHER INFORMATION: Xaa is A, C, G, P, M, V, I, L, Sce, or Sme
```

```
<220> FEATURE:
<221> NAME/KEY: MISC_FEATURE
<222> LOCATION: (29)..(29)
<223> OTHER INFORMATION: Xaa is R, H, or K
<220> FEATURE:
<221> NAME/KEY: MISC_FEATURE
<222> LOCATION: (30)..(31)
<223> OTHER INFORMATION: Xaa is A, C, G, P, M, V, I, L, Sce, or Sme
<220> FEATURE:
<221> NAME/KEY: MISC_FEATURE
<222> LOCATION: (32)..(32)
<223> OTHER INFORMATION: Xaa is D or E
<220> FEATURE:
<221> NAME/KEY: MISC_FEATURE
<222> LOCATION: (33)..(33)
<223> OTHER INFORMATION: Xaa is A, C, G, P, M, V, I, L, Sce, or Sme
<220> FEATURE:
<221> NAME/KEY: MISC_FEATURE
<222> LOCATION: (34)..(34)
<223> OTHER INFORMATION: Xaa is S, T, N or Q
<220> FEATURE:
<221> NAME/KEY: MISC_FEATURE
<222> LOCATION: (35)..(36)
<223> OTHER INFORMATION: Xaa is A, C, G, P, M, V, I, L, Sce, or Sme
<220> FEATURE:
<221> NAME/KEY: MISC_FEATURE
<222> LOCATION: (37)..(38)
<223> OTHER INFORMATION: Xaa is S, T, N or Q
<220> FEATURE:
<221> NAME/KEY: MISC_FEATURE
<222> LOCATION: (39)..(39)
<223> OTHER INFORMATION: Xaa is F, W or Y
<220> FEATURE:
<221> NAME/KEY: MISC_FEATURE
<222> LOCATION: (40)..(41)
<223> OTHER INFORMATION: Xaa is D or E
<220> FEATURE:
<221> NAME/KEY: MISC_FEATURE
<222> LOCATION: (42)..(46)
<223> OTHER INFORMATION: Xaa is A, C, G, P, M, V, I, L, Sce, or Sme
<220> FEATURE:
<221> NAME/KEY: MISC_FEATURE
<222> LOCATION: (47)..(47)
<223> OTHER INFORMATION: Xaa is F, W or Y
<220> FEATURE:
<221> NAME/KEY: MISC_FEATURE
<222> LOCATION: (48)..(48)
<223> OTHER INFORMATION: Xaa is S, T, N or Q
<220> FEATURE:
<221> NAME/KEY: MISC_FEATURE
<222> LOCATION: (49)..(49)
<223> OTHER INFORMATION: Xaa is A, C, G, P, M, V, I, L, Sce, or Sme
<220> FEATURE:
<221> NAME/KEY: MISC_FEATURE
<222> LOCATION: (50)..(50)
<223> OTHER INFORMATION: Xaa is S, T, N or Q
<220> FEATURE:
<221> NAME/KEY: MISC_FEATURE
<222> LOCATION: (51)..(52)
<223> OTHER INFORMATION: Xaa is D or E
<220> FEATURE:
<221> NAME/KEY: MISC_FEATURE
<222> LOCATION: (53)..(53)
<223> OTHER INFORMATION: Xaa is A, C, G, P, M, V, I, L, Sce, or Sme
<220> FEATURE:
<221> NAME/KEY: MISC_FEATURE
<222> LOCATION: (54)..(55)
<223> OTHER INFORMATION: Xaa is S, T, N or Q
<220> FEATURE:
<221> NAME/KEY: MISC_FEATURE
<222> LOCATION: (56)..(56)
<223> OTHER INFORMATION: Xaa is A, C, G, P, M, V, I, L, Sce, or Sme
<220> FEATURE:
<221> NAME/KEY: MISC_FEATURE
<222> LOCATION: (57)..(57)
<223> OTHER INFORMATION: Xaa is F, W or Y
<220> FEATURE:
<221> NAME/KEY: MISC_FEATURE
<222> LOCATION: (58)..(59)
```

```
<223> OTHER INFORMATION: Xaa is A, C, G, P, M, V, I, L, Sce, or Sme
<220> FEATURE:
<221> NAME/KEY: MISC_FEATURE
<222> LOCATION: (60)..(60)
<223> OTHER INFORMATION: Xaa is D or E
<220> FEATURE:
<221> NAME/KEY: MISC_FEATURE
<222> LOCATION: (61)..(62)
<223> OTHER INFORMATION: Xaa is A, C, G, P, M, V, I, L, Sce, or Sme
<220> FEATURE:
<221> NAME/KEY: MISC_FEATURE
<222> LOCATION: (63)..(63)
<223> OTHER INFORMATION: Xaa is R, H, or K
<220> FEATURE:
<221> NAME/KEY: MISC_FEATURE
<222> LOCATION: (65)..(67)
<223> OTHER INFORMATION: Xaa is A, C, G, P, M, V, I, L, Sce, or Sme
<220> FEATURE:
<221> NAME/KEY: MISC_FEATURE
<222> LOCATION: (68)..(69)
<223> OTHER INFORMATION: Xaa is R, H, or K
<220> FEATURE:
<221> NAME/KEY: MISC_FEATURE
<222> LOCATION: (70)..(73)
<223> OTHER INFORMATION: Xaa is A, C, G, P, M, V, I, L, Sce, or Sme
<220> FEATURE:
<221> NAME/KEY: MISC_FEATURE
<222> LOCATION: (74)..(74)
<223> OTHER INFORMATION: Xaa is S, T, N or Q
<220> FEATURE:
<221> NAME/KEY: MISC_FEATURE
<222> LOCATION: (75)..(75)
<223> OTHER INFORMATION: Xaa is A, C, G, P, M, V, I, L, Sce, or Sme
<220> FEATURE:
<221> NAME/KEY: MISC_FEATURE
<222> LOCATION: (76)..(76)
<223> OTHER INFORMATION: Xaa is R, H, or K
<220> FEATURE:
<221> NAME/KEY: MISC_FEATURE
<222> LOCATION: (77)..(77)
<223> OTHER INFORMATION: Xaa is D or E
<220> FEATURE:
<221> NAME/KEY: MISC_FEATURE
<222> LOCATION: (78)..(82)
<223> OTHER INFORMATION: Xaa is A, C, G, P, M, V, I, L, Sce, or Sme
<220> FEATURE:
<221> NAME/KEY: MISC_FEATURE
<222> LOCATION: (83)..(83)
<223> OTHER INFORMATION: Xaa is S, T, N or Q
<220> FEATURE:
<221> NAME/KEY: MISC_FEATURE
<222> LOCATION: (84)..(85)
<223> OTHER INFORMATION: Xaa is A, C, G, P, M, V, I, L, Sce, or Sme
<220> FEATURE:
<221> NAME/KEY: MISC_FEATURE
<222> LOCATION: (86)..(86)
<223> OTHER INFORMATION: Xaa is R, H, or K
<220> FEATURE:
<221> NAME/KEY: MISC_FEATURE
<222> LOCATION: (87)..(88)
<223> OTHER INFORMATION: Xaa is A, C, G, P, M, V, I, L, Sce, or Sme
<220> FEATURE:
<221> NAME/KEY: MISC_FEATURE
<222> LOCATION: (89)..(89)
<223> OTHER INFORMATION: Xaa is R, H, or K
<220> FEATURE:
<221> NAME/KEY: MISC_FEATURE
<222> LOCATION: (90)..(93)
<223> OTHER INFORMATION: Xaa is A, C, G, P, M, V, I, L, Sce, or Sme
<220> FEATURE:
<221> NAME/KEY: MISC_FEATURE
<222> LOCATION: (94)..(94)
<223> OTHER INFORMATION: Xaa is F, W or Y
<220> FEATURE:
<221> NAME/KEY: MISC_FEATURE
<222> LOCATION: (95)..(96)
<223> OTHER INFORMATION: Xaa is S, T, N or Q
<220> FEATURE:
<221> NAME/KEY: MISC_FEATURE
```

```
<222> LOCATION: (97)..(97)
<223> OTHER INFORMATION: Xaa is D or E
<220> FEATURE:
<221> NAME/KEY: MISC_FEATURE
<222> LOCATION: (98)..(98)
<223> OTHER INFORMATION: Xaa is S, T, N or Q
<220> FEATURE:
<221> NAME/KEY: MISC_FEATURE
<222> LOCATION: (99)..(99)
<223> OTHER INFORMATION: Xaa is A, C, G, P, M, V, I, L, Sce, or Sme
<220> FEATURE:
<221> NAME/KEY: MISC_FEATURE
<222> LOCATION: (100)..(100)
<223> OTHER INFORMATION: Xaa is S, T, N or Q
<220> FEATURE:
<221> NAME/KEY: MISC_FEATURE
<222> LOCATION: (101)..(101)
<223> OTHER INFORMATION: Xaa is D or E
<220> FEATURE:
<221> NAME/KEY: MISC_FEATURE
<222> LOCATION: (102)..(102)
<223> OTHER INFORMATION: Xaa is R, H, or K
<220> FEATURE:
<221> NAME/KEY: MISC_FEATURE
<222> LOCATION: (103)..(103)
<223> OTHER INFORMATION: Xaa is A, C, G, P, M, V, I, L, Sce, or Sme
<220> FEATURE:
<221> NAME/KEY: MISC_FEATURE
<222> LOCATION: (104)..(105)
<223> OTHER INFORMATION: Xaa is R, H, or K
<220> FEATURE:
<221> NAME/KEY: MISC_FEATURE
<222> LOCATION: (106)..(106)
<223> OTHER INFORMATION: Xaa is A, C, G, P, M, V, I, L, Sce, or Sme
<220> FEATURE:
<221> NAME/KEY: MISC_FEATURE
<222> LOCATION: (107)..(107)
<223> OTHER INFORMATION: Xaa is F, W or Y
<220> FEATURE:
<221> NAME/KEY: MISC_FEATURE
<222> LOCATION: (108)..(108)
<223> OTHER INFORMATION: Xaa is A, C, G, P, M, V, I, L, Sce, or Sme
<220> FEATURE:
<221> NAME/KEY: MISC_FEATURE
<222> LOCATION: (110)..(110)
<223> OTHER INFORMATION: Xaa is D or E
<220> FEATURE:
<221> NAME/KEY: MISC_FEATURE
<222> LOCATION: (111)..(112)
<223> OTHER INFORMATION: Xaa is A, C, G, P, M, V, I, L, Sce, or Sme
<220> FEATURE:
<221> NAME/KEY: MISC_FEATURE
<222> LOCATION: (113)..(113)
<223> OTHER INFORMATION: Xaa is R, H, or K
<220> FEATURE:
<221> NAME/KEY: MISC_FEATURE
<222> LOCATION: (114)..(114)
<223> OTHER INFORMATION: Xaa is A, C, G, P, M, V, I, L, Sce, or Sme
<220> FEATURE:
<221> NAME/KEY: MISC_FEATURE
<222> LOCATION: (115)..(115)
<223> OTHER INFORMATION: Xaa is R, H, or K
<220> FEATURE:
<221> NAME/KEY: MISC_FEATURE
<222> LOCATION: (116)..(116)
<223> OTHER INFORMATION: Xaa is A, C, G, P, M, V, I, L, Sce, or Sme
<220> FEATURE:
<221> NAME/KEY: MISC_FEATURE
<222> LOCATION: (117)..(117)
<223> OTHER INFORMATION: Xaa is D or E
<220> FEATURE:
<221> NAME/KEY: MISC_FEATURE
<222> LOCATION: (118)..(118)
<223> OTHER INFORMATION: Xaa is A, C, G, P, M, V, I, L, Sce, or Sme
<220> FEATURE:
<221> NAME/KEY: MISC_FEATURE
<222> LOCATION: (119)..(119)
<223> OTHER INFORMATION: Xaa is D or E
<220> FEATURE:
```

```
<221> NAME/KEY: MISC_FEATURE
<222> LOCATION: (120)..(120)
<223> OTHER INFORMATION: Xaa is S, T, N or Q
<220> FEATURE:
<221> NAME/KEY: MISC_FEATURE
<222> LOCATION: (121)..(121)
<223> OTHER INFORMATION: Xaa is A, C, G, P, M, V, I, L, Sce, or Sme
<220> FEATURE:
<221> NAME/KEY: MISC_FEATURE
<222> LOCATION: (122)..(122)
<223> OTHER INFORMATION: Xaa is S, T, N or Q

<400> SEQUENCE: 26

Xaa Xaa Xaa Xaa Xaa Xaa Xaa Xaa Xaa Xaa Xaa Asn Ser Xaa Thr Pro
 1               5                  10                  15

Thr Asp Xaa Ile Ile Xaa Xaa Ile Leu Xaa Xaa Glu Xaa Xaa Xaa Xaa
             20                  25                  30

Xaa Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa Gln
     50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Ser Xaa Xaa Xaa
            100                 105                 110

Xaa Xaa Xaa Xaa Xaa Xaa Xaa Xaa Xaa Xaa
        115                 120

<210> SEQ ID NO 27
<211> LENGTH: 172
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (2)..(2)
<223> OTHER INFORMATION: Xaa is R, H, or K
<220> FEATURE:
<221> NAME/KEY: MISC_FEATURE
<222> LOCATION: (3)..(3)
<223> OTHER INFORMATION: Xaa is A, C, G, P, M, V, I, L, Sce, or Sme
<220> FEATURE:
<221> NAME/KEY: MISC_FEATURE
<222> LOCATION: (4)..(5)
<223> OTHER INFORMATION: Xaa is S, T, N or Q
<220> FEATURE:
<221> NAME/KEY: MISC_FEATURE
<222> LOCATION: (6)..(6)
<223> OTHER INFORMATION: Xaa is R, H, or K
<220> FEATURE:
<221> NAME/KEY: MISC_FEATURE
<222> LOCATION: (7)..(8)
<223> OTHER INFORMATION: Xaa is A, C, G, P, M, V, I, L, Sce, or Sme
<220> FEATURE:
<221> NAME/KEY: MISC_FEATURE
<222> LOCATION: (9)..(9)
<223> OTHER INFORMATION: Xaa is D or E
<220> FEATURE:
<221> NAME/KEY: MISC_FEATURE
<222> LOCATION: (10)..(10)
<223> OTHER INFORMATION: Xaa is R, H, or K
<220> FEATURE:
<221> NAME/KEY: MISC_FEATURE
```

```
<222> LOCATION: (11)..(11)
<223> OTHER INFORMATION: Xaa is A, C, G, P, M, V, I, L, Sce, or Sme
<220> FEATURE:
<221> NAME/KEY: MISC_FEATURE
<222> LOCATION: (12)..(13)
<223> OTHER INFORMATION: Xaa is S, T, N or Q
<220> FEATURE:
<221> NAME/KEY: MISC_FEATURE
<222> LOCATION: (14)..(14)
<223> OTHER INFORMATION: Xaa is R, H, or K
<220> FEATURE:
<221> NAME/KEY: MISC_FEATURE
<222> LOCATION: (15)..(15)
<223> OTHER INFORMATION: Xaa is A, C, G, P, M, V, I, L, Sce, or Sme
<220> FEATURE:
<221> NAME/KEY: MISC_FEATURE
<222> LOCATION: (16)..(16)
<223> OTHER INFORMATION: Xaa is F, W, or Y
<220> FEATURE:
<221> NAME/KEY: MISC_FEATURE
<222> LOCATION: (17)..(18)
<223> OTHER INFORMATION: Xaa is A, C, G, P, M, V, I, L, Sce, or Sme
<220> FEATURE:
<221> NAME/KEY: MISC_FEATURE
<222> LOCATION: (19)..(20)
<223> OTHER INFORMATION: Xaa is D or E
<220> FEATURE:
<221> NAME/KEY: MISC_FEATURE
<222> LOCATION: (21)..(21)
<223> OTHER INFORMATION: Xaa is A, C, G, P, M, V, I, L, Sce, or Sme
<220> FEATURE:
<221> NAME/KEY: MISC_FEATURE
<222> LOCATION: (22)..(22)
<223> OTHER INFORMATION: Xaa is F, W, or Y
<220> FEATURE:
<221> NAME/KEY: MISC_FEATURE
<222> LOCATION: (24)..(24)
<223> OTHER INFORMATION: Xaa is D or E
<220> FEATURE:
<221> NAME/KEY: MISC_FEATURE
<222> LOCATION: (25)..(25)
<223> OTHER INFORMATION: Xaa is S, T, N or Q
<220> FEATURE:
<221> NAME/KEY: MISC_FEATURE
<222> LOCATION: (26)..(28)
<223> OTHER INFORMATION: Xaa is A, C, G, P, M, V, I, L, Sce, or Sme
<220> FEATURE:
<221> NAME/KEY: MISC_FEATURE
<222> LOCATION: (29)..(29)
<223> OTHER INFORMATION: Xaa is D or E
<220> FEATURE:
<221> NAME/KEY: MISC_FEATURE
<222> LOCATION: (30)..(30)
<223> OTHER INFORMATION: Xaa is A, C, G, P, M, V, I, L, Sce, or Sme
<220> FEATURE:
<221> NAME/KEY: MISC_FEATURE
<222> LOCATION: (31)..(31)
<223> OTHER INFORMATION: Xaa is S, T, N or Q
<220> FEATURE:
<221> NAME/KEY: MISC_FEATURE
<222> LOCATION: (32)..(32)
<223> OTHER INFORMATION: Xaa is A, C, G, P, M, V, I, L, Sce, or Sme
<220> FEATURE:
<221> NAME/KEY: MISC_FEATURE
<222> LOCATION: (33)..(33)
<223> OTHER INFORMATION: Xaa is S, T, N or Q
<220> FEATURE:
<221> NAME/KEY: MISC_FEATURE
<222> LOCATION: (34)..(34)
<223> OTHER INFORMATION: Xaa is A, C, G, P, M, V, I, L, Sce, or Sme
<220> FEATURE:
<221> NAME/KEY: MISC_FEATURE
<222> LOCATION: (35)..(36)
<223> OTHER INFORMATION: Xaa is D or E
<220> FEATURE:
<221> NAME/KEY: MISC_FEATURE
<222> LOCATION: (37)..(37)
<223> OTHER INFORMATION: Xaa is A, C, G, P, M, V, I, L, Sce, or Sme
<220> FEATURE:
```

<221> NAME/KEY: MISC_FEATURE
<222> LOCATION: (38)..(39)
<223> OTHER INFORMATION: Xaa is S, T, N or Q
<220> FEATURE:
<221> NAME/KEY: MISC_FEATURE
<222> LOCATION: (40)..(40)
<223> OTHER INFORMATION: Xaa is F, W, or Y
<220> FEATURE:
<221> NAME/KEY: MISC_FEATURE
<222> LOCATION: (41)..(42)
<223> OTHER INFORMATION: Xaa is A, C, G, P, M, V, I, L, Sce, or Sme
<220> FEATURE:
<221> NAME/KEY: MISC_FEATURE
<222> LOCATION: (43)..(43)
<223> OTHER INFORMATION: Xaa is D or E
<220> FEATURE:
<221> NAME/KEY: MISC_FEATURE
<222> LOCATION: (44)..(44)
<223> OTHER INFORMATION: Xaa is A, C, G, P, M, V, I, L, Sce, or Sme
<220> FEATURE:
<221> NAME/KEY: MISC_FEATURE
<222> LOCATION: (45)..(46)
<223> OTHER INFORMATION: Xaa is R, H, or K
<220> FEATURE:
<221> NAME/KEY: MISC_FEATURE
<222> LOCATION: (47)..(47)
<223> OTHER INFORMATION: Xaa is F, W, or Y
<220> FEATURE:
<221> NAME/KEY: MISC_FEATURE
<222> LOCATION: (48)..(48)
<223> OTHER INFORMATION: Xaa is A, C, G, P, M, V, I, L, Sce, or Sme
<220> FEATURE:
<221> NAME/KEY: MISC_FEATURE
<222> LOCATION: (49)..(51)
<223> OTHER INFORMATION: Xaa is D or E
<220> FEATURE:
<221> NAME/KEY: MISC_FEATURE
<222> LOCATION: (52)..(52)
<223> OTHER INFORMATION: Xaa is A, C, G, P, M, V, I, L, Sce, or Sme
<220> FEATURE:
<221> NAME/KEY: MISC_FEATURE
<222> LOCATION: (53)..(53)
<223> OTHER INFORMATION: Xaa is R, H, or K
<220> FEATURE:
<221> NAME/KEY: MISC_FEATURE
<222> LOCATION: (54)..(56)
<223> OTHER INFORMATION: Xaa is A, C, G, P, M, V, I, L, Sce, or Sme
<220> FEATURE:
<221> NAME/KEY: MISC_FEATURE
<222> LOCATION: (57)..(58)
<223> OTHER INFORMATION: Xaa is D or E
<220> FEATURE:
<221> NAME/KEY: MISC_FEATURE
<222> LOCATION: (59)..(59)
<223> OTHER INFORMATION: Xaa is A, C, G, P, M, V, I, L, Sce, or Sme
<220> FEATURE:
<221> NAME/KEY: MISC_FEATURE
<222> LOCATION: (60)..(61)
<223> OTHER INFORMATION: Xaa is S, T, N or Q
<220> FEATURE:
<221> NAME/KEY: MISC_FEATURE
<222> LOCATION: (62)..(62)
<223> OTHER INFORMATION: Xaa is D or E
<220> FEATURE:
<221> NAME/KEY: MISC_FEATURE
<222> LOCATION: (63)..(63)
<223> OTHER INFORMATION: Xaa is A, C, G, P, M, V, I, L, Sce, or Sme
<220> FEATURE:
<221> NAME/KEY: MISC_FEATURE
<222> LOCATION: (64)..(64)
<223> OTHER INFORMATION: Xaa is F, W, or Y
<220> FEATURE:
<221> NAME/KEY: MISC_FEATURE
<222> LOCATION: (65)..(65)
<223> OTHER INFORMATION: Xaa is R, H, or K
<220> FEATURE:
<221> NAME/KEY: MISC_FEATURE
<222> LOCATION: (66)..(68)
<223> OTHER INFORMATION: Xaa is A, C, G, P, M, V, I, L, Sce, or Sme

```
<220> FEATURE:
<221> NAME/KEY: MISC_FEATURE
<222> LOCATION: (69)..(69)
<223> OTHER INFORMATION: Xaa is D or E
<220> FEATURE:
<221> NAME/KEY: MISC_FEATURE
<222> LOCATION: (70)..(71)
<223> OTHER INFORMATION: Xaa is A, C, G, P, M, V, I, L, Sce, or Sme
<220> FEATURE:
<221> NAME/KEY: MISC_FEATURE
<222> LOCATION: (72)..(72)
<223> OTHER INFORMATION: Xaa is S, T, N or Q
<220> FEATURE:
<221> NAME/KEY: MISC_FEATURE
<222> LOCATION: (73)..(73)
<223> OTHER INFORMATION: Xaa is R, H, or K
<220> FEATURE:
<221> NAME/KEY: MISC_FEATURE
<222> LOCATION: (74)..(74)
<223> OTHER INFORMATION: Xaa is A, C, G, P, M, V, I, L, Sce, or Sme
<220> FEATURE:
<221> NAME/KEY: MISC_FEATURE
<222> LOCATION: (75)..(75)
<223> OTHER INFORMATION: Xaa is R, H, or K
<220> FEATURE:
<221> NAME/KEY: MISC_FEATURE
<222> LOCATION: (76)..(76)
<223> OTHER INFORMATION: Xaa is A, C, G, P, M, V, I, L, Sce, or Sme
<220> FEATURE:
<221> NAME/KEY: MISC_FEATURE
<222> LOCATION: (77)..(77)
<223> OTHER INFORMATION: Xaa is D or E
<220> FEATURE:
<221> NAME/KEY: MISC_FEATURE
<222> LOCATION: (78)..(79)
<223> OTHER INFORMATION: Xaa is A, C, G, P, M, V, I, L, Sce, or Sme
<220> FEATURE:
<221> NAME/KEY: MISC_FEATURE
<222> LOCATION: (80)..(80)
<223> OTHER INFORMATION: Xaa is S, T, N or Q
<220> FEATURE:
<221> NAME/KEY: MISC_FEATURE
<222> LOCATION: (82)..(82)
<223> OTHER INFORMATION: Xaa is D or E
<220> FEATURE:
<221> NAME/KEY: MISC_FEATURE
<222> LOCATION: (83)..(83)
<223> OTHER INFORMATION: Xaa is R, H, or K
<220> FEATURE:
<221> NAME/KEY: MISC_FEATURE
<222> LOCATION: (86)..(86)
<223> OTHER INFORMATION: Xaa is F, W, or Y
<220> FEATURE:
<221> NAME/KEY: MISC_FEATURE
<222> LOCATION: (87)..(87)
<223> OTHER INFORMATION: Xaa is A, C, G, P, M, V, I, L, Sce, or Sme
<220> FEATURE:
<221> NAME/KEY: MISC_FEATURE
<222> LOCATION: (89)..(89)
<223> OTHER INFORMATION: Xaa is R, H, or K
<220> FEATURE:
<221> NAME/KEY: MISC_FEATURE
<222> LOCATION: (90)..(90)
<223> OTHER INFORMATION: Xaa is A, C, G, P, M, V, I, L, Sce, or Sme
<220> FEATURE:
<221> NAME/KEY: MISC_FEATURE
<222> LOCATION: (93)..(93)
<223> OTHER INFORMATION: Xaa is R, H, or K
<220> FEATURE:
<221> NAME/KEY: MISC_FEATURE
<222> LOCATION: (94)..(94)
<223> OTHER INFORMATION: Xaa is F, W, or Y
<220> FEATURE:
<221> NAME/KEY: MISC_FEATURE
<222> LOCATION: (96)..(96)
<223> OTHER INFORMATION: Xaa is D or E
<220> FEATURE:
<221> NAME/KEY: MISC_FEATURE
<222> LOCATION: (97)..(98)
```

```
<223> OTHER INFORMATION: Xaa is A, C, G, P, M, V, I, L, Sce, or Sme
<220> FEATURE:
<221> NAME/KEY: MISC_FEATURE
<222> LOCATION: (99)..(99)
<223> OTHER INFORMATION: Xaa is S, T, N or Q
<220> FEATURE:
<221> NAME/KEY: MISC_FEATURE
<222> LOCATION: (100)..(100)
<223> OTHER INFORMATION: Xaa is A, C, G, P, M, V, I, L, Sce, or Sme
<220> FEATURE:
<221> NAME/KEY: MISC_FEATURE
<222> LOCATION: (101)..(101)
<223> OTHER INFORMATION: Xaa is R, H, or K
<220> FEATURE:
<221> NAME/KEY: MISC_FEATURE
<222> LOCATION: (102)..(102)
<223> OTHER INFORMATION: Xaa is S, T, N or Q
<220> FEATURE:
<221> NAME/KEY: MISC_FEATURE
<222> LOCATION: (103)..(103)
<223> OTHER INFORMATION: Xaa is F, W, or Y
<220> FEATURE:
<221> NAME/KEY: MISC_FEATURE
<222> LOCATION: (104)..(108)
<223> OTHER INFORMATION: Xaa is A, C, G, P, M, V, I, L, Sce, or Sme
<220> FEATURE:
<221> NAME/KEY: MISC_FEATURE
<222> LOCATION: (109)..(109)
<223> OTHER INFORMATION: Xaa is S, T, N or Q
<220> FEATURE:
<221> NAME/KEY: MISC_FEATURE
<222> LOCATION: (110)..(110)
<223> OTHER INFORMATION: Xaa is A, C, G, P, M, V, I, L, Sce, or Sme
<220> FEATURE:
<221> NAME/KEY: MISC_FEATURE
<222> LOCATION: (111)..(111)
<223> OTHER INFORMATION: Xaa is D or E
<220> FEATURE:
<221> NAME/KEY: MISC_FEATURE
<222> LOCATION: (112)..(112)
<223> OTHER INFORMATION: Xaa is S, T, N or Q
<220> FEATURE:
<221> NAME/KEY: MISC_FEATURE
<222> LOCATION: (113)..(113)
<223> OTHER INFORMATION: Xaa is A, C, G, P, M, V, I, L, Sce, or Sme
<220> FEATURE:
<221> NAME/KEY: MISC_FEATURE
<222> LOCATION: (114)..(114)
<223> OTHER INFORMATION: Xaa is R, H, or K
<220> FEATURE:
<221> NAME/KEY: MISC_FEATURE
<222> LOCATION: (115)..(115)
<223> OTHER INFORMATION: Xaa is A, C, G, P, M, V, I, L, Sce, or Sme
<220> FEATURE:
<221> NAME/KEY: MISC_FEATURE
<222> LOCATION: (116)..(116)
<223> OTHER INFORMATION: Xaa is D or E
<220> FEATURE:
<221> NAME/KEY: MISC_FEATURE
<222> LOCATION: (117)..(118)
<223> OTHER INFORMATION: Xaa is A, C, G, P, M, V, I, L, Sce, or Sme
<220> FEATURE:
<221> NAME/KEY: MISC_FEATURE
<222> LOCATION: (119)..(119)
<223> OTHER INFORMATION: Xaa is R, H, or K
<220> FEATURE:
<221> NAME/KEY: MISC_FEATURE
<222> LOCATION: (120)..(120)
<223> OTHER INFORMATION: Xaa is S, T, N or Q
<220> FEATURE:
<221> NAME/KEY: MISC_FEATURE
<222> LOCATION: (121)..(122)
<223> OTHER INFORMATION: Xaa is A, C, G, P, M, V, I, L, Sce, or Sme
<220> FEATURE:
<221> NAME/KEY: MISC_FEATURE
<222> LOCATION: (123)..(124)
<223> OTHER INFORMATION: Xaa is R, H, or K
<220> FEATURE:
<221> NAME/KEY: MISC_FEATURE
```

```
<222> LOCATION: (125)..(125)
<223> OTHER INFORMATION: Xaa is A, C, G, P, M, V, I, L, Sce, or Sme
<220> FEATURE:
<221> NAME/KEY: MISC_FEATURE
<222> LOCATION: (127)..(128)
<223> OTHER INFORMATION: Xaa is R, H, or K
<220> FEATURE:
<221> NAME/KEY: MISC_FEATURE
<222> LOCATION: (129)..(129)
<223> OTHER INFORMATION: Xaa is A, C, G, P, M, V, I, L, Sce, or Sme
<220> FEATURE:
<221> NAME/KEY: MISC_FEATURE
<222> LOCATION: (131)..(131)
<223> OTHER INFORMATION: Xaa is S, T, N or Q
<220> FEATURE:
<221> NAME/KEY: MISC_FEATURE
<222> LOCATION: (132)..(132)
<223> OTHER INFORMATION: Xaa is A, C, G, P, M, V, I, L, Sce, or Sme
<220> FEATURE:
<221> NAME/KEY: MISC_FEATURE
<222> LOCATION: (135)..(135)
<223> OTHER INFORMATION: Xaa is D or E
<220> FEATURE:
<221> NAME/KEY: MISC_FEATURE
<222> LOCATION: (136)..(136)
<223> OTHER INFORMATION: Xaa is F, W, or Y
<220> FEATURE:
<221> NAME/KEY: MISC_FEATURE
<222> LOCATION: (139)..(139)
<223> OTHER INFORMATION: Xaa is A, C, G, P, M, V, I, L, Sce, or Sme
<220> FEATURE:
<221> NAME/KEY: MISC_FEATURE
<222> LOCATION: (142)..(142)
<223> OTHER INFORMATION: Xaa is A, C, G, P, M, V, I, L, Sce, or Sme
<220> FEATURE:
<221> NAME/KEY: MISC_FEATURE
<222> LOCATION: (145)..(145)
<223> OTHER INFORMATION: Xaa is F, W, or Y
<220> FEATURE:
<221> NAME/KEY: MISC_FEATURE
<222> LOCATION: (146)..(146)
<223> OTHER INFORMATION: Xaa is A, C, G, P, M, V, I, L, Sce, or Sme
<220> FEATURE:
<221> NAME/KEY: MISC_FEATURE
<222> LOCATION: (149)..(149)
<223> OTHER INFORMATION: Xaa is A, C, G, P, M, V, I, L, Sce, or Sme
<220> FEATURE:
<221> NAME/KEY: MISC_FEATURE
<222> LOCATION: (150)..(150)
<223> OTHER INFORMATION: Xaa is S, T, N or Q
<220> FEATURE:
<221> NAME/KEY: MISC_FEATURE
<222> LOCATION: (152)..(153)
<223> OTHER INFORMATION: Xaa is A, C, G, P, M, V, I, L, Sce, or Sme
<220> FEATURE:
<221> NAME/KEY: MISC_FEATURE
<222> LOCATION: (154)..(154)
<223> OTHER INFORMATION: Xaa is F, W, or Y
<220> FEATURE:
<221> NAME/KEY: MISC_FEATURE
<222> LOCATION: (155)..(157)
<223> OTHER INFORMATION: Xaa is A, C, G, P, M, V, I, L, Sce, or Sme
<220> FEATURE:
<221> NAME/KEY: MISC_FEATURE
<222> LOCATION: (158)..(158)
<223> OTHER INFORMATION: Xaa is R, H, or K
<220> FEATURE:
<221> NAME/KEY: MISC_FEATURE
<222> LOCATION: (159)..(160)
<223> OTHER INFORMATION: Xaa is A, C, G, P, M, V, I, L, Sce, or Sme
<220> FEATURE:
<221> NAME/KEY: MISC_FEATURE
<222> LOCATION: (161)..(161)
<223> OTHER INFORMATION: Xaa is D or E
<220> FEATURE:
<221> NAME/KEY: MISC_FEATURE
<222> LOCATION: (162)..(162)
<223> OTHER INFORMATION: Xaa is A, C, G, P, M, V, I, L, Sce, or Sme
<220> FEATURE:
```

<220> FEATURE:
<221> NAME/KEY: MISC_FEATURE
<222> LOCATION: (163)..(163)
<223> OTHER INFORMATION: Xaa is D or E
<220> FEATURE:
<221> NAME/KEY: MISC_FEATURE
<222> LOCATION: (164)..(164)
<223> OTHER INFORMATION: Xaa is R, H, or K
<220> FEATURE:
<221> NAME/KEY: MISC_FEATURE
<222> LOCATION: (165)..(165)
<223> OTHER INFORMATION: Xaa is S, T, N or Q
<220> FEATURE:
<221> NAME/KEY: MISC_FEATURE
<222> LOCATION: (166)..(166)
<223> OTHER INFORMATION: Xaa is R, H, or K
<220> FEATURE:
<221> NAME/KEY: MISC_FEATURE
<222> LOCATION: (167)..(167)
<223> OTHER INFORMATION: Xaa is A, C, G, P, M, V, I, L, Sce, or Sme
<220> FEATURE:
<221> NAME/KEY: MISC_FEATURE
<222> LOCATION: (168)..(168)
<223> OTHER INFORMATION: Xaa is R, H, or K
<220> FEATURE:
<221> NAME/KEY: MISC_FEATURE
<222> LOCATION: (169)..(169)
<223> OTHER INFORMATION: Xaa is D or E
<220> FEATURE:
<221> NAME/KEY: MISC_FEATURE
<222> LOCATION: (170)..(170)
<223> OTHER INFORMATION: Xaa is A, C, G, P, M, V, I, L, Sce, or Sme
<220> FEATURE:
<221> NAME/KEY: MISC_FEATURE
<222> LOCATION: (171)..(171)
<223> OTHER INFORMATION: Xaa is R, H, or K
<220> FEATURE:
<221> NAME/KEY: MISC_FEATURE
<222> LOCATION: (172)..(172)
<223> OTHER INFORMATION: Xaa is S, T, N or Q

<400> SEQUENCE: 27

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Lys Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Glu Xaa Xaa Ile Ala Xaa Xaa Leu Xaa Xaa Ile Leu Xaa Xaa Met Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Leu Xaa Xaa
        115                 120                 125

Xaa Leu Xaa Xaa Thr Arg Xaa Xaa Gly Ile Xaa Ala Glu Xaa Ala Ala
    130                 135                 140

Xaa Xaa Leu Ala Xaa Xaa Asp Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa
                165                 170

<210> SEQ ID NO 28
<211> LENGTH: 123
<212> TYPE: PRT

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (2)..(2)
<223> OTHER INFORMATION: Xaa is A, C, G, P, M, V, I, L, Sce or Sme
<220> FEATURE:
<221> NAME/KEY: MISC_FEATURE
<222> LOCATION: (3)..(3)
<223> OTHER INFORMATION: Xaa is R, H, or K
<220> FEATURE:
<221> NAME/KEY: MISC_FEATURE
<222> LOCATION: (4)..(6)
<223> OTHER INFORMATION: Xaa is A, C, G, P, M, V, I, L, Sce or Sme
<220> FEATURE:
<221> NAME/KEY: MISC_FEATURE
<222> LOCATION: (7)..(7)
<223> OTHER INFORMATION: Xaa is D or E
<220> FEATURE:
<221> NAME/KEY: MISC_FEATURE
<222> LOCATION: (8)..(8)
<223> OTHER INFORMATION: Xaa is A, C, G, P, M, V, I, L, Sce or Sme
<220> FEATURE:
<221> NAME/KEY: MISC_FEATURE
<222> LOCATION: (9)..(9)
<223> OTHER INFORMATION: Xaa is S, T, N, or Q
<220> FEATURE:
<221> NAME/KEY: MISC_FEATURE
<222> LOCATION: (10)..(10)
<223> OTHER INFORMATION: Xaa is A, C, G, P, M, V, I, L, Sce or Sme
<220> FEATURE:
<221> NAME/KEY: MISC_FEATURE
<222> LOCATION: (11)..(11)
<223> OTHER INFORMATION: Xaa is S, T, N, or Q
<220> FEATURE:
<221> NAME/KEY: MISC_FEATURE
<222> LOCATION: (12)..(12)
<223> OTHER INFORMATION: Xaa is A, C, G, P, M, V, I, L, Sce or Sme
<220> FEATURE:
<221> NAME/KEY: MISC_FEATURE
<222> LOCATION: (13)..(13)
<223> OTHER INFORMATION: Xaa is R, H, or K
<220> FEATURE:
<221> NAME/KEY: MISC_FEATURE
<222> LOCATION: (14)..(14)
<223> OTHER INFORMATION: Xaa is A, C, G, P, M, V, I, L, Sce or Sme
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (16)..(17)
<223> OTHER INFORMATION: Xaa is S, T, N, or Q
<220> FEATURE:
<221> NAME/KEY: MISC_FEATURE
<222> LOCATION: (18)..(19)
<223> OTHER INFORMATION: Xaa is A, C, G, P, M, V, I, L, Sce or Sme
<220> FEATURE:
<221> NAME/KEY: MISC_FEATURE
<222> LOCATION: (20)..(20)
<223> OTHER INFORMATION: Xaa is D or E
<220> FEATURE:
<221> NAME/KEY: MISC_FEATURE
<222> LOCATION: (21)..(22)
<223> OTHER INFORMATION: Xaa is A, C, G, P, M, V, I, L, Sce or Sme
<220> FEATURE:
<221> NAME/KEY: MISC_FEATURE
<222> LOCATION: (23)..(23)
<223> OTHER INFORMATION: Xaa is D or E
<220> FEATURE:
<221> NAME/KEY: MISC_FEATURE
<222> LOCATION: (24)..(24)
<223> OTHER INFORMATION: Xaa is S, T, N, or Q
```

```
<220> FEATURE:
<221> NAME/KEY: MISC_FEATURE
<222> LOCATION: (25)..(25)
<223> OTHER INFORMATION: Xaa is A, C, G, P, M, V, I, L, Sce or Sme
<220> FEATURE:
<221> NAME/KEY: MISC_FEATURE
<222> LOCATION: (26)..(26)
<223> OTHER INFORMATION: Xaa is S, T, N, or Q
<220> FEATURE:
<221> NAME/KEY: MISC_FEATURE
<222> LOCATION: (27)..(27)
<223> OTHER INFORMATION: Xaa is D or E
<220> FEATURE:
<221> NAME/KEY: MISC_FEATURE
<222> LOCATION: (29)..(29)
<223> OTHER INFORMATION: Xaa is A, C, G, P, M, V, I, L, Sce or Sme
<220> FEATURE:
<221> NAME/KEY: MISC_FEATURE
<222> LOCATION: (33)..(33)
<223> OTHER INFORMATION: Xaa is A, C, G, P, M, V, I, L, Sce or Sme
<220> FEATURE:
<221> NAME/KEY: MISC_FEATURE
<222> LOCATION: (35)..(35)
<223> OTHER INFORMATION: Xaa is F, W, or Y
<220> FEATURE:
<221> NAME/KEY: MISC_FEATURE
<222> LOCATION: (36)..(36)
<223> OTHER INFORMATION: Xaa is A, C, G, P, M, V, I, L, Sce or Sme
<220> FEATURE:
<221> NAME/KEY: MISC_FEATURE
<222> LOCATION: (37)..(37)
<223> OTHER INFORMATION: Xaa is D or E
<220> FEATURE:
<221> NAME/KEY: MISC_FEATURE
<222> LOCATION: (38)..(38)
<223> OTHER INFORMATION: Xaa is A, C, G, P, M, V, I, L, Sce or Sme
<220> FEATURE:
<221> NAME/KEY: MISC_FEATURE
<222> LOCATION: (39)..(39)
<223> OTHER INFORMATION: Xaa is D or E
<220> FEATURE:
<221> NAME/KEY: MISC_FEATURE
<222> LOCATION: (40)..(40)
<223> OTHER INFORMATION: Xaa is A, C, G, P, M, V, I, L, Sce or Sme
<220> FEATURE:
<221> NAME/KEY: MISC_FEATURE
<222> LOCATION: (41)..(41)
<223> OTHER INFORMATION: Xaa is R, H, or K
<220> FEATURE:
<221> NAME/KEY: MISC_FEATURE
<222> LOCATION: (42)..(42)
<223> OTHER INFORMATION: Xaa is S, T, N, or Q
<220> FEATURE:
<221> NAME/KEY: MISC_FEATURE
<222> LOCATION: (43)..(43)
<223> OTHER INFORMATION: Xaa is R, H, or K
<220> FEATURE:
<221> NAME/KEY: MISC_FEATURE
<222> LOCATION: (44)..(44)
<223> OTHER INFORMATION: Xaa is F, W, or Y
<220> FEATURE:
<221> NAME/KEY: MISC_FEATURE
<222> LOCATION: (45)..(45)
<223> OTHER INFORMATION: Xaa is A, C, G, P, M, V, I, L, Sce or Sme
<220> FEATURE:
<221> NAME/KEY: MISC_FEATURE
<222> LOCATION: (46)..(46)
<223> OTHER INFORMATION: Xaa is S, T, N, or Q
<220> FEATURE:
<221> NAME/KEY: MISC_FEATURE
<222> LOCATION: (47)..(47)
<223> OTHER INFORMATION: Xaa is A, C, G, P, M, V, I, L, Sce or Sme
<220> FEATURE:
<221> NAME/KEY: MISC_FEATURE
<222> LOCATION: (48)..(48)
<223> OTHER INFORMATION: Xaa is D or E
<220> FEATURE:
<221> NAME/KEY: MISC_FEATURE
<222> LOCATION: (49)..(49)
```

```
<223> OTHER INFORMATION: Xaa is A, C, G, P, M, V, I, L, Sce or Sme
<220> FEATURE:
<221> NAME/KEY: MISC_FEATURE
<222> LOCATION: (50)..(50)
<223> OTHER INFORMATION: Xaa is F, W, or Y
<220> FEATURE:
<221> NAME/KEY: MISC_FEATURE
<222> LOCATION: (51)..(51)
<223> OTHER INFORMATION: Xaa is R, H, or K
<220> FEATURE:
<221> NAME/KEY: MISC_FEATURE
<222> LOCATION: (52)..(52)
<223> OTHER INFORMATION: Xaa is S, T, N, or Q
<220> FEATURE:
<221> NAME/KEY: MISC_FEATURE
<222> LOCATION: (53)..(53)
<223> OTHER INFORMATION: Xaa is A, C, G, P, M, V, I, L, Sce or Sme
<220> FEATURE:
<221> NAME/KEY: MISC_FEATURE
<222> LOCATION: (54)..(54)
<223> OTHER INFORMATION: Xaa is S, T, N, or Q
<220> FEATURE:
<221> NAME/KEY: MISC_FEATURE
<222> LOCATION: (55)..(57)
<223> OTHER INFORMATION: Xaa is A, C, G, P, M, V, I, L, Sce or Sme
<220> FEATURE:
<221> NAME/KEY: MISC_FEATURE
<222> LOCATION: (58)..(58)
<223> OTHER INFORMATION: Xaa is D or E
<220> FEATURE:
<221> NAME/KEY: MISC_FEATURE
<222> LOCATION: (59)..(59)
<223> OTHER INFORMATION: Xaa is R, H, or K
<220> FEATURE:
<221> NAME/KEY: MISC_FEATURE
<222> LOCATION: (60)..(60)
<223> OTHER INFORMATION: Xaa is A, C, G, P, M, V, I, L, Sce or Sme
<220> FEATURE:
<221> NAME/KEY: MISC_FEATURE
<222> LOCATION: (61)..(61)
<223> OTHER INFORMATION: Xaa is F, W, or Y
<220> FEATURE:
<221> NAME/KEY: MISC_FEATURE
<222> LOCATION: (62)..(62)
<223> OTHER INFORMATION: Xaa is A, C, G, P, M, V, I, L, Sce or Sme
<220> FEATURE:
<221> NAME/KEY: MISC_FEATURE
<222> LOCATION: (63)..(63)
<223> OTHER INFORMATION: Xaa is R, H, or K
<220> FEATURE:
<221> NAME/KEY: MISC_FEATURE
<222> LOCATION: (64)..(66)
<223> OTHER INFORMATION: Xaa is A, C, G, P, M, V, I, L, Sce or Sme
<220> FEATURE:
<221> NAME/KEY: MISC_FEATURE
<222> LOCATION: (67)..(67)
<223> OTHER INFORMATION: Xaa is S, T, N, or Q
<220> FEATURE:
<221> NAME/KEY: MISC_FEATURE
<222> LOCATION: (68)..(69)
<223> OTHER INFORMATION: Xaa is A, C, G, P, M, V, I, L, Sce or Sme
<220> FEATURE:
<221> NAME/KEY: MISC_FEATURE
<222> LOCATION: (70)..(70)
<223> OTHER INFORMATION: Xaa is D or E
<220> FEATURE:
<221> NAME/KEY: MISC_FEATURE
<222> LOCATION: (72)..(72)
<223> OTHER INFORMATION: Xaa is R, H, or K
<220> FEATURE:
<221> NAME/KEY: MISC_FEATURE
<222> LOCATION: (77)..(77)
<223> OTHER INFORMATION: Xaa is R, H, or K
<220> FEATURE:
<221> NAME/KEY: MISC_FEATURE
<222> LOCATION: (80)..(81)
<223> OTHER INFORMATION: Xaa is A, C, G, P, M, V, I, L, Sce or Sme
<220> FEATURE:
<221> NAME/KEY: MISC_FEATURE
```

-continued

```
<222> LOCATION: (84)..(84)
<223> OTHER INFORMATION: Xaa is A, C, G, P, M, V, I, L, Sce or Sme
<220> FEATURE:
<221> NAME/KEY: MISC_FEATURE
<222> LOCATION: (87)..(89)
<223> OTHER INFORMATION: Xaa is A, C, G, P, M, V, I, L, Sce or Sme
<220> FEATURE:
<221> NAME/KEY: MISC_FEATURE
<222> LOCATION: (90)..(90)
<223> OTHER INFORMATION: Xaa is D or E
<220> FEATURE:
<221> NAME/KEY: MISC_FEATURE
<222> LOCATION: (91)..(96)
<223> OTHER INFORMATION: Xaa is A, C, G, P, M, V, I, L, Sce or Sme
<220> FEATURE:
<221> NAME/KEY: MISC_FEATURE
<222> LOCATION: (97)..(98)
<223> OTHER INFORMATION: Xaa is D or E
<220> FEATURE:
<221> NAME/KEY: MISC_FEATURE
<222> LOCATION: (99)..(100)
<223> OTHER INFORMATION: Xaa is A, C, G, P, M, V, I, L, Sce or Sme
<220> FEATURE:
<221> NAME/KEY: MISC_FEATURE
<222> LOCATION: (101)..(101)
<223> OTHER INFORMATION: Xaa is S, T, N, or Q
<220> FEATURE:
<221> NAME/KEY: MISC_FEATURE
<222> LOCATION: (102)..(102)
<223> OTHER INFORMATION: Xaa is A, C, G, P, M, V, I, L, Sce or Sme
<220> FEATURE:
<221> NAME/KEY: MISC_FEATURE
<222> LOCATION: (103)..(103)
<223> OTHER INFORMATION: Xaa is S, T, N, or Q
<220> FEATURE:
<221> NAME/KEY: MISC_FEATURE
<222> LOCATION: (104)..(104)
<223> OTHER INFORMATION: Xaa is A, C, G, P, M, V, I, L, Sce or Sme
<220> FEATURE:
<221> NAME/KEY: MISC_FEATURE
<222> LOCATION: (105)..(105)
<223> OTHER INFORMATION: Xaa is D or E
<220> FEATURE:
<221> NAME/KEY: MISC_FEATURE
<222> LOCATION: (106)..(106)
<223> OTHER INFORMATION: Xaa is A, C, G, P, M, V, I, L, Sce or Sme
<220> FEATURE:
<221> NAME/KEY: MISC_FEATURE
<222> LOCATION: (107)..(107)
<223> OTHER INFORMATION: Xaa is R, H, or K
<220> FEATURE:
<221> NAME/KEY: MISC_FEATURE
<222> LOCATION: (108)..(108)
<223> OTHER INFORMATION: Xaa is D or E
<220> FEATURE:
<221> NAME/KEY: MISC_FEATURE
<222> LOCATION: (109)..(109)
<223> OTHER INFORMATION: Xaa is A, C, G, P, M, V, I, L, Sce or Sme
<220> FEATURE:
<221> NAME/KEY: MISC_FEATURE
<222> LOCATION: (110)..(110)
<223> OTHER INFORMATION: Xaa is D or E
<220> FEATURE:
<221> NAME/KEY: MISC_FEATURE
<222> LOCATION: (111)..(111)
<223> OTHER INFORMATION: Xaa is R, H, or K
<220> FEATURE:
<221> NAME/KEY: MISC_FEATURE
<222> LOCATION: (113)..(113)
<223> OTHER INFORMATION: Xaa is S, T, N, or Q
<220> FEATURE:
<221> NAME/KEY: MISC_FEATURE
<222> LOCATION: (118)..(120)
<223> OTHER INFORMATION: Xaa is A, C, G, P, M, V, I, L, Sce or Sme
<220> FEATURE:
<221> NAME/KEY: MISC_FEATURE
<222> LOCATION: (121)..(121)
<223> OTHER INFORMATION: Xaa is R, H, or K
<220> FEATURE:
```

<220> FEATURE:
<221> NAME/KEY: MISC_FEATURE
<222> LOCATION: (122)..(122)
<223> OTHER INFORMATION: Xaa is S, T, N, or Q
<220> FEATURE:
<221> NAME/KEY: MISC_FEATURE
<222> LOCATION: (123)..(123)
<223> OTHER INFORMATION: Xaa is R, H, or K

<400> SEQUENCE: 28

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Lys Ala Xaa Phe Ala Ser
                20                  25                  30

Xaa Gln Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Gly Xaa Asp Ile Ala Thr Xaa Thr Leu Xaa
65                  70              75                  80

Xaa Ala Ser Xaa Cys Ala Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Leu
        100                 105                 110

Xaa Tyr Ala Lys Arg Xaa Xaa Xaa Xaa Xaa Xaa
        115                 120

<210> SEQ ID NO 29
<211> LENGTH: 158
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (2)..(2)
<223> OTHER INFORMATION: Xaa is D or E
<220> FEATURE:
<221> NAME/KEY: MISC_FEATURE
<222> LOCATION: (3)..(3)
<223> OTHER INFORMATION: Xaa is S, T, N or Q
<220> FEATURE:
<221> NAME/KEY: MISC_FEATURE
<222> LOCATION: (4)..(4)
<223> OTHER INFORMATION: Xaa is A, C, G, P, M, V, I, L, Sce or Sme
<220> FEATURE:
<221> NAME/KEY: MISC_FEATURE
<222> LOCATION: (5)..(7)
<223> OTHER INFORMATION: Xaa is S, T, N or Q
<220> FEATURE:
<221> NAME/KEY: MISC_FEATURE
<222> LOCATION: (8)..(8)
<223> OTHER INFORMATION: Xaa is F, W, or Y
<220> FEATURE:
<221> NAME/KEY: MISC_FEATURE
<222> LOCATION: (9)..(9)
<223> OTHER INFORMATION: Xaa is A, C, G, P, M, V, I, L, Sce or Sme
<220> FEATURE:
<221> NAME/KEY: MISC_FEATURE
<222> LOCATION: (10)..(10)
<223> OTHER INFORMATION: Xaa is S, T, N or Q
<220> FEATURE:
<221> NAME/KEY: MISC_FEATURE
<222> LOCATION: (11)..(11)
<223> OTHER INFORMATION: Xaa is A, C, G, P, M, V, I, L, Sce or Sme
<220> FEATURE:
<221> NAME/KEY: MISC_FEATURE

```
<222> LOCATION: (12)..(12)
<223> OTHER INFORMATION: Xaa is S, T, N or Q
<220> FEATURE:
<221> NAME/KEY: MISC_FEATURE
<222> LOCATION: (13)..(14)
<223> OTHER INFORMATION: Xaa is A, C, G, P, M, V, I, L, Sce or Sme
<220> FEATURE:
<221> NAME/KEY: MISC_FEATURE
<222> LOCATION: (15)..(15)
<223> OTHER INFORMATION: Xaa is S, T, N or Q
<220> FEATURE:
<221> NAME/KEY: MISC_FEATURE
<222> LOCATION: (16)..(16)
<223> OTHER INFORMATION: Xaa is A, C, G, P, M, V, I, L, Sce or Sme
<220> FEATURE:
<221> NAME/KEY: MISC_FEATURE
<222> LOCATION: (17)..(17)
<223> OTHER INFORMATION: Xaa is R, H, or K
<220> FEATURE:
<221> NAME/KEY: MISC_FEATURE
<222> LOCATION: (18)..(18)
<223> OTHER INFORMATION: Xaa is D or E
<220> FEATURE:
<221> NAME/KEY: MISC_FEATURE
<222> LOCATION: (19)..(19)
<223> OTHER INFORMATION: Xaa is F, W, or Y
<220> FEATURE:
<221> NAME/KEY: MISC_FEATURE
<222> LOCATION: (20)..(20)
<223> OTHER INFORMATION: Xaa is D or E
<220> FEATURE:
<221> NAME/KEY: MISC_FEATURE
<222> LOCATION: (21)..(21)
<223> OTHER INFORMATION: Xaa is S, T, N or Q
<220> FEATURE:
<221> NAME/KEY: MISC_FEATURE
<222> LOCATION: (22)..(22)
<223> OTHER INFORMATION: Xaa is A, C, G, P, M, V, I, L, Sce or Sme
<220> FEATURE:
<221> NAME/KEY: MISC_FEATURE
<222> LOCATION: (23)..(23)
<223> OTHER INFORMATION: Xaa is S, T, N or Q
<220> FEATURE:
<221> NAME/KEY: MISC_FEATURE
<222> LOCATION: (24)..(24)
<223> OTHER INFORMATION: Xaa is F, W, or Y
<220> FEATURE:
<221> NAME/KEY: MISC_FEATURE
<222> LOCATION: (25)..(27)
<223> OTHER INFORMATION: Xaa is A, C, G, P, M, V, I, L, Sce or Sme
<220> FEATURE:
<221> NAME/KEY: MISC_FEATURE
<222> LOCATION: (28)..(28)
<223> OTHER INFORMATION: Xaa is R, H, or K
<220> FEATURE:
<221> NAME/KEY: MISC_FEATURE
<222> LOCATION: (29)..(30)
<223> OTHER INFORMATION: Xaa is A, C, G, P, M, V, I, L, Sce or Sme
<220> FEATURE:
<221> NAME/KEY: MISC_FEATURE
<222> LOCATION: (31)..(31)
<223> OTHER INFORMATION: Xaa is R, H, or K
<220> FEATURE:
<221> NAME/KEY: MISC_FEATURE
<222> LOCATION: (32)..(32)
<223> OTHER INFORMATION: Xaa is S, T, N or Q
<220> FEATURE:
<221> NAME/KEY: MISC_FEATURE
<222> LOCATION: (33)..(33)
<223> OTHER INFORMATION: Xaa is A, C, G, P, M, V, I, L, Sce or Sme
<220> FEATURE:
<221> NAME/KEY: MISC_FEATURE
<222> LOCATION: (34)..(34)
<223> OTHER INFORMATION: Xaa is F, W, or Y
<220> FEATURE:
<221> NAME/KEY: MISC_FEATURE
<222> LOCATION: (35)..(36)
<223> OTHER INFORMATION: Xaa is A, C, G, P, M, V, I, L, Sce or Sme
<220> FEATURE:
```

-continued

```
<221> NAME/KEY: MISC_FEATURE
<222> LOCATION: (37)..(37)
<223> OTHER INFORMATION: Xaa is D or E
<220> FEATURE:
<221> NAME/KEY: MISC_FEATURE
<222> LOCATION: (38)..(38)
<223> OTHER INFORMATION: Xaa is R, H, or K
<220> FEATURE:
<221> NAME/KEY: MISC_FEATURE
<222> LOCATION: (39)..(39)
<223> OTHER INFORMATION: Xaa is A, C, G, P, M, V, I, L, Sce or Sme
<220> FEATURE:
<221> NAME/KEY: MISC_FEATURE
<222> LOCATION: (40)..(40)
<223> OTHER INFORMATION: Xaa is D or E
<220> FEATURE:
<221> NAME/KEY: MISC_FEATURE
<222> LOCATION: (41)..(41)
<223> OTHER INFORMATION: Xaa is A, C, G, P, M, V, I, L, Sce or Sme
<220> FEATURE:
<221> NAME/KEY: MISC_FEATURE
<222> LOCATION: (42)..(42)
<223> OTHER INFORMATION: Xaa is D or E
<220> FEATURE:
<221> NAME/KEY: MISC_FEATURE
<222> LOCATION: (43)..(45)
<223> OTHER INFORMATION: Xaa is A, C, G, P, M, V, I, L, Sce or Sme
<220> FEATURE:
<221> NAME/KEY: MISC_FEATURE
<222> LOCATION: (46)..(46)
<223> OTHER INFORMATION: Xaa is D or E
<220> FEATURE:
<221> NAME/KEY: MISC_FEATURE
<222> LOCATION: (47)..(47)
<223> OTHER INFORMATION: Xaa is R, H, or K
<220> FEATURE:
<221> NAME/KEY: MISC_FEATURE
<222> LOCATION: (48)..(48)
<223> OTHER INFORMATION: Xaa is A, C, G, P, M, V, I, L, Sce or Sme
<220> FEATURE:
<221> NAME/KEY: MISC_FEATURE
<222> LOCATION: (51)..(51)
<223> OTHER INFORMATION: Xaa is A, C, G, P, M, V, I, L, Sce or Sme
<220> FEATURE:
<221> NAME/KEY: MISC_FEATURE
<222> LOCATION: (55)..(55)
<223> OTHER INFORMATION: Xaa is S, T, N or Q
<220> FEATURE:
<221> NAME/KEY: MISC_FEATURE
<222> LOCATION: (58)..(59)
<223> OTHER INFORMATION: Xaa is A, C, G, P, M, V, I, L, Sce or Sme
<220> FEATURE:
<221> NAME/KEY: MISC_FEATURE
<222> LOCATION: (61)..(61)
<223> OTHER INFORMATION: Xaa is D or E
<220> FEATURE:
<221> NAME/KEY: MISC_FEATURE
<222> LOCATION: (62)..(62)
<223> OTHER INFORMATION: Xaa is S, T, N or Q
<220> FEATURE:
<221> NAME/KEY: MISC_FEATURE
<222> LOCATION: (63)..(64)
<223> OTHER INFORMATION: Xaa is D or E
<220> FEATURE:
<221> NAME/KEY: MISC_FEATURE
<222> LOCATION: (65)..(65)
<223> OTHER INFORMATION: Xaa is A, C, G, P, M, V, I, L, Sce or Sme
<220> FEATURE:
<221> NAME/KEY: MISC_FEATURE
<222> LOCATION: (66)..(66)
<223> OTHER INFORMATION: Xaa is F, W, or Y
<220> FEATURE:
<221> NAME/KEY: MISC_FEATURE
<222> LOCATION: (67)..(67)
<223> OTHER INFORMATION: Xaa is R, H, or K
<220> FEATURE:
<221> NAME/KEY: MISC_FEATURE
<222> LOCATION: (68)..(69)
<223> OTHER INFORMATION: Xaa is A, C, G, P, M, V, I, L, Sce or Sme
```

-continued

```
<220> FEATURE:
<221> NAME/KEY: MISC_FEATURE
<222> LOCATION: (70)..(70)
<223> OTHER INFORMATION: Xaa is R, H, or K
<220> FEATURE:
<221> NAME/KEY: MISC_FEATURE
<222> LOCATION: (71)..(71)
<223> OTHER INFORMATION: Xaa is A, C, G, P, M, V, I, L, Sce or Sme
<220> FEATURE:
<221> NAME/KEY: MISC_FEATURE
<222> LOCATION: (72)..(72)
<223> OTHER INFORMATION: Xaa is R, H, or K
<220> FEATURE:
<221> NAME/KEY: MISC_FEATURE
<222> LOCATION: (73)..(73)
<223> OTHER INFORMATION: Xaa is A, C, G, P, M, V, I, L, Sce or Sme
<220> FEATURE:
<221> NAME/KEY: MISC_FEATURE
<222> LOCATION: (74)..(74)
<223> OTHER INFORMATION: Xaa is R, H, or K
<220> FEATURE:
<221> NAME/KEY: MISC_FEATURE
<222> LOCATION: (75)..(76)
<223> OTHER INFORMATION: Xaa is A, C, G, P, M, V, I, L, Sce or Sme
<220> FEATURE:
<221> NAME/KEY: MISC_FEATURE
<222> LOCATION: (77)..(77)
<223> OTHER INFORMATION: Xaa is D or E
<220> FEATURE:
<221> NAME/KEY: MISC_FEATURE
<222> LOCATION: (78)..(78)
<223> OTHER INFORMATION: Xaa is A, C, G, P, M, V, I, L, Sce or Sme
<220> FEATURE:
<221> NAME/KEY: MISC_FEATURE
<222> LOCATION: (79)..(79)
<223> OTHER INFORMATION: Xaa is D or E
<220> FEATURE:
<221> NAME/KEY: MISC_FEATURE
<222> LOCATION: (80)..(80)
<223> OTHER INFORMATION: Xaa is D or E
<220> FEATURE:
<221> NAME/KEY: MISC_FEATURE
<222> LOCATION: (81)..(82)
<223> OTHER INFORMATION: Xaa is R, H, or K
<220> FEATURE:
<221> NAME/KEY: MISC_FEATURE
<222> LOCATION: (83)..(83)
<223> OTHER INFORMATION: Xaa is S, T, N or Q
<220> FEATURE:
<221> NAME/KEY: MISC_FEATURE
<222> LOCATION: (84)..(84)
<223> OTHER INFORMATION: Xaa is F, W, or Y
<220> FEATURE:
<221> NAME/KEY: MISC_FEATURE
<222> LOCATION: (85)..(85)
<223> OTHER INFORMATION: Xaa is S, T, N or Q
<220> FEATURE:
<221> NAME/KEY: MISC_FEATURE
<222> LOCATION: (86)..(88)
<223> OTHER INFORMATION: Xaa is A, C, G, P, M, V, I, L, Sce or Sme
<220> FEATURE:
<221> NAME/KEY: MISC_FEATURE
<222> LOCATION: (89)..(89)
<223> OTHER INFORMATION: Xaa is F, W, or Y
<220> FEATURE:
<221> NAME/KEY: MISC_FEATURE
<222> LOCATION: (90)..(90)
<223> OTHER INFORMATION: Xaa is A, C, G, P, M, V, I, L, Sce or Sme
<220> FEATURE:
<221> NAME/KEY: MISC_FEATURE
<222> LOCATION: (91)..(91)
<223> OTHER INFORMATION: Xaa is D or E
<220> FEATURE:
<221> NAME/KEY: MISC_FEATURE
<222> LOCATION: (92)..(95)
<223> OTHER INFORMATION: Xaa is A, C, G, P, M, V, I, L, Sce or Sme
<220> FEATURE:
<221> NAME/KEY: MISC_FEATURE
<222> LOCATION: (96)..(96)
```

```
<223> OTHER INFORMATION: Xaa is S, T, N or Q
<220> FEATURE:
<221> NAME/KEY: MISC_FEATURE
<222> LOCATION: (97)..(98)
<223> OTHER INFORMATION: Xaa is A, C, G, P, M, V, I, L, Sce or Sme
<220> FEATURE:
<221> NAME/KEY: MISC_FEATURE
<222> LOCATION: (99)..(99)
<223> OTHER INFORMATION: Xaa is S, T, N or Q
<220> FEATURE:
<221> NAME/KEY: MISC_FEATURE
<222> LOCATION: (100)..(100)
<223> OTHER INFORMATION: Xaa is D or E
<220> FEATURE:
<221> NAME/KEY: MISC_FEATURE
<222> LOCATION: (101)..(101)
<223> OTHER INFORMATION: Xaa is A, C, G, P, M, V, I, L, Sce or Sme
<220> FEATURE:
<221> NAME/KEY: MISC_FEATURE
<222> LOCATION: (102)..(102)
<223> OTHER INFORMATION: Xaa is D or E
<220> FEATURE:
<221> NAME/KEY: MISC_FEATURE
<222> LOCATION: (103)..(103)
<223> OTHER INFORMATION: Xaa is R, H, or K
<220> FEATURE:
<221> NAME/KEY: MISC_FEATURE
<222> LOCATION: (104)..(104)
<223> OTHER INFORMATION: Xaa is D or E
<220> FEATURE:
<221> NAME/KEY: MISC_FEATURE
<222> LOCATION: (105)..(105)
<223> OTHER INFORMATION: Xaa is S, T, N or Q
<220> FEATURE:
<221> NAME/KEY: MISC_FEATURE
<222> LOCATION: (106)..(106)
<223> OTHER INFORMATION: Xaa is A, C, G, P, M, V, I, L, Sce or Sme
<220> FEATURE:
<221> NAME/KEY: MISC_FEATURE
<222> LOCATION: (107)..(109)
<223> OTHER INFORMATION: Xaa is D or E
<220> FEATURE:
<221> NAME/KEY: MISC_FEATURE
<222> LOCATION: (110)..(110)
<223> OTHER INFORMATION: Xaa is A, C, G, P, M, V, I, L, Sce or Sme
<220> FEATURE:
<221> NAME/KEY: MISC_FEATURE
<222> LOCATION: (111)..(111)
<223> OTHER INFORMATION: Xaa is R, H, or K
<220> FEATURE:
<221> NAME/KEY: MISC_FEATURE
<222> LOCATION: (114)..(114)
<223> OTHER INFORMATION: Xaa is A, C, G, P, M, V, I, L, Sce or Sme
<220> FEATURE:
<221> NAME/KEY: MISC_FEATURE
<222> LOCATION: (115)..(115)
<223> OTHER INFORMATION: Xaa is R, H, or K
<220> FEATURE:
<221> NAME/KEY: MISC_FEATURE
<222> LOCATION: (118)..(118)
<223> OTHER INFORMATION: Xaa is A, C, G, P, M, V, I, L, Sce or Sme
<220> FEATURE:
<221> NAME/KEY: MISC_FEATURE
<222> LOCATION: (120)..(120)
<223> OTHER INFORMATION: Xaa is A, C, G, P, M, V, I, L, Sce or Sme
<220> FEATURE:
<221> NAME/KEY: MISC_FEATURE
<222> LOCATION: (121)..(121)
<223> OTHER INFORMATION: Xaa is D or E
<220> FEATURE:
<221> NAME/KEY: MISC_FEATURE
<222> LOCATION: (122)..(123)
<223> OTHER INFORMATION: Xaa is A, C, G, P, M, V, I, L, Sce or Sme
<220> FEATURE:
<221> NAME/KEY: MISC_FEATURE
<222> LOCATION: (124)..(125)
<223> OTHER INFORMATION: Xaa is D or E
<220> FEATURE:
<221> NAME/KEY: MISC_FEATURE
```

```
<222> LOCATION: (126)..(126)
<223> OTHER INFORMATION: Xaa is R, H, or K
<220> FEATURE:
<221> NAME/KEY: MISC_FEATURE
<222> LOCATION: (127)..(127)
<223> OTHER INFORMATION: Xaa is S, T, N or Q
<220> FEATURE:
<221> NAME/KEY: MISC_FEATURE
<222> LOCATION: (128)..(129)
<223> OTHER INFORMATION: Xaa is A, C, G, P, M, V, I, L, Sce or Sme
<220> FEATURE:
<221> NAME/KEY: MISC_FEATURE
<222> LOCATION: (130)..(131)
<223> OTHER INFORMATION: Xaa is S, T, N or Q
<220> FEATURE:
<221> NAME/KEY: MISC_FEATURE
<222> LOCATION: (132)..(132)
<223> OTHER INFORMATION: Xaa is F, W, or Y
<220> FEATURE:
<221> NAME/KEY: MISC_FEATURE
<222> LOCATION: (133)..(133)
<223> OTHER INFORMATION: Xaa is D or E
<220> FEATURE:
<221> NAME/KEY: MISC_FEATURE
<222> LOCATION: (134)..(134)
<223> OTHER INFORMATION: Xaa is A, C, G, P, M, V, I, L, Sce or Sme
<220> FEATURE:
<221> NAME/KEY: MISC_FEATURE
<222> LOCATION: (135)..(135)
<223> OTHER INFORMATION: Xaa is R, H, or K
<220> FEATURE:
<221> NAME/KEY: MISC_FEATURE
<222> LOCATION: (136)..(136)
<223> OTHER INFORMATION: Xaa is A, C, G, P, M, V, I, L, Sce or Sme
<220> FEATURE:
<221> NAME/KEY: MISC_FEATURE
<222> LOCATION: (137)..(137)
<223> OTHER INFORMATION: Xaa is R, H, or K
<220> FEATURE:
<221> NAME/KEY: MISC_FEATURE
<222> LOCATION: (138)..(139)
<223> OTHER INFORMATION: Xaa is D or E
<220> FEATURE:
<221> NAME/KEY: MISC_FEATURE
<222> LOCATION: (140)..(141)
<223> OTHER INFORMATION: Xaa is A, C, G, P, M, V, I, L, Sce or Sme
<220> FEATURE:
<221> NAME/KEY: MISC_FEATURE
<222> LOCATION: (142)..(143)
<223> OTHER INFORMATION: Xaa is S, T, N or Q
<220> FEATURE:
<221> NAME/KEY: MISC_FEATURE
<222> LOCATION: (144)..(144)
<223> OTHER INFORMATION: Xaa is D or E
<220> FEATURE:
<221> NAME/KEY: MISC_FEATURE
<222> LOCATION: (145)..(145)
<223> OTHER INFORMATION: Xaa is S, T, N or Q
<220> FEATURE:
<221> NAME/KEY: MISC_FEATURE
<222> LOCATION: (146)..(146)
<223> OTHER INFORMATION: Xaa is F, W, or Y
<220> FEATURE:
<221> NAME/KEY: MISC_FEATURE
<222> LOCATION: (147)..(147)
<223> OTHER INFORMATION: Xaa is R, H, or K
<220> FEATURE:
<221> NAME/KEY: MISC_FEATURE
<222> LOCATION: (148)..(148)
<223> OTHER INFORMATION: Xaa is A, C, G, P, M, V, I, L, Sce or Sme
<220> FEATURE:
<221> NAME/KEY: MISC_FEATURE
<222> LOCATION: (149)..(149)
<223> OTHER INFORMATION: Xaa is D or E
<220> FEATURE:
<221> NAME/KEY: MISC_FEATURE
<222> LOCATION: (150)..(150)
<223> OTHER INFORMATION: Xaa is R, H, or K
<220> FEATURE:
```

<221> NAME/KEY: MISC_FEATURE
<222> LOCATION: (151)..(152)
<223> OTHER INFORMATION: Xaa is D or E
<220> FEATURE:
<221> NAME/KEY: MISC_FEATURE
<222> LOCATION: (153)..(154)
<223> OTHER INFORMATION: Xaa is F, W, or Y
<220> FEATURE:
<221> NAME/KEY: MISC_FEATURE
<222> LOCATION: (155)..(155)
<223> OTHER INFORMATION: Xaa is R, H, or K
<220> FEATURE:
<221> NAME/KEY: MISC_FEATURE
<222> LOCATION: (156)..(156)
<223> OTHER INFORMATION: Xaa is D or E
<220> FEATURE:
<221> NAME/KEY: MISC_FEATURE
<222> LOCATION: (157)..(157)
<223> OTHER INFORMATION: Xaa is F, W, or Y
<220> FEATURE:
<221> NAME/KEY: MISC_FEATURE
<222> LOCATION: (158)..(158)
<223> OTHER INFORMATION: Xaa is A, C, G, P, M, V, I, L, Sce or Sme

<400> SEQUENCE: 29

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Ile Gly Xaa Arg Ala Ala Xaa Ile Phe Xaa Xaa Asp Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Leu
            100                 105                 110

Ala Xaa Xaa Val Ala Xaa Gln Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa
145                 150                 155
```

<210> SEQ ID NO 30
<211> LENGTH: 113
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (2)..(4)
<223> OTHER INFORMATION: Xaa is A, C, G, P, M, V, I, L, Sce, or Sme
<220> FEATURE:
<221> NAME/KEY: MISC_FEATURE
<222> LOCATION: (5)..(6)
<223> OTHER INFORMATION: Xaa is S, T, N or Q
<220> FEATURE:
<221> NAME/KEY: MISC_FEATURE
<222> LOCATION: (7)..(7)
<223> OTHER INFORMATION: Xaa is F, W, or Y -continued

```
<220> FEATURE:
<221> NAME/KEY: MISC_FEATURE
<222> LOCATION: (8)..(8)
<223> OTHER INFORMATION: Xaa is A, C, G, P, M, V, I, L, Sce, or Sme
<220> FEATURE:
<221> NAME/KEY: MISC_FEATURE
<222> LOCATION: (9)..(10)
<223> OTHER INFORMATION: Xaa is S, T, N or Q
<220> FEATURE:
<221> NAME/KEY: MISC_FEATURE
<222> LOCATION: (11)..(12)
<223> OTHER INFORMATION: Xaa is A, C, G, P, M, V, I, L, Sce, or Sme
<220> FEATURE:
<221> NAME/KEY: MISC_FEATURE
<222> LOCATION: (13)..(13)
<223> OTHER INFORMATION: Xaa is D or E
<220> FEATURE:
<221> NAME/KEY: MISC_FEATURE
<222> LOCATION: (14)..(14)
<223> OTHER INFORMATION: Xaa is R, H, or K
<220> FEATURE:
<221> NAME/KEY: MISC_FEATURE
<222> LOCATION: (16)..(17)
<223> OTHER INFORMATION: Xaa is R, H, or K
<220> FEATURE:
<221> NAME/KEY: MISC_FEATURE
<222> LOCATION: (20)..(21)
<223> OTHER INFORMATION: Xaa is A, C, G, P, M, V, I, L, Sce, or Sme
<220> FEATURE:
<221> NAME/KEY: MISC_FEATURE
<222> LOCATION: (24)..(24)
<223> OTHER INFORMATION: Xaa is F, W, or Y
<220> FEATURE:
<221> NAME/KEY: MISC_FEATURE
<222> LOCATION: (28)..(28)
<223> OTHER INFORMATION: Xaa is S, T, N or Q
<220> FEATURE:
<221> NAME/KEY: MISC_FEATURE
<222> LOCATION: (32)..(33)
<223> OTHER INFORMATION: Xaa is A, C, G, P, M, V, I, L, Sce, or Sme
<220> FEATURE:
<221> NAME/KEY: MISC_FEATURE
<222> LOCATION: (34)..(34)
<223> OTHER INFORMATION: Xaa is R, H, or K
<220> FEATURE:
<221> NAME/KEY: MISC_FEATURE
<222> LOCATION: (35)..(35)
<223> OTHER INFORMATION: Xaa is A, C, G, P, M, V, I, L, Sce, or Sme
<220> FEATURE:
<221> NAME/KEY: MISC_FEATURE
<222> LOCATION: (37)..(37)
<223> OTHER INFORMATION: Xaa is D or E
<220> FEATURE:
<221> NAME/KEY: MISC_FEATURE
<222> LOCATION: (38)..(41)
<223> OTHER INFORMATION: Xaa is A, C, G, P, M, V, I, L, Sce, or Sme
<220> FEATURE:
<221> NAME/KEY: MISC_FEATURE
<222> LOCATION: (42)..(42)
<223> OTHER INFORMATION: Xaa is S, T, N or Q
<220> FEATURE:
<221> NAME/KEY: MISC_FEATURE
<222> LOCATION: (43)..(43)
<223> OTHER INFORMATION: Xaa is F, W, or Y
<220> FEATURE:
<221> NAME/KEY: MISC_FEATURE
<222> LOCATION: (44)..(44)
<223> OTHER INFORMATION: Xaa is R, H, or K
<220> FEATURE:
<221> NAME/KEY: MISC_FEATURE
<222> LOCATION: (45)..(45)
<223> OTHER INFORMATION: Xaa is D or E
<220> FEATURE:
<221> NAME/KEY: MISC_FEATURE
<222> LOCATION: (46)..(47)
<223> OTHER INFORMATION: Xaa is S, T, N or Q
<220> FEATURE:
<221> NAME/KEY: MISC_FEATURE
<222> LOCATION: (48)..(49)
```

```
<223> OTHER INFORMATION: Xaa is A, C, G, P, M, V, I, L, Sce, or Sme
<220> FEATURE:
<221> NAME/KEY: MISC_FEATURE
<222> LOCATION: (50)..(50)
<223> OTHER INFORMATION: Xaa is R, H, or K
<220> FEATURE:
<221> NAME/KEY: MISC_FEATURE
<222> LOCATION: (51)..(52)
<223> OTHER INFORMATION: Xaa is F, W, or Y
<220> FEATURE:
<221> NAME/KEY: MISC_FEATURE
<222> LOCATION: (53)..(53)
<223> OTHER INFORMATION: Xaa is A, C, G, P, M, V, I, L, Sce, or Sme
<220> FEATURE:
<221> NAME/KEY: MISC_FEATURE
<222> LOCATION: (54)..(55)
<223> OTHER INFORMATION: Xaa is S, T, N or Q
<220> FEATURE:
<221> NAME/KEY: MISC_FEATURE
<222> LOCATION: (56)..(56)
<223> OTHER INFORMATION: Xaa is D or E
<220> FEATURE:
<221> NAME/KEY: MISC_FEATURE
<222> LOCATION: (57)..(61)
<223> OTHER INFORMATION: Xaa is A, C, G, P, M, V, I, L, Sce, or Sme
<220> FEATURE:
<221> NAME/KEY: MISC_FEATURE
<222> LOCATION: (62)..(62)
<223> OTHER INFORMATION: Xaa is R, H, or K
<220> FEATURE:
<221> NAME/KEY: MISC_FEATURE
<222> LOCATION: (63)..(63)
<223> OTHER INFORMATION: Xaa is A, C, G, P, M, V, I, L, Sce, or Sme
<220> FEATURE:
<221> NAME/KEY: MISC_FEATURE
<222> LOCATION: (64)..(64)
<223> OTHER INFORMATION: Xaa is D or E
<220> FEATURE:
<221> NAME/KEY: MISC_FEATURE
<222> LOCATION: (65)..(68)
<223> OTHER INFORMATION: Xaa is A, C, G, P, M, V, I, L, Sce, or Sme
<220> FEATURE:
<221> NAME/KEY: MISC_FEATURE
<222> LOCATION: (69)..(69)
<223> OTHER INFORMATION: Xaa is F, W, or Y
<220> FEATURE:
<221> NAME/KEY: MISC_FEATURE
<222> LOCATION: (70)..(71)
<223> OTHER INFORMATION: Xaa is A, C, G, P, M, V, I, L, Sce, or Sme
<220> FEATURE:
<221> NAME/KEY: MISC_FEATURE
<222> LOCATION: (72)..(72)
<223> OTHER INFORMATION: Xaa is S, T, N or Q
<220> FEATURE:
<221> NAME/KEY: MISC_FEATURE
<222> LOCATION: (73)..(73)
<223> OTHER INFORMATION: Xaa is D or E
<220> FEATURE:
<221> NAME/KEY: MISC_FEATURE
<222> LOCATION: (74)..(74)
<223> OTHER INFORMATION: Xaa is A, C, G, P, M, V, I, L, Sce, or Sme
<220> FEATURE:
<221> NAME/KEY: MISC_FEATURE
<222> LOCATION: (75)..(75)
<223> OTHER INFORMATION: Xaa is D or E
<220> FEATURE:
<221> NAME/KEY: MISC_FEATURE
<222> LOCATION: (76)..(76)
<223> OTHER INFORMATION: Xaa is R, H, or K
<220> FEATURE:
<221> NAME/KEY: MISC_FEATURE
<222> LOCATION: (77)..(77)
<223> OTHER INFORMATION: Xaa is A, C, G, P, M, V, I, L, Sce, or Sme
<220> FEATURE:
<221> NAME/KEY: MISC_FEATURE
<222> LOCATION: (78)..(79)
<223> OTHER INFORMATION: Xaa is S, T, N or Q
<220> FEATURE:
<221> NAME/KEY: MISC_FEATURE
```

```
<222> LOCATION: (81)..(81)
<223> OTHER INFORMATION: Xaa is A, C, G, P, M, V, I, L, Sce, or Sme
<220> FEATURE:
<221> NAME/KEY: MISC_FEATURE
<222> LOCATION: (82)..(82)
<223> OTHER INFORMATION: Xaa is S, T, N or Q
<220> FEATURE:
<221> NAME/KEY: MISC_FEATURE
<222> LOCATION: (85)..(85)
<223> OTHER INFORMATION: Xaa is A, C, G, P, M, V, I, L, Sce, or Sme
<220> FEATURE:
<221> NAME/KEY: MISC_FEATURE
<222> LOCATION: (89)..(93)
<223> OTHER INFORMATION: Xaa is A, C, G, P, M, V, I, L, Sce, or Sme
<220> FEATURE:
<221> NAME/KEY: MISC_FEATURE
<222> LOCATION: (94)..(94)
<223> OTHER INFORMATION: Xaa is D or E
<220> FEATURE:
<221> NAME/KEY: MISC_FEATURE
<222> LOCATION: (95)..(95)
<223> OTHER INFORMATION: Xaa is R, H, or K
<220> FEATURE:
<221> NAME/KEY: MISC_FEATURE
<222> LOCATION: (96)..(96)
<223> OTHER INFORMATION: Xaa is A, C, G, P, M, V, I, L, Sce, or Sme
<220> FEATURE:
<221> NAME/KEY: MISC_FEATURE
<222> LOCATION: (97)..(97)
<223> OTHER INFORMATION: Xaa is F, W, or Y
<220> FEATURE:
<221> NAME/KEY: MISC_FEATURE
<222> LOCATION: (98)..(99)
<223> OTHER INFORMATION: Xaa is A, C, G, P, M, V, I, L, Sce, or Sme
<220> FEATURE:
<221> NAME/KEY: MISC_FEATURE
<222> LOCATION: (100)..(101)
<223> OTHER INFORMATION: Xaa is F, W, or Y
<220> FEATURE:
<221> NAME/KEY: MISC_FEATURE
<222> LOCATION: (102)..(102)
<223> OTHER INFORMATION: Xaa is S, T, N or Q
<220> FEATURE:
<221> NAME/KEY: MISC_FEATURE
<222> LOCATION: (103)..(104)
<223> OTHER INFORMATION: Xaa is A, C, G, P, M, V, I, L, Sce, or Sme
<220> FEATURE:
<221> NAME/KEY: MISC_FEATURE
<222> LOCATION: (105)..(105)
<223> OTHER INFORMATION: Xaa is R, H, or K
<220> FEATURE:
<221> NAME/KEY: MISC_FEATURE
<222> LOCATION: (106)..(107)
<223> OTHER INFORMATION: Xaa is A, C, G, P, M, V, I, L, Sce, or Sme
<220> FEATURE:
<221> NAME/KEY: MISC_FEATURE
<222> LOCATION: (108)..(108)
<223> OTHER INFORMATION: Xaa is F, W, or Y
<220> FEATURE:
<221> NAME/KEY: MISC_FEATURE
<222> LOCATION: (109)..(109)
<223> OTHER INFORMATION: Xaa is S, T, N or Q
<220> FEATURE:
<221> NAME/KEY: MISC_FEATURE
<222> LOCATION: (110)..(110)
<223> OTHER INFORMATION: Xaa is A, C, G, P, M, V, I, L, Sce, or Sme
<220> FEATURE:
<221> NAME/KEY: MISC_FEATURE
<222> LOCATION: (111)..(112)
<223> OTHER INFORMATION: Xaa is S, T, N or Q
<220> FEATURE:
<221> NAME/KEY: MISC_FEATURE
<222> LOCATION: (113)..(113)
<223> OTHER INFORMATION: Xaa is F, W, or Y

<400> SEQUENCE: 30

Xaa Xaa Xaa Xaa Xaa Xaa Xaa Xaa Xaa Xaa Xaa Xaa Xaa Xaa His Xaa
1               5                   10                  15
```

Xaa Leu Leu Xaa Xaa Ile Ile Xaa Arg Ile Val Xaa Arg Val Val Xaa
            20              25              30

Xaa Xaa Xaa Glu Xaa Xaa Xaa Xaa Xaa Xaa Xaa Xaa Xaa Xaa Xaa Xaa
        35              40              45

Xaa Xaa Xaa Xaa Xaa Xaa Xaa Xaa Xaa Xaa Xaa Xaa Xaa Xaa Xaa Xaa
 50              55              60

Xaa Xaa Xaa Xaa Xaa Xaa Xaa Xaa Xaa Xaa Xaa Xaa Xaa Xaa Xaa Ile
 65              70              75              80

Xaa Xaa Ala Ala Xaa Thr Ala Val Xaa Xaa Xaa Xaa Xaa Xaa Xaa Xaa
            85              90              95

Xaa Xaa Xaa Xaa Xaa Xaa Xaa Xaa Xaa Xaa Xaa Xaa Xaa Xaa Xaa Xaa
         100             105             110

Xaa

<210> SEQ ID NO 31
<211> LENGTH: 159
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (2)..(2)
<223> OTHER INFORMATION: Xaa is A, C, G, P, M, V, I, L, Sme, or Sce
<220> FEATURE:
<221> NAME/KEY: MISC_FEATURE
<222> LOCATION: (3)..(3)
<223> OTHER INFORMATION: Xaa is D or E
<220> FEATURE:
<221> NAME/KEY: MISC_FEATURE
<222> LOCATION: (5)..(5)
<223> OTHER INFORMATION: Xaa is A, C, G, P, M, V, I, L, Sme, or Sce
<220> FEATURE:
<221> NAME/KEY: MISC_FEATURE
<222> LOCATION: (8)..(8)
<223> OTHER INFORMATION: Xaa is D or E
<220> FEATURE:
<221> NAME/KEY: MISC_FEATURE
<222> LOCATION: (9)..(9)
<223> OTHER INFORMATION: Xaa is A, C, G, P, M, V, I, L, Sme, or Sce
<220> FEATURE:
<221> NAME/KEY: MISC_FEATURE
<222> LOCATION: (11)..(11)
<223> OTHER INFORMATION: Xaa is D or E
<220> FEATURE:
<221> NAME/KEY: MISC_FEATURE
<222> LOCATION: (12)..(12)
<223> OTHER INFORMATION: Xaa is A, C, G, P, M, V, I, L, Sme, or Sce
<220> FEATURE:
<221> NAME/KEY: MISC_FEATURE
<222> LOCATION: (13)..(13)
<223> OTHER INFORMATION: Xaa is S, T, N, or Q
<220> FEATURE:
<221> NAME/KEY: MISC_FEATURE
<222> LOCATION: (17)..(17)
<223> OTHER INFORMATION: Xaa is A, C, G, P, M, V, I, L, Sme, or Sce
<220> FEATURE:
<221> NAME/KEY: MISC_FEATURE
<222> LOCATION: (23)..(23)
<223> OTHER INFORMATION: Xaa is S, T, N, or Q
<220> FEATURE:
<221> NAME/KEY: MISC_FEATURE
<222> LOCATION: (26)..(26)
<223> OTHER INFORMATION: Xaa is D or E
<220> FEATURE:
<221> NAME/KEY: MISC_FEATURE
<222> LOCATION: (28)..(28)

```
<223> OTHER INFORMATION: Xaa is D or E
<220> FEATURE:
<221> NAME/KEY: MISC_FEATURE
<222> LOCATION: (29)..(29)
<223> OTHER INFORMATION: Xaa is A, C, G, P, M, V, I, L, Sme, or Sce
<220> FEATURE:
<221> NAME/KEY: MISC_FEATURE
<222> LOCATION: (30)..(30)
<223> OTHER INFORMATION: Xaa is R, H, or K
<220> FEATURE:
<221> NAME/KEY: MISC_FEATURE
<222> LOCATION: (31)..(32)
<223> OTHER INFORMATION: Xaa is A, C, G, P, M, V, I, L, Sme, or Sce
<220> FEATURE:
<221> NAME/KEY: MISC_FEATURE
<222> LOCATION: (35)..(35)
<223> OTHER INFORMATION: Xaa is A, C, G, P, M, V, I, L, Sme, or Sce
<220> FEATURE:
<221> NAME/KEY: MISC_FEATURE
<222> LOCATION: (37)..(37)
<223> OTHER INFORMATION: Xaa is S, T, N, or Q
<220> FEATURE:
<221> NAME/KEY: MISC_FEATURE
<222> LOCATION: (38)..(38)
<223> OTHER INFORMATION: Xaa is A, C, G, P, M, V, I, L, Sme, or Sce
<220> FEATURE:
<221> NAME/KEY: MISC_FEATURE
<222> LOCATION: (43)..(43)
<223> OTHER INFORMATION: Xaa is A, C, G, P, M, V, I, L, Sme, or Sce
<220> FEATURE:
<221> NAME/KEY: MISC_FEATURE
<222> LOCATION: (46)..(46)
<223> OTHER INFORMATION: Xaa is D or E
<220> FEATURE:
<221> NAME/KEY: MISC_FEATURE
<222> LOCATION: (51)..(51)
<223> OTHER INFORMATION: Xaa is R, H, or K
<220> FEATURE:
<221> NAME/KEY: MISC_FEATURE
<222> LOCATION: (52)..(52)
<223> OTHER INFORMATION: Xaa is S, T, N, or Q
<220> FEATURE:
<221> NAME/KEY: MISC_FEATURE
<222> LOCATION: (54)..(54)
<223> OTHER INFORMATION: Xaa is A, C, G, P, M, V, I, L, Sme, or Sce
<220> FEATURE:
<221> NAME/KEY: MISC_FEATURE
<222> LOCATION: (58)..(58)
<223> OTHER INFORMATION: Xaa is A, C, G, P, M, V, I, L, Sme, or Sce
<220> FEATURE:
<221> NAME/KEY: MISC_FEATURE
<222> LOCATION: (59)..(59)
<223> OTHER INFORMATION: Xaa is D or E
<220> FEATURE:
<221> NAME/KEY: MISC_FEATURE
<222> LOCATION: (60)..(60)
<223> OTHER INFORMATION: Xaa is A, C, G, P, M, V, I, L, Sme, or Sce
<220> FEATURE:
<221> NAME/KEY: MISC_FEATURE
<222> LOCATION: (63)..(64)
<223> OTHER INFORMATION: Xaa is A, C, G, P, M, V, I, L, Sme, or Sce
<220> FEATURE:
<221> NAME/KEY: MISC_FEATURE
<222> LOCATION: (65)..(65)
<223> OTHER INFORMATION: Xaa is F, W, or Y
<220> FEATURE:
<221> NAME/KEY: MISC_FEATURE
<222> LOCATION: (66)..(66)
<223> OTHER INFORMATION: Xaa is A, C, G, P, M, V, I, L, Sme, or Sce
<220> FEATURE:
<221> NAME/KEY: MISC_FEATURE
<222> LOCATION: (84)..(84)
<223> OTHER INFORMATION: Xaa is S, T, N, or Q
<220> FEATURE:
<221> NAME/KEY: MISC_FEATURE
<222> LOCATION: (87)..(87)
<223> OTHER INFORMATION: Xaa is A, C, G, P, M, V, I, L, Sme, or Sce
<220> FEATURE:
<221> NAME/KEY: MISC_FEATURE
```

```
<222> LOCATION: (91)..(92)
<223> OTHER INFORMATION: Xaa is D or E
<220> FEATURE:
<221> NAME/KEY: MISC_FEATURE
<222> LOCATION: (94)..(94)
<223> OTHER INFORMATION: Xaa is A, C, G, P, M, V, I, L, Sme, or Sce
<220> FEATURE:
<221> NAME/KEY: MISC_FEATURE
<222> LOCATION: (103)..(103)
<223> OTHER INFORMATION: Xaa is D or E
<220> FEATURE:
<221> NAME/KEY: MISC_FEATURE
<222> LOCATION: (104)..(104)
<223> OTHER INFORMATION: Xaa is R, H, or K
<220> FEATURE:
<221> NAME/KEY: MISC_FEATURE
<222> LOCATION: (106)..(107)
<223> OTHER INFORMATION: Xaa is R, H, or K
<220> FEATURE:
<221> NAME/KEY: MISC_FEATURE
<222> LOCATION: (112)..(112)
<223> OTHER INFORMATION: Xaa is A, C, G, P, M, V, I, L, Sme, or Sce
<220> FEATURE:
<221> NAME/KEY: MISC_FEATURE
<222> LOCATION: (126)..(126)
<223> OTHER INFORMATION: Xaa is R, H, or K
<220> FEATURE:
<221> NAME/KEY: MISC_FEATURE
<222> LOCATION: (127)..(127)
<223> OTHER INFORMATION: Xaa is S, T, N, or Q
<220> FEATURE:
<221> NAME/KEY: MISC_FEATURE
<222> LOCATION: (133)..(133)
<223> OTHER INFORMATION: Xaa is A, C, G, P, M, V, I, L, Sme, or Sce
<220> FEATURE:
<221> NAME/KEY: MISC_FEATURE
<222> LOCATION: (135)..(136)
<223> OTHER INFORMATION: Xaa is D or E
<220> FEATURE:
<221> NAME/KEY: MISC_FEATURE
<222> LOCATION: (141)..(141)
<223> OTHER INFORMATION: Xaa is R, H, or K
<220> FEATURE:
<221> NAME/KEY: MISC_FEATURE
<222> LOCATION: (142)..(142)
<223> OTHER INFORMATION: Xaa is F, W, or Y
<220> FEATURE:
<221> NAME/KEY: MISC_FEATURE
<222> LOCATION: (144)..(144)
<223> OTHER INFORMATION: Xaa is D or E
<220> FEATURE:
<221> NAME/KEY: MISC_FEATURE
<222> LOCATION: (153)..(153)
<223> OTHER INFORMATION: Xaa is R, H, or K
<220> FEATURE:
<221> NAME/KEY: MISC_FEATURE
<222> LOCATION: (155)..(155)
<223> OTHER INFORMATION: Xaa is S, T, N, or Q
<220> FEATURE:
<221> NAME/KEY: MISC_FEATURE
<222> LOCATION: (157)..(157)
<223> OTHER INFORMATION: Xaa is S, T, N, or Q
<220> FEATURE:
<221> NAME/KEY: MISC_FEATURE
<222> LOCATION: (158)..(158)
<223> OTHER INFORMATION: Xaa is A, C, G, P, M, V, I, L, Sme, or Sce
<220> FEATURE:
<221> NAME/KEY: MISC_FEATURE
<222> LOCATION: (159)..(159)
<223> OTHER INFORMATION: Xaa is R, H, or K

<400> SEQUENCE: 31

Xaa Xaa Xaa Val Xaa Ile Gly Xaa Xaa Lys Xaa Xaa Xaa Gly Met Glu
1               5                   10                  15

Xaa Ala Ala Val Tyr Leu Xaa Pro Ile Xaa Met Xaa Xaa Xaa Xaa Xaa
            20                  25                  30
```

```
Asp Leu Xaa Ala Xaa Xaa Ala Asp Ile His Xaa Glu Ala Xaa Ile His
             35                  40                  45

Ala Leu Xaa Xaa Asn Xaa Asn Gly Phe Xaa Xaa Xaa Phe Trp Xaa Xaa
 50                  55                  60

Xaa Xaa Thr Ile Ala Tyr Ala Leu Ala Asn Ala Asp Thr Gly Ala Ile
 65                  70                  75                  80

Lys Thr Gly Xaa Leu Met Xaa Met Val Ala Xaa Xaa Gly Xaa His Tyr
                 85                  90                  95

Gly Ala Asn Ile Ala Met Xaa Xaa Asp Xaa Xaa Gly Gly Phe Gly Xaa
            100                 105                 110

Gly Thr Tyr Ala Leu Thr Phe Leu Ile Ser Asn Pro Glu Xaa Xaa Gly
            115                 120                 125

Phe Gly Arg His Xaa Asp Xaa Xaa Thr Gly Val Gly Xaa Xaa Phe Xaa
130                 135                 140

Pro Phe Val Val Thr Tyr Phe Phe Xaa Tyr Xaa Gly Xaa Xaa Xaa
145                 150                 155
```

```
<210> SEQ ID NO 32
<211> LENGTH: 184
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (2)..(2)
<223> OTHER INFORMATION: Xaa is S, T, N, or Q
<220> FEATURE:
<221> NAME/KEY: MISC_FEATURE
<222> LOCATION: (11)..(11)
<223> OTHER INFORMATION: Xaa is S, T, N, or Q
<220> FEATURE:
<221> NAME/KEY: MISC_FEATURE
<222> LOCATION: (17)..(17)
<223> OTHER INFORMATION: Xaa is A, C, G, P, M, V, I, L, Sce or Sme
<220> FEATURE:
<221> NAME/KEY: MISC_FEATURE
<222> LOCATION: (22)..(22)
<223> OTHER INFORMATION: Xaa is A, C, G, P, M, V, I, L, Sce or Sme
<220> FEATURE:
<221> NAME/KEY: MISC_FEATURE
<222> LOCATION: (25)..(25)
<223> OTHER INFORMATION: Xaa is R, H or K
<220> FEATURE:
<221> NAME/KEY: MISC_FEATURE
<222> LOCATION: (26)..(26)
<223> OTHER INFORMATION: Xaa is S, T, N, or Q
<220> FEATURE:
<221> NAME/KEY: MISC_FEATURE
<222> LOCATION: (28)..(28)
<223> OTHER INFORMATION: Xaa is S, T, N, or Q
<220> FEATURE:
<221> NAME/KEY: MISC_FEATURE
<222> LOCATION: (30)..(30)
<223> OTHER INFORMATION: Xaa is D or E
<220> FEATURE:
<221> NAME/KEY: MISC_FEATURE
<222> LOCATION: (31)..(31)
<223> OTHER INFORMATION: Xaa is A, C, G, P, M, V, I, L, Sce or Sme
<220> FEATURE:
<221> NAME/KEY: MISC_FEATURE
<222> LOCATION: (34)..(34)
<223> OTHER INFORMATION: Xaa is S, T, N, or Q
<220> FEATURE:
<221> NAME/KEY: MISC_FEATURE
<222> LOCATION: (35)..(35)
<223> OTHER INFORMATION: Xaa is R, H or K
```

```
<220> FEATURE:
<221> NAME/KEY: MISC_FEATURE
<222> LOCATION: (36)..(36)
<223> OTHER INFORMATION: Xaa is S, T, N, or Q
<220> FEATURE:
<221> NAME/KEY: MISC_FEATURE
<222> LOCATION: (38)..(38)
<223> OTHER INFORMATION: Xaa is S, T, N, or Q
<220> FEATURE:
<221> NAME/KEY: MISC_FEATURE
<222> LOCATION: (39)..(39)
<223> OTHER INFORMATION: Xaa is A, C, G, P, M, V, I, L, Sce or Sme
<220> FEATURE:
<221> NAME/KEY: MISC_FEATURE
<222> LOCATION: (49)..(49)
<223> OTHER INFORMATION: Xaa is D or E
<220> FEATURE:
<221> NAME/KEY: MISC_FEATURE
<222> LOCATION: (50)..(51)
<223> OTHER INFORMATION: Xaa is A, C, G, P, M, V, I, L, Sce or Sme
<220> FEATURE:
<221> NAME/KEY: MISC_FEATURE
<222> LOCATION: (54)..(55)
<223> OTHER INFORMATION: Xaa is S, T, N, or Q
<220> FEATURE:
<221> NAME/KEY: MISC_FEATURE
<222> LOCATION: (58)..(58)
<223> OTHER INFORMATION: Xaa is D or E
<220> FEATURE:
<221> NAME/KEY: MISC_FEATURE
<222> LOCATION: (61)..(63)
<223> OTHER INFORMATION: Xaa is S, T, N, or Q
<220> FEATURE:
<221> NAME/KEY: MISC_FEATURE
<222> LOCATION: (65)..(65)
<223> OTHER INFORMATION: Xaa is A, C, G, P, M, V, I, L, Sce or Sme
<220> FEATURE:
<221> NAME/KEY: MISC_FEATURE
<222> LOCATION: (66)..(66)
<223> OTHER INFORMATION: Xaa is D or E
<220> FEATURE:
<221> NAME/KEY: MISC_FEATURE
<222> LOCATION: (68)..(69)
<223> OTHER INFORMATION: Xaa is A, C, G, P, M, V, I, L, Sce or Sme
<220> FEATURE:
<221> NAME/KEY: MISC_FEATURE
<222> LOCATION: (70)..(70)
<223> OTHER INFORMATION: Xaa is D or E
<220> FEATURE:
<221> NAME/KEY: MISC_FEATURE
<222> LOCATION: (71)..(71)
<223> OTHER INFORMATION: Xaa is S, T, N, or Q
<220> FEATURE:
<221> NAME/KEY: MISC_FEATURE
<222> LOCATION: (72)..(73)
<223> OTHER INFORMATION: Xaa is A, C, G, P, M, V, I, L, Sce or Sme
<220> FEATURE:
<221> NAME/KEY: MISC_FEATURE
<222> LOCATION: (75)..(75)
<223> OTHER INFORMATION: Xaa is A, C, G, P, M, V, I, L, Sce or Sme
<220> FEATURE:
<221> NAME/KEY: MISC_FEATURE
<222> LOCATION: (76)..(76)
<223> OTHER INFORMATION: Xaa is S, T, N, or Q
<220> FEATURE:
<221> NAME/KEY: MISC_FEATURE
<222> LOCATION: (79)..(79)
<223> OTHER INFORMATION: Xaa is A, C, G, P, M, V, I, L, Sce or Sme
<220> FEATURE:
<221> NAME/KEY: MISC_FEATURE
<222> LOCATION: (82)..(83)
<223> OTHER INFORMATION: Xaa is A, C, G, P, M, V, I, L, Sce or Sme
<220> FEATURE:
<221> NAME/KEY: MISC_FEATURE
<222> LOCATION: (85)..(85)
<223> OTHER INFORMATION: Xaa is A, C, G, P, M, V, I, L, Sce or Sme
<220> FEATURE:
<221> NAME/KEY: MISC_FEATURE
<222> LOCATION: (86)..(86)
```

```
<223> OTHER INFORMATION: Xaa is S, T, N, or Q
<220> FEATURE:
<221> NAME/KEY: MISC_FEATURE
<222> LOCATION: (88)..(88)
<223> OTHER INFORMATION: Xaa is A, C, G, P, M, V, I, L, Sce or Sme
<220> FEATURE:
<221> NAME/KEY: MISC_FEATURE
<222> LOCATION: (89)..(90)
<223> OTHER INFORMATION: Xaa is S, T, N, or Q
<220> FEATURE:
<221> NAME/KEY: MISC_FEATURE
<222> LOCATION: (91)..(91)
<223> OTHER INFORMATION: Xaa is A, C, G, P, M, V, I, L, Sce or Sme
<220> FEATURE:
<221> NAME/KEY: MISC_FEATURE
<222> LOCATION: (92)..(92)
<223> OTHER INFORMATION: Xaa is D or E
<220> FEATURE:
<221> NAME/KEY: MISC_FEATURE
<222> LOCATION: (93)..(94)
<223> OTHER INFORMATION: Xaa is R, H or K
<220> FEATURE:
<221> NAME/KEY: MISC_FEATURE
<222> LOCATION: (95)..(95)
<223> OTHER INFORMATION: Xaa is S, T, N, or Q
<220> FEATURE:
<221> NAME/KEY: MISC_FEATURE
<222> LOCATION: (106)..(106)
<223> OTHER INFORMATION: Xaa is A, C, G, P, M, V, I, L, Sce or Sme
<220> FEATURE:
<221> NAME/KEY: MISC_FEATURE
<222> LOCATION: (109)..(109)
<223> OTHER INFORMATION: Xaa is A, C, G, P, M, V, I, L, Sce or Sme
<220> FEATURE:
<221> NAME/KEY: MISC_FEATURE
<222> LOCATION: (110)..(110)
<223> OTHER INFORMATION: Xaa is S, T, N, or Q
<220> FEATURE:
<221> NAME/KEY: MISC_FEATURE
<222> LOCATION: (122)..(122)
<223> OTHER INFORMATION: Xaa is S, T, N, or Q
<220> FEATURE:
<221> NAME/KEY: MISC_FEATURE
<222> LOCATION: (127)..(127)
<223> OTHER INFORMATION: Xaa is R, H or K
<220> FEATURE:
<221> NAME/KEY: MISC_FEATURE
<222> LOCATION: (128)..(129)
<223> OTHER INFORMATION: Xaa is A, C, G, P, M, V, I, L, Sce or Sme
<220> FEATURE:
<221> NAME/KEY: MISC_FEATURE
<222> LOCATION: (130)..(130)
<223> OTHER INFORMATION: Xaa is F, W, or Y
<220> FEATURE:
<221> NAME/KEY: MISC_FEATURE
<222> LOCATION: (132)..(133)
<223> OTHER INFORMATION: Xaa is A, C, G, P, M, V, I, L, Sce or Sme
<220> FEATURE:
<221> NAME/KEY: MISC_FEATURE
<222> LOCATION: (161)..(161)
<223> OTHER INFORMATION: Xaa is R, H or K
<220> FEATURE:
<221> NAME/KEY: MISC_FEATURE
<222> LOCATION: (162)..(162)
<223> OTHER INFORMATION: Xaa is A, C, G, P, M, V, I, L, Sce or Sme
<220> FEATURE:
<221> NAME/KEY: MISC_FEATURE
<222> LOCATION: (164)..(165)
<223> OTHER INFORMATION: Xaa is A, C, G, P, M, V, I, L, Sce or Sme
<220> FEATURE:
<221> NAME/KEY: MISC_FEATURE
<222> LOCATION: (175)..(175)
<223> OTHER INFORMATION: Xaa is D or E
<220> FEATURE:
<221> NAME/KEY: MISC_FEATURE
<222> LOCATION: (176)..(176)
<223> OTHER INFORMATION: Xaa is A, C, G, P, M, V, I, L, Sce or Sme
<220> FEATURE:
<221> NAME/KEY: MISC_FEATURE
```

```
<222> LOCATION: (179)..(179)
<223> OTHER INFORMATION: Xaa is R, H or K
<220> FEATURE:
<221> NAME/KEY: MISC_FEATURE
<222> LOCATION: (180)..(180)
<223> OTHER INFORMATION: Xaa is S, T, N, or Q
<220> FEATURE:
<221> NAME/KEY: MISC_FEATURE
<222> LOCATION: (181)..(182)
<223> OTHER INFORMATION: Xaa is A, C, G, P, M, V, I, L, Sce or Sme
<220> FEATURE:
<221> NAME/KEY: MISC_FEATURE
<222> LOCATION: (183)..(183)
<223> OTHER INFORMATION: Xaa is D or E
<220> FEATURE:
<221> NAME/KEY: MISC_FEATURE
<222> LOCATION: (184)..(184)
<223> OTHER INFORMATION: Xaa is A, C, G, P, M, V, I, L, Sce or Sme

<400> SEQUENCE: 32

Xaa Xaa Gln Ala Ile Gly Ile Leu Glu Leu Xaa Ser Ile Ala Lys Gly
 1               5                  10                  15

Xaa Glu Leu Gly Asp Xaa Met Leu Xaa Xaa Ala Xaa Val Xaa Xaa Leu
            20                  25                  30

Val Xaa Xaa Xaa Ile Xaa Xaa Gly Lys Phe Leu Leu Met Leu Gly Gly
        35                  40                  45

Xaa Xaa Xaa Ala Ile Xaa Xaa Ala Ile Xaa Thr Gly Xaa Xaa Xaa Ala
50                  55                  60

Xaa Xaa Met Xaa Xaa Xaa Xaa Xaa Leu Xaa Xaa Ile His Xaa Ser
65                  70                  75                  80

Val Xaa Xaa Ala Xaa Xaa Gly Xaa Xaa Xaa Xaa Xaa Xaa Xaa Ala
            85                  90                  95

Val Gly Ile Val Glu Thr Trp Ser Val Xaa Ala Cys Xaa Xaa Ala Ala
        100                 105                 110

Asp Leu Ala Val Lys Gly Ser Asn Val Xaa Leu Val Arg Val Xaa Xaa
        115                 120                 125

Xaa Xaa Gly Xaa Xaa Gly Lys Cys Tyr Met Val Ala Gly Asp Val
    130                 135                 140

Leu Asp Val Ala Ala Val Ala Thr Ala Ser Leu Ala Ala Gly Ala
145                 150                 155                 160

Xaa Xaa Leu Xaa Xaa Tyr Ala Ser Ile Ile Pro Arg Pro His Xaa Xaa
            165                 170                 175

Met Trp Xaa Xaa Xaa Xaa Xaa Xaa
            180

<210> SEQ ID NO 33
<211> LENGTH: 103
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (24)..(25)
<223> OTHER INFORMATION: Xaa is D or E
<220> FEATURE:
<221> NAME/KEY: MISC_FEATURE
<222> LOCATION: (26)..(26)
<223> OTHER INFORMATION: Xaa is R, H, or K
<220> FEATURE:
<221> NAME/KEY: MISC_FEATURE
<222> LOCATION: (41)..(41)
```

```
<223> OTHER INFORMATION: Xaa is F, W, or Y
<220> FEATURE:
<221> NAME/KEY: MISC_FEATURE
<222> LOCATION: (44)..(44)
<223> OTHER INFORMATION: Xaa is S, T, N, or Q
<220> FEATURE:
<221> NAME/KEY: MISC_FEATURE
<222> LOCATION: (45)..(45)
<223> OTHER INFORMATION: Xaa is A, C, G, P, M, V, I, L, Sce, or Sme
<220> FEATURE:
<221> NAME/KEY: MISC_FEATURE
<222> LOCATION: (61)..(61)
<223> OTHER INFORMATION: Xaa is S, T, N, or Q
<220> FEATURE:
<221> NAME/KEY: MISC_FEATURE
<222> LOCATION: (62)..(62)
<223> OTHER INFORMATION: Xaa is R, H, or K
<220> FEATURE:
<221> NAME/KEY: MISC_FEATURE
<222> LOCATION: (65)..(65)
<223> OTHER INFORMATION: Xaa is A, C, G, P, M, V, I, L, Sce, or Sme
<220> FEATURE:
<221> NAME/KEY: MISC_FEATURE
<222> LOCATION: (66)..(66)
<223> OTHER INFORMATION: Xaa is R, H, or K
<220> FEATURE:
<221> NAME/KEY: MISC_FEATURE
<222> LOCATION: (69)..(69)
<223> OTHER INFORMATION: Xaa is D or E
<220> FEATURE:
<221> NAME/KEY: MISC_FEATURE
<222> LOCATION: (70)..(70)
<223> OTHER INFORMATION: Xaa is R, H, or K
<220> FEATURE:
<221> NAME/KEY: MISC_FEATURE
<222> LOCATION: (72)..(72)
<223> OTHER INFORMATION: Xaa is R, H, or K
<220> FEATURE:
<221> NAME/KEY: MISC_FEATURE
<222> LOCATION: (73)..(73)
<223> OTHER INFORMATION: Xaa is A, C, G, P, M, V, I, L, Sce, or Sme
<220> FEATURE:
<221> NAME/KEY: MISC_FEATURE
<222> LOCATION: (76)..(76)
<223> OTHER INFORMATION: Xaa is A, C, G, P, M, V, I, L, Sce, or Sme
<220> FEATURE:
<221> NAME/KEY: MISC_FEATURE
<222> LOCATION: (77)..(77)
<223> OTHER INFORMATION: Xaa is F, W, or Y
<220> FEATURE:
<221> NAME/KEY: MISC_FEATURE
<222> LOCATION: (78)..(78)
<223> OTHER INFORMATION: Xaa is S, T, N, or Q
<220> FEATURE:
<221> NAME/KEY: MISC_FEATURE
<222> LOCATION: (79)..(79)
<223> OTHER INFORMATION: Xaa is A, C, G, P, M, V, I, L, Sce, or Sme
<220> FEATURE:
<221> NAME/KEY: MISC_FEATURE
<222> LOCATION: (88)..(88)
<223> OTHER INFORMATION: Xaa is A, C, G, P, M, V, I, L, Sce, or Sme
<220> FEATURE:
<221> NAME/KEY: MISC_FEATURE
<222> LOCATION: (89)..(89)
<223> OTHER INFORMATION: Xaa is D or E
<220> FEATURE:
<221> NAME/KEY: MISC_FEATURE
<222> LOCATION: (92)..(92)
<223> OTHER INFORMATION: Xaa is R, H, or K
<220> FEATURE:
<221> NAME/KEY: MISC_FEATURE
<222> LOCATION: (93)..(93)
<223> OTHER INFORMATION: Xaa is D or E
<220> FEATURE:
<221> NAME/KEY: MISC_FEATURE
<222> LOCATION: (96)..(96)
<223> OTHER INFORMATION: Xaa is D or E
<220> FEATURE:
<221> NAME/KEY: MISC_FEATURE
```

```
<222> LOCATION: (99)..(99)
<223> OTHER INFORMATION: Xaa is R, H, or K
<220> FEATURE:
<221> NAME/KEY: MISC_FEATURE
<222> LOCATION: (100)..(100)
<223> OTHER INFORMATION: Xaa is D or E

<400> SEQUENCE: 33

Xaa Glu Glu Val Val Leu Ile Thr Val Pro Ser Ala Leu Val Ala Val
1               5                   10                  15

Lys Ile Ala His Ala Leu Val Xaa Xaa Xaa Leu Ala Ala Cys Val Asn
            20                  25                  30

Ile Val Pro Gly Leu Thr Ser Ile Xaa Arg Trp Xaa Xaa Ser Val Val
        35                  40                  45

Ser Asp His Glu Leu Leu Leu Val Lys Thr Thr Xaa Xaa Ala Phe
    50                  55                  60

Xaa Xaa Leu Lys Xaa Xaa Val Xaa Xaa Leu His Xaa Xaa Xaa Xaa Pro
65              70                  75                  80

Glu Ile Val Ala Leu Pro Ile Xaa Xaa Gly Asn Xaa Xaa Tyr Leu Xaa
            85                  90                  95

Trp Leu Xaa Xaa Asn Thr Gly
            100

<210> SEQ ID NO 34
<211> LENGTH: 122
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (14)..(14)
<223> OTHER INFORMATION: Xaa is D or E
<220> FEATURE:
<221> NAME/KEY: MISC_FEATURE
<222> LOCATION: (35)..(35)
<223> OTHER INFORMATION: Xaa is A, C, G, P, M, V, I, L, Sce, Sme
<220> FEATURE:
<221> NAME/KEY: MISC_FEATURE
<222> LOCATION: (37)..(37)
<223> OTHER INFORMATION: Xaa is S, T, N, or Q
<220> FEATURE:
<221> NAME/KEY: MISC_FEATURE
<222> LOCATION: (39)..(39)
<223> OTHER INFORMATION: Xaa is F, W, or Y
<220> FEATURE:
<221> NAME/KEY: MISC_FEATURE
<222> LOCATION: (40)..(40)
<223> OTHER INFORMATION: Xaa is D or E
<220> FEATURE:
<221> NAME/KEY: MISC_FEATURE
<222> LOCATION: (51)..(52)
<223> OTHER INFORMATION: Xaa is D or E
<220> FEATURE:
<221> NAME/KEY: MISC_FEATURE
<222> LOCATION: (69)..(69)
<223> OTHER INFORMATION: Xaa is R, H, or K
<220> FEATURE:
<221> NAME/KEY: MISC_FEATURE
<222> LOCATION: (79)..(79)
<223> OTHER INFORMATION: Xaa is A, C, G, P, M, V, I, L, Sce, Sme
<220> FEATURE:
<221> NAME/KEY: MISC_FEATURE
<222> LOCATION: (81)..(82)
<223> OTHER INFORMATION: Xaa is A, C, G, P, M, V, I, L, Sce, Sme
<220> FEATURE:
<221> NAME/KEY: MISC_FEATURE
```

```
<222> LOCATION: (85)..(85)
<223> OTHER INFORMATION: Xaa is A, C, G, P, M, V, I, L, Sce, Sme
<220> FEATURE:
<221> NAME/KEY: MISC_FEATURE
<222> LOCATION: (86)..(86)
<223> OTHER INFORMATION: Xaa is R, H, or K
<220> FEATURE:
<221> NAME/KEY: MISC_FEATURE
<222> LOCATION: (97)..(97)
<223> OTHER INFORMATION: Xaa is D or E
<220> FEATURE:
<221> NAME/KEY: MISC_FEATURE
<222> LOCATION: (99)..(99)
<223> OTHER INFORMATION: Xaa is A, C, G, P, M, V, I, L, Sce, Sme
<220> FEATURE:
<221> NAME/KEY: MISC_FEATURE
<222> LOCATION: (101)..(101)
<223> OTHER INFORMATION: Xaa is D or E
<220> FEATURE:
<221> NAME/KEY: MISC_FEATURE
<222> LOCATION: (102)..(102)
<223> OTHER INFORMATION: Xaa is R, H, or K
<220> FEATURE:
<221> NAME/KEY: MISC_FEATURE
<222> LOCATION: (104)..(104)
<223> OTHER INFORMATION: Xaa is R, H, or K
<220> FEATURE:
<221> NAME/KEY: MISC_FEATURE
<222> LOCATION: (110)..(110)
<223> OTHER INFORMATION: Xaa is D or E
<220> FEATURE:
<221> NAME/KEY: MISC_FEATURE
<222> LOCATION: (112)..(112)
<223> OTHER INFORMATION: Xaa is A, C, G, P, M, V, I, L, Sce, Sme
<220> FEATURE:
<221> NAME/KEY: MISC_FEATURE
<222> LOCATION: (113)..(113)
<223> OTHER INFORMATION: Xaa is R, H, or K
<220> FEATURE:
<221> NAME/KEY: MISC_FEATURE
<222> LOCATION: (116)..(116)
<223> OTHER INFORMATION: Xaa is A, C, G, P, M, V, I, L, Sce, Sme
<220> FEATURE:
<221> NAME/KEY: MISC_FEATURE
<222> LOCATION: (117)..(117)
<223> OTHER INFORMATION: Xaa is D or E
<220> FEATURE:
<221> NAME/KEY: MISC_FEATURE
<222> LOCATION: (118)..(118)
<223> OTHER INFORMATION: Xaa is A, C, G, P, M, V, I, L, Sce, Sme
<220> FEATURE:
<221> NAME/KEY: MISC_FEATURE
<222> LOCATION: (119)..(119)
<223> OTHER INFORMATION: Xaa is D or E
<220> FEATURE:
<221> NAME/KEY: MISC_FEATURE
<222> LOCATION: (120)..(120)
<223> OTHER INFORMATION: Xaa is S, T, N, or Q
<220> FEATURE:
<221> NAME/KEY: MISC_FEATURE
<222> LOCATION: (121)..(121)
<223> OTHER INFORMATION: Xaa is A, C, G, P, M, V, I, L, Sce, Sme
<220> FEATURE:
<221> NAME/KEY: MISC_FEATURE
<222> LOCATION: (122)..(122)
<223> OTHER INFORMATION: Xaa is S, T, N, or Q

<400> SEQUENCE: 34

Xaa Val Arg Gly Ile Arg Gly Ala Ile Thr Val Glu Glu Xaa Thr Pro
1               5                   10                  15

Ala Ala Ile Leu Ala Ala Thr Ile Glu Leu Leu Leu Lys Met Leu Glu
            20                  25                  30

Ala Asn Xaa Ile Xaa Ser Xaa Xaa Glu Leu Ala Ala Val Ile Phe Thr
        35                  40                  45

Val Thr Xaa Xaa Leu Thr Ser Ala Phe Pro Ala Glu Ala Ala Arg Leu
```

```
                50                  55                  60
Ile Gly Met His Xaa Val Pro Leu Leu Ser Ala Arg Glu Val Xaa Val
 65                  70                  75                  80

Xaa Xaa Ser Leu Xaa Xaa Val Ile Arg Val Leu Ala Leu Trp Asn Thr
                 85                  90                  95

Xaa Thr Xaa Gln Xaa Xaa Val Xaa His Val Tyr Leu Asn Xaa Ala Xaa
            100                 105                 110

Xaa Leu Arg Xaa Xaa Xaa Xaa Xaa Xaa Xaa
            115                 120

<210> SEQ ID NO 35
<211> LENGTH: 177
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or optionally absent
<220> FEATURE:
<221> NAME/KEY: MISC_FEATURE
<222> LOCATION: (2)..(2)
<223> OTHER INFORMATION: Xaa is S, T, N or Q
<220> FEATURE:
<221> NAME/KEY: MISC_FEATURE
<222> LOCATION: (3)..(3)
<223> OTHER INFORMATION: Xaa is R, H or K
<220> FEATURE:
<221> NAME/KEY: MISC_FEATURE
<222> LOCATION: (16)..(16)
<223> OTHER INFORMATION: Xaa is S, T, N or Q
<220> FEATURE:
<221> NAME/KEY: MISC_FEATURE
<222> LOCATION: (17)..(19)
<223> OTHER INFORMATION: Xaa is A, C, G, P, M, V, I, L, Sce, or Sme
<220> FEATURE:
<221> NAME/KEY: MISC_FEATURE
<222> LOCATION: (20)..(20)
<223> OTHER INFORMATION: Xaa is S, T, N or Q
<220> FEATURE:
<221> NAME/KEY: MISC_FEATURE
<222> LOCATION: (21)..(21)
<223> OTHER INFORMATION: Xaa is A, C, G, P, M, V, I, L, Sce, or Sme
<220> FEATURE:
<221> NAME/KEY: MISC_FEATURE
<222> LOCATION: (37)..(37)
<223> OTHER INFORMATION: Xaa is S, T, N or Q
<220> FEATURE:
<221> NAME/KEY: MISC_FEATURE
<222> LOCATION: (39)..(39)
<223> OTHER INFORMATION: Xaa is D or E
<220> FEATURE:
<221> NAME/KEY: MISC_FEATURE
<222> LOCATION: (42)..(42)
<223> OTHER INFORMATION: Xaa is A, C, G, P, M, V, I, L, Sce, or Sme
<220> FEATURE:
<221> NAME/KEY: MISC_FEATURE
<222> LOCATION: (44)..(44)
<223> OTHER INFORMATION: Xaa is F, W, or Y
<220> FEATURE:
<221> NAME/KEY: MISC_FEATURE
<222> LOCATION: (45)..(45)
<223> OTHER INFORMATION: Xaa is S, T, N or Q
<220> FEATURE:
<221> NAME/KEY: MISC_FEATURE
<222> LOCATION: (51)..(51)
<223> OTHER INFORMATION: Xaa is S, T, N or Q
<220> FEATURE:
<221> NAME/KEY: MISC_FEATURE
<222> LOCATION: (52)..(52)
<223> OTHER INFORMATION: Xaa is D or E
<220> FEATURE:
<221> NAME/KEY: MISC_FEATURE
```

```
<222> LOCATION: (53)..(53)
<223> OTHER INFORMATION: Xaa is A, C, G, P, M, V, I, L, Sce, or Sme
<220> FEATURE:
<221> NAME/KEY: MISC_FEATURE
<222> LOCATION: (56)..(56)
<223> OTHER INFORMATION: Xaa is S, T, N or Q
<220> FEATURE:
<221> NAME/KEY: MISC_FEATURE
<222> LOCATION: (59)..(59)
<223> OTHER INFORMATION: Xaa is A, C, G, P, M, V, I, L, Sce, or Sme
<220> FEATURE:
<221> NAME/KEY: MISC_FEATURE
<222> LOCATION: (63)..(64)
<223> OTHER INFORMATION: Xaa is D or E
<220> FEATURE:
<221> NAME/KEY: MISC_FEATURE
<222> LOCATION: (65)..(65)
<223> OTHER INFORMATION: Xaa is S, T, N or Q
<220> FEATURE:
<221> NAME/KEY: MISC_FEATURE
<222> LOCATION: (66)..(66)
<223> OTHER INFORMATION: Xaa is D or E
<220> FEATURE:
<221> NAME/KEY: MISC_FEATURE
<222> LOCATION: (80)..(81)
<223> OTHER INFORMATION: Xaa is R, H or K
<220> FEATURE:
<221> NAME/KEY: MISC_FEATURE
<222> LOCATION: (89)..(89)
<223> OTHER INFORMATION: Xaa is D or E
<220> FEATURE:
<221> NAME/KEY: MISC_FEATURE
<222> LOCATION: (90)..(90)
<223> OTHER INFORMATION: Xaa is A, C, G, P, M, V, I, L, Sce, or Sme
<220> FEATURE:
<221> NAME/KEY: MISC_FEATURE
<222> LOCATION: (93)..(93)
<223> OTHER INFORMATION: Xaa is D or E
<220> FEATURE:
<221> NAME/KEY: MISC_FEATURE
<222> LOCATION: (95)..(95)
<223> OTHER INFORMATION: Xaa is A, C, G, P, M, V, I, L, Sce, or Sme
<220> FEATURE:
<221> NAME/KEY: MISC_FEATURE
<222> LOCATION: (105)..(105)
<223> OTHER INFORMATION: Xaa is A, C, G, P, M, V, I, L, Sce, or Sme
<220> FEATURE:
<221> NAME/KEY: MISC_FEATURE
<222> LOCATION: (106)..(106)
<223> OTHER INFORMATION: Xaa is D or E
<220> FEATURE:
<221> NAME/KEY: MISC_FEATURE
<222> LOCATION: (108)..(108)
<223> OTHER INFORMATION: Xaa is A, C, G, P, M, V, I, L, Sce, or Sme
<220> FEATURE:
<221> NAME/KEY: MISC_FEATURE
<222> LOCATION: (109)..(109)
<223> OTHER INFORMATION: Xaa is R, H or K
<220> FEATURE:
<221> NAME/KEY: MISC_FEATURE
<222> LOCATION: (110)..(110)
<223> OTHER INFORMATION: Xaa is D or E
<220> FEATURE:
<221> NAME/KEY: MISC_FEATURE
<222> LOCATION: (124)..(124)
<223> OTHER INFORMATION: Xaa is R, H or K
<220> FEATURE:
<221> NAME/KEY: MISC_FEATURE
<222> LOCATION: (126)..(126)
<223> OTHER INFORMATION: Xaa is D or E
<220> FEATURE:
<221> NAME/KEY: MISC_FEATURE
<222> LOCATION: (135)..(135)
<223> OTHER INFORMATION: Xaa is D or E
<220> FEATURE:
<221> NAME/KEY: MISC_FEATURE
<222> LOCATION: (152)..(152)
<223> OTHER INFORMATION: Xaa is F, W, or Y
<220> FEATURE:
```

```
<221> NAME/KEY: MISC_FEATURE
<222> LOCATION: (156)..(156)
<223> OTHER INFORMATION: Xaa is A, C, G, P, M, V, I, L, Sce, or Sme
<220> FEATURE:
<221> NAME/KEY: MISC_FEATURE
<222> LOCATION: (158)..(158)
<223> OTHER INFORMATION: Xaa is D or E
<220> FEATURE:
<221> NAME/KEY: MISC_FEATURE
<222> LOCATION: (161)..(161)
<223> OTHER INFORMATION: Xaa is F, W, or Y
<220> FEATURE:
<221> NAME/KEY: MISC_FEATURE
<222> LOCATION: (165)..(165)
<223> OTHER INFORMATION: Xaa is S, T, N or Q
<220> FEATURE:
<221> NAME/KEY: MISC_FEATURE
<222> LOCATION: (166)..(166)
<223> OTHER INFORMATION: Xaa is D or E
<220> FEATURE:
<221> NAME/KEY: MISC_FEATURE
<222> LOCATION: (170)..(170)
<223> OTHER INFORMATION: Xaa is R, H or K
<220> FEATURE:
<221> NAME/KEY: MISC_FEATURE
<222> LOCATION: (173)..(173)
<223> OTHER INFORMATION: Xaa is R, H or K
<220> FEATURE:
<221> NAME/KEY: MISC_FEATURE
<222> LOCATION: (174)..(174)
<223> OTHER INFORMATION: Xaa is A, C, G, P, M, V, I, L, Sce, or Sme
<220> FEATURE:
<221> NAME/KEY: MISC_FEATURE
<222> LOCATION: (175)..(175)
<223> OTHER INFORMATION: Xaa is R, H or K
<220> FEATURE:
<221> NAME/KEY: MISC_FEATURE
<222> LOCATION: (176)..(176)
<223> OTHER INFORMATION: Xaa is A, C, G, P, M, V, I, L, Sce, or Sme
<220> FEATURE:
<221> NAME/KEY: MISC_FEATURE
<222> LOCATION: (177)..(177)
<223> OTHER INFORMATION: Xaa is R, H or K

<400> SEQUENCE: 35

Xaa Xaa Xaa Ala Lys Ile Gly Ile Val Thr Val Ser Asp Arg Ala Xaa
 1               5                  10                  15

Xaa Xaa Xaa Xaa Xaa Asp Ile Ser Gly Lys Ala Ile Ile Leu Ala Leu
             20                  25                  30

Asn Leu Tyr Leu Xaa Ser Xaa Trp Glu Xaa Ile Xaa Xaa Val Ile Pro
         35                  40                  45

Asp Glu Xaa Xaa Xaa Ile Glu Xaa Thr Leu Xaa Lys Met Ala Xaa Xaa
 50                  55                  60

Xaa Xaa Cys Cys Leu Ile Val Thr Thr Gly Thr Gly Pro Ala Xaa
 65                  70                  75                  80

Xaa Asp Val Thr Pro Glu Ala Thr Xaa Xaa Val Cys Xaa Arg Xaa Met
             85                  90                  95

Pro Gly Phe Gly Glu Leu Met Arg Xaa Xaa Ser Xaa Xaa Xaa Val Pro
        100                 105                 110

Thr Ala Ile Leu Ser Arg Gln Thr Ala Gly Leu Xaa Gly Xaa Ser Leu
        115                 120                 125

Ile Val Asn Leu Pro Gly Xaa Pro Ala Ser Ile Ser Asp Cys Leu Leu
130                 135                 140

Ala Val Phe Pro Ala Ile Pro Xaa Cys Ile Asp Xaa Met Xaa Gly Pro
145                 150                 155                 160

Xaa Leu Glu Cys Xaa Xaa Ala Met Ile Xaa Pro Phe Xaa Xaa Xaa Xaa
                165                 170                 175
```

Xaa

```
<210> SEQ ID NO 36
<211> LENGTH: 122
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (14)..(14)
<223> OTHER INFORMATION: Xaa is D or E
<220> FEATURE:
<221> NAME/KEY: MISC_FEATURE
<222> LOCATION: (32)..(32)
<223> OTHER INFORMATION: Xaa is D or E
<220> FEATURE:
<221> NAME/KEY: MISC_FEATURE
<222> LOCATION: (33)..(33)
<223> OTHER INFORMATION: Xaa is A, C, G, P, M, V, I, L, Sce, or Sme
<220> FEATURE:
<221> NAME/KEY: MISC_FEATURE
<222> LOCATION: (35)..(35)
<223> OTHER INFORMATION: Xaa is A, C, G, P, M, V, I, L, Sce, or Sme
<220> FEATURE:
<221> NAME/KEY: MISC_FEATURE
<222> LOCATION: (37)..(37)
<223> OTHER INFORMATION: Xaa is S, T, N, or Q
<220> FEATURE:
<221> NAME/KEY: MISC_FEATURE
<222> LOCATION: (39)..(39)
<223> OTHER INFORMATION: Xaa is F, W, or Y
<220> FEATURE:
<221> NAME/KEY: MISC_FEATURE
<222> LOCATION: (41)..(41)
<223> OTHER INFORMATION: Xaa is D or E
<220> FEATURE:
<221> NAME/KEY: MISC_FEATURE
<222> LOCATION: (51)..(52)
<223> OTHER INFORMATION: Xaa is D or E
<220> FEATURE:
<221> NAME/KEY: MISC_FEATURE
<222> LOCATION: (57)..(57)
<223> OTHER INFORMATION: Xaa is F, W, or Y
<220> FEATURE:
<221> NAME/KEY: MISC_FEATURE
<222> LOCATION: (68)..(68)
<223> OTHER INFORMATION: Xaa is R, H, or K
<220> FEATURE:
<221> NAME/KEY: MISC_FEATURE
<222> LOCATION: (79)..(79)
<223> OTHER INFORMATION: Xaa is A, C, G, P, M, V, I, L, Sce, or Sme
<220> FEATURE:
<221> NAME/KEY: MISC_FEATURE
<222> LOCATION: (81)..(82)
<223> OTHER INFORMATION: Xaa is A, C, G, P, M, V, I, L, Sce, or Sme
<220> FEATURE:
<221> NAME/KEY: MISC_FEATURE
<222> LOCATION: (85)..(85)
<223> OTHER INFORMATION: Xaa is A, C, G, P, M, V, I, L, Sce, or Sme
<220> FEATURE:
<221> NAME/KEY: MISC_FEATURE
<222> LOCATION: (86)..(86)
<223> OTHER INFORMATION: Xaa is R, H, or K
<220> FEATURE:
<221> NAME/KEY: MISC_FEATURE
<222> LOCATION: (97)..(97)
<223> OTHER INFORMATION: Xaa is D or E
<220> FEATURE:
<221> NAME/KEY: MISC_FEATURE
<222> LOCATION: (99)..(99)
<223> OTHER INFORMATION: Xaa is A, C, G, P, M, V, I, L, Sce, or Sme
<220> FEATURE:
<221> NAME/KEY: MISC_FEATURE
```

-continued

```
<222> LOCATION: (101)..(101)
<223> OTHER INFORMATION: Xaa is D or E
<220> FEATURE:
<221> NAME/KEY: MISC_FEATURE
<222> LOCATION: (102)..(102)
<223> OTHER INFORMATION: Xaa is R, H, or K
<220> FEATURE:
<221> NAME/KEY: MISC_FEATURE
<222> LOCATION: (104)..(105)
<223> OTHER INFORMATION: Xaa is R, H, or K
<220> FEATURE:
<221> NAME/KEY: MISC_FEATURE
<222> LOCATION: (107)..(107)
<223> OTHER INFORMATION: Xaa is F, W, or Y
<220> FEATURE:
<221> NAME/KEY: MISC_FEATURE
<222> LOCATION: (112)..(112)
<223> OTHER INFORMATION: Xaa is A, C, G, P, M, V, I, L, Sce, or Sme
<220> FEATURE:
<221> NAME/KEY: MISC_FEATURE
<222> LOCATION: (113)..(113)
<223> OTHER INFORMATION: Xaa is R, H, or K
<220> FEATURE:
<221> NAME/KEY: MISC_FEATURE
<222> LOCATION: (114)..(114)
<223> OTHER INFORMATION: Xaa is A, C, G, P, M, V, I, L, Sce, or Sme
<220> FEATURE:
<221> NAME/KEY: MISC_FEATURE
<222> LOCATION: (115)..(115)
<223> OTHER INFORMATION: Xaa is R, H, or K
<220> FEATURE:
<221> NAME/KEY: MISC_FEATURE
<222> LOCATION: (116)..(116)
<223> OTHER INFORMATION: Xaa is A, C, G, P, M, V, I, L, Sce, or Sme
<220> FEATURE:
<221> NAME/KEY: MISC_FEATURE
<222> LOCATION: (117)..(117)
<223> OTHER INFORMATION: Xaa is D or E
<220> FEATURE:
<221> NAME/KEY: MISC_FEATURE
<222> LOCATION: (118)..(118)
<223> OTHER INFORMATION: Xaa is A, C, G, P, M, V, I, L, Sce, or Sme
<220> FEATURE:
<221> NAME/KEY: MISC_FEATURE
<222> LOCATION: (119)..(119)
<223> OTHER INFORMATION: Xaa is D or E
<220> FEATURE:
<221> NAME/KEY: MISC_FEATURE
<222> LOCATION: (120)..(120)
<223> OTHER INFORMATION: Xaa is S, T, N, or Q
<220> FEATURE:
<221> NAME/KEY: MISC_FEATURE
<222> LOCATION: (121)..(121)
<223> OTHER INFORMATION: Xaa is A, C, G, P, M, V, I, L, Sce, or Sme
<220> FEATURE:
<221> NAME/KEY: MISC_FEATURE
<222> LOCATION: (122)..(122)
<223> OTHER INFORMATION: Xaa is S, T, N, or Q

<400> SEQUENCE: 36

Xaa Val Arg Gly Ile Arg Gly Ala Ile Thr Val Asn Ser Xaa Thr Pro
1               5                   10                  15

Thr Ser Ile Ile Ile Ala Thr Ile Leu Leu Leu Glu Lys Met Leu Xaa
                20                  25                  30

Xaa Asn Xaa Ile Xaa Ser Xaa Glu Xaa Leu Ala Ala Val Ile Phe Thr
                35                  40                  45

Val Thr Xaa Xaa Leu Thr Ser Ala Xaa Pro Ala Glu Ala Ala Arg Gln
            50                  55                  60

Ile Gly Met Xaa Arg Val Pro Leu Leu Ser Arg Glu Val Xaa Val
65              70                  75                  80

Xaa Xaa Ser Leu Xaa Xaa Val Ile Arg Val Leu Ala Leu Trp Asn Thr
                85                  90                  95
```

```
Xaa Thr Xaa Gln Xaa Xaa Val Xaa Xaa Val Xaa Leu Ser Glu Ala Xaa
            100                 105                 110

Xaa Xaa Xaa Xaa Xaa Xaa Xaa Xaa Xaa Xaa
        115                 120

<210> SEQ ID NO 37
<211> LENGTH: 172
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (2)..(2)
<223> OTHER INFORMATION: Xaa is R, H or K
<220> FEATURE:
<221> NAME/KEY: MISC_FEATURE
<222> LOCATION: (3)..(3)
<223> OTHER INFORMATION: Xaa is A, C, G, P, M, V, I, L, Sce, or Sme
<220> FEATURE:
<221> NAME/KEY: MISC_FEATURE
<222> LOCATION: (4)..(5)
<223> OTHER INFORMATION: Xaa is S, T, N or Q
<220> FEATURE:
<221> NAME/KEY: MISC_FEATURE
<222> LOCATION: (6)..(6)
<223> OTHER INFORMATION: Xaa is R, H or K
<220> FEATURE:
<221> NAME/KEY: MISC_FEATURE
<222> LOCATION: (7)..(8)
<223> OTHER INFORMATION: Xaa is A, C, G, P, M, V, I, L, Sce, or Sme
<220> FEATURE:
<221> NAME/KEY: MISC_FEATURE
<222> LOCATION: (9)..(9)
<223> OTHER INFORMATION: Xaa is D or E
<220> FEATURE:
<221> NAME/KEY: MISC_FEATURE
<222> LOCATION: (10)..(10)
<223> OTHER INFORMATION: Xaa is R, H or K
<220> FEATURE:
<221> NAME/KEY: MISC_FEATURE
<222> LOCATION: (11)..(11)
<223> OTHER INFORMATION: Xaa is A, C, G, P, M, V, I, L, Sce, or Sme
<220> FEATURE:
<221> NAME/KEY: MISC_FEATURE
<222> LOCATION: (12)..(13)
<223> OTHER INFORMATION: Xaa is S, T, N or Q
<220> FEATURE:
<221> NAME/KEY: MISC_FEATURE
<222> LOCATION: (14)..(14)
<223> OTHER INFORMATION: Xaa is R, H or K
<220> FEATURE:
<221> NAME/KEY: MISC_FEATURE
<222> LOCATION: (15)..(15)
<223> OTHER INFORMATION: Xaa is A, C, G, P, M, V, I, L, Sce, or Sme
<220> FEATURE:
<221> NAME/KEY: MISC_FEATURE
<222> LOCATION: (16)..(16)
<223> OTHER INFORMATION: Xaa is F, W or Y
<220> FEATURE:
<221> NAME/KEY: MISC_FEATURE
<222> LOCATION: (17)..(18)
<223> OTHER INFORMATION: Xaa is A, C, G, P, M, V, I, L, Sce, or Sme
<220> FEATURE:
<221> NAME/KEY: MISC_FEATURE
<222> LOCATION: (19)..(20)
<223> OTHER INFORMATION: Xaa is D or E
<220> FEATURE:
<221> NAME/KEY: MISC_FEATURE
<222> LOCATION: (21)..(21)
<223> OTHER INFORMATION: Xaa is A, C, G, P, M, V, I, L, Sce, or Sme
<220> FEATURE:
<221> NAME/KEY: MISC_FEATURE
```

```
<222> LOCATION: (22)..(22)
<223> OTHER INFORMATION: Xaa is F, W or Y
<220> FEATURE:
<221> NAME/KEY: MISC_FEATURE
<222> LOCATION: (24)..(24)
<223> OTHER INFORMATION: Xaa is D or E
<220> FEATURE:
<221> NAME/KEY: MISC_FEATURE
<222> LOCATION: (25)..(25)
<223> OTHER INFORMATION: Xaa is S, T, N or Q
<220> FEATURE:
<221> NAME/KEY: MISC_FEATURE
<222> LOCATION: (28)..(28)
<223> OTHER INFORMATION: Xaa is A, C, G, P, M, V, I, L, Sce, or Sme
<220> FEATURE:
<221> NAME/KEY: MISC_FEATURE
<222> LOCATION: (29)..(29)
<223> OTHER INFORMATION: Xaa is D or E
<220> FEATURE:
<221> NAME/KEY: MISC_FEATURE
<222> LOCATION: (46)..(46)
<223> OTHER INFORMATION: Xaa is R, H or K
<220> FEATURE:
<221> NAME/KEY: MISC_FEATURE
<222> LOCATION: (49)..(51)
<223> OTHER INFORMATION: Xaa is D or E
<220> FEATURE:
<221> NAME/KEY: MISC_FEATURE
<222> LOCATION: (53)..(53)
<223> OTHER INFORMATION: Xaa is R, H or K
<220> FEATURE:
<221> NAME/KEY: MISC_FEATURE
<222> LOCATION: (58)..(58)
<223> OTHER INFORMATION: Xaa is D or E
<220> FEATURE:
<221> NAME/KEY: MISC_FEATURE
<222> LOCATION: (64)..(64)
<223> OTHER INFORMATION: Xaa is F, W or Y
<220> FEATURE:
<221> NAME/KEY: MISC_FEATURE
<222> LOCATION: (73)..(73)
<223> OTHER INFORMATION: Xaa is R, H or K
<220> FEATURE:
<221> NAME/KEY: MISC_FEATURE
<222> LOCATION: (75)..(75)
<223> OTHER INFORMATION: Xaa is R, H or K
<220> FEATURE:
<221> NAME/KEY: MISC_FEATURE
<222> LOCATION: (76)..(76)
<223> OTHER INFORMATION: Xaa is A, C, G, P, M, V, I, L, Sce, or Sme
<220> FEATURE:
<221> NAME/KEY: MISC_FEATURE
<222> LOCATION: (77)..(77)
<223> OTHER INFORMATION: Xaa is D or E
<220> FEATURE:
<221> NAME/KEY: MISC_FEATURE
<222> LOCATION: (80)..(80)
<223> OTHER INFORMATION: Xaa is S, T, N or Q
<220> FEATURE:
<221> NAME/KEY: MISC_FEATURE
<222> LOCATION: (82)..(82)
<223> OTHER INFORMATION: Xaa is D or E
<220> FEATURE:
<221> NAME/KEY: MISC_FEATURE
<222> LOCATION: (83)..(83)
<223> OTHER INFORMATION: Xaa is R, H or K
<220> FEATURE:
<221> NAME/KEY: MISC_FEATURE
<222> LOCATION: (89)..(89)
<223> OTHER INFORMATION: Xaa is R, H or K
<220> FEATURE:
<221> NAME/KEY: MISC_FEATURE
<222> LOCATION: (93)..(93)
<223> OTHER INFORMATION: Xaa is R, H or K
<220> FEATURE:
<221> NAME/KEY: MISC_FEATURE
<222> LOCATION: (96)..(96)
<223> OTHER INFORMATION: Xaa is D or E
<220> FEATURE:
```

```
<221> NAME/KEY: MISC_FEATURE
<222> LOCATION: (97)..(97)
<223> OTHER INFORMATION: Xaa is A, C, G, P, M, V, I, L, Sce, or Sme
<220> FEATURE:
<221> NAME/KEY: MISC_FEATURE
<222> LOCATION: (99)..(99)
<223> OTHER INFORMATION: Xaa is S, T, N or Q
<220> FEATURE:
<221> NAME/KEY: MISC_FEATURE
<222> LOCATION: (100)..(100)
<223> OTHER INFORMATION: Xaa is A, C, G, P, M, V, I, L, Sce, or Sme
<220> FEATURE:
<221> NAME/KEY: MISC_FEATURE
<222> LOCATION: (101)..(101)
<223> OTHER INFORMATION: Xaa is R, H or K
<220> FEATURE:
<221> NAME/KEY: MISC_FEATURE
<222> LOCATION: (102)..(102)
<223> OTHER INFORMATION: Xaa is S, T, N or Q
<220> FEATURE:
<221> NAME/KEY: MISC_FEATURE
<222> LOCATION: (103)..(103)
<223> OTHER INFORMATION: Xaa is F, W or Y
<220> FEATURE:
<221> NAME/KEY: MISC_FEATURE
<222> LOCATION: (104)..(104)
<223> OTHER INFORMATION: Xaa is A, C, G, P, M, V, I, L, Sce, or Sme
<220> FEATURE:
<221> NAME/KEY: MISC_FEATURE
<222> LOCATION: (111)..(111)
<223> OTHER INFORMATION: Xaa is D or E
<220> FEATURE:
<221> NAME/KEY: MISC_FEATURE
<222> LOCATION: (123)..(123)
<223> OTHER INFORMATION: Xaa is R, H or K
<220> FEATURE:
<221> NAME/KEY: MISC_FEATURE
<222> LOCATION: (131)..(131)
<223> OTHER INFORMATION: Xaa is S, T, N or Q
<220> FEATURE:
<221> NAME/KEY: MISC_FEATURE
<222> LOCATION: (135)..(135)
<223> OTHER INFORMATION: Xaa is D or E
<220> FEATURE:
<221> NAME/KEY: MISC_FEATURE
<222> LOCATION: (136)..(136)
<223> OTHER INFORMATION: Xaa is F, W or Y
<220> FEATURE:
<221> NAME/KEY: MISC_FEATURE
<222> LOCATION: (154)..(154)
<223> OTHER INFORMATION: Xaa is F, W or Y
<220> FEATURE:
<221> NAME/KEY: MISC_FEATURE
<222> LOCATION: (162)..(162)
<223> OTHER INFORMATION: Xaa is A, C, G, P, M, V, I, L, Sce, or Sme
<220> FEATURE:
<221> NAME/KEY: MISC_FEATURE
<222> LOCATION: (163)..(163)
<223> OTHER INFORMATION: Xaa is D or E
<220> FEATURE:
<221> NAME/KEY: MISC_FEATURE
<222> LOCATION: (164)..(164)
<223> OTHER INFORMATION: Xaa is R, H or K
<220> FEATURE:
<221> NAME/KEY: MISC_FEATURE
<222> LOCATION: (165)..(165)
<223> OTHER INFORMATION: Xaa is S, T, N or Q
<220> FEATURE:
<221> NAME/KEY: MISC_FEATURE
<222> LOCATION: (166)..(166)
<223> OTHER INFORMATION: Xaa is R, H or K
<220> FEATURE:
<221> NAME/KEY: MISC_FEATURE
<222> LOCATION: (167)..(167)
<223> OTHER INFORMATION: Xaa is A, C, G, P, M, V, I, L, Sce, or Sme
<220> FEATURE:
<221> NAME/KEY: MISC_FEATURE
<222> LOCATION: (168)..(168)
<223> OTHER INFORMATION: Xaa is R, H or K
```

<220> FEATURE:
<221> NAME/KEY: MISC_FEATURE
<222> LOCATION: (169)..(169)
<223> OTHER INFORMATION: Xaa is D or E
<220> FEATURE:
<221> NAME/KEY: MISC_FEATURE
<222> LOCATION: (170)..(170)
<223> OTHER INFORMATION: Xaa is A, C, G, P, M, V, I, L, Sce, or Sme
<220> FEATURE:
<221> NAME/KEY: MISC_FEATURE
<222> LOCATION: (171)..(171)
<223> OTHER INFORMATION: Xaa is R, H or K
<220> FEATURE:
<221> NAME/KEY: MISC_FEATURE
<222> LOCATION: (172)..(172)
<223> OTHER INFORMATION: Xaa is S, T, N or Q

<400> SEQUENCE: 37

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Lys Xaa Xaa Pro Ile Xaa Xaa Ala Asn Gly
            20                  25                  30

Thr Leu Asp Glu Leu Thr Ser Phe Ile Gly Glu Ala Lys Xaa Tyr Val
            35                  40                  45

Xaa Xaa Xaa Met Xaa Gly Ile Leu Glu Xaa Ile Gln Asn Asp Ile Xaa
        50                  55                  60

Lys Ile Met Gly Glu Ile Gly Ser Xaa Gly Xaa Xaa Xaa Gly Ile Xaa
65              70                  75                  80

Glu Xaa Xaa Ile Ala Trp Leu Leu Xaa Leu Ile Leu Xaa Tyr Met Xaa
            85                  90                  95

Xaa Val Xaa Xaa Xaa Xaa Xaa Leu Pro Gly Gly Thr Leu Xaa Ser
            100                 105                 110

Ala Lys Leu Asp Val Cys Arg Thr Ile Ala Xaa Arg Ala Leu Arg Lys
            115                 120                 125

Val Leu Xaa Val Thr Arg Xaa Xaa Gly Ile Gly Ala Glu Ala Ala Ala
            130                 135                 140

Tyr Leu Leu Ala Leu Ser Asp Leu Leu Xaa Leu Leu Ala Arg Val Ile
145                 150                 155                 160

Glu Xaa Xaa Xaa Xaa Xaa Xaa Xaa Xaa Xaa Xaa Xaa
                165                 170
```

<210> SEQ ID NO 38
<211> LENGTH: 123
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (13)..(13)
<223> OTHER INFORMATION: Xaa is R, H, or K
<220> FEATURE:
<221> NAME/KEY: MISC_FEATURE
<222> LOCATION: (15)..(15)
<223> OTHER INFORMATION: Xaa is D or E
<220> FEATURE:
<221> NAME/KEY: MISC_FEATURE
<222> LOCATION: (17)..(108)
<223> OTHER INFORMATION: Xaa is S, T, N or Q
<220> FEATURE:
<221> NAME/KEY: MISC_FEATURE
<222> LOCATION: (20)..(20)
<223> OTHER INFORMATION: Xaa is D or E -continued

```
<220> FEATURE:
<221> NAME/KEY: MISC_FEATURE
<222> LOCATION: (24)..(24)
<223> OTHER INFORMATION: Xaa is S, T, N or Q
<220> FEATURE:
<221> NAME/KEY: MISC_FEATURE
<222> LOCATION: (33)..(33)
<223> OTHER INFORMATION: Xaa is A, C, G, P, M, V, I, L, Sce, or Sme
<220> FEATURE:
<221> NAME/KEY: MISC_FEATURE
<222> LOCATION: (39)..(39)
<223> OTHER INFORMATION: Xaa is D or E
<220> FEATURE:
<221> NAME/KEY: MISC_FEATURE
<222> LOCATION: (42)..(42)
<223> OTHER INFORMATION: Xaa is S, T, N or Q
<220> FEATURE:
<221> NAME/KEY: MISC_FEATURE
<222> LOCATION: (43)..(43)
<223> OTHER INFORMATION: Xaa is R, H, or K
<220> FEATURE:
<221> NAME/KEY: MISC_FEATURE
<222> LOCATION: (46)..(46)
<223> OTHER INFORMATION: Xaa is S, T, N or Q
<220> FEATURE:
<221> NAME/KEY: MISC_FEATURE
<222> LOCATION: (48)..(48)
<223> OTHER INFORMATION: Xaa is D or E
<220> FEATURE:
<221> NAME/KEY: MISC_FEATURE
<222> LOCATION: (51)..(51)
<223> OTHER INFORMATION: Xaa is R, H, or K
<220> FEATURE:
<221> NAME/KEY: MISC_FEATURE
<222> LOCATION: (54)..(54)
<223> OTHER INFORMATION: Xaa is S, T, N or Q
<220> FEATURE:
<221> NAME/KEY: MISC_FEATURE
<222> LOCATION: (56)..(57)
<223> OTHER INFORMATION: Xaa is A, C, G, P, M, V, I, L, Sce, or Sme
<220> FEATURE:
<221> NAME/KEY: MISC_FEATURE
<222> LOCATION: (58)..(58)
<223> OTHER INFORMATION: Xaa is D or E
<220> FEATURE:
<221> NAME/KEY: MISC_FEATURE
<222> LOCATION: (70)..(70)
<223> OTHER INFORMATION: Xaa is D or E
<220> FEATURE:
<221> NAME/KEY: MISC_FEATURE
<222> LOCATION: (72)..(72)
<223> OTHER INFORMATION: Xaa is R, H, or K
<220> FEATURE:
<221> NAME/KEY: MISC_FEATURE
<222> LOCATION: (90)..(90)
<223> OTHER INFORMATION: Xaa is D or E
<220> FEATURE:
<221> NAME/KEY: MISC_FEATURE
<222> LOCATION: (97)..(98)
<223> OTHER INFORMATION: Xaa is D or E
<220> FEATURE:
<221> NAME/KEY: MISC_FEATURE
<222> LOCATION: (108)..(108)
<223> OTHER INFORMATION: Xaa is D or E
<220> FEATURE:
<221> NAME/KEY: MISC_FEATURE
<222> LOCATION: (111)..(111)
<223> OTHER INFORMATION: Xaa is R, H, or K
<220> FEATURE:
<221> NAME/KEY: MISC_FEATURE
<222> LOCATION: (118)..(120)
<223> OTHER INFORMATION: Xaa is A, C, G, P, M, V, I, L, Sce, or Sme
<220> FEATURE:
<221> NAME/KEY: MISC_FEATURE
<222> LOCATION: (121)..(121)
<223> OTHER INFORMATION: Xaa is R, H, or K
<220> FEATURE:
<221> NAME/KEY: MISC_FEATURE
<222> LOCATION: (122)..(122)
```

<223> OTHER INFORMATION: Xaa is S, T, N or Q
<220> FEATURE:
<221> NAME/KEY: MISC_FEATURE
<222> LOCATION: (123)..(123)
<223> OTHER INFORMATION: Xaa is R, H, or K

<400> SEQUENCE: 38

Xaa Pro His Leu Val Ile Glu Ala Thr Ala Asn Leu Xaa Leu Xaa Thr
1               5                   10                  15

Xaa Pro Gly Xaa Leu Leu Glu Xaa Ala Asn Lys Ser Leu Phe Ala Ser
            20                  25                  30

Xaa Gln Phe Gly Glu Ala Xaa Ile Lys Xaa Xaa Phe Val Xaa Leu Xaa
        35                  40                  45

Ala Tyr Xaa Gln Gly Xaa Ala Xaa Xaa Xaa Arg Ala Tyr Leu His Ala
    50                  55                  60

Cys Leu Ser Ile Leu Xaa Gly Xaa Asp Ile Ala Thr Arg Thr Leu Leu
65                  70                  75                  80

Gly Ala Ser Leu Cys Ala Val Leu Ala Xaa Ala Val Ala Gly Gly Gly
                85                  90                  95

Xaa Xaa Gly Val Gln Val Ser Val Glu Val Arg Xaa Met Glu Xaa Leu
            100                 105                 110

Ser Tyr Ala Lys Arg Xaa Xaa Xaa Xaa Xaa Xaa
            115                 120

<210> SEQ ID NO 39
<211> LENGTH: 158
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (2)..(2)
<223> OTHER INFORMATION: Xaa is D or E
<220> FEATURE:
<221> NAME/KEY: MISC_FEATURE
<222> LOCATION: (3)..(3)
<223> OTHER INFORMATION: Xaa is S, T, N or Q
<220> FEATURE:
<221> NAME/KEY: MISC_FEATURE
<222> LOCATION: (4)..(4)
<223> OTHER INFORMATION: Xaa is A, C, G, P, M, V, I, L, Sce, Sme
<220> FEATURE:
<221> NAME/KEY: MISC_FEATURE
<222> LOCATION: (19)..(19)
<223> OTHER INFORMATION: Xaa is F, W, or Y
<220> FEATURE:
<221> NAME/KEY: MISC_FEATURE
<222> LOCATION: (20)..(20)
<223> OTHER INFORMATION: Xaa is D or E
<220> FEATURE:
<221> NAME/KEY: MISC_FEATURE
<222> LOCATION: (21)..(21)
<223> OTHER INFORMATION: Xaa is S, T, N or Q
<220> FEATURE:
<221> NAME/KEY: MISC_FEATURE
<222> LOCATION: (30)..(30)
<223> OTHER INFORMATION: Xaa is A, C, G, P, M, V, I, L, Sce, Sme
<220> FEATURE:
<221> NAME/KEY: MISC_FEATURE
<222> LOCATION: (31)..(31)
<223> OTHER INFORMATION: Xaa is R, H, or K
<220> FEATURE:
<221> NAME/KEY: MISC_FEATURE
<222> LOCATION: (38)..(38)
<223> OTHER INFORMATION: Xaa is R, H, or K

```
<220> FEATURE:
<221> NAME/KEY: MISC_FEATURE
<222> LOCATION: (45)..(45)
<223> OTHER INFORMATION: Xaa is A, C, G, P, M, V, I, L, Sce, Sme
<220> FEATURE:
<221> NAME/KEY: MISC_FEATURE
<222> LOCATION: (46)..(46)
<223> OTHER INFORMATION: Xaa is D or E
<220> FEATURE:
<221> NAME/KEY: MISC_FEATURE
<222> LOCATION: (62)..(62)
<223> OTHER INFORMATION: Xaa is S, T, N or Q
<220> FEATURE:
<221> NAME/KEY: MISC_FEATURE
<222> LOCATION: (63)..(64)
<223> OTHER INFORMATION: Xaa is D or E
<220> FEATURE:
<221> NAME/KEY: MISC_FEATURE
<222> LOCATION: (65)..(65)
<223> OTHER INFORMATION: Xaa is A, C, G, P, M, V, I, L, Sce, Sme
<220> FEATURE:
<221> NAME/KEY: MISC_FEATURE
<222> LOCATION: (67)..(67)
<223> OTHER INFORMATION: Xaa is R, H, or K
<220> FEATURE:
<221> NAME/KEY: MISC_FEATURE
<222> LOCATION: (79)..(79)
<223> OTHER INFORMATION: Xaa is D or E
<220> FEATURE:
<221> NAME/KEY: MISC_FEATURE
<222> LOCATION: (82)..(82)
<223> OTHER INFORMATION: Xaa is R, H, or K
<220> FEATURE:
<221> NAME/KEY: MISC_FEATURE
<222> LOCATION: (83)..(83)
<223> OTHER INFORMATION: Xaa is S, T, N or Q
<220> FEATURE:
<221> NAME/KEY: MISC_FEATURE
<222> LOCATION: (84)..(84)
<223> OTHER INFORMATION: Xaa is F, W, or Y
<220> FEATURE:
<221> NAME/KEY: MISC_FEATURE
<222> LOCATION: (87)..(87)
<223> OTHER INFORMATION: Xaa is A, C, G, P, M, V, I, L, Sce, Sme
<220> FEATURE:
<221> NAME/KEY: MISC_FEATURE
<222> LOCATION: (89)..(89)
<223> OTHER INFORMATION: Xaa is F, W, or Y
<220> FEATURE:
<221> NAME/KEY: MISC_FEATURE
<222> LOCATION: (94)..(95)
<223> OTHER INFORMATION: Xaa is A, C, G, P, M, V, I, L, Sce, Sme
<220> FEATURE:
<221> NAME/KEY: MISC_FEATURE
<222> LOCATION: (96)..(96)
<223> OTHER INFORMATION: Xaa is S, T, N or Q
<220> FEATURE:
<221> NAME/KEY: MISC_FEATURE
<222> LOCATION: (97)..(98)
<223> OTHER INFORMATION: Xaa is A, C, G, P, M, V, I, L, Sce, Sme
<220> FEATURE:
<221> NAME/KEY: MISC_FEATURE
<222> LOCATION: (99)..(99)
<223> OTHER INFORMATION: Xaa is S, T, N or Q
<220> FEATURE:
<221> NAME/KEY: MISC_FEATURE
<222> LOCATION: (100)..(100)
<223> OTHER INFORMATION: Xaa is D or E
<220> FEATURE:
<221> NAME/KEY: MISC_FEATURE
<222> LOCATION: (101)..(101)
<223> OTHER INFORMATION: Xaa is A, C, G, P, M, V, I, L, Sce, Sme
<220> FEATURE:
<221> NAME/KEY: MISC_FEATURE
<222> LOCATION: (102)..(102)
<223> OTHER INFORMATION: Xaa is D or E
<220> FEATURE:
<221> NAME/KEY: MISC_FEATURE
<222> LOCATION: (103)..(103)
```

```
<223> OTHER INFORMATION: Xaa is R, H, or K
<220> FEATURE:
<221> NAME/KEY: MISC_FEATURE
<222> LOCATION: (104)..(104)
<223> OTHER INFORMATION: Xaa is D or E
<220> FEATURE:
<221> NAME/KEY: MISC_FEATURE
<222> LOCATION: (105)..(105)
<223> OTHER INFORMATION: Xaa is S, T, N or Q
<220> FEATURE:
<221> NAME/KEY: MISC_FEATURE
<222> LOCATION: (109)..(109)
<223> OTHER INFORMATION: Xaa is D or E
<220> FEATURE:
<221> NAME/KEY: MISC_FEATURE
<222> LOCATION: (115)..(115)
<223> OTHER INFORMATION: Xaa is R, H, or K
<220> FEATURE:
<221> NAME/KEY: MISC_FEATURE
<222> LOCATION: (121)..(121)
<223> OTHER INFORMATION: Xaa is D or E
<220> FEATURE:
<221> NAME/KEY: MISC_FEATURE
<222> LOCATION: (123)..(123)
<223> OTHER INFORMATION: Xaa is A, C, G, P, M, V, I, L, Sce, Sme
<220> FEATURE:
<221> NAME/KEY: MISC_FEATURE
<222> LOCATION: (125)..(125)
<223> OTHER INFORMATION: Xaa is D or E
<220> FEATURE:
<221> NAME/KEY: MISC_FEATURE
<222> LOCATION: (126)..(126)
<223> OTHER INFORMATION: Xaa is R, H, or K
<220> FEATURE:
<221> NAME/KEY: MISC_FEATURE
<222> LOCATION: (127)..(127)
<223> OTHER INFORMATION: Xaa is S, T, N or Q
<220> FEATURE:
<221> NAME/KEY: MISC_FEATURE
<222> LOCATION: (133)..(133)
<223> OTHER INFORMATION: Xaa is D or E
<220> FEATURE:
<221> NAME/KEY: MISC_FEATURE
<222> LOCATION: (134)..(134)
<223> OTHER INFORMATION: Xaa is A, C, G, P, M, V, I, L, Sce, Sme
<220> FEATURE:
<221> NAME/KEY: MISC_FEATURE
<222> LOCATION: (136)..(136)
<223> OTHER INFORMATION: Xaa is A, C, G, P, M, V, I, L, Sce, Sme
<220> FEATURE:
<221> NAME/KEY: MISC_FEATURE
<222> LOCATION: (137)..(137)
<223> OTHER INFORMATION: Xaa is R, H, or K
<220> FEATURE:
<221> NAME/KEY: MISC_FEATURE
<222> LOCATION: (138)..(139)
<223> OTHER INFORMATION: Xaa is D or E
<220> FEATURE:
<221> NAME/KEY: MISC_FEATURE
<222> LOCATION: (140)..(141)
<223> OTHER INFORMATION: Xaa is A, C, G, P, M, V, I, L, Sce, Sme
<220> FEATURE:
<221> NAME/KEY: MISC_FEATURE
<222> LOCATION: (142)..(142)
<223> OTHER INFORMATION: Xaa is S, T, N or Q
<220> FEATURE:
<221> NAME/KEY: MISC_FEATURE
<222> LOCATION: (145)..(145)
<223> OTHER INFORMATION: Xaa is S, T, N or Q
<220> FEATURE:
<221> NAME/KEY: MISC_FEATURE
<222> LOCATION: (147)..(147)
<223> OTHER INFORMATION: Xaa is R, H, or K
<220> FEATURE:
<221> NAME/KEY: MISC_FEATURE
<222> LOCATION: (151)..(152)
<223> OTHER INFORMATION: Xaa is D or E
<220> FEATURE:
<221> NAME/KEY: MISC_FEATURE
```

```
<222> LOCATION: (155)..(155)
<223> OTHER INFORMATION: Xaa is R, H, or K
<220> FEATURE:
<221> NAME/KEY: MISC_FEATURE
<222> LOCATION: (156)..(156)
<223> OTHER INFORMATION: Xaa is D or E
<220> FEATURE:
<221> NAME/KEY: MISC_FEATURE
<222> LOCATION: (157)..(157)
<223> OTHER INFORMATION: Xaa is F, W, or Y
<220> FEATURE:
<221> NAME/KEY: MISC_FEATURE
<222> LOCATION: (158)..(158)
<223> OTHER INFORMATION: Xaa is A, C, G, P, M, V, I, L, Sce, Sme

<400> SEQUENCE: 39

Xaa Xaa Xaa Xaa Asn Thr Ser Phe Leu Ser Pro Ser Leu Val Thr Ile
1               5                   10                  15

Arg Asp Xaa Xaa Xaa Gly Gln Phe Ala Val Leu Arg Ile Xaa Xaa Thr
            20                  25                  30

Gly Phe Pro Ala Asp Xaa Gly Asp Ile Asp Leu Cys Xaa Xaa Lys Met
        35                  40                  45

Ile Gly Val Arg Ala Ala Gln Ile Phe Leu Gly Asp Asp Xaa Xaa Xaa
50                  55                  60

Xaa Phe Xaa Gly Pro His Ile Arg Ile Arg Cys Val Asp Ile Xaa Asp
65                  70                  75                  80

Lys Xaa Xaa Xaa Asn Ala Xaa Val Xaa Val Asp Leu Ile Xaa Xaa Xaa
                85                  90                  95

Xaa Xaa Xaa Xaa Xaa Xaa Xaa Xaa Ala Glu Glu Xaa Ala Lys Leu
            100                 105                 110

Ala Leu Xaa Val Ala Leu Gln Val Xaa Ile Xaa Asp Xaa Xaa Xaa Cys
        115                 120                 125

Val Thr Gln Phe Xaa Xaa Lys Xaa Xaa Xaa Xaa Xaa Xaa Xaa Ser Asp
    130                 135                 140

Xaa Phe Xaa Pro Asp Lys Xaa Xaa Tyr Tyr Xaa Xaa Xaa Xaa
145                 150                 155

<210> SEQ ID NO 40
<211> LENGTH: 113
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is any amino acid or is optionally absent
<220> FEATURE:
<221> NAME/KEY: MISC_FEATURE
<222> LOCATION: (11)..(11)
<223> OTHER INFORMATION: Xaa is A, C, G, P, M, V, I, L, Sce, or Sme
<220> FEATURE:
<221> NAME/KEY: MISC_FEATURE
<222> LOCATION: (13)..(13)
<223> OTHER INFORMATION: Xaa is D or E
<220> FEATURE:
<221> NAME/KEY: MISC_FEATURE
<222> LOCATION: (14)..(14)
<223> OTHER INFORMATION: Xaa is R, H, or K
<220> FEATURE:
<221> NAME/KEY: MISC_FEATURE
<222> LOCATION: (16)..(17)
<223> OTHER INFORMATION: Xaa is R, H, or K
<220> FEATURE:
<221> NAME/KEY: MISC_FEATURE
<222> LOCATION: (33)..(33)
<223> OTHER INFORMATION: Xaa is A, C, G, P, M, V, I, L, Sce, or Sme
<220> FEATURE:
```

```
<221> NAME/KEY: MISC_FEATURE
<222> LOCATION: (35)..(35)
<223> OTHER INFORMATION: Xaa is A, C, G, P, M, V, I, L, Sce, or Sme
<220> FEATURE:
<221> NAME/KEY: MISC_FEATURE
<222> LOCATION: (45)..(45)
<223> OTHER INFORMATION: Xaa is D or E
<220> FEATURE:
<221> NAME/KEY: MISC_FEATURE
<222> LOCATION: (46)..(46)
<223> OTHER INFORMATION: Xaa is S, T, N or Q
<220> FEATURE:
<221> NAME/KEY: MISC_FEATURE
<222> LOCATION: (55)..(55)
<223> OTHER INFORMATION: Xaa is S, T, N or Q
<220> FEATURE:
<221> NAME/KEY: MISC_FEATURE
<222> LOCATION: (56)..(56)
<223> OTHER INFORMATION: Xaa is D or E
<220> FEATURE:
<221> NAME/KEY: MISC_FEATURE
<222> LOCATION: (57)..(57)
<223> OTHER INFORMATION: Xaa is A, C, G, P, M, V, I, L, Sce, or Sme
<220> FEATURE:
<221> NAME/KEY: MISC_FEATURE
<222> LOCATION: (66)..(67)
<223> OTHER INFORMATION: Xaa is A, C, G, P, M, V, I, L, Sce, or Sme
<220> FEATURE:
<221> NAME/KEY: MISC_FEATURE
<222> LOCATION: (69)..(69)
<223> OTHER INFORMATION: Xaa is F, W, or Y
<220> FEATURE:
<221> NAME/KEY: MISC_FEATURE
<222> LOCATION: (71)..(71)
<223> OTHER INFORMATION: Xaa is A, C, G, P, M, V, I, L, Sce, or Sme
<220> FEATURE:
<221> NAME/KEY: MISC_FEATURE
<222> LOCATION: (72)..(72)
<223> OTHER INFORMATION: Xaa is S, T, N or Q
<220> FEATURE:
<221> NAME/KEY: MISC_FEATURE
<222> LOCATION: (75)..(75)
<223> OTHER INFORMATION: Xaa is D or E
<220> FEATURE:
<221> NAME/KEY: MISC_FEATURE
<222> LOCATION: (90)..(90)
<223> OTHER INFORMATION: Xaa is A, C, G, P, M, V, I, L, Sce, or Sme
<220> FEATURE:
<221> NAME/KEY: MISC_FEATURE
<222> LOCATION: (92)..(92)
<223> OTHER INFORMATION: Xaa is A, C, G, P, M, V, I, L, Sce, or Sme
<220> FEATURE:
<221> NAME/KEY: MISC_FEATURE
<222> LOCATION: (94)..(94)
<223> OTHER INFORMATION: Xaa is D or E
<220> FEATURE:
<221> NAME/KEY: MISC_FEATURE
<222> LOCATION: (102)..(102)
<223> OTHER INFORMATION: Xaa is S, T, N or Q
<220> FEATURE:
<221> NAME/KEY: MISC_FEATURE
<222> LOCATION: (104)..(104)
<223> OTHER INFORMATION: Xaa is A, C, G, P, M, V, I, L, Sce, or Sme
<220> FEATURE:
<221> NAME/KEY: MISC_FEATURE
<222> LOCATION: (108)..(108)
<223> OTHER INFORMATION: Xaa is F, W, or Y
<220> FEATURE:
<221> NAME/KEY: MISC_FEATURE
<222> LOCATION: (111)..(112)
<223> OTHER INFORMATION: Xaa is S, T, N or Q
<220> FEATURE:
<221> NAME/KEY: MISC_FEATURE
<222> LOCATION: (113)..(113)
<223> OTHER INFORMATION: Xaa is F, W, or Y

<400> SEQUENCE: 40

Xaa Pro Val Ile Gln Thr Phe Val Ser Thr Xaa Leu Xaa Xaa His Xaa
```

```
              1               5                  10                 15
Xaa Leu Leu Leu Ala Ile Ile Tyr Arg Ile Val Thr Arg Val Val Leu
               20                 25                 30

Xaa Lys Xaa Glu Asp Leu Val Met Met Thr Phe His Xaa Xaa Thr Pro
               35                 40                 45

Met His Phe Phe Gly Ser Xaa Xaa Xaa Val Ala Cys Val Arg Val Glu
               50                 55                 60

Ala Xaa Xaa Gly Xaa Gly Xaa Xaa Glu Pro Xaa Lys Val Thr Ser Ile
 65                 70                 75                 80

Val Thr Ala Ala Ile Thr Ala Val Cys Xaa Ile Xaa Ala Xaa Arg Ile
               85                 90                 95

Phe Val Leu Tyr Phe Xaa Pro Xaa His Cys Gly Xaa Asn Gly Xaa Xaa
               100                105                110

Xaa
```

<210> SEQ ID NO 41
<211> LENGTH: 159
<212> TYPE: PRT
<213> ORGANISM: Artificial Sequence
<220> FEATURE:
<223> OTHER INFORMATION: Synthetic

<400> SEQUENCE: 41

```
Met Gly Glu Val Pro Ile Gly Asp Pro Lys Glu Leu Asn Gly Met Glu
 1               5                 10                 15

Ile Ala Ala Val Tyr Leu Gln Pro Ile Glu Met Glu Pro Arg Gly Ile
               20                 25                 30

Asp Leu Ala Ala Ser Leu Ala Asp Ile His Leu Glu Ala Asp Ile His
               35                 40                 45

Ala Leu Lys Asn Asn Pro Asn Gly Phe Pro Glu Gly Phe Trp Met Pro
               50                 55                 60

Tyr Leu Thr Ile Ala Tyr Glu Leu Lys Asn Thr Asp Thr Gly Ala Ile
 65                 70                 75                 80

Lys Arg Gly Thr Leu Met Pro Met Val Ala Asp Asp Gly Pro His Tyr
               85                 90                 95

Gly Ala Asn Ile Ala Met Glu Lys Asp Lys Lys Gly Gly Phe Gly Val
               100                105                110

Gly Asn Tyr Glu Leu Thr Phe Tyr Ile Ser Asn Pro Glu Lys Gln Gly
               115                120                125

Phe Gly Arg His Val Asp Glu Glu Thr Gly Val Gly Lys Trp Phe Glu
               130                135                140

Pro Phe Lys Val Asp Tyr Lys Phe Lys Tyr Thr Gly Thr Pro Lys
145                 150                155
```

<210> SEQ ID NO 42
<211> LENGTH: 184
<212> TYPE: PRT
<213> ORGANISM: Artificial Sequence
<220> FEATURE:
<223> OTHER INFORMATION: Synthetic

<400> SEQUENCE: 42

```
Met Ser Gln Ala Ile Gly Ile Leu Glu Leu Thr Ser Ile Ala Lys Gly
 1               5                 10                 15

Met Glu Leu Gly Asp Ala Met Leu Lys Ser Ala Asn Val Asp Leu Leu
               20                 25                 30

Val Ser Lys Thr Ile Cys Pro Gly Lys Phe Leu Leu Met Leu Gly Gly
```

```
                35                  40                  45

Asp Ile Gly Ala Ile Gln Gln Ala Ile Glu Thr Gly Thr Ser Gln Ala
 50                  55                  60

Gly Glu Met Leu Val Asp Ser Leu Val Leu Ala Asn Ile His Pro Ser
 65                  70                  75                  80

Val Leu Pro Ala Ile Ser Gly Leu Asn Ser Val Asp Lys Arg Gln Ala
                 85                  90                  95

Val Gly Ile Val Glu Thr Trp Ser Val Ala Ala Cys Ile Ser Ala Ala
                100                 105                 110

Asp Arg Ala Val Lys Gly Ser Asn Val Thr Leu Val Arg Val His Met
                115                 120                 125

Ala Phe Gly Ile Gly Gly Lys Cys Tyr Met Val Val Ala Gly Asp Val
                130                 135                 140

Ser Asp Val Asn Asn Ala Val Thr Val Ala Ser Glu Ser Ala Gly Glu
145                 150                 155                 160

Lys Gly Leu Leu Val Tyr Arg Ser Val Ile Pro Arg Pro His Glu Ala
                165                 170                 175

Met Trp Arg Gln Met Val Glu Gly
                180

<210> SEQ ID NO 43
<211> LENGTH: 103
<212> TYPE: PRT
<213> ORGANISM: Artificial Sequence
<220> FEATURE:
<223> OTHER INFORMATION: Synthetic

<400> SEQUENCE: 43

Met Glu Glu Val Val Leu Ile Thr Val Pro Ser Glu Glu Val Ala Arg
 1               5                  10                  15

Thr Ile Ala Lys Ala Leu Val Glu Glu Arg Leu Ala Ala Cys Val Asn
                20                  25                  30

Ile Val Pro Gly Leu Thr Ser Ile Tyr Arg Trp Gln Gly Glu Val Val
                35                  40                  45

Glu Asp Gln Glu Leu Leu Leu Leu Val Lys Thr Thr Thr His Ala Phe
 50                  55                  60

Pro Lys Leu Lys Glu Arg Val Lys Ala Leu His Pro Tyr Thr Val Pro
 65                  70                  75                  80

Glu Ile Val Ala Leu Pro Ile Ala Glu Gly Asn Arg Glu Tyr Leu Asp
                 85                  90                  95

Trp Leu Arg Glu Asn Thr Gly
                100

<210> SEQ ID NO 44
<211> LENGTH: 122
<212> TYPE: PRT
<213> ORGANISM: Artificial Sequence
<220> FEATURE:
<223> OTHER INFORMATION: Synthetic

<400> SEQUENCE: 44

Met Val Arg Gly Ile Arg Gly Ala Ile Thr Val Glu Glu Asp Thr Pro
 1               5                  10                  15

Glu Ala Ile His Gln Ala Thr Arg Glu Leu Leu Leu Lys Met Leu Glu
                20                  25                  30

Ala Asn Gly Ile Gln Ser Tyr Glu Glu Leu Ala Ala Val Ile Phe Thr
                35                  40                  45
```

```
Val Thr Glu Asp Leu Thr Ser Ala Phe Pro Ala Glu Ala Arg Gln
 50                  55                  60

Ile Gly Met His Arg Val Pro Leu Leu Ser Ala Arg Glu Val Pro Val
 65                  70                  75                  80

Pro Gly Ser Leu Pro Arg Val Ile Arg Val Leu Ala Leu Trp Asn Thr
                 85                  90                  95

Asp Thr Pro Gln Asp Arg Val Arg His Val Tyr Leu Arg Glu Ala Val
             100                 105                 110

Arg Leu Arg Pro Asp Leu Glu Ser Ala Gln
        115                 120
```

<210> SEQ ID NO 45
<211> LENGTH: 14
<212> TYPE: PRT
<213> ORGANISM: Artificial Sequence
<220> FEATURE:
<223> OTHER INFORMATION: Synthetic

<400> SEQUENCE: 45

```
Leu Glu Gly Gly Asp Ser Leu Asp Met Leu Glu Trp Ser Leu
 1               5                  10
```

<210> SEQ ID NO 46
<211> LENGTH: 177
<212> TYPE: PRT
<213> ORGANISM: Artificial Sequence
<220> FEATURE:
<223> OTHER INFORMATION: Synthetic

<400> SEQUENCE: 46

```
Met Ser Lys Ala Lys Ile Gly Ile Val Thr Val Ser Asp Arg Ala Ser
 1               5                  10                  15

Ala Gly Ile Tyr Glu Asp Ile Ser Gly Lys Ala Ile Ile Asp Thr Leu
                 20                  25                  30

Asn Asp Tyr Leu Thr Ser Glu Trp Glu Pro Ile Tyr Gln Val Ile Pro
             35                  40                  45

Asp Glu Gln Asp Val Ile Glu Thr Thr Leu Ile Lys Met Ala Asp Glu
 50                  55                  60

Gln Asp Cys Cys Leu Ile Val Thr Thr Gly Gly Thr Gly Pro Ala Lys
 65                  70                  75                  80

Arg Asp Val Thr Pro Glu Ala Thr Glu Ala Val Cys Asp Arg Met Met
                 85                  90                  95

Pro Gly Phe Gly Glu Leu Met Arg Ala Glu Ser Leu Lys Phe Val Pro
             100                 105                 110

Thr Ala Ile Leu Ser Arg Gln Thr Ala Gly Leu Arg Gly Asp Ser Leu
         115                 120                 125

Ile Val Asn Leu Pro Gly Lys Pro Lys Ser Ile Arg Glu Cys Leu Asp
     130                 135                 140

Ala Val Phe Pro Ala Ile Pro Tyr Cys Ile Asp Leu Met Glu Gly Pro
145                 150                 155                 160

Tyr Leu Glu Cys Asn Glu Ala Val Ile Lys Pro Phe Arg Pro Lys Ala
                 165                 170                 175

Lys
```

<210> SEQ ID NO 47
<211> LENGTH: 172
<212> TYPE: PRT
<213> ORGANISM: Artificial Sequence
<220> FEATURE:

<223> OTHER INFORMATION: Synthetic

<400> SEQUENCE: 47

Met Arg Ile Thr Thr Lys Val Gly Asp Lys Gly Ser Thr Arg Leu Phe
1               5                   10                  15

Gly Gly Glu Glu Val Trp Lys Asp Ser Pro Ile Ile Glu Ala Asn Gly
            20                  25                  30

Thr Leu Asp Glu Leu Thr Ser Phe Ile Gly Glu Ala Lys His Tyr Val
        35                  40                  45

Asp Glu Glu Met Lys Gly Ile Leu Glu Glu Ile Gln Asn Asp Ile Tyr
    50                  55                  60

Lys Ile Met Gly Glu Ile Gly Ser Lys Gly Lys Ile Glu Gly Ile Ser
65                  70                  75                  80

Glu Glu Arg Ile Lys Trp Leu Glu Gly Leu Ile Ser Arg Tyr Glu Glu
                85                  90                  95

Met Val Asn Leu Lys Ser Phe Val Leu Pro Gly Gly Thr Leu Glu Ser
            100                 105                 110

Ala Lys Leu Asp Val Cys Arg Thr Ile Ala Arg Arg Ala Glu Arg Lys
        115                 120                 125

Val Ala Thr Val Leu Arg Glu Phe Gly Ile Gly Lys Glu Ala Leu Val
    130                 135                 140

Tyr Leu Asn Arg Leu Ser Asp Leu Leu Phe Leu Ala Arg Val Ile
145                 150                 155                 160

Glu Ile Glu Lys Asn Lys Leu Lys Glu Val Arg Ser
                165                 170

<210> SEQ ID NO 48
<211> LENGTH: 123
<212> TYPE: PRT
<213> ORGANISM: Artificial Sequence
<220> FEATURE:
<223> OTHER INFORMATION: Synthetic

<400> SEQUENCE: 48

Met Pro His Leu Val Ile Glu Ala Thr Ala Asn Leu Arg Leu Glu Thr
1               5                   10                  15

Ser Pro Gly Glu Leu Leu Glu Gln Ala Asn Ala Ala Leu Phe Ala Ser
            20                  25                  30

Gly Gln Phe Gly Glu Ala Asp Ile Lys Ser Arg Phe Val Thr Leu Glu
        35                  40                  45

Ala Tyr Arg Gln Gly Thr Ala Ala Val Glu Arg Ala Tyr Leu His Ala
    50                  55                  60

Cys Leu Ser Ile Leu Asp Gly Arg Asp Ala Ala Thr Arg Gln Ala Leu
65                  70                  75                  80

Gly Glu Ser Leu Cys Glu Val Leu Ala Gly Ala Val Ala Gly Gly Gly
                85                  90                  95

Glu Glu Gly Val Gln Val Ser Val Glu Val Arg Glu Met Glu Arg Ala
            100                 105                 110

Ser Tyr Ala Lys Arg Val Val Ala Arg Gln Arg
        115                 120

<210> SEQ ID NO 49
<211> LENGTH: 158
<212> TYPE: PRT
<213> ORGANISM: Artificial Sequence
<220> FEATURE:
<223> OTHER INFORMATION: Synthetic

<400> SEQUENCE: 49

Met Glu Ser Val Asn Thr Ser Phe Leu Ser Pro Ser Leu Val Thr Ile
1               5                   10                  15

Arg Asp Phe Asp Asn Gly Gln Phe Ala Val Leu Arg Ile Gly Arg Thr
            20                  25                  30

Gly Phe Pro Ala Asp Lys Gly Asp Ile Asp Leu Cys Leu Asp Lys Met
        35                  40                  45

Lys Gly Val Arg Asp Ala Gln Gln Ser Ile Gly Asp Thr Glu Phe
    50                  55                  60

Gly Phe Lys Gly Pro His Ile Arg Ile Arg Cys Val Asp Ile Asp Asp
65              70                  75                  80

Lys His Thr Tyr Asn Ala Met Val Tyr Val Asp Leu Ile Val Gly Thr
            85                  90                  95

Gly Ala Ser Glu Val Glu Arg Glu Thr Ala Glu Leu Ala Lys Glu
        100                 105                 110

Lys Leu Arg Ala Ala Leu Gln Val Asp Ile Ala Asp Glu His Ser Cys
    115                 120                 125

Val Thr Gln Phe Glu Met Lys Leu Arg Glu Glu Leu Leu Ser Ser Asp
    130                 135                 140

Ser Phe His Pro Asp Lys Asp Glu Tyr Tyr Lys Asp Phe Leu
145                 150                 155

<210> SEQ ID NO 50
<211> LENGTH: 113
<212> TYPE: PRT
<213> ORGANISM: Artificial Sequence
<220> FEATURE:
<223> OTHER INFORMATION: Synthetic

<400> SEQUENCE: 50

Met Pro Val Ile Gln Thr Phe Val Ser Thr Pro Leu Asp His His Lys
1               5                   10                  15

Arg Glu Asn Leu Ala Gln Val Tyr Arg Ala Val Thr Arg Asp Val Leu
            20                  25                  30

Gly Lys Pro Glu Asp Leu Val Met Met Thr Phe His Asp Ser Thr Pro
        35                  40                  45

Met His Phe Phe Gly Ser Thr Asp Pro Val Ala Cys Val Arg Val Glu
50                  55                  60

Ala Leu Gly Gly Tyr Gly Pro Ser Glu Pro Glu Lys Val Thr Ser Ile
65              70                  75                  80

Val Thr Ala Ala Ile Thr Lys Glu Cys Gly Ile Val Ala Asp Arg Ile
            85                  90                  95

Phe Val Leu Tyr Phe Ser Pro Leu His Cys Gly Trp Asn Gly Thr Asn
        100                 105                 110

Phe

<210> SEQ ID NO 51
<211> LENGTH: 8
<212> TYPE: PRT
<213> ORGANISM: Artificial Sequence
<220> FEATURE:
<223> OTHER INFORMATION: Synthetic

<400> SEQUENCE: 51

Leu Glu His His His His His His
1               5

```
<210> SEQ ID NO 52
<211> LENGTH: 142
<212> TYPE: DNA
<213> ORGANISM: Artificial Sequence
<220> FEATURE:
<223> OTHER INFORMATION: Synthetic

<400> SEQUENCE: 52
taatgcttaa gtcgaacaga aagtaatcgt attgtacacg gccgcataat cgaaattaat      60
acgactcact atagggggaat tgtgagcgga taacaattcc ccatcttagt atattagtta    120
agtataagaa ggagatatac at                                              142
```

SELF-ASSEMBLING PROTEIN NANOSTRUCTURES

CROSS-REFERENCE TO RELATED APPLICATIONS

This application is a U.S. National Phase of International Application No. PCT/US2014/015371, filed Feb. 7, 2014, which claims priority to U.S. Provisional Application Ser. No. 61/762,194 filed Feb. 7, 2013, the disclosures of which are hereby incorporated by reference in their entireties.

BACKGROUND OF THE INVENTION

Unless otherwise indicated herein, the materials described in this section are not prior art to the claims in this application and are not admitted to be prior art by inclusion in this section.

Molecular self-assembly is an elegant and powerful approach to patterning matter on the atomic scale. Recent years have seen advances in the development of self-assembling biomaterials, particularly those composed of nucleic acids. DNA has been used to create, for example, nanoscale shapes and patterns, molecular containers, and three-dimensional macroscopic crystals. Methods for designing self-assembling proteins have progressed more slowly, yet the functional and physical properties of proteins make them attractive as building blocks for the development of advanced functional materials.

In any self-assembling structure, interactions between the subunits are required to drive assembly. Previous approaches to designing self-assembling proteins have satisfied this requirement in various ways, including the use of relatively simple and well-understood coiled-coil and helical bundle interactions, engineered disulfide bonds, chemical cross-links, metal-mediated interactions, templating by non-biological materials in conjunction with computational protein interface design, or genetic fusion of multiple protein domains or fragments which naturally self-associate.

In some scenarios, computational modeling and design of molecules can aid researchers in investigating the molecules. For example, computational protein design can provide valuable reagents for biomedical and biochemical research, identify sequences compatible with a given protein backbone, and design protein folds.

SUMMARY

In one aspect, isolated nanostructures are provided, comprising
(a) a plurality of first proteins that self-interact to form a first multimeric substructure comprising at least one axis of rotational symmetry;
(b) a plurality of second proteins that self-interact to form a second multimeric substructure comprising at least one axis of rotational symmetry;
wherein multiple copies of the first multimeric substructure and the second multimeric substructure interact with each other at one or more symmetrically repeated, non-natural, non-covalent protein-protein interfaces that orient the first multimeric substructures and the second multimeric substructures such that their symmetry axes are aligned with symmetry axes of the same kind in a designated mathematical symmetry group.

The nanostructures of the invention may, for example, have a mathematical symmetry group is selected from the group consisting of tetrahedral point group symmetry, octahedral point group symmetry, and icosahedral point group symmetry. In one embodiment, the first multimeric substructure comprises a dimer, trimer, tetramer, or pentamer of the first protein, and wherein the second multimeric substructure comprises a dimer or trimer of the second protein. In another embodiment, the first multimeric substructure comprises a trimer of the first protein, and wherein the second multimeric substructure comprises a dimer of the second protein. In a further embodiment, the first multimeric substructure comprises a trimer of the first protein, and wherein the second multimeric substructure comprises a trimer of the second protein. In another embodiment, the first protein and the second protein may be between 30-250 amino acids in length. In a still further embodiment, each symmetrically repeated instance of the non-natural, non-covalent protein-protein interface between the first multimeric substructure and the second multimeric substructure buries between 1000-2000 Å$^2$ of solvent-accessible surface area (SASA) on the first multimeric substructure and the second multimeric substructure. In another embodiment, each symmetrically repeated, non-natural, non-covalent protein-protein interface between the first multimeric substructure and the second multimeric substructure has a shape complementary value between 0.5-0.8. In a further embodiment, at least 50% of the atomic contacts comprising each symmetrically repeated, non-natural, non-covalent protein-protein interface between the first multimeric substructure and the second multimeric substructure is formed from amino acid residues residing in elements of alpha helix and/or beta strand secondary structure. Exemplary first and second proteins are disclosed herein.

In another aspect, the invention provides isolated proteins, comprising an amino acid sequence selected from the group consisting of SEQ ID NOS: 1-40, multimeric assemblies comprising a plurality of identical isolated protein monomers, recombinant nucleic acid encoding the isolated proteins, recombinant expression vector comprising the recombinant nucleic acids operatively linked to a promoter, and recombinant host cells, comprising the recombinant expression vectors of the invention, as well as kits comprising one or more of the compositions of the invention.

In a further aspect, a method is provided. A computing device generates a plurality of representations of a first protein building block. The computing device generates a plurality of representations of a second protein building block, where the first protein building block differs from the second protein building block. The computing device generates an arrangement of the plurality of representations of the first protein building block and the plurality of representations of the second protein building block according to symmetric operations of a designated mathematical symmetry group. The computing device computationally determines a docked configuration of the arrangement of the plurality of representations of the first protein building block and the plurality of representations of the second protein building block by at least generating at least one interface for each protein building block of the arrangement that is suitable for computational protein-protein interface design. The computing device computationally modifies amino acid sequences of the plurality of representations of the first protein building block and the plurality of representations of the second protein building block in the docked configuration to specify a plurality of representations of protein-protein interfaces. The plurality of representations of protein-protein interfaces include one or more representations of protein-protein interfaces between the first protein building block and the second protein building block that are energetically favorable to drive self-assembly of the protein building blocks comprising the modified amino acid sequences to the docked configuration. The computing device generates an output that is based on at least one representation of the group consisting of: a representation of the docked configuration, at least one representation of the plurality of representations of the protein-protein interfaces, and at least one representation of the representations of the first protein building block and the representations of the second protein building block having modified amino acid sequences.

BRIEF DESCRIPTION OF THE DRAWINGS

FIG. 10 shows the amino acid sequence of an exemplary protein (T32-28A) of the invention (SEQ ID NOs: 1, 11, 21, 31).

FIG. 11 shows the amino acid sequence of an exemplary protein (T32-28B) of the invention (SEQ ID NOs: 2, 12, 22, 32).

FIG. 12 shows the amino acid sequence of an exemplary protein (T33-09A) of the invention (SEQ ID NOs: 3, 13, 23, 33).

FIG. 13 shows the amino acid sequence of an exemplary protein (T33-09B) of the invention (SEQ ID NOs: 4, 14, 24, 34).

FIG. 14 shows the amino acid sequence of an exemplary protein (T33-15A) of the invention (SEQ ID NOs: 5, 15, 25, 35).

FIG. 15 shows the amino acid sequence of an exemplary protein (T33-15B) of the invention (SEQ ID NOs: 6, 16, 26, 36).

FIG. 16 shows the amino acid sequence of an exemplary protein (T33-21A) of the invention (SEQ ID NOs: 7, 17, 27, 37).

FIG. 17 shows the amino acid sequence of an exemplary protein (T33-21B) of the invention (SEQ ID NOs: 8, 18, 28, 38).

FIG. 18 shows the amino acid sequence of an exemplary protein (T33-28A) of the invention (SEQ ID NOs: 9, 19, 29, 39).

FIG. 19 shows the amino acid sequence of an exemplary protein (T33-28B) of the invention (SEQ ID NOs: 10, 20, 30, 40).

DETAILED DESCRIPTION

Natural protein assemblies are most often held together by many weak, noncovalent interactions which together form large, highly complementary, low energy protein-protein interfaces. Such interfaces spontaneously self-assemble and allow precise definition of the orientation of subunits relative to one another, which is critical for obtaining the desired material with high accuracy. Designing assemblies with these properties has been difficult due to the complexities of modeling protein structures and energetics.

A general computational method for designing self-assembling protein materials is disclosed, involving symmetrical docking of protein building blocks in a target symmetric architecture.

In some embodiments of the general computational method, the protein building blocks can include two or more distinct protein building blocks. Then, classes of nanomaterials can be constructed from docked configurations of the two or more distinct protein building blocks. Using multiple distinct protein building blocks can provide greater control over the assembly process and new functions. The nanomaterials can be engineered to encapsulate biomolecules of interest and deliver them to the cytosol of cultured cells to demonstrate their potential as next-generation targeted delivery vehicles.

The methods described herein can be used to design nanomaterials that combine several features of fundamental importance for their use in therapeutic applications. The nanomaterials can be designed with atomic-level accuracy that 1) underlies protein structure-function relationships, 2) is critical for the design of function, and 3) is currently inaccessible to other classes of materials such as synthetic nanoparticles or liposomes. Modular materials can be derived from these methods that enable the facile development of a variety of sophisticated functionalities. The nanomaterials can be "smart" materials that can respond in vitro or in vivo to therapeutically relevant environmental cues such as changes in pH.

Multi-component materials can enable design of larger cage-like assemblies with greater internal loading capacities, control over the initiation of assembly through mixing of separately purified components, and independent functionalization of each component. These three features are important for many potential downstream applications, including targeted delivery, vaccine design, and biosynthetic pathway engineering.

Software can simultaneously model multiple distinct subunit types in all of the symmetry groups relevant to protein structure, including helical, point group, layer group, and space group symmetries. The software can contain functionality for designing symmetric nanostructures, efficiently calculating scores, and sampling symmetric degrees of freedom.

Example Operations

Figure 1:
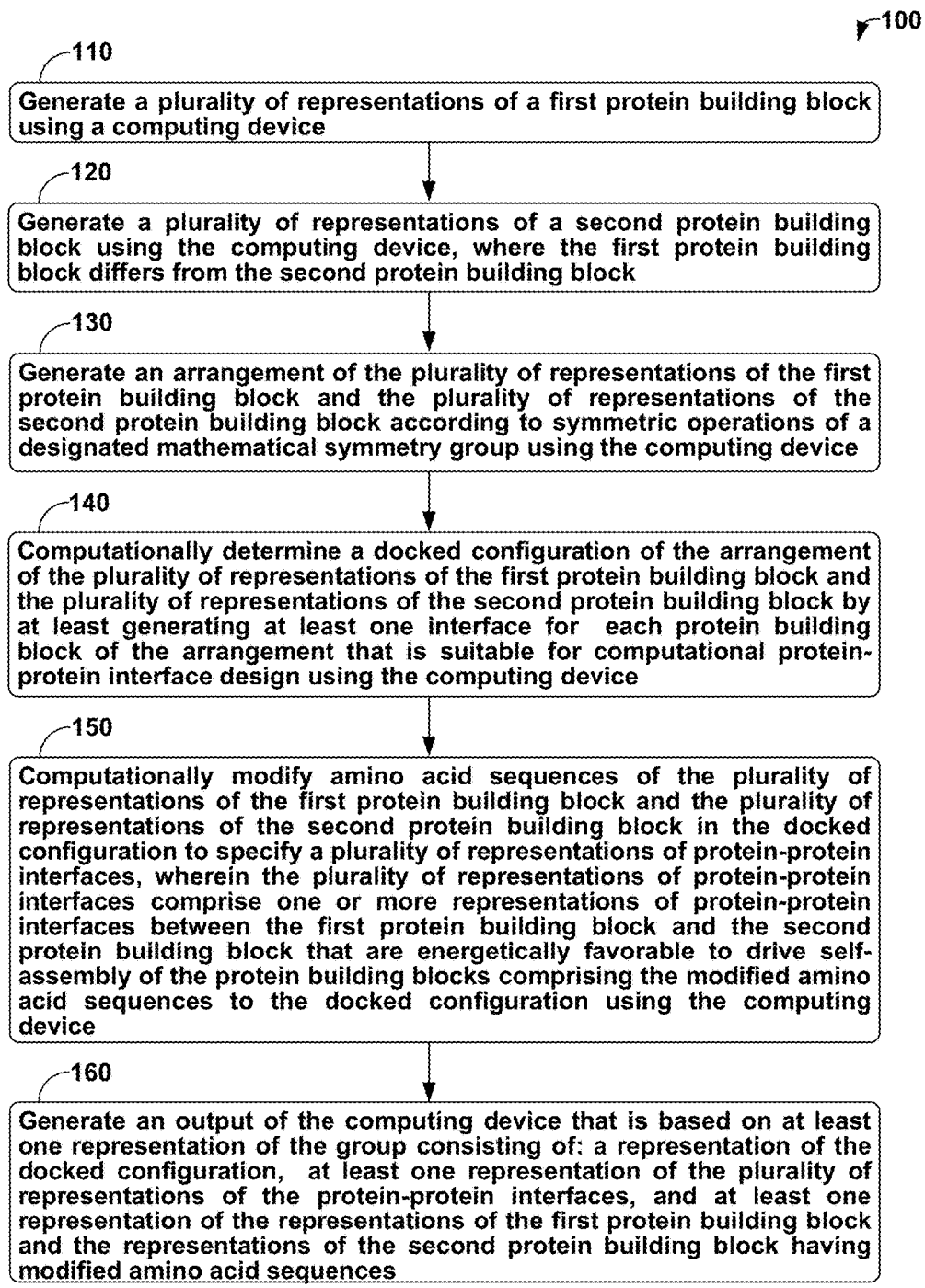
FIG. 1 is a flow chart of an example method.

FIG. 1 is a flow chart of an example method 100. Method 100 can begin at block 110, where a computing device, such as computing device 1000 described below in the context of at least FIG. 9A, can generate a plurality of representations of a first protein building block. At block 120, the computing device can generate a plurality of representations of a second protein building block, where the first protein building block differs from the second protein building block. In some embodiments, each of the first and second protein building blocks can include a synthetic polypeptide.

At block 130, the computing device can generate an arrangement of the plurality of representations of the first protein building block and the plurality of representations of the second protein building block according to symmetric operations of a designated mathematical symmetry group. In some embodiments, each of the plurality of the first and second protein building blocks can include a protein that shares an axis of symmetry with the designated mathematical symmetry group. In other embodiments, the designated mathematical symmetry group can conform to a symmetry selected from tetrahedral point group symmetry, octahedral point group symmetry, and icosahedral point group symmetry. In still other embodiments, generating the arrangement of the plurality of representations of the first protein building block and the plurality of representations of the second protein building block can include computationally aligning symmetry axes of the first protein building block and the second protein building block with at least one axis in the designated mathematical symmetry group.

At block 140, the computing device can computationally determine a docked configuration of the arrangement of the plurality of representations of the first protein building block and the plurality of representations of the second protein building block by at least generating at least one interface for each protein building block of the arrangement that is suitable for computational protein-protein interface design.

In some embodiments, determining a docked configuration of the plurality of the first and second protein building blocks can additionally include sampling rotational degrees of freedom and translational degrees of freedom for each of the first and second protein building blocks. In particular of these embodiments, sampling the rotational degrees of freedom and the translational degrees of freedom can include: selecting a rotational value for a rotational degree of freedom for each of the first and second protein building blocks; selecting a translational value for a translational degree of freedom for each of the first and second protein building blocks; determining a sampled representation of the first protein building block based on the selected rotational value for the first protein building block and the selected translational value for the first protein building block; determining a sampled representation of the second protein building block based on the selected rotational value for the second protein building block and the selected translational value for the second protein building block; and determining a designability measure for the docked configuration using the sampled representation of the first protein building block and the sampled representation of the second protein building block.

In more particular of these embodiments, determining the designability measure of the docked configuration can include determining a number of beta carbon contacts within a specified distance threshold between the sampled representation of the first protein building block and the sampled representation of the second protein building block in the docked configuration based on the values of the selected rotational and translational degrees of freedom.

At block 150, the computing device can computationally modify amino acid sequences of the plurality of representations of the first protein building block and the plurality of representations of the second protein building block in the docked configuration to specify a plurality of representations of protein-protein interfaces. The plurality of representations of protein-protein interfaces can include one or more representations of protein-protein interfaces between the first protein building block and the second protein building block that are energetically favorable to drive self-assembly of the protein building blocks comprising the modified amino acid sequences to the docked configuration using the computing device.

In some embodiments, computationally modifying the amino acid sequences of the plurality of representations of the first protein building block and the plurality of representations of the second protein building block can include selecting a selected representation of one or more amino acid sequences associated with a representation of at least one protein building block of the plurality of representations of the first protein building block and the plurality of representations of the second protein building block. In particular of these embodiments, computationally modifying the amino acid sequences of the plurality of representations of the first protein building block and the plurality of representations of the second protein building block can include computationally mutating an amino acid sequence of the selected representation of one or more amino acid sequences. In other embodiments, computationally modifying the amino acid sequences of the plurality of representations of the first protein building block and the plurality of representations of the second protein building block can include evaluating an energy of an amino acid mutation using a computational score function.

At block 160, the computing device can generate an output of the computing device that is based on at least one representation of the group consisting of: a representation of the docked configuration, at least one representation of the plurality of representations of the protein-protein interfaces, and at least one representation of the representations of the first protein building block and the representations of the second protein building block having modified amino acid sequences.

Figure 2:
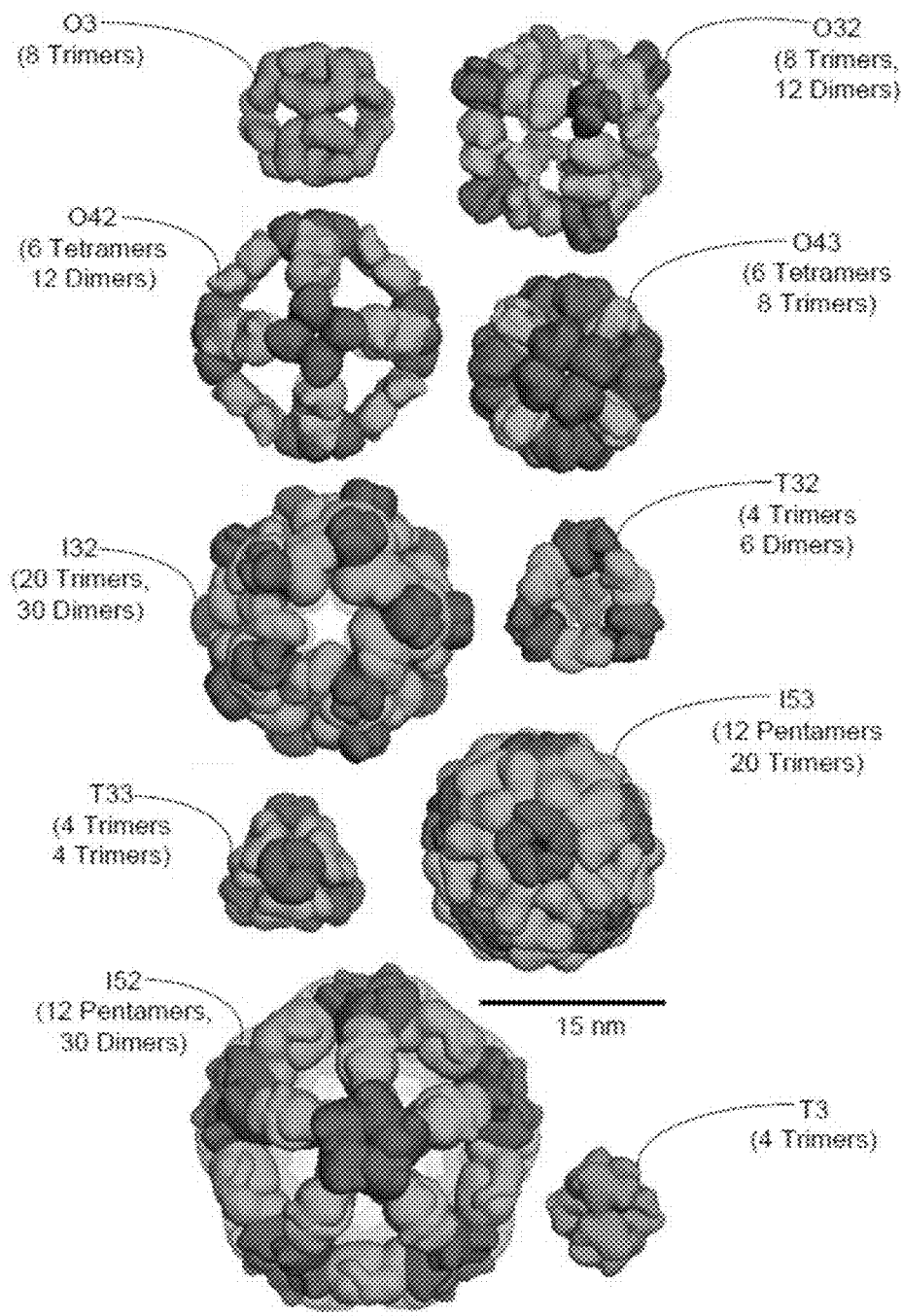
FIG. 2 depicts example protein architectures.

FIG. 2 depicts example protein architectures that can be designed using the method, in accordance with an example embodiment. FIG. 2 shows ten example architectures arranged roughly into two columns with architectures labeled O3, O42, I32, T32, I52 in the column, and labeled O32, O43, T32, I53, and T3 in the right column. The right column of architectures also includes a reference line indicating a reference distance of 15 nanometers within FIG. 2.

An architecture is labeled in FIG. 2 as either Xy or Xyz, where X is a letter, and y and z are numbers. The letter X represents the symmetry of the architecture: T for tetrahedral symmetry, O for octahedral symmetry, and I for icosahedral symmetry. The number y indicates a number of monomers in a first building block used to build the architecture and the number z indicates a number of monomers in a second building block used to build the architecture. If the number z is not present, then only one type of building block is used to build the structure. For examples, the O3 architecture at the top of the left column of FIG. 2, is an octahedral structure made up of one trimeric building block, the T33 architecture toward the bottom of the left column of FIG. 2 is a tetrahedral structure made up of two different types of trimer building blocks, and the I52 architecture at the bottom of the left column of FIG. 2 is an icosahedral structure made up of two multimer building blocks: a pentamer and a dimer.

FIG. 2 also indicates how many of each type of building block are utilized to build the structure. In the T32 architecture shown in the middle of the right column of FIG. 2 and in FIG. 3F, the structure is assembled from 4 trimers aligned along the tetrahedral three-fold symmetry axes and 6 dimers aligned along the two-fold symmetry axes. The T33 architecture (also shown in FIG. 3A-E) is constructed from four copies of one trimer and four copies of a second trimer, with the three-fold symmetry axis of each trimer aligned at opposite poles of each tetrahedral three-fold symmetry axis.

Accurate Design of Coassembling Multi-Component Protein Nanomaterials

The self-assembly of proteins into highly ordered nanoscale architectures is a hallmark of biological systems. Compared to homooligomers, assemblies formed from multiple distinct components offer a wider range of possible structures due to their combinatorial nature, greater control over the timing of assembly, and enhanced modularity through independently addressable building blocks. Disclosed is a general computational method for designing protein nanomaterials in which two distinct types of subunits coassemble to a target symmetric architecture. The information necessary to direct assembly is encoded in designed protein-protein interfaces that precisely define the relative orientations of the building blocks. This method has been used to design five novel 24-subunit cage-like protein nanomaterials in two distinct symmetric architectures. The designed pairs of proteins self-assemble to form highly homogeneous nanocages when co-expressed in E. coli, and the assembly of two of the materials can be initiated upon demand by mixing independently produced components. Crystal structures of the materials are in close agreement with the computational design models at the level of both the designed interfaces and the overall architectures. The accuracy of the method and the universe of two-component materials that it makes accessible pave the way for the design of functional protein nanomaterials tailored to specific applications.

The level of structural complexity available to self-assembled nanomaterials generally increases with the number of unique molecular components used to construct the material. DNA nanotechnology provides an extreme example of this phenomenon: strategies have been developed for encoding specific and directional interactions between hundreds of distinct DNA strands, allowing the construction of nanoscale objects with essentially arbitrary structures. Here the structural and functional range of designed protein materials is expanded with a general computational method for designing two-component coassembling protein nanomaterials with high accuracy.

Software can be used to model multi-component systems; that is, systems consisting of multiple distinct protein subunits, each associated with a distinct symmetry group. Within the updated framework we disclose herein, each distinct subunit can be modified independently of one another, with the changes propagated to all symmetrically related copies.

Figures 3A, 3B, 3C:
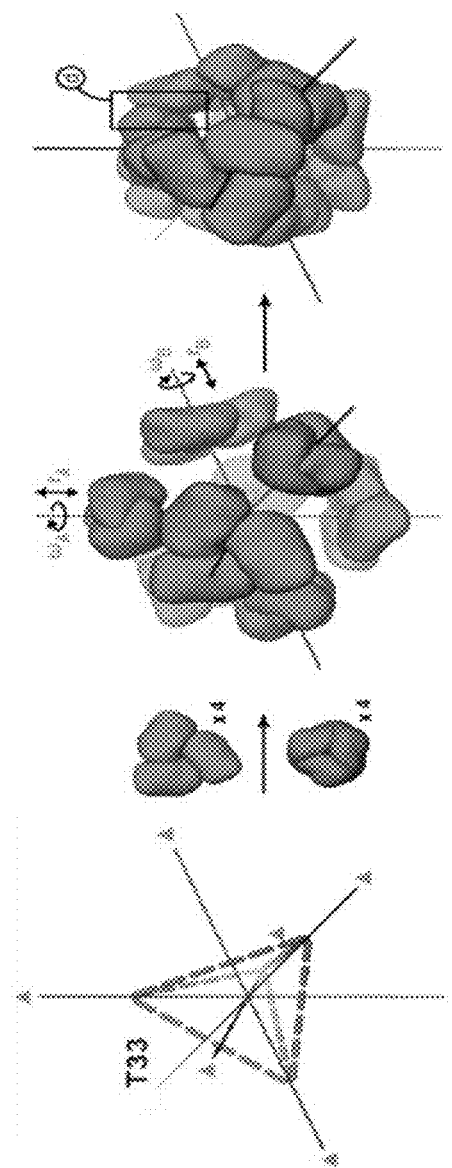
FIGS. 3A-3F shows a method for building protein architectures.

FIGS. 3A-3F shows a method for building two-component symmetric protein nanostructures. FIGS. 3A-3E illustrates this method using a dual tetrahedral architecture (designated in FIG. 2 and FIG. 3A as T33) as an example. In the T33 architecture, four copies each of two distinct, naturally trimeric building blocks are aligned at opposite poles of the three-fold symmetry axes of a tetrahedron as shown in FIG. 3A. This alignment places one set of building blocks at the vertices of the T33 tetrahedron and the second set of building blocks at the centers of the faces of the T33 tetrahedron, totaling twelve subunits of each protein.

Figure 3D:
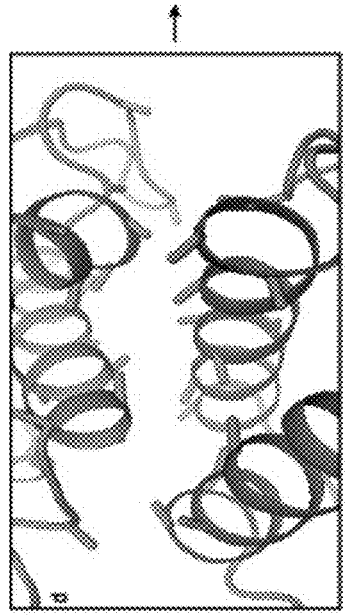
Figure 3E:
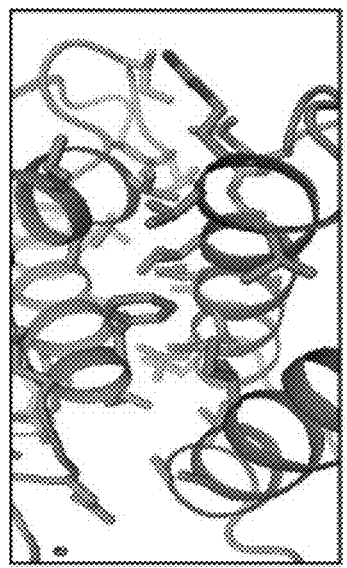

Each trimeric building block is allowed to rotate around and translate along its three-fold symmetry axis as indicated in FIG. 3B; other rigid body moves are disallowed because they would lead to asymmetry. These four degrees of freedom can be systematically explored during docking to identify configurations with interfaces that are suitable for design, as shown in FIG. 3C. The docking score function can maximize the number of inter-building block neighbors per residue and can favor residues in highly anchored regions of the protein structure that are unlikely to change conformation upon mutation of surface side chains as shown in FIG. 3D. A design algorithm, such as but not limited to the RosettaDesign™ algorithm, can be used to sample the identities and configurations of the side chains near the inter-building block interface, generating interfaces with features resembling those found in natural protein assemblies such as well-packed hydrophobic cores surrounded by polar rims, such as shown in FIG. 3E. The end result is a pair of new amino acid sequences, one for each building block, predicted to stabilize the modeled interface and therefore spontaneously drive assembly to the specific target configuration. These docking and design procedures were implemented in software to enable the simultaneous modeling of multiple distinct symmetrically arranged protein components. In particular, different components can be moved independently of one another while maintaining their internal degrees of freedom. This enables the design strategy described above to be generalized to a wide variety of symmetric architectures in which multiple symmetric building blocks are combined in geometrically specific ways. Combining even two symmetry elements can give rise to a large number of distinct symmetric architectures with a range of possible morphologies, including those with dihedral and cubic point group symmetries, as well as helical, layer, and space group symmetries.

As shown in the non-limiting examples that follow, the designed interfaces can drive assembly of cage-like nanomaterials that closely match the computational design models: the backbone RMSD over all 24 subunits in each material range from 1.0 to 2.6 Å. The precise control over interface geometry offered by our method thus enables the design of two-component protein nanomaterials with diverse nanoscale features such as surfaces, pores, and internal volumes with high accuracy.

The method described here can provide a general route to designing multi-component protein-based nanomaterials and molecular machines with programmable structures and functions. The capability to design highly homogeneous protein nanostructures with atomic-level accuracy and controllable assembly can open new opportunities in targeted drug delivery, vaccine design, plasmonics, and other applications that can benefit from the precise patterning of matter on the sub-nanometer to hundred nanometer scale.

Multi-Component Symmetric Modeling

The herein-described methods and techniques are not limited to use of RosettaDesign™, the Rosetta™ software suite, or any other specific software package. For example, other software programs could be used in conjunction with this method to model multi-component symmetric protein nanostructures. As will be understood by those of skill in the art, the implementation of the design methods of the invention described below is non-limiting, and the methods are in no way limited to the implementation disclosed herein.

Figure 4A:
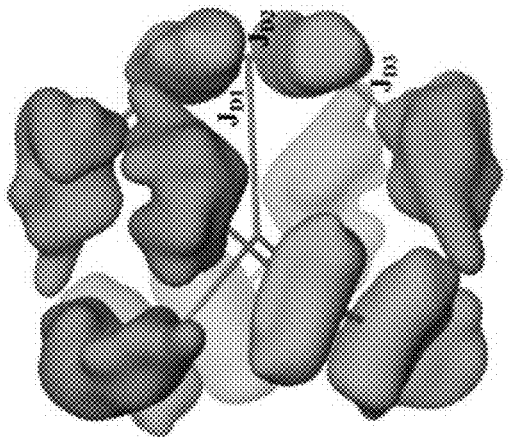
FIGS. 4A, 4B, and 4C show three different symmetric fold tree representations using an example two-component architecture with D3 symmetry.
Figure 4B:
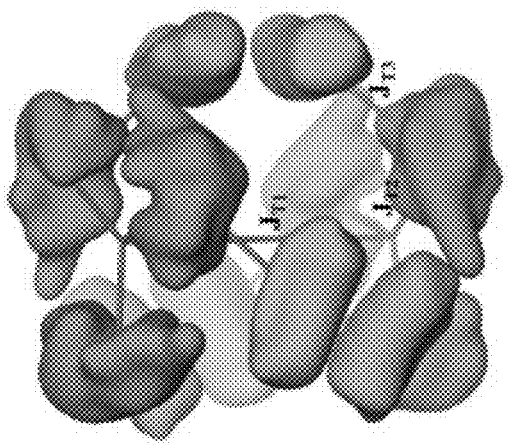
Figure 4C:
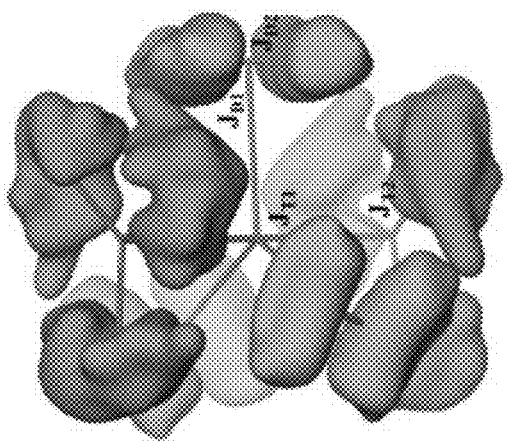

As an example embodiment, the Rosetta™ software package was modified for multi-component symmetric modeling. Rosetta's symmetric modeling framework was updated out to enable modeling of multi-component systems; that is, systems consisting of multiple distinct protein subunits, each associated with a distinct symmetry group. Within this updated framework, each distinct subunit can be modified independently of one another, with the changes propagated to all symmetrically related copies. All of Rosetta's design and modeling functionality accessible to one-component symmetries is now accessible for multi-component symmetries as well, including efficient scoring calculations and sampling of symmetric degrees of freedom. These changes to Rosetta's symmetry machinery are illustrated in FIGS. 4A-4C and described briefly below. In both the one-component examples shown in FIGS. 4A and 4B and the multi-component example of FIG. 4C, the symmetry of a given target architecture is passed to Rosetta in the form of a symmetry definition file.

FIGS. 4A, 4B, and 4C show three different symmetric fold tree representations of an example D32 architecture. In each of FIGS. 4A, 4B, and 4C, the D32 architecture is made up of two trimeric building blocks, each shown in a relatively dark gray color, and three dimeric building blocks each shown in a relatively light gray color, arranged with D3 point group symmetry. Following the strategy described above, arranging the building blocks with D3 point group symmetry is accomplished by aligning the three-fold symmetry axes of the trimeric building blocks along the three-fold axis in D3 point group symmetry and the two-fold symmetry axes of the dimeric building blocks along the two-fold axes in D3 point group symmetry. In the examples shown in FIGS. 4A-4C, rigid body degrees of freedom (RB DOFs) are shown using gray lines. FIGS. 4A and 4B show examples with one component symmetry. FIG. 4A shows RB DOF $J_{D3}$ connecting the master dimer subunit to the master trimer subunit. RB DOF $J_{D3}$ is a child of RB DOFs $J_{D1}$ and $J_{D2}$ controlling the master dimer subunit; in this case the positions of the trimeric subunits depend on the positions of the dimeric subunits. That is, the RB DOFs of the trimeric building blocks shown in FIG. 4A depend on the RB DOFs of the dimeric building blocks.

In the example shown in FIG. 4B, RB DOF $J_{T3}$ connecting the master trimer subunit to the master dimer subunit is a child of RB DOFs $J_{T1}$ and $J_{T2}$ controlling the master trimer subunit. Then, in FIG. 4B, the positions, and thus the RB DOFs, of the dimeric subunits depend on the positions, and thus the RB DOFs, of the trimeric subunits. FIG. 4C shows an example with multi-component symmetry. With multi-component symmetric modeling the RB DOFs controlling the master trimer subunit ($J_{T1}$ and $J_{T2}$) are independent of the RB DOFs controlling the master dimer subunit ($J_{D1}$ and $J_{D2}$); in the example of FIG. 4C, the positions of the dimeric subunits do not depend on the positions of the trimeric subunits and vice versa.

In some embodiments, only a single connection was allowed from the symmetric fold tree into the asymmetric unit. Thus, when modeling a system with multiple distinct symmetric components, only one such component could have its internal DOFs preserved. For example, in the D32 system shown in FIGS. 4A and 4B, if only one connection into the asymmetric unit is allowed, then one must choose to connect the two subunits in the asymmetric unit to either the three-fold axis (middle panel) or the two-fold axis (left panel). If both are connected to the three-fold axis, rotations around this connection will correctly preserve the internal DOFs of the trimer, but disrupt the internal DOFs of the dimer such as shown in FIG. 4B.

Other embodiments can enable multiple connections from the symmetric fold tree into the asymmetric unit, as the multi-component extension of symmetric modeling in Rosetta allows the asymmetric unit to be broken down into substructures that are independently managed by the symmetric fold tree. Using a multi-component symmetric fold tree in our D32 example allows the trimer to connect directly to the three-fold axis and the dimer to connect directly to the two-fold axis, thus any motions allowed by the symmetric architecture preserve the internal DOFs of both building blocks as shown in FIG. 5C.

In both the one-component and multi-component case, the symmetry of a given target architecture; e.g., T32 and T33 architectures, can be passed to Rosetta in the form of a symmetry definition file. The multi-component symmetry definition file syntax can be largely the same as the one-component syntax, with the additional requirement that the jumps connecting the protein subunits to the fold tree must specify which component is connected to each symmetry element.

Herein we define a symmetric architecture as a conceptual representation of a known mathematical symmetry group comprising at least one element of rotational symmetry, in which one or more of the elements of symmetry are explicitly considered; along each of the considered symmetry elements, multimeric protein building blocks with matching elements of symmetry can be aligned such that the symmetry elements of the building blocks and the designated symmetry group are collinear. Known mathematical symmetry groups with multiple different types of symmetry elements can be considered (for instance, octahedral point group symmetry contains two-fold, three-fold, and four-fold rotational symmetry elements); modeling nanostructures possessing these symmetries can require multiple distinct multimeric protein building blocks with distinct symmetries. In this way, a symmetric architecture defines: 1) the overall symmetry of the nanostructure being modeled, 2) the symmetries of the one or more distinct multimeric building blocks making up the symmetric nanostructure, and 3) the relative orientations of the symmetry axes of the one or more multimeric building blocks.

As a non-limiting example, a symmetric framework can be provided to model systems in two different symmetric architectures with tetrahedral point group symmetry. In one architecture, the assembly can be constructed from 4 trimers aligned along the tetrahedral three-fold symmetry axes and 6 dimers aligned along the two-folds; this architecture can be referred to as T32 (tetrahedron constructed from 3mers and 2mers). The second architecture, T33, can be constructed from four copies of one trimer and four copies of a second trimer, with the three-fold of each trimer aligned at opposite poles of each tetrahedral three-fold. Throughout the docking and design process the relative orientation of each of the two subunits within the trimers and/or dimers was maintained while allowing the trimeric or dimeric building blocks to translate along and rotate about the tetrahedral three-fold or two-fold symmetry axes.

The method disclosed herein can be used to model and design synthetic nanostructures possessing a wide variety of symmetries. In addition to the two-component tetrahedral symmetric architectures discussed above, nanostructures possessing octahedral or icosahedral point group symmetries can be modeled using the method, as well as nanostructures possessing dihedral point group symmetries, helical or line group symmetries, plane or layer group symmetries, or space group symmetries. In each symmetry, multimeric protein building blocks can be aligned along a subset of one or more of the elements of symmetry in the symmetry group in order to generate a synthetic nanostructure with the desired overall symmetry. The relative orientations of symmetry elements in all of the aforementioned symmetry group are known, and the symmetry definition file disclosed herein provides one general and non-limiting mechanism for providing this information to the computational design method.

Two-Component Symmetric Docking

The herein-described methods and techniques are discussed herein in the context of an example embodiment of the Rosetta™ software suite. However, there herein-described methods and techniques are not limited to use of RosettaDesign™, the Rosetta™ software suite, or any other specific software package. For example, other software programs could be used in conjunction with this method to computationally dock multi-component symmetric protein nanostructures. As will be understood by those of skill in the art, the implementation of the design methods of the invention described below is non-limiting, and the methods are in no way limited to the implementation disclosed herein. An application, tc_dock, was written within Rosetta™ to dock two distinct oligomeric building blocks into higher order symmetries in order to identify docked configurations predicted to be suitable for interface design. The required inputs for the tc_dock application are one PDB file containing a single subunit of the first scaffold component and a second PDB file containing a single subunit of the second scaffold component.

Sets of homodimeric and homotrimeric protein structures were curated to be input to our docking and design protocol. First, the PISA database was searched for all homodimeric or homotrimeric proteins passing the default criteria for dissociation energy, accessible surface area, buried surface area, percent buried surface area, and average chain length. The IDs obtained from PISA were then provided as input for the advanced search tool in the Protein Data Bank to select proteins clustered at 90% sequence identity with: 1) X-ray resolution less than 2 Å, 2) chain lengths of 75 to 200 amino acids, and 3) *Escherichia coli* as the host organism for protein expression. One trimeric protein that did not pass our automated selection criteria, PDB ID 3FTT, was added because of previous experience indicating it may serve as a successful design scaffold.

Coordinates for each of the selected PDB IDs were downloaded from the biological assemblies in the PDB and standardized for input to Rosetta. For biological assemblies containing multiple models with one chain per model, each model was treated as a separate chain. For assemblies containing multiple models with multiple chains per model, only the first model was considered. Alternative side chains and HETATM records were removed, selenomethionines replaced with methionines, and the chain with the lowest average RMSD (as calculated by the super command in PyMOL) to all other chains was selected to be the input chain for design. Residues with missing main chain atoms were removed from the design input chain and its residues renumbered starting from 1. A new biological assembly was created in PyMOL by superimposing copies of the design input chain onto all other chains, and the assembly's symmetry axis was aligned along the vector [0, 0, 1] and its center of mass translated to the origin. Assemblies were discarded that were found to be too asymmetric, as assessed by the dispersion of symmetry axes implied by each tuple of symmetrically related atoms. For PDB IDs with multiple biological assemblies, the assembly with the lowest biological unit number found to match the expected C2 or C3 symmetry was chosen for design. The final set of 1,161 homodimeric proteins is listed in Table 1 below. And the final set of 200 homotrimeric proteins is listed in Table 2 below.

TABLE 1

```
1a1x__1 1a3c__1 1ag9__1 1alu__1 1alv__1 1az5__1 1b0x__1 1b8z__1 1bgf__1
1bm9__1 1btk__1 1buo__1 1byf__1 1byr__1 1c02__1 1cdc__1 1ci4__1 1ciz__2
1coz__1 1cxq__1 1d7j__3 1d9c__1 1dnl__1 1dz3__1 1e7l__1 1ecs__1 1eeq__1 1ek3__1
1ep0__1 1esr__1 1etx__1 1evx__1 1ex2__1 1ext__1 1eyv__1 1f1e__1 1f1g__1 1f1m__1
1f9f__1 1f9z__1 1fit__1 1fmb__1 1fux__1 1fzv__1 1g2i__1 1g2q__1 1g8q__1 1gd7__1
1gvj__1 1gvp__1 1gy6__1 1gy7__1 1gyx__1 1h8x__1 1he7__1 1hgx__1 1ht9__1 1hur__1
1i0r__1 1i12__1 1i3c__1 1i4y__1 1i9d__2 1ic2__2 1ihr__1 1ilk__1 1iq6__1 1is6__1
1ixl__2 1izm__1 1j24__1 1j27__2 1j2r__1 1j3m__1 1j3q__1 1j55__1 1j7g__1 1j8b__1
1j98__1 1jc4__1 1jhc__1 1jhg__1 1jk3__2 1jr8__1 1jrl__2 1jya__1 1k04__1
1k2e__1 1k3s__1 1k66__1 1k8u__1 1k9u__1 1kcq__2 1k19__2 1kll__1 1kso__1 1l1q__1
1l3p__1 1l8s__1 1lgp__1 1lj9__1 1lq9__1 1ly1__1 1m0d__1 1m1f__1 1m2d__1 1m4i__1
1mi8__1 1mjh__1 1mk4__1
1mka__1 1mkk__1 1mp9__1 1msc__1 1mxi__1 1my6__1 1my7__1 1n99__1 1n91__2
1ng2__2 1njh__1 1nki__1 1np6__1 1nqd__1 1nrz__5 1ns5__1 1nu3__1 1nxm__1 1nzn__2
1o22__1 1o3u__1 1o4t__1 1o4w__1 1o50__1 1o6a__1 1o6d__2 1oh0__1 1ohp__1 1oiv__1
1on2__1 1oqc__1 1oru__1 1ovs__2 1p6o__1 1pbj__2 1pdo__1 1psr__1 1puc__1 1pvm__1
1py9__1 1pzw__1 1q08__1 1q7s__3 1q8b__2 1q98__1 1q9u__1 1qip__1 1qou__1 1qto__1
1qwi__1 1rlt__1 1rlu__1 1r29__1 1r5q__2 1r7j__1 1r71__1 1r9c__1 1rdo__1 1rfy__1
1rlk__2 1rxq__2 1s4k__1 1s67__1 1s7i__1 1s7z__2 1s99__1 1sd4__1 1sei__1 1sgm__1
1sh8__1 1sjw__2 1sjy__1 1sk4__2 1sl8__2 1snd__1 1t82__1 1t92__1 1tc5__1 1tfe__1
1tgj__1 1to4__1 1tu1__1 1tuh__1 1tuv__2 1tuw__1 1tvd__1 1twu__1 1u2w__1 1u3y__1
1u5f__2 1u69__2 1u7i__1 1uat__2 1udv__1 1ues__1 1ukk__1 1usc__1 1usm__1
1usp__1 1ut7__1 1uww__1 1uz3__1 1v05__1 1v2z__1 1v70__1 1v8y__1 1v96__1 1v9y__1
1vc1__1 1vh5__1
1via__1 1vj2__1 1vje__1 1vjl__1 1vkc__1 1vki__1 1v17__1 1vq3__2 1vr7__1
1vzg__1 1w53__1 1wc9__1 1wkq__1 1w1t__1 1wn2__1 1woc__1 1wpn__1 1wu9__1 1wwc__2
1wwi__2 1wz3__1 1x0j__1 1x2i__1 1x6i__1 1x82__1 1x8d__1 1xe1__2 1xfs__1 1xhn__1
1xqa__1 1xrk__1 1xs0__1 1xso__1 1xsq__1 1xty__1 1xvq__2 1y0b__1 1y0h__1 1y0u__1
1y5h__1 1y7r__1 1y9q__1 1y9w__1 1yb3__2 1ybx__1 1ybz__2 1yfu__1 1ygt__1 1yhf__2
1yib__1 1ylk__1 1ylm__1 1yo3__1 1yoa__1 1yr0__1 1ysp__2 1z0p__1 1z2w__3 1z4e__1
1z9n__1 1z9p__1 1zb9__1 1zdn__3 1zhq__1 1zhv__2 1zj6__2 1zlj__1 1zn8__1 1zo2__1
1zop__1 1zps__1 1zpv__1 1zpw__2 1ztd__1 1zva__1 1zwy__1 1zxk__1 2a15__1 2a67__1
2a6c__1 2a72__1 2a8n__1 2a9s__1 2aan__2 2aao__3 2akp__3 2aps__1 2aqs__1 2asf__1
2auw__2 2b06__1 2b0a__1 2b0v__2 2b18__1 2b1y__1 2b3s__3 2b5a__1 2b5g__1
2b6h__2 2b8m__1 2b9a__1 2bbe__2 2bdr__1 2bnl__1 2bsj__1 2bz1__1 2c2i__1 2c9q__1
2car__1 2cvd__1
2cvi__1 2cwz__1 2cyy__1 2d37__1 2d4p__2 2d4u__1 2d5m__1 2d7v__1 2d8d__1
2dc3__1 2dc4__1 2dlb__1 2dm9__1 2dob__2 2dp9__1 2dpf__1 2dql__1 2duy__2 2dvk__1
2dxq__1 2elf__2 2eln__1 2e6u__1 2e8e__1 2eb1__1 2ebb__1 2ecu__1 2een__1 2ef8__1
```

TABLE 1-continued

2efv__1 2egd__1 2eh3__1 2ehp__12ei5__1 2eiq__3 2ejn__1 2eo4__1 2erb__3 2esu__2
2f22__1 2f4p__1 2f5g__1 2f62__1 2f99__22f9h__1 2fa1__1 2fa5__1 2fbh__1 2fbn__1
2fck__1 2fd5__1 2fe3__1 2fex__1 2fhq__1 2fip__12fiu__1 2fj9__2 2fjt__1 2fl4__1
2fpr__1 2fq4__1 2fr2__2 2fre__1 2ftr__1 2fu4__1 2fyq__12fyx__1 2g0c__2 2g0i__1
2g1u__1 2g3a__1 2g3r__2 2g7s__1 2g84__1 2gax__3 2gbt__1 2ge7__12gen__1 2gff__1
2glz__1 2goj__1 2gpc__1 2gu9__1 2gux__1 2gxg__1 2gyq__1 2gzv__2 2h1t__12h2b__1
2h8e__1 2h9u__1 2ha8__1 2hbo__1 2hcm__1 2hhg__2 2hhz__1 2hiq__1 2hkv__1
2h10__12hlj__1 2hng__1 2hq9__1 2hql__1 2hs1__1 2hsb__1 2htd__1 2huh__1 2hur__2
2hyt__1 2hzc__2
2hzt__2 2i02__1 2i51__1 2i7a__1 2i7d__1 2i8b__1 2i8d__1 2i8t__1 2ia1__1
2ict__2 2id1__12iek__1 2if5__1 2ifx__1 2ig6__1 2igi__1 2ikk__1 2imj__1 2iml__1
2ims__1 2imz__1 2inb__12isy__1 2iu5__1 2ivy__1 2iwq__1 2ixk__1 2j6b__1 2j6y__1
2j7j__1 2j8m__1 2jar__1 2jba 12jdj__1 2je3__1 2jlj__1 2lig__1 2nlv__1 2nrk__1
2nsa__2 2nwv__1 2nx4__1 2nx8__1 2nyb__12nyc__1 2nyi__1 2nz7__1 2nzo__1 2o08__1
2o28__1 2o38__1 2o4t__1 2o6f__1 2o70__1 2o7m__12o95__1 2o99__1 2oa2__1 2oai__1
2ob5__1 2od4__1 2od6__1 2oda__1 2oee__1 2ogi__1 2oik__12okf__1 2oku__1 2olm__1
2omo__1 2onf__1 2oo2__1 2ooj__1 2ook__1 2opo__1 2oqk__2 2oqm__12oso__1 2ou3__1
2ou5__1 2ou6__1 2ouf__1 2ovs__1 2owp__1 2oyn__1 2oyz__1 2ozh__1 2ozj__12p08__1
2p09__1 2p12__1 2p25__1 2p3w__1 2p5q__1 2p7o__1 2p84__1 2p8g__1 2p8i__1
2p92__12pa7__1 2pey__1 2pfb__1 2pfi__1 2pfw__1 2pjs__1 2pk8__1 2pkh__1 2pmr__1
2pn0__1 2pn2__1
2pq3__2 2pqv__1 2prx__1 2pwo__1 2pyt__1 2q03__1 2q0y__1 2q20__1 2q24__1
2q2f__1 2q2h__12q2i__1 2q30__1 2q3p__1 2q3t__1 2q3x__1 2q4n__1 2q5c__3 2q79__1
2q82__1 2q8o__1 2q9k__12q9r__1 2qe9__1 2qhk__1 2qjw__1 2qkp__1 2ql8__1 2qml__2
2qmm__1 2qnd__3 2qnl__1 2qnt__12qqz__1 2qrr__1 2qsi__1 2qsw__1 2qtr__1 2qud__1
2qvm__2 2qx0__1 2r0x__1 2rli__1 2r47__12r4i__1 2r6u__1 2r6v__1 2r78__1 2rbb__1
2rc3__1 2rcz__1 2rey__1 2rh0__1 2rhm__1 2ril__12riq__1 2rk3__1 2rk9__1 2rkf__1
2rkh__1 2uv4__1 2v57__1 2v90__1 2vez__1 2vkl__1 2voc__12vpk__1 2vs0__1 2vsv__1
2vvp__1 2vvw__1 2w1r__1 2w2a__1 2w31__1 2w4e__1 2w7w__1 2wb6__12wce__1 2wcr__1
2wcu__1 2wcw__1 2wfc__1 2wnx__1 2wp7__1 2wra__1 2wtg__1 2wzo__1 2x3g__12x5c__1
2x5h__1 2x5r__1 2x7z__1 2xbq__1 2xdp__1 2xf1__1 2xhf__1 2xr4__1 2xrh__1
2xxc__12y0o__1 2y39__1 2y6w__1 2y78__1 2yfd__1 2ykz__1 2yqy__3 2ysk__1 2yvo__1
2ywl__1 2yxh__1
2yz1__3 2yzk__1 2z10__1 2z6d__1 2z8u__1 2z98__1 2zcm__1 2zdo__1 2zdp__1
2zej__1 2zgl__12znd__1 2zpm__2 2zvy__1 2zw2__1 2zxy__1 3a2y__2 3a5p__1 3a6r__1
3a6s__3 3acd__1 3agx__13ah7__1 3aly__3 3b02__1 3b09__1 3b33__1 3b47__1 3b5g__1
3b5t__1 3b76__1 3b7c__1 3b7h__13b9c__1 3bb9__1 3bcw__1 3bde__1 3bln__1 3bm1__1
3bm7__1 3bmz__1 3bn7__1 3bpj__1 3bpv__13bqx__1 3bri__1 3bs3__1 3but__1 3by8__2
3byr__1 3bzh__1 3bzt__1 3c0f__1 3c1d__3 3c1q__13c3m__1 3c97__1 3can__1 3cb0__1
3cby__1 3ce1__1 3cex__1 3cjd__1 3cje__1 3cjn__1 3cm3__13cng__1 3cnk__1 3cnu__1
3cp3__1 3ct6__1 3cu3__1 3czt__1 3d00__1 3d0f__1 3d0j__1 3d0w__13d5p__1 3d7a__1
3db7__1 3dcm__1 3df8__1 3dib__2 3dlo__1 3dm8__1 3dmc__1 3dn7__1 3dnx__13do8__1
3dpj__1 3dr6__1 3dsb__1 3dz8__1 3e10__1 3e17__1 3e2c__1 3e39__1 3e4v__1
3e5h__13e8o__1 3ebt__1 3ec6__1 3ec9__1 3ecf__1 3f3x__1 3f43__1 3f7e__1 3f7l__1
3f8h__1 3f8x__1
3f9s__1 3fcd__1 3fcn__1 3fd7__3 3ff0__1 3ffy__1 3fg9__1 3fgv__1 3fgy__1
3fh1__1 3fjs__13fkc__2 3flj__1 3fm2__1 3fm5__1 3fmb__1 3fn7__1 3fov__1 3fqm__1
3frq__1 3ful__1 3fv6__13fwz__1 3fx7__1 3fxh__1 3fyb__1 3fyn__1 3g0k__1 3g13__1
3g14__1 3g16__1 3g26__1 3g2b 13g46__1 3g7p__1 3g8g__1 3g8k__1 3g8z__1 3gby__1
3gdw__1 3gfa__1 3ggq__1 3ggu__1 3ghj__13gla__1 3glv__1 3gm5__1 3gpv__1 3grd__1
3guz__1 3gwk__1 3gwn__1 3gxh__3 3gya__2 3gyd__13gzr__1 3h05__1 3h0n__1 3h0x__2
3h1s__1 3h2d__1 3h36__1 3h3h__1 3h4o__1 3h4y__1 3h51__13h6q__1 3h8h__2 3h8u__1
3h95__1 3ha2__1 3ha9__2 3hcz__2 3hdc__1 3hf5__1 3hhv__1 3hiu__13hix__5 3hk4__2
3hm4__1 3hmf__2 3hmz__1 3hoi__1 3hqx__1 3hr7__1 3ht1__1 3huh__1 3hup__13hvv__1
3hx9__1 3hyq__2 3hzb__1 3hzp__1 3i24__1 3i3g__1 3ial__1 3ia8__3 3ibm__1
3ifj__33ift__2 3igr__2 3iis__1 3ijm__1 3ilx__1 3in8__1 3inq__1 3ip0__2 3ir3__1
3itf__1 3ix3__1
3jrz__1 3jtf__1 3jtw__1 3jtz__1 3jum__1 3jx9__1 3k0z__1 3k1e__1 3k21__1
3k2v__1 3k3v__23k67__1 3k69__1 3k86__1 3kb5__2 3kbe__1 3kbq__1 3kby__1 3kg0__2
3kgz__1 3kk4__1 3kkg__13kl1__1 3kol__1 3kor__1 3kpc__1 3ksh__1 3ksv__1 3kuv__1
3kwk__1 3kyz__1 3l18__1 3l1e__13l1n__2 3l34__1 3l3u__1 3l46__1 3l7h__1 3l7x__1
3l8u__1 3l9y__1 3lag__1 3las__1 3lb5__13lby__1 3le4__1 3le5__1 3leq__2 3lf6__1
3lfh__1 3lfp__1 3lfr__1 3lhc__1 3lhr__1 3lin__13lio__1 3llv__2 3lmo__1 3lqn__1
3lqy__2 3lr0__1 3lte__1 3lw3__1 3lwc__1 3lx7__1 3lyd__13lyg__1 3lyh__1 3lyx__1
3lza__1 3lz1__1 3m1e__1 3m5b__1 3m6j__1 3m8e__1 3m9z__1 3mcw__13mdp__1 3mgd__1
3mgm__1 3mhx__1 3mmh__1 3mng__1 3msh__1 3mti__1 3mtq__1 3mws__1 3myf__13n1s__1
3n4j__1 3n4w__1 3n6y__3 3n8b__1 3nad__1 3nbc__1 3neu__1 3nfc__1 3nj2__1
3njc__13nl9__1 3nqn__1 3nr1__1 3nrh__3 3nrp__1 3ny5__1 3nym__1 3o0m__1 3o10__1
3olc__1 3o2e__2
3o2r__1 3o79__3 3oa4__1 3obh__1 3oga__1 3ogh__1 3ohe__1 3oj7__1 3oji__1
3okx__1 3oms__13on4__1 3oni__2 3oop__1 3ose__2 3ov8__1 3oxp__1 3p0t__1 3p2t__2
3pc6__1 3pg6__1 3pmd__13pn3__3 3pp9__1 3pr6__2 3pu7__1 3q20__1 3q34__1 3q3y__3
3q62__1 3q63__1 3q64__1 3q6a__13q7r__1 3q8i__2 3q90__1 3qbm__1 3qdo__1 3qfl__1
3qh6__2 3qmq__1 3qoo__1 3qp4__1 3qp8__13qs2__1 3qu1__1 3qzx__1 3r0n__1 3r5g__1
3r68__2 3r6a__1 3r6f__1 3rcp__2 3rd1__1 3rem__13rfi__2 3rkc__1 3rmh__1 3rmu__1
3rob__1 3rqi__1 3rt2__2 3s2r__1 3s45__1 3s6f__1 3s8i__13s9f__1 3sb1__1 3sd2__1
3sk2__1 3sl__2 3sl7__1 3slz__1 3smd__2 3smj__3 3son__1 3soy__13svi__2 3sxm__1
3sz7__2 3szj__1 3t1s__1 3t43__1 3t46__2 3t8r__1 3t90__1 3t9y__1 3td4__43teq__1
3tgn__1 3tgv__1 3tj8__1 3tk0__1 3tnj__1 3tol__1 3trc__1 3typ__1 3tys__1
3u04__13u15__1 3u1d__1 3u2a__1 3u5v__1 3u6g__1 3u80__1 3ub6__1 3ucb__1 3ucg__1

TABLE 1-continued

3ufe__1 3uh9__1
3uie__1 3ulb__1 3ups__1 3urr__1 3uv0__1 3ux2__1 3vjz__1 3vk6__1 3vp5__1
3vq1__1 3vub__13zrd__1 3zve__1 3zw5__1 3zxc__1 3zxq__1 3zy7__1 4a1i__1 4a5k__1
4a5n__1 4ae4__1 4aeq__14ag7__1 4agh__1 4alg__1 4avp__1 4ax2__1 4b4p__1 4b6i__1
4di0__1 4duq__1 4e08__1 4e0h__14e2g__1 4e74__1 4e7p__1 4eae__1 4egu__1 4em8__1
4err__1 4es1__1 4eun__1 4ew5__1 4ew7__14exo__1 4exr__1 4ezg__1 4f82__1 4f8y__1
4fak__1 4fiv__1 4flb__1 4fld__1 4g5a__1 4g6x__14gdh__1 4ghj__1 4giw__1 4go7__1
4gs3__2 4gwb__1

TABLE 2

1buu__1 1dbf__1 1dg6__1 1di6__1 1f7l__1 1fth__1 1gr3__1 1gu9__1 1gx1__1
1h7z__1 1h9m__11hfo__1 1idp__1 1iv2__1 1jd1__1 1jlj__1 1jq0__1 1jw8__2 1knb__1
1kr4__1 1lr0__2 1n2m__11nog__1 1nza__1 1o5j__1 1o91__1 1ocy__1 1oni__1 1ox3__1
1p11__2 1pwb__1 1q5h__1 1q5x__11qu1__1 1rlh__2 1s55__1 1seh__1 1sjn__1 1t0a__1
1tcz__1 1td4__1 1u5x__1 1u9d__2 1ufy__11uku__1 1usn__2 1uuy__1 1uxa__1 1v3w__1
1ve0__1 1vfj__1 1vhf__2 1vmf__1 1vmh__1 1vph__11woz__1 1wy1__1 1x25__1 1xhd__2
1yq5__1 2aa1__1 2bcm__1 2brj__1 2bt9__1 2bzv__1 2chc__12cu5__1 2cvl__1 2dt4__1
2e7a__1 2ed6__1 2eg2__1 2f0c__1 2fb6__2 2fvh__1 2g2d__1 2gdg__12gr8__1 2gw8__1
2h6l__1 2hx0__1 2ibl__1 2ieq__1 2ig8__1 2is8__1 2j2j__1 2j9c__1 2jb7__12nuh__2
2oj6__1 2oll__1 2otm__1 2p2o__1 2p6c__1 2p6h__1 2p6y__1 2p9o__1 2pii__1
2qg8__12qih__1 2r32__1 2r6q__1 2rfr__1 2rie__1 2tnf__1 2uyk__1 2vnl__1 2w5p__1
2wds__1 2wh7__1
2wkb__1 2wpq__1 2wq4__1 2x4j__1 2xcz__1 2xdh__1 2xdj__1 2xx6__1 2y75__2
2yzj__1 2zhz__13aqe__7 3b64__1 3b81__1 3bsw__1 3bzq__1 3c6v__1 3cc0__1 3ci3__1
3cp1__1 3d01__1 3d9x__13da0__1 3djh__1 3e6q__1 3eby__1 3efg__1 3ehw__1 3ejc__1
3ejv__1 3emf__1 3f09__1 3f0d__13f4f__1 3fq3__3 3ftt__1 3fuy__1 3fwt__1 3fwu__1
3gqh__1 3h5i__1 3h6x__1 3htn__1 3hwu__13hza__1 3i3f__1 3i7t__1 3ixc__1 3jv1__1
3k6a__1 3kan__1 3kjj__1 3laa__1 3lqw__1 3m1x__13mc3__1 3mci__1 3mdx__1 3mf7__1
3mhy__1 3mko__1 3mqh__1 3mxu__2 3n79__1 3ne3__2 3nfd__13o46__1 3oiu__2 3opk__1
3p48__1 3pzy__1 3qc7__1 3qr7__1 3quw__1 3r1w__1 3r3r__2 3rwn__13so2__1 3ta2__1
3tio__1 3tq5__1 3tqz__1 3uv9__2 3v4d__1 3vi6__2 3zw0__14aff__1 4g2k__14gb5__1
4gdz__1

The subunits can be arranged at the origin according to the symmetry specified by command-line options or through a user-provided symmetry definition file. Then the full space of contacting symmetric configurations can be sampled by systematically varying the translational and rotational degrees of freedom (DOFs) in the system. In order to test all four possible orientations of the two building blocks (inside/inside, inside/outside, outside/inside, outside/outside) two separate docking runs can be performed in which the orientation of one of the building blocks is reversed by setting the Rosetta command-line option tcdock::reverse to true. Configurations in which backbone or beta carbon atoms from different building blocks clash (distance between backbone amide nitrogen and carbonyl oxygen atoms <=2.6 Å; distance between all other backbone/beta carbon atom pairs <=3.0 Å) can be discarded.

In each non-clashing configuration, a designability score can be calculated. For example, the designability score can be calculated as the sum of the number of beta carbon contacts between building blocks (where a contact is defined as two beta carbon atoms within 12 Å), weighted by the type of secondary structures on which the contacting positions exist (by setting the Rosetta tcdock::cb_weight_secstruct command line option to true) and the average degree of connectivity (the number of amino acid positions within a user-specified distance threshold within the multimeric building block) of the contacting positions (by setting the Rosetta tcdock::cb_weight_average_degree command line option to true). This designability measure favors the selection of docked configurations with large numbers of contacting residues on well-anchored regions of protein structure. In addition to inter-component contacts, which can be contacts between building blocks of the two different components, two-component systems can also possess intra-component contacts or contacts between building blocks of the same component. The Rosetta command-line options tcdock::intra, tcdock::intra1, and tcdock::intra2 control the contribution to the designability score of intra-component contacts for both components, for component 1, and for component 2, respectively.

Data and PDB files can be output for a user-defined number of top scoring configurations (set by the Rosetta tcdock::topx command-line option). The data, which can be saved by redirecting the output of the run to a log file, includes the rigid body DOFs, the designability score, the number of carbon beta contacts between building blocks, the number of contacting residues between building blocks, the average score per carbon beta contact, and the average score per contacting residue.

In one example, the 1161 dimers and 200 trimers listed in the scaffold sets listed in Tables 1 and 2 provided 232,200 unique pairwise combinations of trimers with dimers, and 19,900 unique pairwise combinations of trimers. Docking was carried out for each of these unique combinations with or without the tcdock::reverse option set to true, for a total of 504,200 independent docking trajectories. The tcdock::intra option was set to false such that intra-component contacts were not included in the calculated scores.

For each unique scaffold combination, the 3 top scoring T33 docks were selected. This set of 59,700 distinct configurations was ranked by the average designability score per residue and the top 1,000 used as input for interface design. For T32, data was output for the 40 top scoring docked configurations per docking trajectory. This set of 18,576,000 distinct configurations was filtered to remove all configurations with less than 80 contacting residues between building blocks and ranked by the average designability score per residue. This set was filtered to retain only the one top ranked configuration for each unique scaffold pair and the top 1,000 configurations were used as input for interface design.

Two-Component Symmetric Interface Design

The herein-described methods and techniques are not limited to use of RosettaDesign, the Rosetta software suite, or any other specific software package. For example, other software programs could be used in conjunction with this method to design new amino acid sequences at protein-protein interfaces. As will be understood by those of skill in the art, the implementation of the design methods of the invention described below is non-limiting, and the methods are in no way limited to the implementation disclosed herein.

A set of protein-protein interface design protocols was developed within Rosetta to identify mutations predicted to drive assembly of two distinct protein building blocks into higher order symmetric complexes. The design functionality was broken into modular components and implemented within the RosettaScripts™ framework in order to facilitate future code development and to provide users the ability to modify each step of the design process without having to change the underlying C++ code.

The design process can have four stages: I) interface design, II) shape complementarity optimization, III) automated reversion, and IV) resfile-based refinement. The protocols used in each stage can take as input a symmetry definition file and a PDB file containing a single subunit of both scaffold proteins; the latter can be produced by concatenating the two scaffold protein PDB files used as input for docking and changing the chain of the second subunit to be "B". In addition, initial values for the translational and rotational symmetric rigid body DOFs can be specified through user-defined variables. All design calculations can be performed on the two independent subunits and propagated symmetrically.

Stage I.

Interface design can involve carrying out multiple design trajectories for each docked configuration. At the start of each trajectory, the symmetric rigid body DOFs can be perturbed in order to sample nearby docked configurations. The behavior of these perturbations can be set by the user, including specifying whether to sample values from a user-defined grid of angles and displacements or randomly from user-defined uniform or Gaussian distributions of angles and displacements. Trajectories yielding docked configurations with clashing backbones (distance between backbone amide nitrogen and carbonyl oxygen atoms <=2.6 Å; distance between all other backbone/beta carbon atom pairs <=3.0 Å) can be discarded prior to interface design based on user-defined cutoff values for the number of clashing atoms.

In each of the remaining trajectories, interface residues can be selected according to the some or all of the following three criteria: 1) the residue has a beta carbon (alpha carbon in the case of glycine) within a user-defined cutoff distance to a beta carbon (alpha carbon in the case of glycine) in a different building block (in this study the default 10 Å cutoff was used), 2) the residue has a nonzero solvent accessible surface area when the protein subunits are in the unbound state, and 3), with the exception of residues that have high Lennard-Jones repulsive scores (fa_rep), the residue does not make contacts (any heavy atoms within 5 Å) with other subunits in the same oligomeric building block. Residues matching all three criteria can be considered designable, with the exception of proline and glycine, which are restricted to repacking. In some scenarios, criterion 3 is not enforced.

Residues fulfilling criteria 1 and 2 can be termed "interface positions" and criteria 1, 2, and 3 can be termed "design positions". Then, all design positions are also interface positions, but not all interface positions are design positions. These positions can be updated at multiple points throughout design stages I through IV; appending any positions that newly satisfy the selection criteria to the previously defined sets. All residues not in the selected sets remain fixed throughout the design process. In addition, mutations to proline, glycine, or cysteine are prohibited unless explicitly specified otherwise by the user via a resfile (see stage IV). Optionally, a reduced amino acid set can be used during Stage I such that only the native amino acid and mutations to a subset of the 20 common amino acids are allowed at each design position.

Once the design positions have been selected, an initial round of design can be carried out using the standard RosettaDesign™ algorithm and a version of the Rosetta™ scorefunction, soft_rep, in which the Lennard-Jones repulsive term (fa_rep) is down-weighted to favor tightly packed interfaces. The scorefunction can be then set to score12 and the Rosetta energy is minimized through a series of small changes to the design position side chain configurations and the symmetric rigid body DOFs (i.e., the side chains and rigid body DOFS are symmetrically minimized). Designs with contacting interface areas not meeting user-defined thresholds can be discarded. For those designs passing the interface area cutoffs, the design positions can be updated and a second round of interface design is carried out using the standard RosettaDesign™ algorithm with the score12 score function. The design position side chains can be repacked and the interface position side chains and rigid body DOFs can be subjected to at least one round of minimization.

Several metrics can be used to gauge the quality of the interfaces resulting from this first stage of design and to select designs to carry forward to shape complementarity optimization in Stage II. These metrics include, but are not limited to: 1) the number of buried unsatisfied hydrogen bonds at the designed interface, 2) the shape complementarity of the designed interface, and 3) the predicted binding energy of the interface, defined as the difference in energy between the bound and unbound (individual building blocks) state following repacking of the side chains at the design positions and minimization of the side chains at the interface positions in the unbound state. For each passing design, the values of the final rigid body DOFs can be output to a scorefile along with the metric values and the standard score12 score terms, and a resfilecan be generated containing each of the design positions and their amino acid identities.

In one example, 100 independent design trajectories were run for each of the top 1000 docked T32 and T33 configurations (supra vide). At the start of each trajectory, the building blocks were displaced 2 Å away from the assembly's center of mass along their symmetry axes, and the translational rigid body DOFs were perturbed by sampling randomly from a Gaussian distribution with a standard deviation of 0.75 Å and the rotational rigid body DOFs were perturbed by sampling randomly from a Gaussian distribution with a standard deviation of 2 degrees. Trajectories yielding more than 8 clashing backbone atoms were removed from further design considerations. A reduced amino acid set was employed during this stage of the design process such that only mutations to the following 8 amino acids were allowed: alanine, aspartate, isoleucine, leucine, asparagine, serine, threonine, and valine. Additionally, during all RosettaDesign™ steps in all stages, the chi2 angle for aromatic side chains being repacked or designed was restricted to between 70 and 110 degrees.

T32 design trajectories yielding contacting interface areas of less than 1,100 Å$^2$ or greater than 2,000 Å$^2$ following the first round of design were discarded. The passing T32 designs were further filtered at the end of Stage I to remove those that had more than 45 mutations or 8 buried unsatisfied hydrogen bonds at the designed interface, a predicted binding energy greater than −12 REU, or a shape complementarity score of less than 0.60. The T33 design trajectories were filtered based on contacting interface areas at the end of Stage I rather than after the first round of design, discarding those that yielded contacting interface areas of less than 600 Å$^2$. The passing T33 designs were further filtered to remove those with more than 100 mutations or 10 buried unsatisfied hydrogen bonds at the designed interface, a predicted binding energy greater than −12 REU, or a shape complementarity of less than 0.55. The resulting 1,292 T32 designs and 593 T33 designs were subjected to the protocol described in Stage II below.

Stage II:

Stage II involves to regenerate the initial design from the two input scaffolds: 1) the rigid body DOFs output from Stage I are used to reposition the subunits in the fully assembled state, 2) the interface positions are re-selected using the same criteria as before, with the exception that all positions specified in the input resfile are included regardless of whether or not they fulfill the criteria in the input state, 3) the resfile output from stage I is used as input to the RosettaDesign algorithm to reintroduce the initial design mutations, and 4) the interface position side chains are subjected to one or more rounds of minimization and/or repacking.

Then, optimization techniques, such as greedy optimization, can test individual reversions to native amino acids at all mutated residues. A custom reversion score can be used in which individual mutations are filtered to remove those that increase the number of buried unsatisfied hydrogen bonds at the designed interface and scored according to the sum of the predicted binding energy, the total Rosetta energy, and a residue type constraint energy favoring the native amino acid. The potential reversions can be combined one at a time proceeding from the individually best scoring to worst scoring reversions at each position, only accepting those that do not increase the number of buried unsatisfied hydrogen bonds at the designed interface and improve the reversion score in the context of all previously accepted mutations. In some embodiments, the buried unsatisfied hydrogen bond criterion is optional; for example, this criterion was used for the T32 designs, but not T33.

Following another one or more rounds of interface position side chain minimization and/or repacking, optimization techniques are used to increase the shape complementarity of the designed interfaces. Mutations to all amino acids except cysteine, glycine, and proline can be tested individually at each design position as defined by the input resfile. Each mutation can be ranked by the shape complementarity of the design interface if the mutation does not: 1) increase the total Rosetta energy by more than 2.0 Rosetta energy units (REU), 2) decrease the predicted binding energy by 1.0 REU, 3) introduce any new unsatisfied hydrogen bonds, or 4) increase the fa_dun component of the score, which can be an internal energy of side chain rotamers as defined by statistics from the Dunbrack library, by more than 2.5 REU (the fa_dun criterion is optional; it was used for the T32 designs, but not T33). Next, mutations cam be combined one at a time proceeding from the best scoring to worst scoring individual mutations, only accepting those that still pass the same three or four criteria and improve the shape complementarity in the context of all previously accepted mutations. During both the reversion and shape complementarity optimization, all of the interface positions can be subjected to at least one round of minimization, repacking, and minimization prior to evaluating the effects of each mutation.

In addition to the standard Rosetta scores, the following metrics, and perhaps others, can used to assess the quality of each design following one or more rounds of interface position side chain minimization and/or repacking: 1) the total number of mutations, 2) the number of buried unsatisfied hydrogen bonds at the interface, 3) the average degree of each design position, 4) the RosettaHoles packing score, 5) the average total Rosetta energy, fa_atr, fa_rep, and fa_dun for each filter position, 6) the contacting interface area, 7) the predicted binding energy, 8) the shape complementarity, and 9) the change in predicted binding energy resulting from individual mutations of each interface side chain to alanine (i.e., a computational alanine scan of the designed interface). Those designs passing a set of user-defined thresholds for each metric are subsequently subjected to visual inspection to further filter the designs. A scorefile with the metric values and the standard score12 score terms, and a resfile containing the design positions and their amino acid identities is generated for each design at the end of Stage II.

In one example, the T32 designs resulting from Stage II were filtered to remove those with a shape complementarity score less than 0.65, predicted binding energies of greater than −25 REU, a positive Rosetta holes score for the designed interface, an interface area less than 1,200 Å$^2$, or more than 1 buried unsatisfied hydrogen bond at the designed interface. The 283 passing T32 designs were visually inspected and manually curated down to a list of 68 designs that were subjected to the reversion protocol outlined in Stage III. The T33 designs resulting from Stage II were filtered, visually inspected and manually curated down to a list of 38 designs that were subjected to the reversion protocol outlined in Stage III Stage III:

The third stage in the design process can identify, via an automated computational process, mutated residues predicted not to be critical for assembly and to revert them back to their native amino acid identities. This helps to minimize the number of mutations being made to the scaffold proteins and reduces the amount of refinement required in Stage IV.

Stage III can be begin by regenerating the design from the two input scaffolds using the rigid body DOFs from stage I and the resfile output from stage II: 1) the rigid body DOFs can be used to reposition the subunits in the fully assembled state, 2) the interface positions can be re-selected in the same manner as in Stage II, 3) the resfile can be used as input to the RosettaDesign algorithm to reintroduce the initial design mutations, and 4) at least one round of interface position side chain and rigid body DOF minimization, side chain repacking, and minimization is performed.

Next, greedy optimization or another optimization algorithm can be used to revert mutations to the native amino identities as follows. During the first part of the optimization algorithm, each reversion can be tested individually and ranked by the change in shape complementarity if the reversion does not: 1) decrease the predicted binding energy by more than 2.0 REU, 2) increase the number of buried unsatisfied hydrogen bonds at the interface, or 3) decrease the shape complementarity of the interface by more than 0.02. During the second part of the optimization algorithm, reversions that passed the first part can be combined one at a time proceeding from the best scoring to the worst scoring individual mutations, only accepting those that still pass the three criteria above in the context of all previously accepted mutations. Then, optimization can be terminated if a mutation passes these criteria but causes the predicted binding energy to be greater than a user-defined threshold (in one example, −15 REU was used for T32 designs and −17 REU for T33 designs) or the shape complementarity to be less than 0.65. During both parts of optimization, all interface positions can be subjected to at least one round of minimization, repacking, and minimization prior to evaluating the effects of each mutation. Furthermore, during the second part, the reference structure for measuring the change in shape complementarity can be reset after each accepted mutation.

Following at least one round of rigid body and side chain minimization, side chain repacking, and minimization, the full suite of additional metrics can be evaluated (as outlined at the end of Stage II) with the additional calculation of a Boltzmann weighted estimation of the probability of each designed side chain configuration in the bound versus the unbound state. For each design, the values of the final rigid body DOFs are output to a score file along with the additional metrics and the standard score12 score terms, and a resfile is generated containing the interface positions and their amino acid identities.

In one example, all 68 T32 designs and 38 T33 designs resulting from Stage III were run through the resfile-based refinement protocols outlined in Stage IV below.

Stage IV:

Stage IV of the design process can involve one or more iterations of resfile-based redesign with user-guided mutations. In each iteration of the process, a combination of visual inspection and analysis of the design metrics can be used to generate modified resfiles for each design, with each modified resfilecontaining a small number of user-defined mutations relative to a correspondingresfile output from Stage III. Two different protocols, resfile_optimize and resfile_design, can be used to test the user-defined mutations. In both protocols, the starting configuration can be generated from the two input scaffolds using the rigid body DOFs from the previous round of design.

The resfile_optimize protocol uses greedy optimization to test the user-defined mutations. First the reverted design resulting from Stage III can be regenerated using the unmodified resfile output from Stage III together with the standard RosettaDesign™ algorithm, and the side chains specified in the resfile are minimized, repacked, and minimized. Next, user-defined mutations can be tested individually at each design position. Each mutation can be ranked by the change in shape complementarity of the designed interface, if the mutation does not decrease the predicted binding energy by greater than 2.0 REU or decrease the shape complementarity of the designed interface by more than 0.02. The passing mutations are then combined one at a time proceeding from the best ranked to the worst ranked individual mutations, only accepting those that still do not decrease the binding energy by more than 2.0 REU or the shape complementarity by more than 0.02 in the context of all previously accepted mutations. Optimization can be terminated if a mutation passes these criteria, but causes the predicted binding energy to be greater than −15 REU or the shape complementarity to be less than 0.63. All positions specified in the input resfile can be subjected to at least one round of minimization, repacking, and minimization prior to evaluating the effects of each mutation. Furthermore, during the combining stage, the reference structure for measuring the change in predicted binding energy and the change in the shape complementarity can be reset after each accepted mutation.

The resfile_design protocol involves taking the starting design configuration generated using the rigid body DOFs from the previous round of design and applying the standard RosettaDesign algorithm with the user-defined resfile.

In both protocols, the symmetric rigid body DOFs and the side chains specified in the input resfile are minimized, side chains repacked, and minimized prior to calculating the full suite of design metrics. This process can be iterated until designs are obtained which are deemed suitable for experimental testing or until the user decides the designs are no longer worth pursuing.

Example Computing Environment

Figure 8:
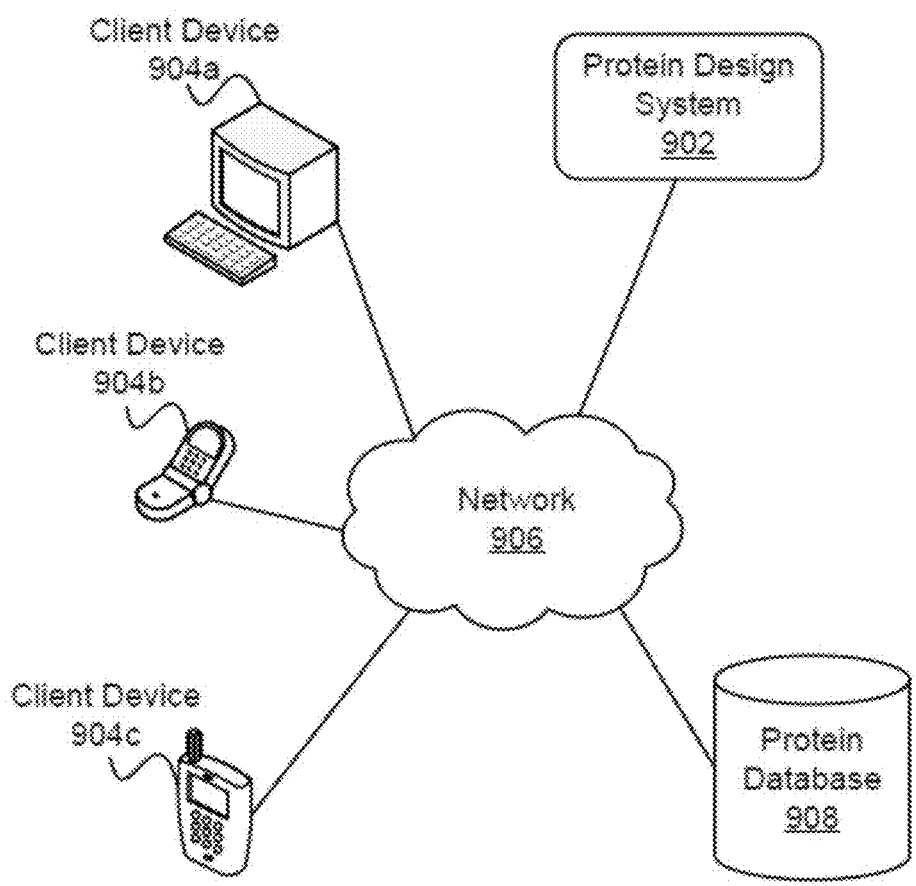
FIG. 8 is a block diagram of an example computing network.

FIG. 8 is a block diagram of an example computing network. Some or all of the above-mentioned techniques disclosed herein, such as but not limited to techniques disclosed as part of and/or being performed by software, the Rosetta™ software suite, RosettaDesign™, Rosetta™ applications, and/or other herein-described computer software and computer hardware, can be part of and/or performed by a computing device. For example, FIG. 8 shows protein design system 902 configured to communicate, via network 906, with client devices 904*a*, 904*b*, and 904*c* and protein database 908. In some embodiments, protein design system 902 and/or protein database 908 can be a computing device configured to perform some or all of the herein described methods and techniques, such as but not limited to, method 100 and functionality described as being part of or related to the Rosetta™ software suite. Protein database 908 can, in some embodiments, store information related to and/or used by the Rosetta™ software suite.

Network 906 may correspond to a LAN, a wide area network (WAN), a corporate intranet, the public Internet, or any other type of network configured to provide a communications path between networked computing devices. Network 906 may also correspond to a combination of one or more LANs, WANs, corporate intranets, and/or the public Internet.

Although FIG. 8 only shows three client devices 904*a*, 904*b*, 904*c*, distributed application architectures may serve tens, hundreds, or thousands of client devices. Moreover, client devices 904*a*, 904*b*, 904*c* (or any additional client devices) may be any sort of computing device, such as an ordinary laptop computer, desktop computer, network terminal, wireless communication device (e.g., a cell phone or smart phone), and so on. In some embodiments, client devices 904*a*, 904*b*, 904*c* can be dedicated to problem solving/using the Rosetta software suite. In other embodiments, client devices 904*a*, 904*b*, 904*c* can be used as general purpose computers that are configured to perform a number of tasks and need not be dedicated to problem solving. In still other embodiments, part or all of the functionality of protein design system 902 and/or protein database 908 can be incorporated in a client device, such as client device 904*a*, 904*b*, and/or 904*c*.

Computing Device Architecture

Figure 9A:
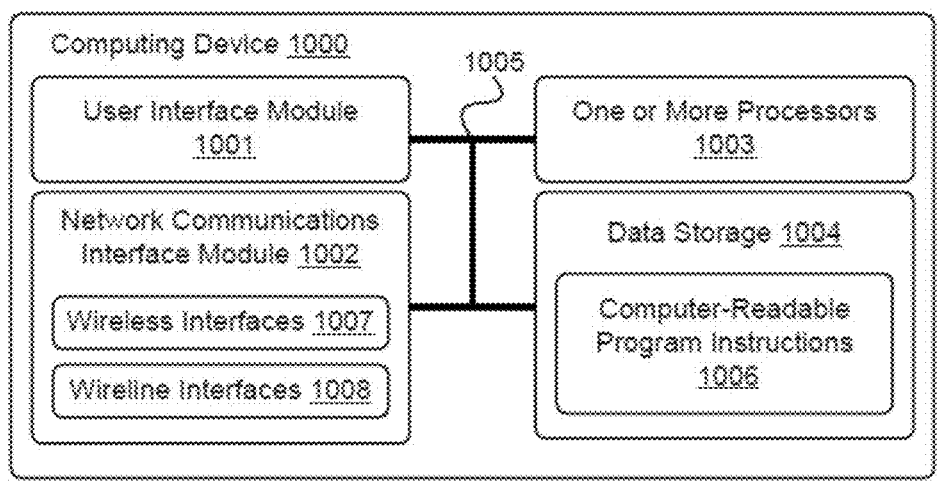
FIG. 9A is a block diagram of an example computing device.

FIG. 9A is a block diagram of an example computing device (e.g., system) In particular, computing device 1000 shown in FIG. 9A can be configured to: include components of and/or perform one or more functions of protein design system 902, client device 904a, 904b, 904c, network 906, and/or protein database 908 and/or carry out part or all of any herein-described methods and techniques, such as but not limited to method 100. Computing device 1000 may include a user interface module 1001, a network-communication interface module 1002, one or more processors 1003, and data storage 1004, all of which may be linked together via a system bus, network, or other connection mechanism 1005.

User interface module 1001 can be operable to send data to and/or receive data from external user input/output devices. For example, user interface module 1001 can be configured to send and/or receive data to and/or from user input devices such as a keyboard, a keypad, a touch screen, a computer mouse, a track ball, a joystick, a camera, a voice recognition module, and/or other similar devices. User interface module 1001 can also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, either now known or later developed. User interface module 1001 can also be configured to generate audible output(s), such as a speaker, speaker jack, audio output port, audio output device, earphones, and/or other similar devices.

Network-communications interface module 1002 can include one or more wireless interfaces 1007 and/or one or more wireline interfaces 1008 that are configurable to communicate via a network, such as network 906 shown in FIG. 8. Wireless interfaces 1007 can include one or more wireless transmitters, receivers, and/or transceivers, such as a Bluetooth transceiver, a Zigbee transceiver, a Wi-Fi transceiver, a WiMAX transceiver, and/or other similar type of wireless transceiver configurable to communicate via a wireless network. Wireline interfaces 1008 can include one or more wireline transmitters, receivers, and/or transceivers, such as an Ethernet transceiver, a Universal Serial Bus (USB) transceiver, or similar transceiver configurable to communicate via a twisted pair, one or more wires, a coaxial cable, a fiber-optic link, or a similar physical connection to a wireline network.

In some embodiments, network communications interface module 1002 can be configured to provide reliable, secured, and/or authenticated communications. For each communication described herein, information for ensuring reliable communications (i.e., guaranteed message delivery) can be provided, perhaps as part of a message header and/or footer (e.g., packet/message sequencing information, encapsulation header(s) and/or footer(s), size/time information, and transmission verification information such as CRC and/or parity check values). Communications can be made secure (e.g., be encoded or encrypted) and/or decrypted/decoded using one or more cryptographic protocols and/or algorithms, such as, but not limited to, DES, AES, RSA, Diffie-Hellman, and/or DSA. Other cryptographic protocols and/or algorithms can be used as well or in addition to those listed herein to secure (and then decrypt/decode) communications.

Processors 1003 can include one or more general purpose processors and/or one or more special purpose processors (e.g., digital signal processors, application specific integrated circuits, etc.). Processors 1003 can be configured to execute computer-readable program instructions 1006 contained in data storage 1004 and/or other instructions as described herein. Data storage 1004 can include one or more computer-readable storage media that can be read and/or accessed by at least one of processors 1003. The one or more computer-readable storage media can include volatile and/or non-volatile storage components, such as optical, magnetic, organic or other memory or disc storage, which can be integrated in whole or in part with at least one of processors 1003. In some embodiments, data storage 1004 can be implemented using a single physical device (e.g., one optical, magnetic, organic or other memory or disc storage unit), while in other embodiments, data storage 1004 can be implemented using two or more physical devices.

Data storage 1004 can include computer-readable program instructions 1006 and perhaps additional data. For example, in some embodiments, data storage 1004 can store part or all of data utilized by a protein design system and/or a protein database; e.g., protein designs system 902, protein database 908. In some embodiments, data storage 1004 can additionally include storage required to perform at least part of the herein-described methods and techniques and/or at least part of the functionality of the herein-described devices and networks.

Figure 9B:
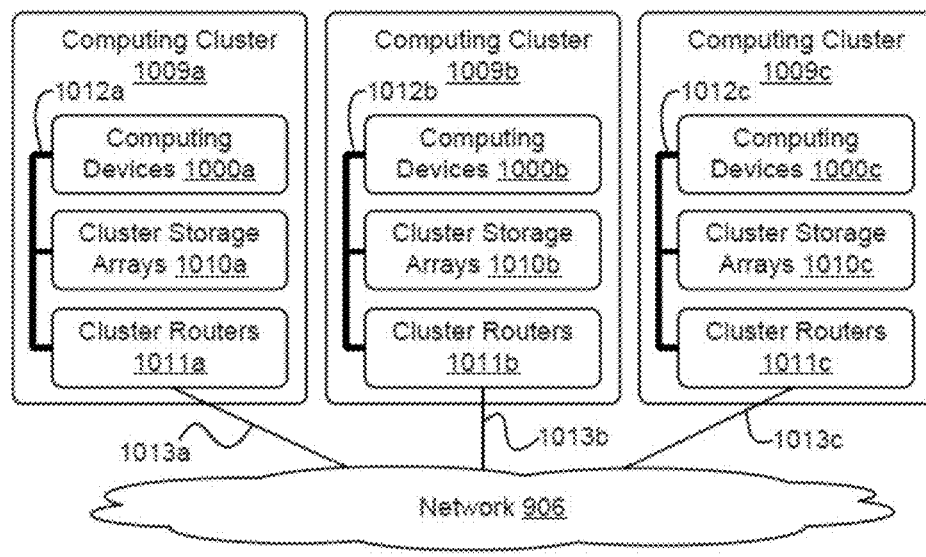
FIG. 9B depicts an example cloud-based server system.

FIG. 9B depicts a network 906 of computing clusters 1009a, 1009b, 1009c arranged as a cloud-based server system in accordance with an example embodiment. Data and/or software for protein design system 902 can be stored on one or more cloud-based devices that store program logic and/or data of cloud-based applications and/or services. In some embodiments, protein design system 902 can be a single computing device residing in a single computing center. In other embodiments, protein design system 902 can include multiple computing devices in a single computing center, or even multiple computing devices located in multiple computing centers located in diverse geographic locations.

In some embodiments, data and/or software for protein design system 902 can be encoded as computer readable information stored in tangible computer readable media (or computer readable storage media) and accessible by client devices 904a, 904b, and 904c, and/or other computing devices. In some embodiments, data and/or software for protein design system 902 can be stored on a single disk drive or other tangible storage media, or can be implemented on multiple disk drives or other tangible storage media located at one or more diverse geographic locations.

FIG. 9B depicts a cloud-based server system in accordance with an example embodiment. In FIG. 9B, the functions of protein design system 902 can be distributed among three computing clusters 1009a, 1009b, and 1008c. Computing cluster 1009a can include one or more computing devices 1000a, cluster storage arrays 1010a, and cluster routers 1011a connected by a local cluster network 1012a. Similarly, computing cluster 1009b can include one or more computing devices 1000b, cluster storage arrays 1010b, and cluster routers 1011b connected by a local cluster network 1012b. Likewise, computing cluster 1009c can include one or more computing devices 1000c, cluster storage arrays 1010c, and cluster routers 1011c connected by a local cluster network 1012c.

In some embodiments, each of the computing clusters 1009a, 1009b, and 1009c can have an equal number of computing devices, an equal number of cluster storage arrays, and an equal number of cluster routers. In other embodiments, however, each computing cluster can have different numbers of computing devices, different numbers of cluster storage arrays, and different numbers of cluster routers. The number of computing devices, cluster storage arrays, and cluster routers in each computing cluster can depend on the computing task or tasks assigned to each computing cluster.

In computing cluster 1009a, for example, computing devices 1000a can be configured to perform various computing tasks of protein design system 902. In one embodiment, the various functionalities of protein design system 902 can be distributed among one or more of computing devices 1000a, 1000b, and 1000c. Computing devices 1000b and 1000c in computing clusters 1009b and 1009c can be configured similarly to computing devices 1000a in computing cluster 1009a. On the other hand, in some embodiments, computing devices 1000a, 1000b, and 1000c can be configured to perform different functions.

In some embodiments, computing tasks and stored data associated with protein design system 902 can be distributed across computing devices 1000a, 1000b, and 1000c based at least in part on the processing requirements of protein design system 902, the processing capabilities of computing devices 1000a, 1000b, and 1000c, the latency of the network links between the computing devices in each computing cluster and between the computing clusters themselves, and/or other factors that can contribute to the cost, speed, fault-tolerance, resiliency, efficiency, and/or other design goals of the overall system architecture.

The cluster storage arrays 1010a, 1010b, and 1010c of the computing clusters 1009a, 1009b, and 1009c can be data storage arrays that include disk array controllers configured to manage read and write access to groups of hard disk drives. The disk array controllers, alone or in conjunction with their respective computing devices, can also be configured to manage backup or redundant copies of the data stored in the cluster storage arrays to protect against disk drive or other cluster storage array failures and/or network failures that prevent one or more computing devices from accessing one or more cluster storage arrays.

Similar to the manner in which the functions of protein design system 902 can be distributed across computing devices 1000a, 1000b, and 1000c of computing clusters 1009a, 1009b, and 1009c, various active portions and/or backup portions of these components can be distributed across cluster storage arrays 1010a, 1010b, and 1010c. For example, some cluster storage arrays can be configured to store one portion of the data and/or software of protein design system 902, while other cluster storage arrays can store a separate portion of the data and/or software of protein design system 902. Additionally, some cluster storage arrays can be configured to store backup versions of data stored in other cluster storage arrays.

The cluster routers 1011a, 1011b, and 1011c in computing clusters 1009a, 1009b, and 1009c can include networking equipment configured to provide internal and external communications for the computing clusters. For example, the cluster routers 1011a in computing cluster 1009a can include one or more internet switching and routing devices configured to provide (i) local area network communications between the computing devices 1000a and the cluster storage arrays 1001a via the local cluster network 1012a, and (ii) wide area network communications between the computing cluster 1009a and the computing clusters 1009b and 1009c via the wide area network connection 1013a to network 906. Cluster routers 1011b and 1011c can include network equipment similar to the cluster routers 1011a, and cluster routers 1011b and 1011c can perform similar networking functions for computing clusters 1009b and 1009b that cluster routers 1011a perform for computing cluster 1009a.

In some embodiments, the configuration of the cluster routers 1011a, 1011b, and 1011c can be based at least in part on the data communication requirements of the computing devices and cluster storage arrays, the data communications capabilities of the network equipment in the cluster routers 1011a, 1011b, and 1011c, the latency and throughput of local networks 1012a, 1012b, 1012c, the latency, throughput, and cost of wide area network links 1013a, 1013b, and 1013c, and/or other factors that can contribute to the cost, speed, fault-tolerance, resiliency, efficiency and/or other design goals of the moderation system architecture.

Nanostructures and Proteins

The present invention provides synthetic nanostructures comprising (a) a plurality of first proteins that self-interact to form a first multimeric substructure comprising at least one axis of rotational symmetry;

(b) a plurality of second proteins that self-interact to form a second multimeric substructure comprising at least one axis of rotational symmetry;

wherein multiple copies of the first multimeric substructure and the second multimeric substructure interact with each other at symmetrically repeated, non-natural, non-covalent protein-protein interfaces that orient the first multimeric substructures and the second multimeric substructures such that their symmetry axes are aligned with symmetry axes of the same kind in a designated mathematical symmetry group.

The nanostructures of the invention can be used for any suitable purpose, including but not limited to delivery vehicles, as the nanostructures can encapsulate molecules of interest and/or the first and second proteins can be modified to bind to molecules of interest (diagnostics, therapeutics, detectable molecules for imaging and other applications, etc.)

The nanostructures of the invention are synthetic, in that they are not naturally occurring. The first protein and the second protein are non-naturally occurring proteins that can be produced by any suitable means, including recombinant production or chemical synthesis. Each member of the plurality of first proteins is identical to each other, and each member of the plurality of second proteins is identical to each other. The first proteins and the second proteins are different. There are no specific primary amino acid sequence requirements for the first and second proteins. As described in detail herein, the inventors disclose methods for designing the synthetic nanostructures of the invention, where the nanostructures are not dependent on specific primary amino acid sequences of the first and second proteins that make up the multimeric structures that interact to form the nanostructures of the invention. As will be understood by those of skill in the art, the design methods of the invention can produce a wide variety of nanostructures made of a wide variety of subunit proteins, and the methods are in no way limited to the subunit proteins disclosed herein.

As used herein, a "plurality" means at least two; in various embodiments, there are at least 2, 3, 4, 5, 6 or more first proteins in the first multimeric substructure and second proteins in the second multimeric substructure.

The number of first proteins in the first multimeric substructure may be the same or different than the number of second proteins in the second multimeric substructure. In one exemplary embodiment, the first multimeric substructure comprises a trimer of the first protein, and wherein the second multimeric substructure comprises a dimer of the second protein. In a further exemplary embodiment, the first multimeric substructure comprises a trimer of the first protein, and wherein the second multimeric substructure comprises a trimer of the second protein.

The first and second proteins may be of any suitable length for a given purpose of the resulting nanostructure. In one embodiment, the first protein and the second protein are typically between 30-250 amino acids in length; the length of the first protein and the second protein may be the same or different. In various further embodiments, the first protein and the second protein are between 30-225, 30-200, 30-175, 50-250, 50-225, 50-200, 50-175, 75-250, 75-225, 75-200, 75-175, 100-250, 100-225, 100-200, 100-175, 125-250, 125-225, 125-200, 125-175, 150-250, 150-225, 150-200, and 150-175 amino acids in length.

In another embodiment, the first protein and the second protein comprise or consist of proteins selected from the following pairs of first and second proteins:

(a) T32-28A (SEQ ID NO: 11) and T32-28B SEQ ID NO: 12);

(b) T33-09A SEQ ID NO: 13) and T33-09B SEQ ID NO: 14);

(c) T33-15A SEQ ID NO: 15) and T33-15B SEQ ID NO: 16);

(d) T33-21A SEQ ID NO: 17) and T33-21B SEQ ID NO: 18); and (e) T33-28A SEQ ID NO: 19) and T33-28B SEQ ID NO: 20).

FIGS. 10-19 show the primary amino acid sequences of the proteins noted and allowable substitutions. Each figure includes four columns, which show:

1) The residue position in the protein
2) The identity of that residue in the designed sequence
3) The allowed amino acids at that position within our genus (labeled 1-4, indicating the AAs at that position in the different SEQ ID NOs for the relevant protein); and
4) The solvent-accessible surface area (SASA) of that residue in crystal structures (T32-28, T33-15, T33-21, and T33-28) or computationally designed models (T33-09) of the nanostructures.

In some embodiments certain residues can be any amino acid residue ("any"); such residues with a solvent-accessible surface area of greater than 50 square Angstroms are defined as being present on the polypeptide surface, and thus can be substituted with a different amino acid as desired for a given purpose without disruption of protein structure or multimer assembly (for example, SEQ ID NOS: 11-20). In various other embodiments, these same residues can be modified by conservative substitutions (for example, SEQ ID NOS:21-30).

As further shown in the table, certain other residues can only be substituted with conservative amino acid substitutions. Such residues have a solvent-accessible surface area of less than or equal to 50 square Angstroms and are present in the polypeptide interior, and thus can be modified only by conservative substitutions to maintain overall protein structure to permit multimer assembly. As used here, "conservative amino acid substitution" means that:

hydrophobic amino acids (Ala, Cys, Gly, Pro, Met, Sce, Sme, Val, Ile, Leu) can only be substituted with other hydrophobic amino acids;
hydrophobic amino acids with bulky side chains (Phe, Tyr, Trp) can only be substituted with other hydrophobic amino acids with bulky side chains;
amino acids with positively charged side chains (Arg, His, Lys) can only be substituted with other amino acids with positively charged side chains;
amino acids with negatively charged side chains (Asp, Glu) can only be substituted with other amino acids with negatively charged side chains; and
amino acids with polar uncharged side chains (Ser, Thr, Asn, Gln) can only be substituted with other amino acids with polar uncharged side chains.

Certain other residues in the proteins are invariant; these residues have one or more atoms within 5 Angstroms of one or more atoms across the interface between the first and second multimeric substructures, and are therefore directly involved in self-assembly.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

In a further embodiment, the first protein and the second protein comprise or consist of proteins selected from the following pairs of first and second proteins:

(a) T32-28A (SEQ ID NO: 21) and T32-28B SEQ ID NO: 22);

(b) T33-09A SEQ ID NO: 23) and T33-09B SEQ ID NO: 24);

(c) T33-15A SEQ ID NO: 25) and T33-15B SEQ ID NO: 26);

(d) T33-21A SEQ ID NO: 27) and T33-21B SEQ ID NO: 28); and (e) T33-28A SEQ ID NO: 29) and T33-28B SEQ ID NO: 30

In another embodiment, the first protein and the second protein comprise or consist of proteins selected from the following pairs of first and second proteins:

(a) T32-28A (SEQ ID NO: 31) and T32-28B SEQ ID NO: 32);

(b) T33-09A SEQ ID NO: 33) and T33-09B SEQ ID NO: 34);

(c) T33-15A SEQ ID NO: 35) and T33-15B SEQ ID NO: 36);

(d) T33-21A SEQ ID NO: 37) and T33-21B SEQ ID NO: 38); and (e) T33-28A SEQ ID NO: 39) and T33-28B SEQ ID NO: 40).

In one embodiment, the first protein and the second protein comprise or consist of proteins selected from the following pairs of first and second proteins:

(a) T32-28A (SEQ ID NO: 11, 21, or 31) and T32-28B SEQ ID NO: 12, 22, or 32), wherein the first protein is at least 70% identical to the amino acid sequence of SEQ ID NO: 1 and the second protein is at least 70% identical to the amino acid sequence of SEQ ID NO: 2;

(b) T33-09A SEQ ID NO: 13, 23, or 33) and T33-09B SEQ ID NO: 14, 24, or 34), wherein the first protein is at least 70% identical to the amino acid sequence of SEQ ID NO: 3 and the second protein is at least 70% identical to the amino acid sequence of SEQ ID NO: 4;

(c) T33-15A SEQ ID NO: 15, 25, or 35) and T33-15B SEQ ID NO: 16, 26, or 36), wherein the first protein is at least 70% identical to the amino acid sequence of SEQ ID NO: 5 and the second protein is at least 70% identical to the amino acid sequence of SEQ ID NO: 6;

(d) T33-21A SEQ ID NO: 17, 27, or 37) and T33-21B SEQ ID NO: 18, 28, or 38), wherein the first protein is at least 70% identical to the amino acid sequence of SEQ ID NO: 7 and the second protein is at least 70% identical to the amino acid sequence of SEQ ID NO: 8; and (e) T33-28A SEQ ID NO: 19, 29, or 39) and T33-28B SEQ ID NO: 20, 30, or 40), wherein the first protein is at least 70% identical to the amino acid sequence of SEQ ID NO: 9 and the second protein is at least 70% identical to the amino acid sequence of SEQ ID NO: 10.

In various further embodiments, the first and second proteins are at least 75%, 80%, 85%, 90%, 91%, 92%, 93%, 94%, 95%, 96%, 97%, or 98% identical to the amino acid sequence of the designed protein.

In various further embodiments, the first and second proteins comprise or consist of proteins selected from the following pairs of first and second proteins (a)
T32-28A (SEQ ID NO: 1)
MGEVPIGDPKELNGMEIAAVYLQPIEMEPRGIDLAASLADIHLEAD

IHALKNNPNGFPEGFWMPYLTIAYALANADTGAIKTGTLMPMVADD

GPHYGANIAMEKDKKGGFGVGTYALTFLISNPEKQGFGRHVDEETG

VGKWFEPFVVTYFFKYTGTPK;
and

T32-28B (SEQ ID NO: 2)
MSQAIGILELTSIAKGMELGDAMLKSANVDLLVSKTISPGKFLLML

GGDIGAIQQAIETGTSQAGEMLVDSLVLANIHPSVLPAISGLNSVD

KRQAVGIVETWSVAACISAADLAVKGSNVTLVRVHMAFGIGGKCYM

VVAGDVLDVAAAVATASLAAGAKGLLVYASIIPRPHEAMWRQMVEG;

(b)
T33-09A (SEQ ID NO: 3)
MEEVVLITVPSALVAVKIAHALVEERLAACVNIVPGLTSIYRWQGS

VVSDHELLLLVKTTTHAFPKLKERVKALHPYTVPEIVALPIAEGNR

EYLDWLRENTG;
and

T33-09B (SEQ ID NO: 4)
MVRGIRGAITVEEDTPAAILAATIELLLKMLEANGIQSYEELAAVI

FTVTEDLTSAFPAEAARLIGMHRVPLLSAREVPVPGSLPRVIRVLA

LWNTDTPQDRVRHVYLNEAVRLRPDLESAQ;

(c)
T33-15A (SEQ ID NO: 5)
MSKAKIGIVTVSDRASAGITADISGKAIILALNLYLTSEWEPIYQV

IPDEQDVIETTLIKMADEQDCCLIVTTGGTGPAKRDVTPEATEAVC

DRMMPGFGELMRAESLKEVPTAILSRQTAGLRGDSLIVNLPGDPAS

ISDCLLAVFPAIPYCIDLMEGPYLECNEAMIKPFRPKAK;
and

T33-15B (SEQ ID NO: 6)
MVRGIRGAITVNSDTPTSIIIATILLLEKMLEANGIQSYEELAAVI

FTVTEDLTSAFPAEAARQIGMHRVPLLSAREVPVPGSLPRVIRVLA

LWNTDTPQDRVRHVYLSEAVRLRPDLESAQ;

(d)
T33-21A (SEQ ID NO: 7)
MRITTKVGDKGSTRLFGGEEVWKDSPIIEANGTLDELTSFIGEAKH

YVDEEMKGILEEIQNDIYKIMGEIGSKGKIEGISEERIAWLLKLIL

RYMEMVNLKSFVLPGGTLESAKLDVCRTIARRALRKVLTVTREFGI

GAEAAAYLLALSDLLFLLARVIEIEKNKLKEVRS;
and

T33-21B (SEQ ID NO: 8)
MPHLVIEATANLRLETSPGELLEQANKALFASGQFGEADIKSRFVT

LEAYRQGTAAVERAYLHACLSILDGRDIATRTLLGASLCAVLAEAV

AGGGEEGVQVSVEVREMERLSYAKRVVARQR;
and (e)
T33-28A (SEQ ID NO: 9)
MESVNTSFLSPSLVTIRDFDNGQFAVLRIGRTGFPADKGDIDLCLD

KMIGVRAAQIFLGDDTEDGFKGPHIRIRCVDIDDKHTYNAMVYVDL

IVGTGASEVERETAEEEAKLALRVALQVDIADEHSCVTQFEMKLRE

ELLSSDSFHPDKDEYYKDFL;
and

T33-28B (SEQ ID NO: 10)
MPVIQTFVSTPLDHHKRLLLAIIYRIVTRVVLGKPEDLVMMTFHDS

TPMHFFGSTDPVACVRVEALGGYGPSEPEKVTSIVTAAITAVCGIV

ADRIFVLYFSPLHCGWNGTNF.

As shown in the examples that follow, these non-naturally occurring protein pairs self-interact to form multimeric substructures, which can interact to form the nanostructures of the invention. As will be understood by those of skill in the art, the design methods of the invention can produce a wide variety of nanostructures made of a wide variety of subunit proteins, and the methods are in no way limited to these particular protein pairs; they are merely exemplary.

The plurality of the first proteins self-interact to form a first multimeric substructure and the plurality of the second proteins self-interact to form a second multimeric substructure, where each multimeric substructure comprises at least one axis of rotational symmetry. As will be understood by those of skill in the art, the self-interaction is a non-covalent protein-protein interaction. Any suitable non-covalent interaction(s) can drive self-interaction of the proteins to form the multimeric substructure, including but not limited to one or more of electrostatic interactions, π-effects, van der Waals forces, hydrogen bonding, and hydrophobic effects. The self-interaction in each of the two different multimeric substructures may be natural or synthetic in origin; that is, the synthetic proteins making up the nanostructures of the invention may be synthetic variations of natural proteins that self-interact to form multimeric substructures, or they may be fully synthetic proteins that have no amino acid sequence relationships to known natural proteins.

As used herein, "at least one axis of rotational symmetry" means at least one axis of symmetry around which the substructure can be rotated without changing the appearance of the substructure. In one embodiment, one or both of the substructures have cyclic symmetry, meaning rotation about a single axis (for example, a three-fold axis in the case of a trimeric protein; generally, multimeric substructures with n subunits and cyclic symmetry will have n-fold rotational symmetry, sometimes denoted as $C_n$ symmetry). In other embodiments, one or both substructures possess symmetries comprising multiple rotational symmetry axes, including but not limited to dihedral symmetry (cyclic symmetry plus an orthogonal two-fold rotational axis) and the cubic point group symmetries including tetrahedral, octahedral, and icosahedral point group symmetry (multiple kinds of rotational axes). The first multimeric substructure and the second multimeric substructure may comprise the same or different rotational symmetry properties. In one non-limiting embodiment, the first multimeric substructure comprises a dimer, trimer, tetramer, or pentamer of the first protein, and wherein the second multimeric substructure comprises a dimer or trimer of the second protein. In a further non-limiting embodiment, the first multimeric protein comprises a trimeric protein, and the second multimeric protein comprises a dimeric protein. In another non-limiting embodiment,
the first multimeric protein comprises a trimeric protein, and the second multimeric protein comprises a different trimeric protein.

Figure 3F:
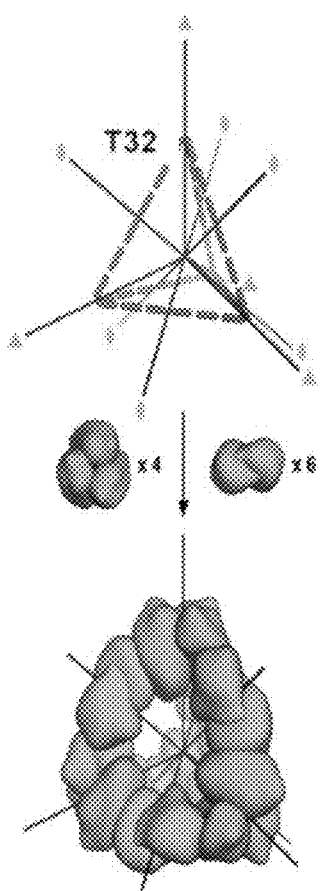

In the nanostructures of the invention, there are at least two identical copies of the first multimeric substructure and at least two identical copies of the second multimeric substructure in the nanostructure. In general, the number of copies of each of the first and second multimeric substructures is dictated by the number of symmetry axes in the designated mathematical symmetry group of the nanostructure that match the symmetry axes in each multimeric substructure. This relationship arises from the requirement that the symmetry axes of each copy of each multimeric substructure must be aligned to symmetry axes of the same kind in the synthetic nanostructure. By way of non-limiting example, a synthetic nanostructure with tetrahedral point group symmetry can comprise exactly four copies of a first trimeric substructure aligned along the exactly four three-fold symmetry axes passing through the center and vertices of a tetrahedron. Likewise, the same non-limiting example tetrahedral nanostructure can comprise six (but not five, seven, or any other number) copies of a dimeric substructure aligned along the six two-fold symmetry axes passing through the center and edges of the tetrahedron (an example of a synthetic nanostructure with this symmetric architecture, referred to here as T32, is shown in FIG. 3F). In general, although every copy of each multimeric substructure must have its symmetry axes aligned to symmetry axes of the same kind in the synthetic nanostructure, not all symmetry axes in the synthetic nanostructure must have a multimeric building block aligned to them. By way of non-limiting example, we can consider a synthetic nanostructure with icosahedral point group symmetry comprising multiple copies of each of a first multimeric substructure and a second multimeric substructure. There are 30 two-fold, 20 three-fold, and 12 five-fold rotational symmetry axes in icosahedral point group symmetry. The nanostructures of the invention are those in which two different multimeric substructures are aligned along all instances of two types of symmetry axes in a designated mathematical symmetry group. Therefore, the nanostructures in this non-limiting example could include icosahedral nanostructures comprising 30 dimeric substructures and 20 trimeric substructures, or 30 dimeric substructures and 12 pentameric substructures, or 20 trimeric substructures and 12 pentameric substructures. In each case, one of the three types of symmetry axes is left unoccupied by multimeric substructures.

The interaction between the first and second multimeric substructures is a non-natural (e.g., not an interaction seen in a naturally occurring protein multimer), non-covalent interaction; this can comprise any suitable non-covalent interaction(s), including but not limited to one or more of electrostatic interactions, π-effects, van der Waals forces, hydrogen bonding, and hydrophobic effects. The interaction occurs at multiple identical interfaces (symmetrical) between the first and second multimeric substructures, wherein the interfaces can be continuous or discontinuous. This symmetric repetition of the non-covalent protein-protein interfaces between the first and second multimeric substructures results from the overall symmetry of the subject nanostructures; because each protein molecule of each of the first and second multimeric substructures is in a symmetrically equivalent position in the nanostructure, the interactions between them are also symmetrically equivalent.

Non-covalent interactions between the first multimeric substructures and the second multimeric substructures orient the substructures such that their symmetry axes are aligned with symmetry axes of the same kind in a designated mathematical symmetry group as described above. This feature provides for the formation of regular, defined nanostructures, as opposed to irregular or imprecisely defined structures or aggregates. Several structural features of the non-covalent interactions between the first multimeric substructures and the second multimeric substructures help to provide a specific orientation between substructures. Generally, large interfaces that are complementary both chemically and geometrically and comprise many individually weak atomic interactions tend to provide highly specific orientations between protein molecules. In one embodiment of the subject invention, therefore, each symmetrically repeated instance of the non-natural, non-covalent protein-protein interface between the first multimeric substructure and the second multimeric substructure may bury between 1000-2000 $Å^2$ of solvent-accessible surface area (SASA) on the first multimeric substructure and the second multimeric substructure combined. SASA is a standard measurement of the surface area of molecules commonly used by those skilled in the art; many computer programs exist that can calculate both SASA and the change in SASA upon burial of a given interface for a given protein structure. A commonly used measure of the geometrical complementarity of protein-protein interfaces is the Shape Complementarity ($S_c$) value of Lawrence and Colman (*J. Mol. Biol.* 234:946-50 (1993)). In a further embodiment, each symmetrically repeated, non-natural, non-covalent protein-protein interface between the first multimeric substructure and the second multimeric substructure has an $S_c$ value between 0.5-0.8. Finally, in order to provide a specific orientation between the first multimeric substructures and the second multimeric substructures, in many embodiments the interface between them may be formed by relatively rigid portions of each of the protein substructures. This feature ensures that flexibility within each protein molecule does not lead to imprecisely defined orientations between the first and second multimeric substructures. Secondary structures in proteins, that is alpha helices and beta strands, generally make a large number of atomic interactions with the rest of the protein structure and therefore occupy a rigidly fixed position. Therefore, in one embodiment, at least 50% of the atomic contacts comprising each symmetrically repeated, non-natural, non-covalent protein-protein interface between the first multimeric substructure and the second multimeric substructure are formed from amino acid residues residing in elements of alpha helix and/or beta strand secondary structure.

The nanostructures of the invention are capable of forming a variety of different structural classes based on the designated mathematical symmetry group of each nanostructure. As the teachings above indicate, the nanostructures comprise multiple copies of a first multimeric substructure and multiple copies of a second multimeric substructure that interact at one or more symmetrically repeated, non-covalent protein-protein interfaces that orient the first multimeric substructures and the second multimeric substructures such that their symmetry axes are aligned with symmetry axes of the same kind in a designated mathematical symmetry group. There are many symmetry groups that comprise multiple types of symmetry axes, including but not limited to dihedral symmetries, cubic point group symmetries, line or helical symmetries, plane or layer symmetries, and space group symmetries. Collectively, the nanostructures of the invention may possess any symmetry that comprises at least two types of symmetry axes; however, each individual nanostructure possesses a single, mathematically defined symmetry that results from the interface between the first and second multimeric substructures orienting them such that their symmetry axes align to those in a designated mathematically symmetry group. Individual nanostructures possessing different symmetries may find use in different applications; for instance, nanostructures possessing cubic point group symmetries may form hollow shell- or cage-like structures that could be useful, for example, for packaging or encapsulating molecules of interest, while nanostructures possessing plane group symmetries will tend to form regularly repeating two-dimensional protein layers that could be used, for example, to array molecules, nanostructures, or other functional elements of interest at regular intervals.

In one embodiment, the mathematical symmetry group is selected from the group consisting of tetrahedral point group symmetry, octahedral point group symmetry, and icosahedral point group symmetry.

As will be apparent to those of skill in the art, the ability to widely modify surface amino acid residues without disruption of the protein structure permits many types of modifications to endow the resulting self-assembled multimers with a variety of functions. In one non-limiting embodiment, the protein can be modified to facilitate covalent linkage to a "cargo" of interest. In one non-limiting example, the protein can be modified, such as by introduction of various cysteine residues at defined positions to facilitate linkage to one or more antigens of interest, such that an assembly of the protein would provide a scaffold to provide a large number of antigens for delivery as a vaccine to generate an improved immune response (similar to the use of virus-like particles). In another non-limiting embodiment, the protein of the invention may be modified by linkage (covalent or non-covalent) with a moiety to help facilitate "endosomal escape." For applications that involve delivering molecules of interest to a target cell, such as targeted delivery, a critical step can be escape from the endosome—a membrane-bound organelle that is the entry point of the delivery vehicle into the cell. Endosomes mature into lysosomes, which degrade their contents. Thus, if the delivery vehicle does not somehow "escape" from the endosome before it becomes a lysosome, it will be degraded and will not perform its function. There are a variety of lipids or organic polymers that disrupt the endosome and allow escape into the cytosol. Thus, in this embodiment, the first or second protein can be modified, for example, by introducing cysteine residues that will allow chemical conjugation of such a lipid or organic polymer to the monomer or resulting multimer surface.

In a further aspect, the present invention provides isolated proteins, comprising or consisting of an amino acid sequence selected from the group consisting of (a) T32-28A (SEQ ID NO: 11);
(b) T32-28B SEQ ID NO: 12);
(c) T33-09A SEQ ID NO: 13);
(d) T33-09B SEQ ID NO: 14);
(e) T33-15A SEQ ID NO: 15);
(f) T33-15B SEQ ID NO: 16);
(g) T33-21A SEQ ID NO: 17);
(h) T33-21B SEQ ID NO: 18);
(i) T33-28A SEQ ID NO: 19); and
(j) T33-28B SEQ ID NO: 20).

The isolated proteins of the invention can be used, for example, to prepare the nanostructures of the invention. In some embodiments, the isolated proteins may be produced in the same time and place; for instance, they may be expressed recombinantly in the same bacterial or eukaryotic cell. In other embodiments, each protein may be produced separately from the other, either by recombinant expression in separate bacterial or eukaryotic cells or by protein synthesis in separate vessels. The isolated proteins of the invention can be modified in a number of ways, including but not limited to the ways described above, either before or after assembly of the nanostructures of the invention. As a non-limiting example, the T33-15A protein and the T33-15B protein could be produced by recombinant expression in separate cultures of bacterial cells and purified independently of one another. Prior to mixing the two proteins, each protein could be modified chemically to introduce additional functionality as described above. The modified proteins could then be mixed to initiate assembly of a modified T33-15 nanostructure that comprises multiple copies of each of the T33-15A and T33-15B proteins. Alternatively, the T33-15A and T33-15B proteins could be produced recombinantly in the same cell to produce the assembled T33-15 nanostructure of the invention, which could then be modified as desired.

FIGS. 10-19 show the primary amino acid sequences of the proteins noted and allowable substitutions, as discussed above. In another embodiment, the isolated proteins comprise or consist of an amino acid sequence selected from the group consisting of:

(a) T32-28A (SEQ ID NO: 21);
(b) T32-28B SEQ ID NO: 22);
(c) T33-09A SEQ ID NO: 23);
(d) T33-09B SEQ ID NO: 24);
(e) T33-15A SEQ ID NO: 25);
(f) T33-15B SEQ ID NO: 26);
(g) T33-21A SEQ ID NO: 27);
(h) T33-21B SEQ ID NO: 28);
(i) T33-28A SEQ ID NO: 29); and
(j) T33-28B SEQ ID NO: 30).

In another embodiment, the isolated proteins comprise or consist of an amino acid sequence selected from the group consisting of:

(a) T32-28A (SEQ ID NO: 31);
(b) T32-28B SEQ ID NO: 32);
(c) T33-09A SEQ ID NO: 32);
(d) T33-09B SEQ ID NO: 34);
(e) T33-15A SEQ ID NO: 35);
(f) T33-15B SEQ ID NO: 36);
(g) T33-21A SEQ ID NO: 37);
(h) T33-21B SEQ ID NO: 38);
(i) T33-28A SEQ ID NO: 39); and
(j) T33-28B SEQ ID NO: 40).

In another embodiment, the isolated proteins comprise or consist of an amino acid sequence:

(A) T32-28A (SEQ ID NO: 11, 21, or 31), wherein the protein is at least 70% identical to the amino acid sequence of SEQ ID NO: 1;

(B) T32-28B SEQ ID NO: 12, 22, or 32), wherein the protein is at least 70% identical to the amino acid sequence of SEQ ID NO: 2;

(C) T33-09A SEQ ID NO: 13, 23, or 33), wherein the protein is at least 70% identical to the amino acid sequence of SEQ ID NO: 3;

(D) T33-09B SEQ ID NO: 14, 24, or 34), wherein the protein is at least 70% identical to the amino acid sequence of SEQ ID NO: 4;

(E) T33-15A SEQ ID NO: 15, 25, or 35), wherein the protein is at least 70% identical to the amino acid sequence of SEQ ID NO: 5;

(F) T33-15B SEQ ID NO: 16, 26, or 36), wherein the protein is at least 70% identical to the amino acid sequence of SEQ ID NO: 6;

(G) T33-21A SEQ ID NO: 17, 27, or 37), wherein the protein is at least 70% identical to the amino acid sequence of SEQ ID NO: 7;

(H) T33-21B SEQ ID NO: 18, 28, or 38), wherein the protein is at least 70% identical to the amino acid sequence of SEQ ID NO: 8;

(I) T33-28A SEQ ID NO: 19, 29, or 39), wherein the protein is at least 70% identical to the amino acid sequence of SEQ ID NO: 9; and (J) T33-28B SEQ ID NO: 20, 30, or 40), wherein the protein is at least 70% identical to the amino acid sequence of SEQ ID NO: 10.

In various further embodiments, the protein of any one of (A)-(J) is at least 75%, 80%, 85%, 90%, 91%, 92%, 93%, 94%, 95%, 96%, 97%, or 98% identical to the amino acid sequence of the designed protein.

In a further embodiment, the isolated protein comprises or consists of an amino acid sequence selected from the group consisting of: SEQ ID NOS: 1-10.

As used throughout the present application, the term "protein" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may be linked to any other moiety as deemed useful for a given purpose. Such linkage can be covalent or non-covalent as is understood by those of skill in the art.

In one non-limiting embodiment, the protein can be modified to facilitate covalent linkage to a "cargo" of interest. In one non-limiting example, the protein can be modified, such as by introduction of various cysteine residues at defined positions to facilitate linkage to one or more antigens of interest, such that an assembly of the protein would provide a scaffold to provide a large number of antigens for delivery as a vaccine to generate an improved immune response (similar to the use of virus-like particles). In another non-limiting embodiment, the protein of the invention may be modified by linkage (covalent or non-covalent) with a moiety to help facilitate "endosomal escape."

In a further aspect, the present invention provides multimers, comprising a plurality of identical protein monomers according to any embodiment or combination of embodiments of the proteins of the invention. As is disclosed herein, proteins of the invention are capable of self-interacting into multimeric substructures (i.e.: dimers, trimers, hexamers, pentamers, hexamers, etc.) formed from self-assembly of a plurality of a single protein monomer of the invention (i.e., "homo-multimeric assemblies"). As used herein, a "plural-ity" means 2 or more. In various embodiments, the multimeric assembly comprises 2, 3, 4, 5, 6, or more identical protein monomers. The multimeric assemblies can be used for any purpose, including but not limited to creating the nanostructures of the present invention.

In another aspect, the present invention provides isolated nucleic acids encoding a protein of the present invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the proteins of the invention.

In a further aspect, the present invention provides recombinant expression vectors comprising the isolated nucleic acid of any embodiment or combination of embodiments of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited to plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; Gene Transfer and Expression Protocols, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In another aspect, the present invention provides host cells that have been transfected with the recombinant expression vectors disclosed herein, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, 2$^{nd}$ Ed. (R. I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide.

In a further aspect, the present invention provides kits comprising:
 (a) one or more of the isolated proteins, multimeric protein assemblies, or nanostructures of the invention;
 (b) one or more recombinant nucleic acids of the invention;
 (c) one or more recombinant expression vectors comprising recombinant nucleic acids of the invention; and/or
 (d) one or more recombinant host cell, comprising recombinant expression vectors of the invention.

Nanostructure and Protein Examples

Two example distinct tetrahedral architectures have been considered in detail: the T33 architecture described above and the T32 architecture shown in FIGS. 2 and 3F, in which the materials are formed from four trimeric and six dimeric building blocks aligned along the three-fold and two-fold tetrahedral symmetry axes. In an experiment, all pairwise combinations of a set of 1,161 dimeric and 200 trimeric protein building blocks of known structure were docked in the T32 and T33 architectures. This resulted in a large set of potential novel nanomaterials: 232,200 and 19,900 docked protein pairs, respectively, with a given pair often yielding several distinct promising docked configurations. Interface sequence design calculations were carried out on the 1,000 highest scoring docked configurations in each architecture, and the designs were evaluated based on the predicted binding energy, shape complementarity, size, and number of buried unsatisfied hydrogen bonding groups (vide supra).

After filtering on these criteria, 30 T32 and 30 T33 materials were selected for experimental characterization. The 60 designs were derived from 39 distinct trimeric and 19 dimeric proteins, and contained an average of 19 amino acid mutations per pair of subunits compared to the native sequences. The designed interfaces reside mostly on elements of secondary structure, both α-helices and β-strands, with nearby loops often making minor contributions.

Synthetic genes encoding each designed pair of proteins were cloned in tandem in a single expression vector to allow inducible co-expression in *E. coli*. Polyacrylamide gel electrophoresis (PAGE) under non-denaturing (native) conditions was used to rapidly screen the assembly state of the designed proteins in clarified cell lysates. Several designed protein pairs yielded single bands that migrated more slowly than the wild-type proteins from which they were derived, suggesting assembly to higher-order species. These proteins were subcloned to introduce a hexahistidine tag at the C terminus of one of the two subunits and purified by nickel affinity chromatography and size exclusion chromatography (SEC). Five pairs of designed proteins, one T32 design (T32-28) and four T33 designs (T33-09, T33-15, T33-21, and T33-28), co-purified off of the nickel column and yielded dominant peaks at the expected size of approximately 24 subunits when analyzed by SEC, such as shown in FIG. 5A.

Figure 5A:
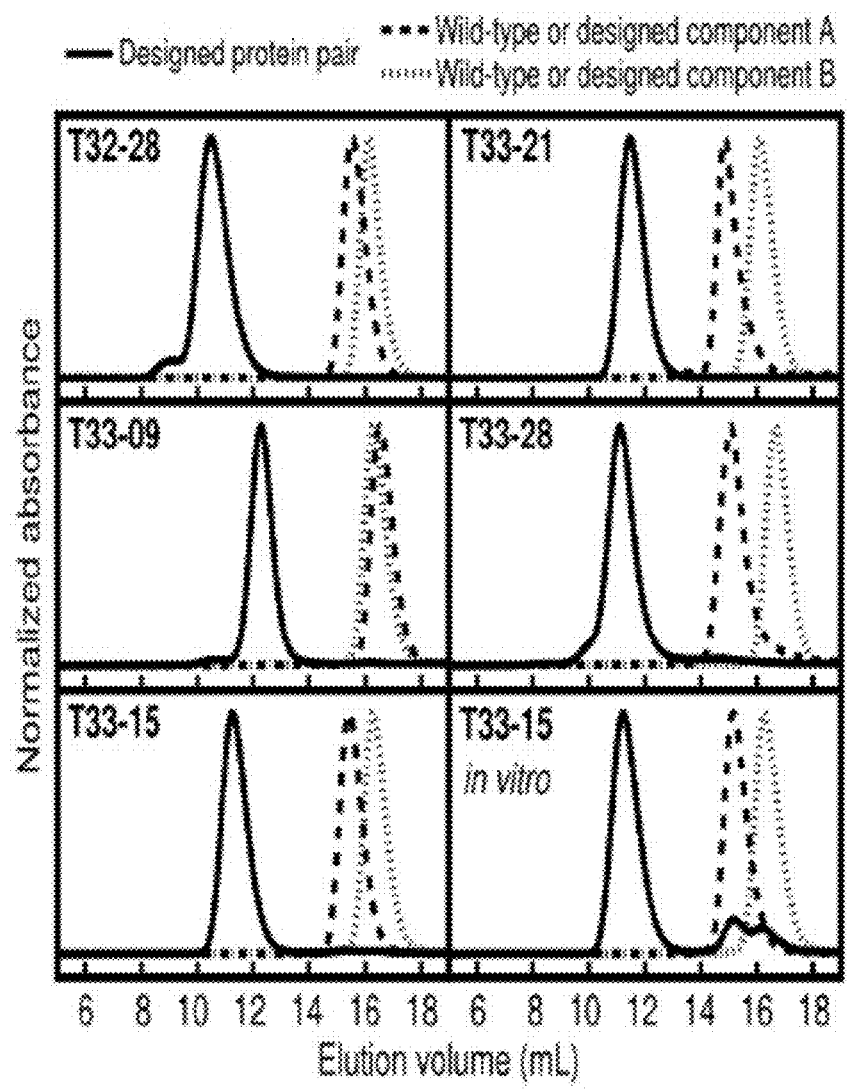
FIG. 5A shows SEC chromatograms of designed pairs of proteins and wild-type oligomeric proteins.

FIG. 5A shows SEC chromatograms of the designed pairs of proteins (solid lines) and the wild-type oligomeric proteins from which they were derived (dashed and dotted lines). The co-expressed designed proteins elute at the volumes expected for the target 24-subunit nanomaterials, while the wild-type proteins elute as dimers or trimers. The T33-15 in vitro panel shows chromatograms for the individually produced and purified designed components (T33-15A and T33-15B [dashed and dotted lines]) as well as a stoichiometric mixture of the two components (solid line).

Figure 5B:
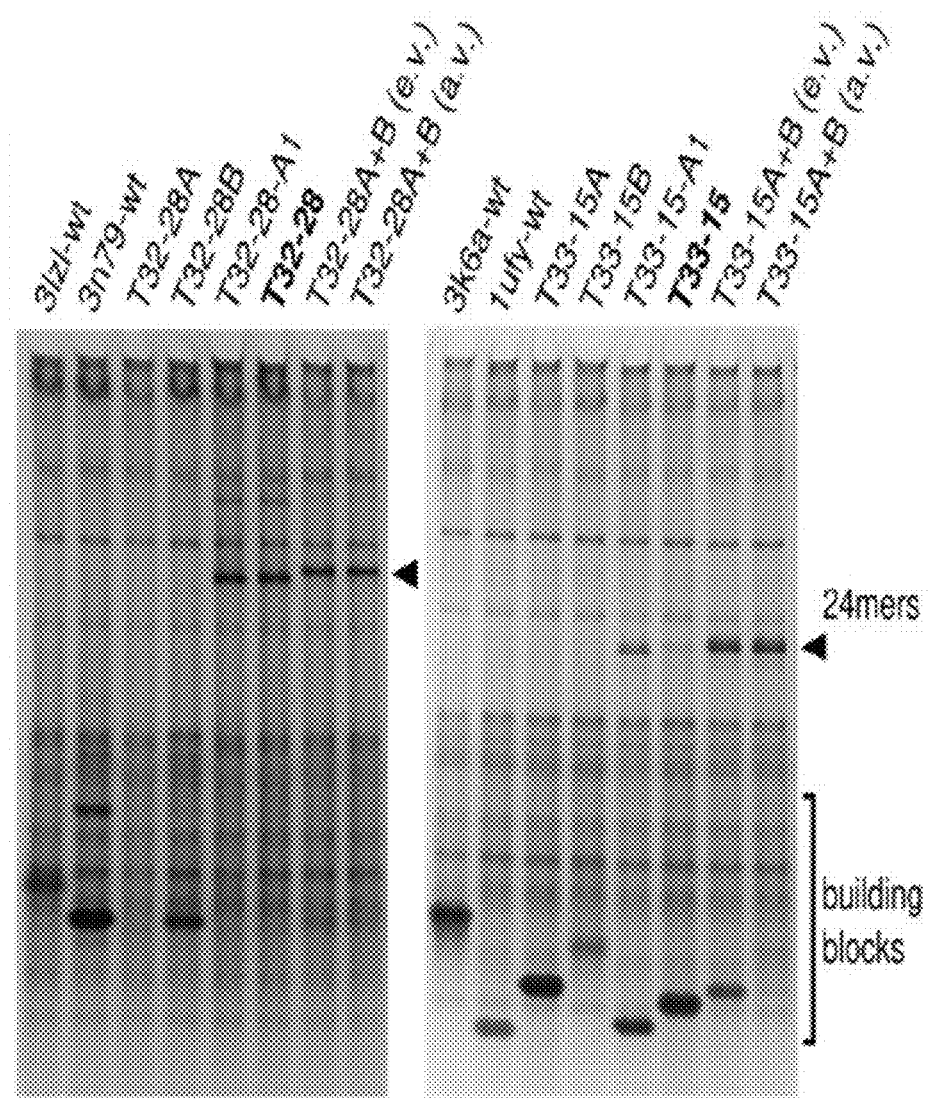
FIG. 5B shows a native PAGE analysis of in vitro-assembled T32-28 and T33-15 in cell lysates.
Figure 5C:
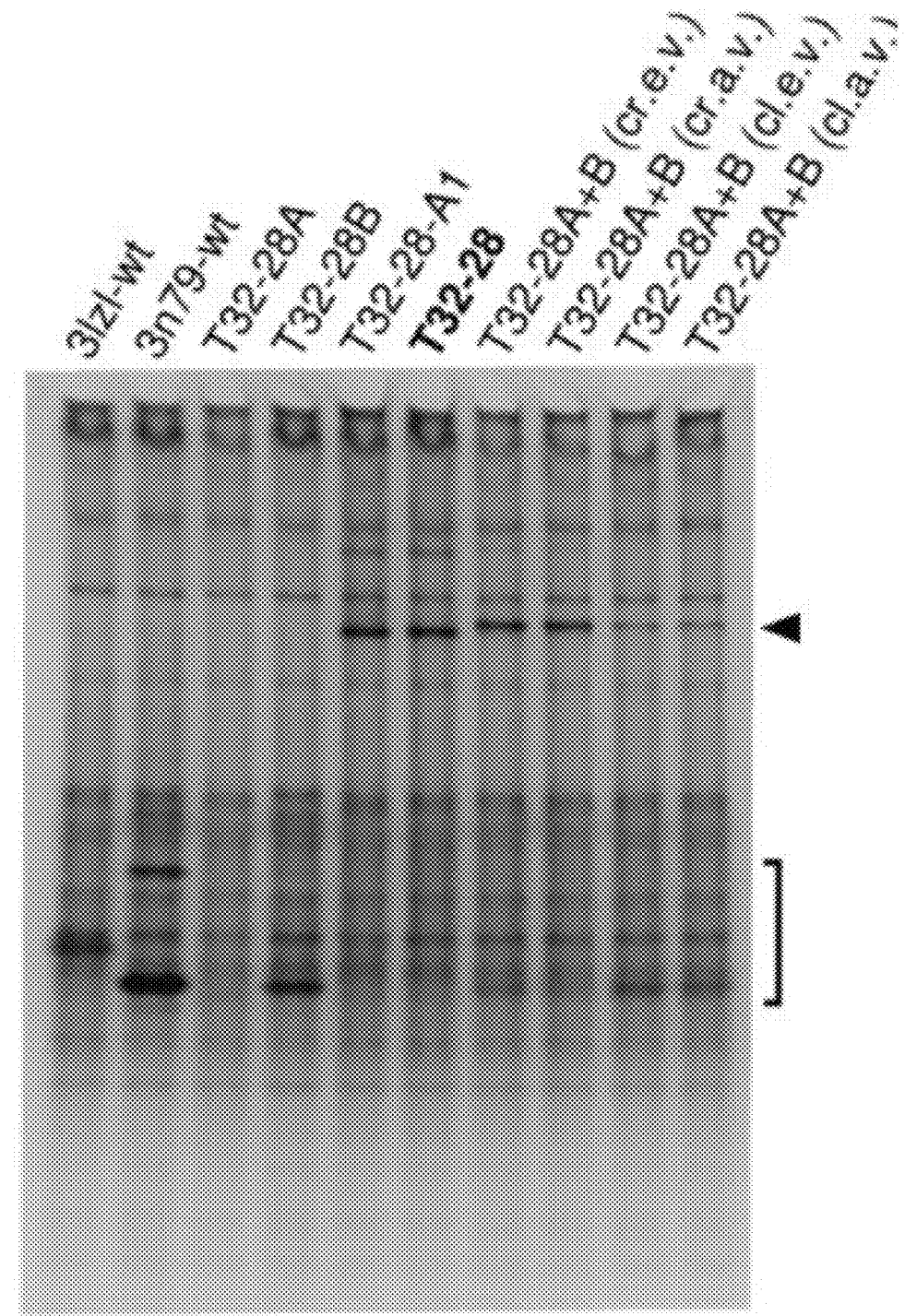
FIGS. 5C-5G show respective native PAGE analyses of in vitro-assembled T32-28, T33-09, T33-15, T33-21, and T33-28 in cell lysates.
Figure 5D:
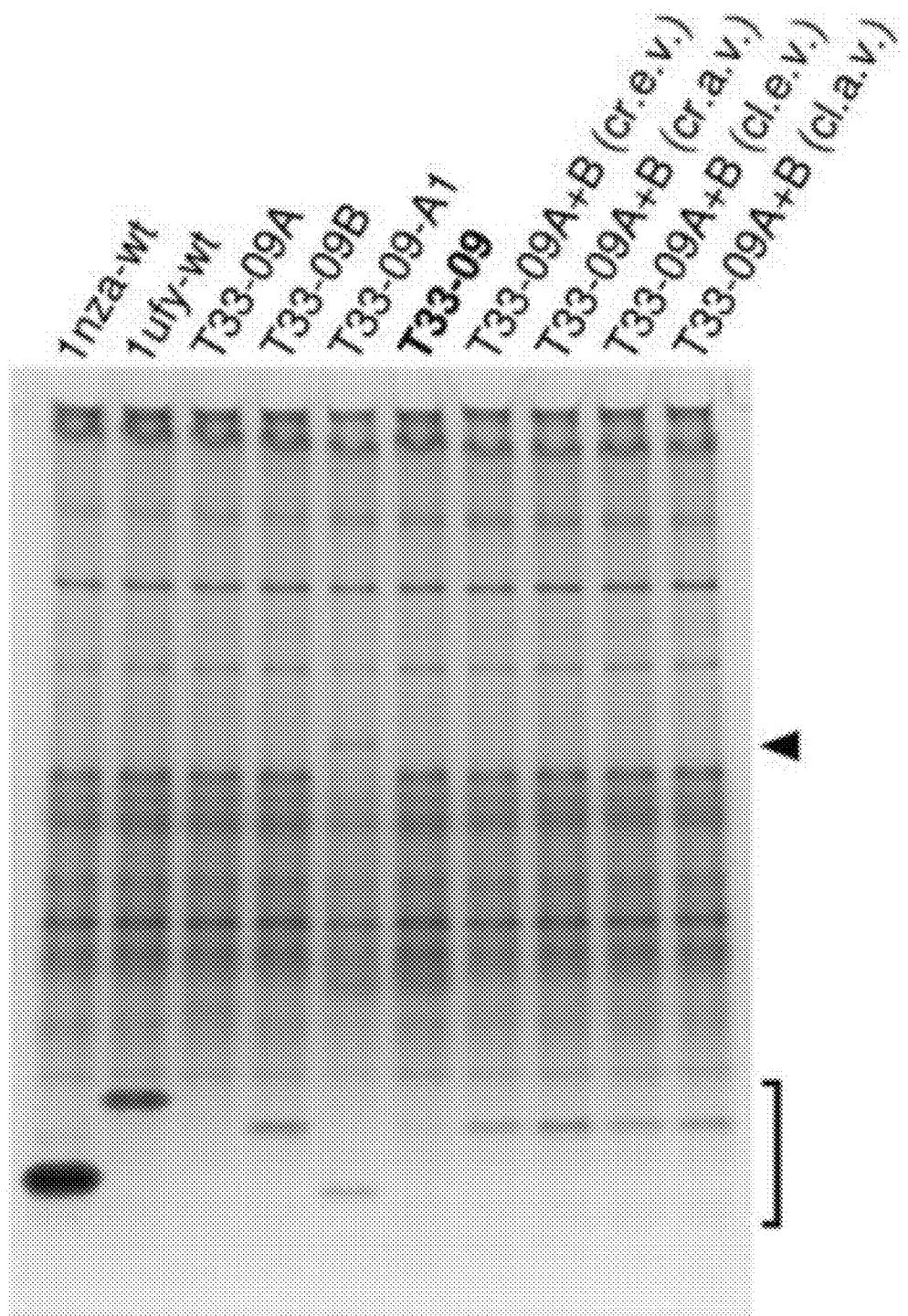

FIG. 5B shows a native PAGE analysis of in vitro-assembled T32-28 (left panel) and T33-15 (right panel) in cell lysates. In FIG. 5B, lysates of the co-expressed design components (lanes 5-6) contain slowly migrating species (arrows) not present in lysates of the wild-type and individually expressed components (lanes 1-4). Mixing equal volumes (e.v.) of crude lysates containing the individual designed components yields the same assemblies (lane 7), although some unassembled building blocks remain due to unequal levels of expression (particularly for T33-15). When the differences in expression levels are accounted for by mixing adjusted volumes of lysates (a.v.), more efficient assembly is observed (lane 8).

FIGS. 5C-5G respectively show native PAGE analyses of in vitro-assembled T32-28, T33-09, T33-15, T33-21, and T33-28 in cell lysates. In FIGS. 5C-5G, lane 1 is from cells expressing the wild-type scaffold for component A and lane 2 the wild-type scaffold for component B. Lanes 3-4 are from cells expressing the individual design components and lanes 5-6 the co-expressed components. Lanes 7-8 are from samples mixed as crude lysates (cr.e.v or cr.a.v), while lanes 9-10 are from samples mixed as cleared lysates (cl.e.v. or cl.a.v.). Lanes 7 and 9 are from lysates mixed with equal volumes (cr.e.v. or cl.e.v.), while lanes 8 and 10 are from lysates mixed with adjusted volumes (cr.a.v. or cl.a.v.). Lane 5 is from cells expressing the C-terminally A1-tagged constructs; all other lanes are from cells expressing the C-terminally His-tagged constructs. An arrow is positioned next to each gel indicating the migration of 24-subunit assemblies and the gel regions containing unassembled building blocks are bracketed. Each gel was stained with GelCode™ Blue (Thermo Scientific).

Figure 5E:
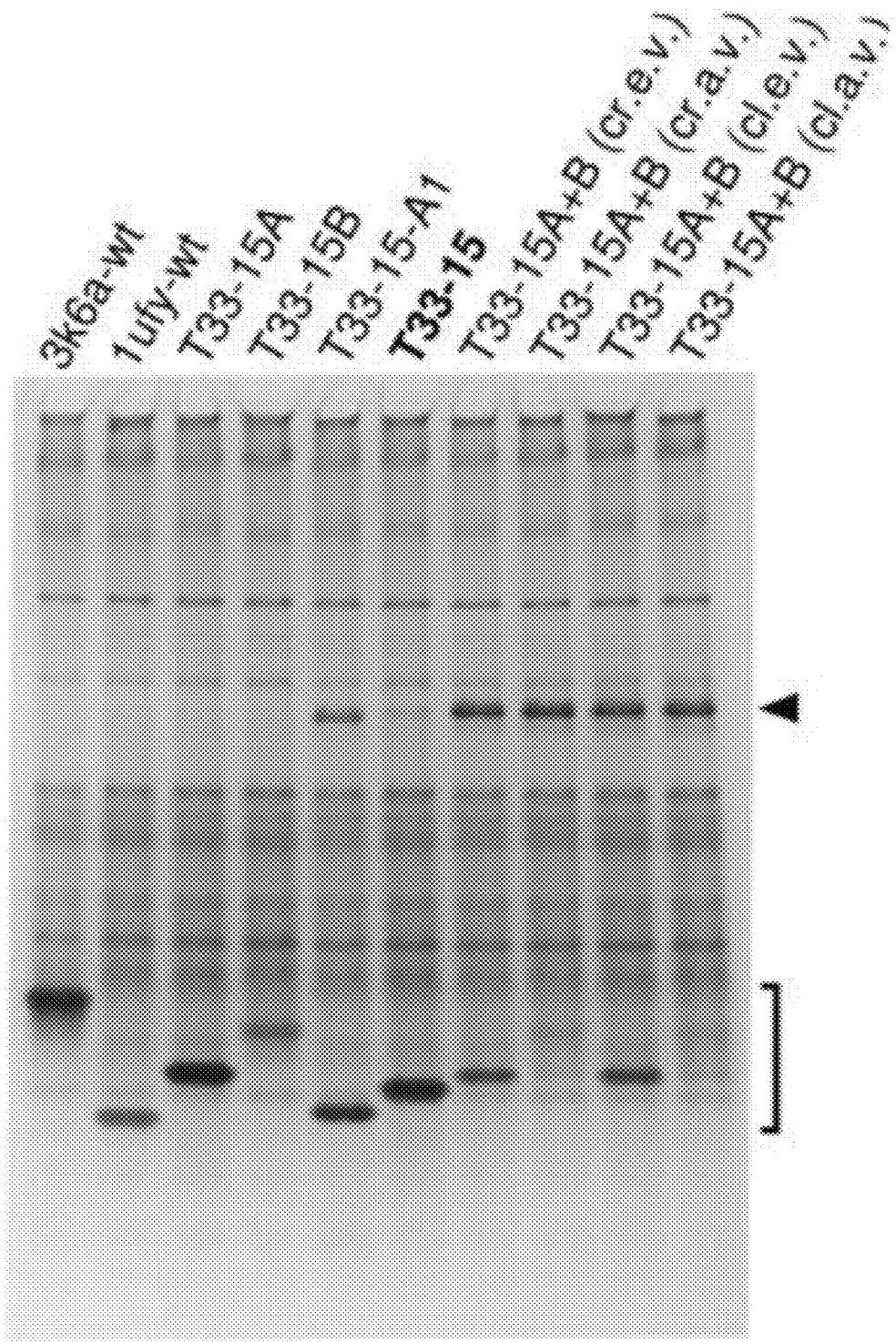
Figure 5F:
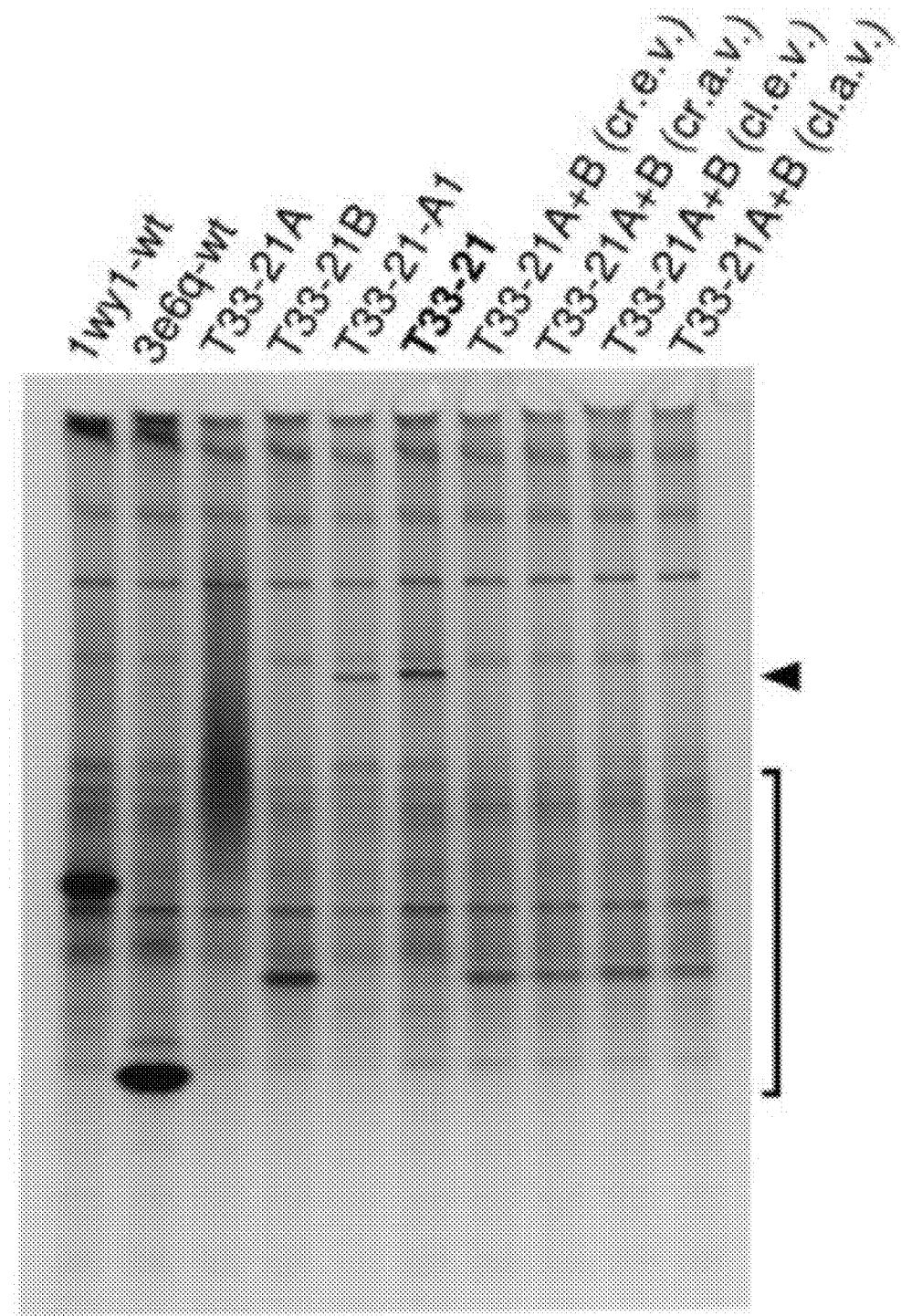
Figure 5G:
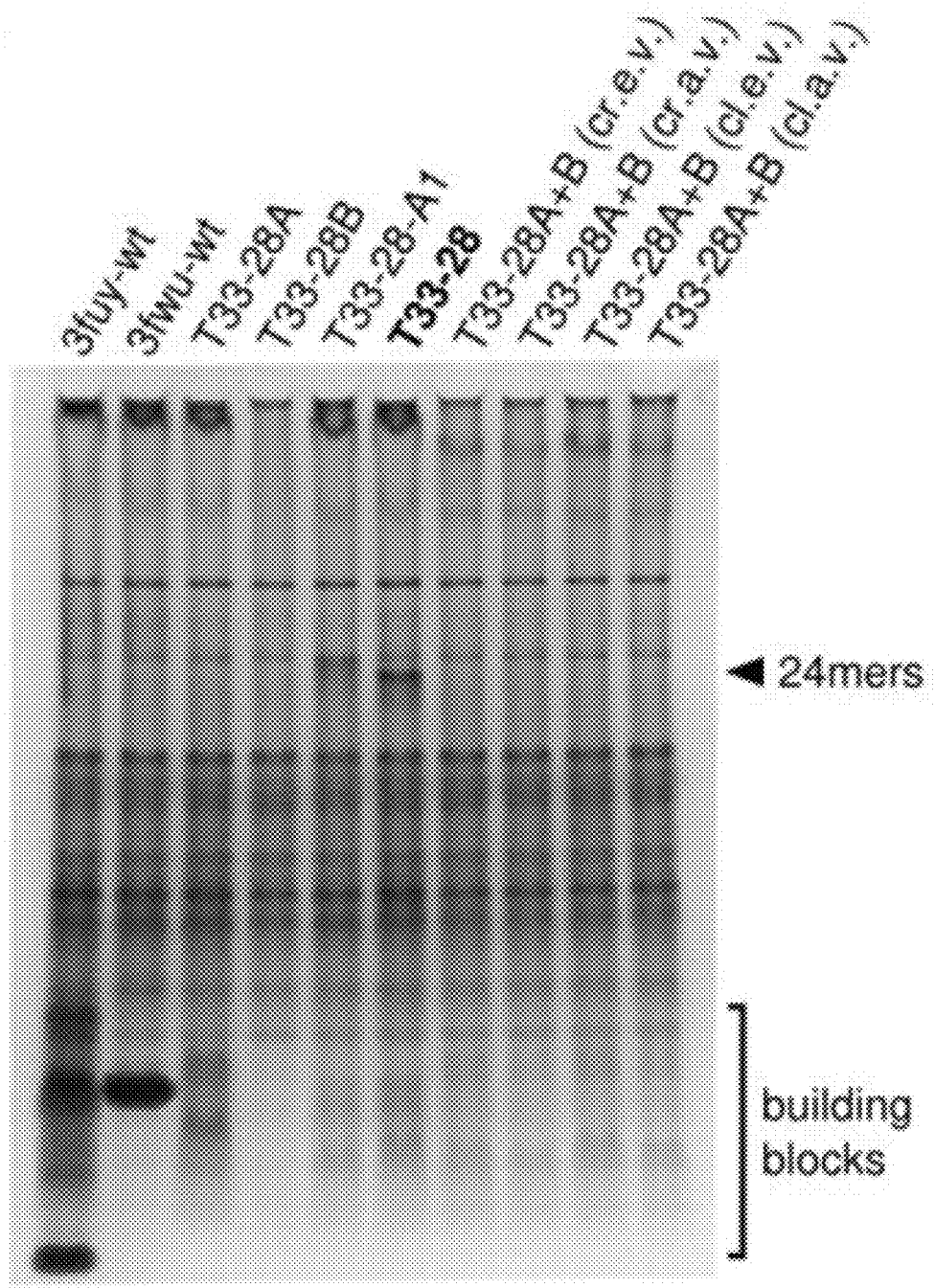

The ability of each material to assemble in vitro was tested by expressing the two components in separate *E. coli* cultures and mixing them at various points after cell lysis. Native PAGE revealed that in two cases, T33-15 shown in FIG. 5E and T32-28 shown in FIG. 5G, the two separately expressed components efficiently assembled to the designed materials in vitro when equal volumes of cell lysates were mixed as indicated in FIGS. 5B, 5C, and 5E. Adjusting the volume of each lysate in the mixture to account for differences in the level of soluble expression of the two components allowed for more quantitative assembly. In the case of T33-15, the two components of the material could also be purified independently: T33-15A and T33-15B each eluted from the SEC column as trimers in isolation. After mixing the two purified components in a 1:1 molar ratio and two hour incubation at room temperature, the mixture eluted from the SEC column as predominantly the 24mer assembly, with small amounts of residual trimeric building blocks remaining as shown in FIG. 5A. The assembly of our designed materials can thus be controlled by simply mixing the two components.

Figure 6A:
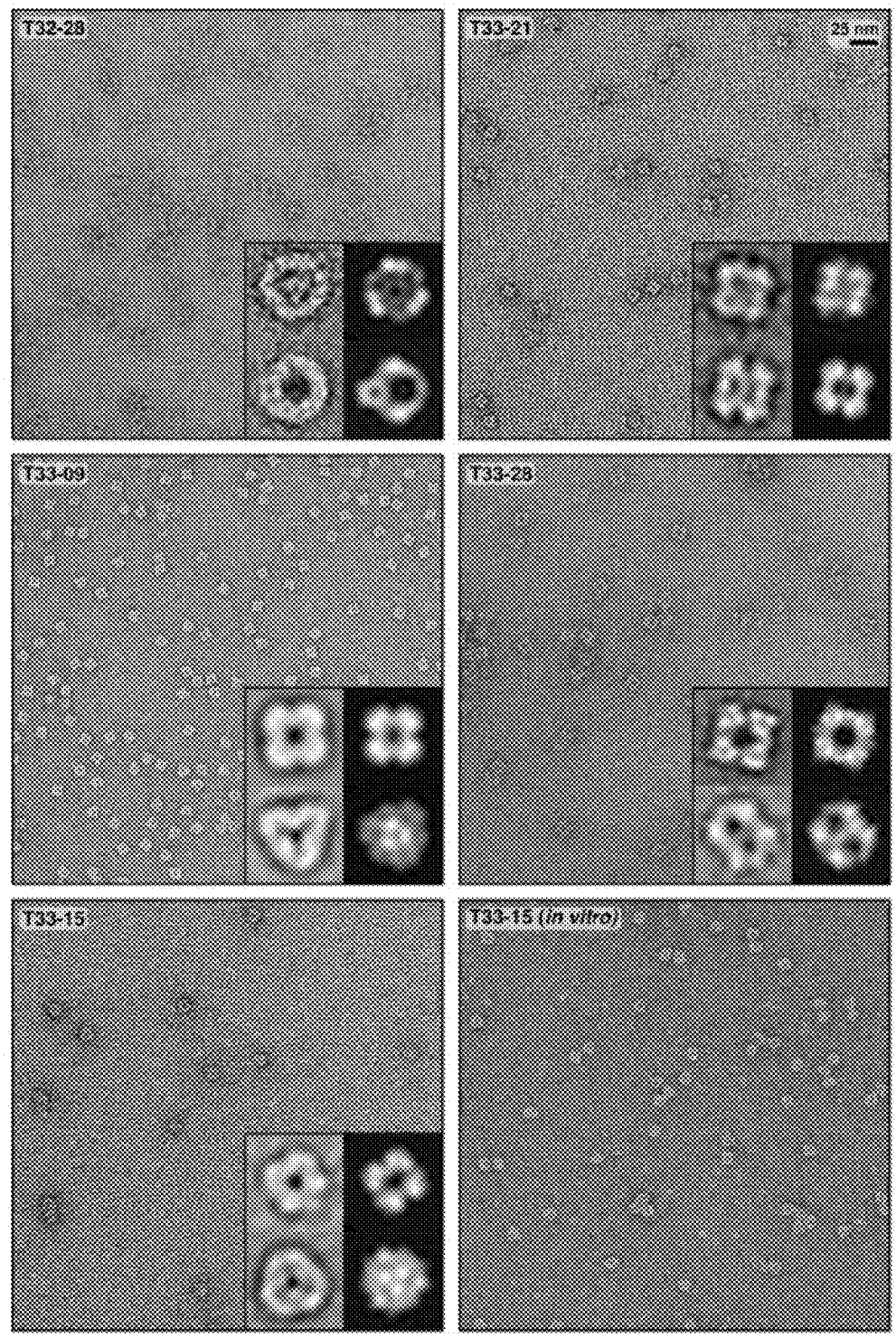
FIGS. 6A and 6B each show electron micrographs of designed two-component protein nanomaterials.
Figure 6B:
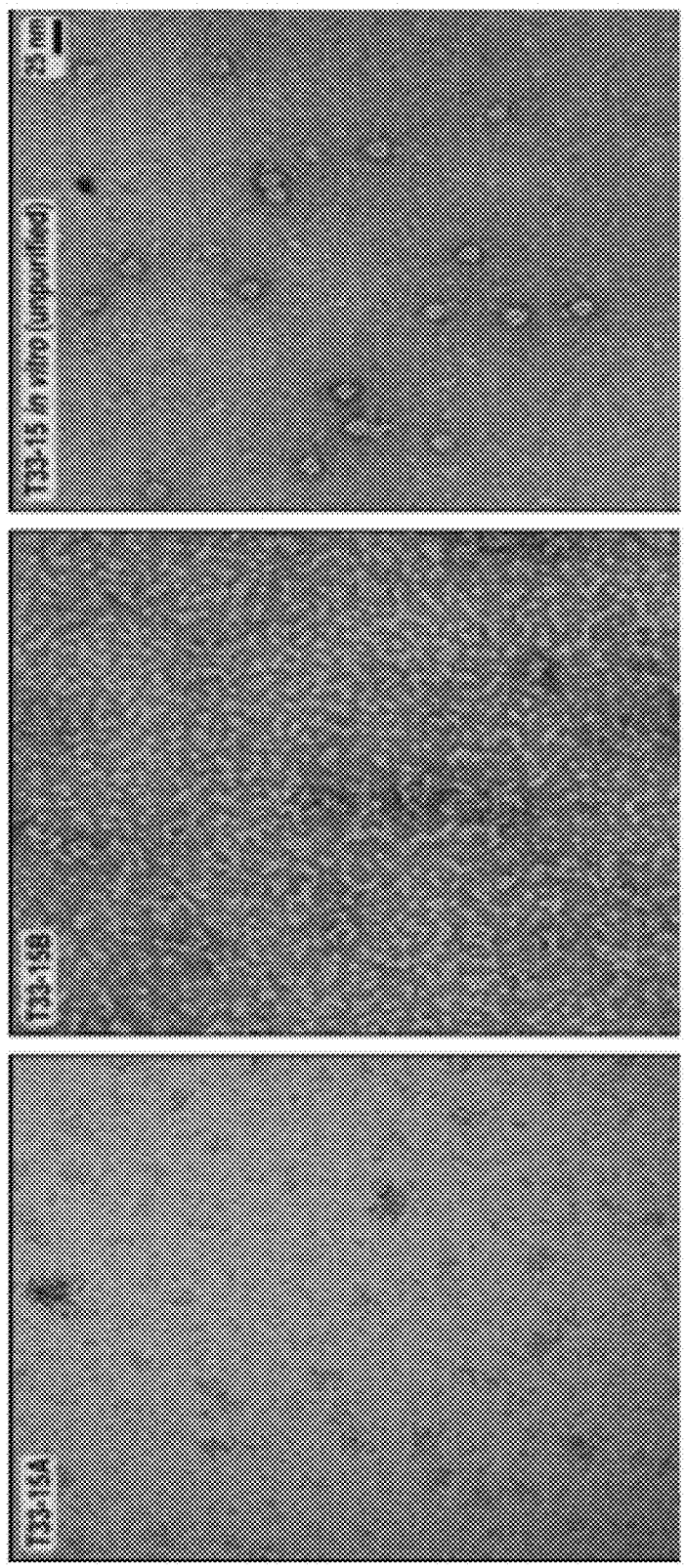

FIGS. 6A and 6B shows electron micrographs of designed two-component protein nanomaterials. FIG. 6A shows negative stain electron microscopy of the five designed materials confirmed that they assemble specifically to the target architectures (FIG. 2). For each material, fields of remarkably monodisperse particles of the expected size and symmetry were observed, confirming the homogeneity of the materials suggested by SEC. Particle averaging yielded images that recapitulate features of the computational design models at low resolution. For example, class averages of T33-09 revealed roughly square or triangle-shaped structures with well-defined internal cavities that closely resemble projections calculated from the computational design model along its two-fold and three-fold axes as shown in FIG. 2, T33-09 inset.

FIG. 6B shows electron micrographs of in vitro-assembled T33-15 (unpurified) and T33-15A and T33-15B in isolation. Negative stain electron micrographs of independently purified T33-15 components (left and middle panels) and unpurified, in vitro-assembled T33-15 (right panel) are shown to scale (scale bar: 25 nm). Micrographs of T33-15 assembled in vitro as described above were indistinguishable from those of co-expressed T33-15 as shown in FIGS. 6A and 6B, demonstrating that the same material is obtained using both methods X-ray crystal structures were solved four of the designed materials (T32-28, T33-15, T33-21, and T33-28) to resolutions ranging from 2.1 to 4.5 Å. Table 3 provides crystallographic statistics for T32-28, T33-15, and T33-28 data collection and refinement, where statistics in parentheses refer to the highest resolution shell.

TABLE 3

|  | T32-28 (PDB ID 4NWN) | T33-15 (PDB ID 4NWO) | T33-28 (PDB ID 4NWR) |
| --- | --- | --- | --- |
| Wavelength (Å) | 0.9793 | 0.9792 | 0.9793 |
| Resolution range (Å) | 93.93-4.5 (4.66-4.5) | 75.49-2.8 (2.901-2.8) | 94.21-3.5 (3.625-3.5) |
| Space group | $P3_121$ | F432 | $P2_1$ |
| Unit cell [a/b/c (Å)] | 246.01 246.01 290.94 | 213.52 213.52 213.52 | 124.91 189.25 376.83 |
| Unit cell [α/β/γ (°)] | 90 90 120 | 90 90 90 | 90 90.02 90 |
| Total reflections | 436516 (44096) | 146590 (14934) | 808494 (85695) |
| Unique reflections | 59814 (5903) | 10783 (1045) | 217956 (21869) |
| Multiplicity | 7.3 (7.5) | 13.6 (14.3) | 3.7 (3.9) |
| Completeness (%) | 98.31 (97.93) | 99.91 (100.00) | 98.80 (99.57) |
| Mean I/sigma (I) | 13.20 (2.17) | 19.80 (2.16) | 8.95 (2.39) |
| Wilson B-factor | 184 | 79.32 | 90.49 |
| R-merge | 0.1383 (0.9457) | 0.1234 (1.767) | 0.144 (0.6014) |
| R-meas | 0.1492 | 0.1282 | 0.1683 |
| CC1/2 | 0.997 (0.586) | 0.999 (0.718) | 0.994 (0.685) |
| CC* | 0.999 (0.859) | 1 (0.914) | 0.998 (0.902) |
| R-work | 0.2971 (0.3574) | 0.2020 (0.3181) | 0.2614 (0.3126) |
| R-free | 0.3429 (0.3937) | 0.2515 (0.3765) | 0.2987 (0.3639) |
| Number of non-hydrogen atoms | 20307 | 2011 | 88861 |
| macromolecules | 20307 | 2008 | 88861 |
| ligands | 0 | 1 | 0 |
| water | 0 | 2 | 0 |
| Protein residues | 4075 | 285 | 12686 |
| RMS(bonds) | 0.003 | 0.003 | 0.002 |
| RMS(angles) | 0.55 | 0.77 | 0.49 |
| Ramachandran favored (%) | 97 | 98 | 97 |
| Ramachandran outliers (%) | 0.15 | 0 | 0 |
| Clashscore | 0.89 | 2.26 | 4.61 |
| Average B-factor | 216.2 | 72.6 | 91.7 |
| macromolecules | 216.2 | 72.6 | 91.7 |
| ligands |  | 111.5 |  |
| solvent |  | 56.6 |  |

Table 4 shows crystallographic statistics for T33-21 data collection and refinement, with Statistics in parentheses refer to the highest resolution shell.

|  | T33-21 R32 (PDB ID 4NWP) | T33-21 F4₁32 (PDB ID 4NWQ) |
| --- | --- | --- |
| Wavelength (Å) | 1.0393 | 0.9716 |
| Resolution range (Å) | 93.78-2.1 (2.175-2.1) | 96.23-2.8 (2.9-2.8) |
| Space group | R32 | F4₁32 |
| Unit cell [a/b/c (Å)] | 113.35 113.35 634.88 | 272.18 272.18 272.18 |
| Unit cell [α/β/γ (°)] | 90 90 120 | 90 90 90 |
| Total reflections | 901047 (89024) | 431476 (43290) |
| Unique reflections | 92425 (9127) | 21830 (2129) |
| Multiplicity | 9.7 (9.8) | 19.8 (20.3) |
| Completeness (%) | 99.94 (99.97) | 99.99 (99.95) |
| Mean I/sigma (I) | 14.46 (2.48) | 20.89 (3.14) |
| Wilson B-factor | 37.68 | 69 |
| R-merge | 0.1123 (1.179) | 0.1215 (1.203) |
| R-meas | 0.1187 | 0.1248 |
| CC1/2 | 0.998 (0.749) | 0.999 (0.878) |
| CC* | 1 (0.925) | 1 (0.967) |
| R-work | 0.1879 (0.3925) | 0.1815 (0.3340) |
| R-free | 0.2183 (0.4478) | 0.1958 (0.3804) |
| Number of non-hydrogen atoms | 8248 | 2112 |
| macromolecules | 7882 | 2041 |
| ligands | 141 | 55 |
| water | 225 | 16 |
| Protein residues | 1046 | 269 |
| RMS(bonds) | 0.004 | 0.001 |
| RMS(angles) | 0.67 | 0.41 |
| Ramachandran favored (%) | 100 | 99 |
| Ramachandran outliers (%) | 0 | 0 |
| Clashscore | 1.87 | 1.2 |
| Average B-factor | 42.5 | 73.1 |
| macromolecules | 42.2 | 72.5 |
| ligands | 64.5 | 98.8 |
| solvent | 40.6 | 64 |

Figure 7:
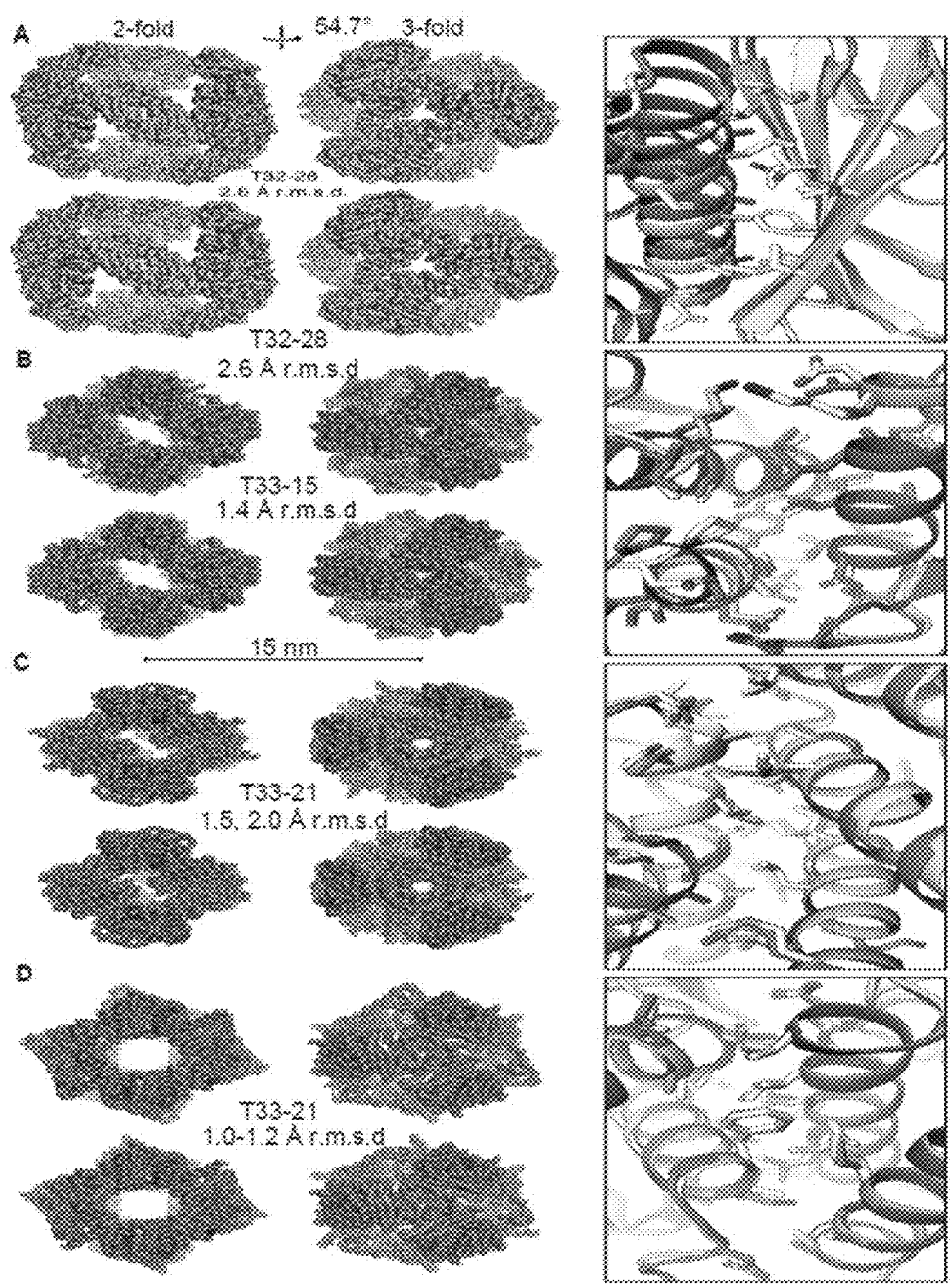
FIG. 7 shows computational design models and crystal structures of designed two-component protein nanomaterials

In the provided cases, the structures can reveal that the inter-building block interfaces were designed with high accuracy: comparing a pair of chains from each structure to the computationally designed model yields backbone root mean square deviations (RMSD) between 0.5 and 1.2 Å, as indicated on the right side of FIG. 7 and Table 5 below.

sponding names in the design models. In the case of T33-28, four different sets of RMSD calculations were carried out; one for each of the four cages contained in the asymmetric unit of 4NWR.

In the structures with resolutions that permit detailed analysis of side chain configurations (T33-15 and two inde-

| Design model | Crystal Structure | Global RMSD (Å) | 2 Chain RMSD (Å) | Contents of asymmetric unit | Structure used for superposition |
| --- | --- | --- | --- | --- | --- |
| T32-28 | 4NWN | 2.586 | 1.246 | One cage (24 subunits) | Asymmetric unit |
| T33-15 | 4NWO | 1.433 | 0.876 | One chain of each component (2 subunits) | One cage generated by 32 components of F432 crystal symmetry |
| T33-21 | 4NWP | 1.962 | 0.924 | 4 chains of each component (8 subunits) | One cage generated from one crystallographic 3-fold |
| T33-21 | 4NWQ | 1.482 | 0.765 | One chain of each component (2 subunits) | One cage generated from crystallographic 2-folds and 3-folds |
| T33-28 | 4NWR | 0.965 | 0.503 | Four complete cages (96 subunits) | One complete cage from the asymmetric unit |
| T33-28 | 4NWR | 0.965 | 0.548 | Four complete cages (96 subunits) | One complete cage from the asymmetric unit |
| T33-28 | 4NWR | 1.195 | 0.567 | Four complete cages (96 subunits) | One complete cage from the asymmetric unit |
| T33-28 | 4NWR | 1.212 | 0.477 | Four complete cages (96 subunits) | One complete cage from the asymmetric unit |

For Table 5, global RMSDs were calculated over all 24 subunits of each design model and corresponding subunits in each crystal structure and 2 chain RMSDs were calculated over chains A and B of each design model and corresponding subunits in each crystal structure. 24 subunits composing one complete cage were derived from each crystal structure as indicated and the chains renamed to match the corresponding pendent crystal forms of T33-21), 87/113 side chains at the designed interfaces can adopt the predicted conformations as indicated in Tables 6 and 7 below. Table 6 shows a side chain chi value comparison of T33-15 crystal structure (PDB ID 4NWO) with the design model. The numbers reported are the differences in the value of each side chain chi value for each amino acid resolved in the crystal structure.

TABLE 6

| Residue | Δchi1 | Δchi2 | Δchi3 | Δchi4 | Δchi5 |
|---|---|---|---|---|---|
| I9 | 1.6 | 4.2 | | | |
| T10 | 4.8 | | | | |
| V11 | 1.1 | | | | |
| N12 | −0.8 | −3.4 | | | |
| S13 | −8.3 | | | | |
| T15 | −0.5 | | | | |
| P16 | 2.0 | −0.7 | −0.9 | 2.4 | |
| T17 | 135.3 | | | | |
| S18 | 116.3 | | | | |
| I20 | 1.3 | −13.5 | | | |
| I21 | 4.8 | −1.4 | | | |
| I24 | −7.1 | −4.4 | | | |
| L25 | −1.1 | −6.8 | | | |
| E28 | −103.8 | −14.8 | 79.8 | | |
| K29 | −16.6 | — | — | — | |
| E32 | — | — | — | | |
| Q64 | 90.3 | 145.9 | −25.5 | | |
| I65 | −1.8 | 1.7 | | | |
| R86 | −5.2 | −8.2 | −1.3 | −3.6 | 7.5 |
| L108 | 1.6 | −0.6 | | | |
| S109 | 3.9 | | | | |
| E110 | — | — | — | | |
| T140 | — | | | | |
| I143 | 2.2 | −9.0 | | | |
| K146 | 100.0 | 3.9 | — | — | |
| I149 | −98.7 | −11.1 | | | |
| L150 | 0.8 | −9.1 | | | |
| N153 | 13.3 | 4.6 | | | |
| L154 | 3.5 | 3.4 | | | |

TABLE 6-continued

| Residue | Δchi1 | Δchi2 | Δchi3 | Δchi4 | Δchi5 |
|---|---|---|---|---|---|
| E226 | — | — | — | | |
| S227 | −1.3 | | | | |
| K229 | — | — | — | — | |
| E230 | — | — | — | | |
| V231 | — | | | | |
| D255 | −9.8 | 4.6 | | | |
| P256 | −4.9 | 3.3 | −0.2 | −3.0 | |
| S258 | −10.3 | | | | |
| S260 | 0.5 | | | | |
| D261 | 2.4 | 18.8 | | | |
| L264 | 103.8 | 108.6 | | | |
| N285 | −6.7 | −7.6 | | | |
| M288 | −8.4 | 2.0 | −10.2 | | |
| I289 | −4.5 | −3.3 | | | |
| Pass | 29 | 23 | 4 | 3 | 1 |
| Fail | 7 | 2 | 2 | 0 | 0 |

In Table 6, residue numbers refer to positions in the T33-15 design model, the "pass" values are the number of residues where |Δchi|≤25 m, and the "fail" values are the number of residues where |Δchi|>25. Residues with missing atoms in the crystal structure, for which a Δchi value could not be determined, are indicated with a dash. All Δchi values are reported in degrees.

Table 7 shows side chain chi value comparison of T33-21 crystal structures (PDB IDs 4NWP and 4NWQ) with the design model.

TABLE 7

| | T33-21 vs. 4NWP | | | | | T33-21 vs. 4NWQ | | | | |
|---|---|---|---|---|---|---|---|---|---|---|
| Residue[1] | Δchi1 | Δchi2 | Δchi3 | Δchi4 | Δchi5 | Δchi1 | Δchi2 | Δchi3 | Δchi4 | Δchi5 |
| K52 | — | — | — | — | | 108.5 | −0.1 | 0.7 | −1.5 | |
| E54 | 1.4 | — | — | | | 4.4 | −7.1 | 2.8 | | |
| S57 | 9.5 | | | | | 6.0 | | | | |
| E58 | 13.8 | — | — | | | 82.2 | 90.5 | −38.0 | | |
| E59 | — | — | — | | | −97.1 | 95.5 | 14.7 | | |
| R60 | −0.2 | 4.1 | −4.2 | 18.9 | −0.2 | 2.1 | 5.4 | −8.1 | −3.2 | 0.0 |
| I61 | 0.7 | −8.0 | | | | −6.4 | −13.6 | | | |
| W63 | 3.0 | −3.3 | | | | 2.3 | 1.6 | | | |
| L65 | −5.1 | 12.7 | | | | −11.2 | −3.6 | | | |
| K66 | 110.0 | −1.8 | 121.6 | 120.9 | | 106.5 | −25.5 | −119.7 | 1.4 | |
| I68 | 2.4 | −10.0 | | | | −1.1 | −12.1 | | | |
| L69 | 0.1 | 3.0 | | | | −3.0 | −1.3 | | | |
| M72 | 33.0 | −0.3 | 2.5 | | | 1.1 | −3.8 | 11.4 | | |
| L102 | −4.7 | 9.6 | | | | −4.7 | 8.0 | | | |
| R103 | −7.4 | −5.5 | −5.4 | −3.4 | 0.3 | −7.8 | −5.2 | −5.3 | −1.5 | 0.7 |
| L106 | −2.0 | −10.6 | | | | −4.8 | −13.7 | | | |
| T109 | −7.4 | | | | | −9.8 | | | | |
| R110 | −102.3 | 14.3 | −4.1 | 39.6 | 0.1 | −106.9 | 19.8 | −1.9 | 17.6 | 0.4 |
| I114 | −6.7 | −20.3 | | | | −4.2 | 4.6 | | | |
| E117 | 0.3 | 168.2 | −55.5 | | | −16.4 | 160.2 | 5.0 | | |
| L123 | −2.2 | 1.4 | | | | −2.2 | 1.8 | | | |
| D127 | −9.4 | 2.5 | | | | −9.8 | 14.0 | | | |
| D145 | — | — | | | | — | — | | | |
| K175 | 3.5 | — | — | — | | −1.8 | −5.0 | 2.6 | −0.6 | |
| D221 | 13.3 | −21.7 | | | | 19.4 | −17.7 | | | |
| I222 | 109.5 | 110.2 | | | | 100.6 | −9.5 | | | |
| T224 | −4.6 | | | | | −4.7 | | | | |
| R225 | −15.7 | −6.2 | 0.4 | −9.4 | 1.0 | −12.3 | −1.4 | −6.0 | 2.4 | 0.2 |
| T226 | −5.1 | | | | | −1.8 | | | | |
| L227 | 4.5 | 0.5 | | | | 5.3 | 0.3 | | | |
| S231 | 111.7 | | | | | −4.9 | | | | |
| C233 | −7.9 | | | | | −2.1 | | | | |
| V235 | −1.6 | | | | | −6.8 | | | | |
| E238 | — | — | — | | | −11.4 | 0.6 | 16.9 | | |
| E258 | 14.0 | −7.2 | 62.5 | | | −1.1 | −13.0 | 84.3 | | |
| R259 | −4.5 | 3.5 | −52.7 | 73.8 | −1.2 | 2.6 | −5.9 | −120.7 | −85.6 | 0.0 |
| L260 | 20.9 | −12.0 | | | | 6.8 | −3.3 | | | |
| S261 | 0.9 | | | | | 4.1 | | | | |
| Y262 | −11.7 | 2.4 | | | | −5.4 | −6.2 | | | |
| K264 | 12.2 | −1.4 | −9.0 | 7.4 | | 6.6 | −1.7 | −129.1 | 7.8 | |

TABLE 7-continued

| | T33-21 vs. 4NWP | | | | | T33-21 vs. 4NWQ | | | | |
|---|---|---|---|---|---|---|---|---|---|---|
| Residue[1] | Δchi1 | Δchi2 | Δchi3 | Δchi4 | Δchi5 | Δchi1 | Δchi2 | Δchi3 | Δchi4 | Δchi5 |
| R265 | 90.0 | −33.2 | 139.5 | −16.2 | 0.1 | 3.3 | 2.0 | 11.5 | −6.7 | 0.1 |
| Pass | 31 | 23 | 6 | 5 | 6 | 34 | 28 | 12 | 9 | 6 |
| Fail | 6 | 3 | 5 | 3 | 0 | 6 | 4 | 5 | 1 | 0 |

In Table 7, residue numbers refer to positions in the T33-21 design model, the "pass" values are the number of residues where |Δchi|≤25 m, and the "fail" values are the number of residues where |Δchi|>25. Residues with missing atoms in the crystal structure, for which a Δchi value could not be determined, are indicated with a dash. All Δchi values are reported in degrees.

As intended, the designed interfaces can drive assembly of cage-like nanomaterials that closely match the computational design models: the backbone RMSD over all 24 subunits in each material range from 1.0 to 2.6 Å. The precise control over interface geometry offered by our method thus enables the design of two-component protein nanomaterials with diverse nanoscale features such as surfaces, pores, and internal volumes with high accuracy.

The method described here can provide a general route to designing multi-component protein-based nanomaterials and molecular machines with programmable structures and functions. The capability to design highly homogeneous protein nanostructures with atomic-level accuracy and controllable assembly can open new opportunities in targeted drug delivery, vaccine design, plasmonics, and other applications that can benefit from the precise patterning of matter on the sub-nanometer to hundred nanometer scale.

Experimental Methods

Amino Acid Sequences.

Enumerated below are the amino acid sequences for the five successful designs that were characterized in detail in this study (T32-28, T33-09, T33-15, T33-21, and T33-28) along with the wild-type proteins from which these designs were derived (referred to by their Protein Data Bank accession numbers followed by the suffix "-wt"). As described in the main text, each designed material comprises a pair of designed proteins. The two components are referred to here by the name of the designed material followed by the suffix "A" or "B". The amino acid sequences of the two C-terminal tags used in this study are also presented.

3lzl-wt (dimeric scaffold for T32-28A)
(SEQ ID NO: 41)
MGEVPIGDPKELNGMEIAAVYLQPIEMEPRGIDLAASLADIHLEADI

HALKNNPNGFPEGFWMPYLTIAYELKNTDTGAIKRGTLMPMVADDGP

HYGANIAMEKDKKGGFGVGNYELTFYISNPEKQGFGRHVDEETGVGK

WFEPPFKVDYKFKYTGTPK

3n79-wt (trimeric scaffold for T32-28B)
(SEQ ID NO: 42)
MSQAIGILELTSIAKGMELGDAMLKSANVDLLVSKTICPGKFLLMLG

GDIGAIQQAIETGTSQAGEMLVDSLVLANIHPSVLPAISGLNSVDKR

QAVGIVETWSVAACISAADRAVKGSNVTLVRVHMAFGIGGKCYMVVA

GDVSDVNNAVTVASESAGEKGLLVYRSVIPRPHEAMWRQMVEG

1nza-wt (trimeric scaffold for T33-09A)
(SEQ ID NO: 43)
MEEVVLITVPSEEVARTIAKALVEERLAACVNIVPGLTSIYRWQGEV

VEDQELLLLVKTTTHAFPKLKERVKALHPYTVPEIVALPIAEGNREY

LDWLRENTG

1ufy-wt (trimeric scaffold for T33-09B and T33-15B)
(SEQ ID NO: 44)
MVRGIRGAITVEEDTPEAIHQATRELLLKMLEANGIQSYEELAAVIF

TVTEDLTSAFPAEAARQIGMHRVPLLSAREVPVPGSLPRVIRVLALW

NTDTPQDRVRHVYLREAVRLRPDLESAQ

3k6a-wt (trimeric scaffold for T33-15A)
(SEQ ID NO: 46)
MSKAKIGIVTVSDRASAGIYEDISGKAIIDTLNDYLTSEWEPIYQVI

PDEQDVIETTLIKMADEQDCCLIVTTGGTGPAKRDVTPEATEAVCDR

MMPGFGELMRAESLKFVPTAILSRQTAGLRGDSLIVNLPGKPKSIRE

CLDAVFPAIPYCIDLMEGPYLECNEAVIKPFRPKAK

1wyl-wt (trimeric scaffold for T33-21A)
(SEQ ID NO: 47)
MRITTKVGDKGSTRLFGGEEVWKDSPIIEANGTLDELTSFIGEAKHY

VDEEMKGILEEIQNDIYKIMGEIGSKGKIEGISEERIKWLEGLISRY

EEMVNLKSFVLPGGTLESAKLDVCRTIARRAERKVATVLREFGIGKE

ALVYLNRLSDLLFLLARVIEIEKNKLKEVR

3e6q-wt (trimeric scaffold for T33-21B)
(SEQ ID NO: 48)
MPHLVIEATANLRLETSPGELLEQANAALFASGQFGEADIKSRFVTL

EAYRQGTAAVERAYLHACLSILDGRDAATRQALGESLCEVLAGAVAG

GGEEGVQVSVEVREMERASYAKRVVARQR

3fuy-wt (trimeric scaffold for T33-28A)
(SEQ ID NO: 49)
MESVNTSFLSPSLVTIRDFDNGQFAVLRIGRTGFPADKGDIDLCLDK

MKGVRDAQQSIGDDTEFGFKGPHIRIRCVDIDDKHTYNAMVYVDLIV

GTGASEVERETAEELAKEKLRAALQVDIADEHSCVTQFEMKLREELL

SSDSFHPDKDEYYKDFL

3fwu-wt (trimeric scaffold for T33-28B)
(SEQ ID NO: 50)
MPVIQTFVSTPLDHHKRENLAQVYRAVTRDVLGKPEDLVMMTFHDST

PMHFFGSTDPVACVRVEALGGYGPSEPEKVTSIVTAAITKECGIVAD

RIFVLYFSPLHCGWNGTNF

-continued

T32-28A
(SEQ ID NO: 1)
MGEVPIGDPKELNGMEIAAVYLQPIEMEPRGIDLAASLADIHLEADI

HALKNNPNGFPEGFWMPYLTIAYALANADTGAIKTGTLMPMVADDGP

HYGANIAMEKDKKGGFGVGTYALTFLISNPEKQGFGRHVDEETGVGK

WFEPFVVTYFFKYTGTPK

T32-28B
(SEQ ID NO: 2)
MSQAIGILELTSIAKGMELGDAMLKSANVDLLVSKTISPGKFLLMLG

GDIGAIQQAIETGTSQAGEMLVDSLVLANIHPSVLPAISGLNSVDKR

QAVGIVETWSVAACISAADLAVKGSNVTLVRVHMAFGIGGKCYMVVA

GDVLDVAAAVATASLAAGAKGLLVYASIIPRPHEAMWRQMVEG

T33-09A
(SEQ ID NO: 3)
MEEVVLITVPSALVAVKIAHALVEERLAACVNIVPGLTSIYRWQGSV

VSDHELLLLVKTTTHAFPKLKERVKALHPYTVPEIVALPIAEGNREY

LDWLRENTG

T33-09B
(SEQ ID NO: 4)
MVRGIRGAITVEEDTPAAILAATIELLLKMLEANGIQSYEELAAVIF

TVTEDLTSAFPAEAARLIGMHRVPLLSAREVPVPGSLPRVIRVLALW

NTDTPQDRVRHVYLNEAVRLRPDLESAQ

T33-15A
(SEQ ID NO: 5)
MSKAKIGIVTVSDRASAGITADISGKAIILALNLYLTSEWEPIYQVI

PDEQDVIETTLIKMADEQDCCLIVTTGGTGPAKRDVTPEATEAVCDR

MMPGFGELMRAESLKEVPTAILSRQTAGLRGDSLIVNLPGDPASISD

CLLAVFPAIPYCIDLMEGPYLECNEAMIKPFRPKAK

T33-15B
(SEQ ID NO: 6)
MVRGIRGAITVNSDTPTSIIIATILLLEKMLEANGIQSYEELAAVIF

TVTEDLTSAFPAEAARQIGMHRVPLLSAREVPVPGSLPRVIRVLALW

NTDTPQDRVRHVYLSEAVRLRPDLESAQ

T33-21A
(SEQ ID NO: 7)
MRITTKVGDKGSTRLFGGEEVWKDSPIIEANGTLDELTSFIGEAKHY

VDEEMKGILEEIQNDIYKIMGEIGSKGKIEGISEERIAWLLKLILRY

MEMVNLKSFVLPGGTLESAKLDVCRTIARRALRKVLTVTREFGIGAE

AAAYLLALSDLLFLLARVIEIEKNKLKEVR

T33-21B
(SEQ ID NO: 8)
MPHLVIEATANLRLETSPGELLEQANKALFASGQFGEADIKSRFVTL

EAYRQGTAAVERAYLHACLSILDGRDIATRTLLGASLCAVLAEAVAG

GGEEGVQVSVEVREMERLSYAKRVVARQR

T33-28A
(SEQ ID NO: 9)
MESVNTSFLSPSLVTIRDFDNGQFAVLRIGRTGFPADKGDIDLCLDK

MIGVRAAQIFLGDDTEDGFKGPHIRIRCVDIDDKHTYNAMVYVDLIV

GTGASEVERETAEEEAKLALRVALQVDIADEHSCVTQFEMKLREELL

SSDSFHPDKDEYYKDFL

T33-28B
(SEQ ID NO: 10)
MPVIQTFVSTPLDHHKRLLLAIIYRIVTRVVLGKPEDLVMMTFHDST

PMHFFGSTDPVACVRVEALGGYGPSEPEKVTSIVTAAITAVCGIVAD

RIFVLYFSPLHCGWNGTNF

A1 tag (for fluorescent labeling and lysate screening)
(SEQ ID NO: 45)
LEGGDSLDMLEWSL hexahistidine tag (for purification)
(SEQ ID NO: 51)
LEHHHHHH Protein Expression, Lysate Screening, and Purification.

Codon-optimized genes encoding the designed and corresponding wild-type proteins were either purchased (Gen9) or constructed from sets of purchased oligonucleotides (Integrated DNA Technologies) by recursive PCR All genes were cloned using the Gibson assembly method into a variant of the pET29b expression vector (Novagen) that had been digested by NdeI and XhoI restriction endonucleases. The genes encoding the wild-type proteins were each cloned into the vector individually, while the genes encoding the designed proteins were cloned in pairs along with the following intergenic region derived from the pETDuet-1 vector (Novagen):

(SEQ ID NO: 52)
5'TAATGCTTAAGTCGAACAGAAAGTAATCGTATTGTACACGGCCGC

ATAATCGAAATTAATACGACTCACTATAGGGGAATTGTGAGCGGATA

ACAATTCCCCATCTTAGTATATTAGTTAAGTATAAGAAGGAGATATA

CAT-3'

The constructs for the designed protein pairs thus possessed the following set of elements from 5' to 3': NdeI restriction site, upstream gene, intergenic region, downstream gene, XhoI restriction site. The upstream genes encoded components denoted with the suffix "A" above; the downstream genes encoded the "B" components. This allowed for co-expression of the designed protein pairs in which both the upstream and downstream gene had their own T7 promoter/lac operator and ribosome binding site.

The pET29b variant used for the initial constructs appended the A1 peptide tag (vide supra) to the C terminus of each wild-type gene and to the downstream gene of each designed protein pair for fluorescent labeling via the AcpS system. For purification purposes, vectors encoding C-terminally His-tagged versions of the designed protein pairs, the individual protein components, and the corresponding wild-types were subsequently constructed by subcloning (via Gibson assembly) into the standard pET29b vector between the NdeI and XhoI restriction sites. As with the A1 peptide tag, the hexahistidine tag was only appended to the downstream component in the co-expression constructs.

Expression plasmids were transformed into BL21 (DE3) E. coli cells. Cells were grown in LB medium supplemented with 50 mg L$^{-1}$ of kanamycin (Sigma) at 37° C. until an $OD_{600}$ of 0.8 was reached. Protein expression was induced by addition of 0.5 mM isopropyl-thio-β-D-galactopyranoside (Sigma) and allowed to proceed for either 5 h at 22° C. or 3 h at 37° C. before cells were harvested by centrifugation.

The designed proteins were screened for assembly by subjecting cleared lysates to native (non-denaturing) PAGE as described previously in the context of at least FIGS. 5A-5G. Single bands for each of the five successful materials were visible when stained with GelCode™ Blue (Thermo Scientific). In these initial screens, all constructs were tested under both the 22° C. and the 37° C. expression conditions. Based on these results, in all subsequent work T32-28, T33-28, and the corresponding wild-type proteins were expressed at 22° C., while T33-09, T33-15, T33-21, and the corresponding wild-type proteins were expressed at 37° C.

For purification, cells were lysed by sonication in 50 mM TRIS pH 8.0, 250 mM NaCl, 1 mM DTT, 20 mM imidazole supplemented with 1 mM phenylmethanesulfonyl fluoride, and the lysates were cleared by centrifugation and filtered through 0.22 µM filters (Millipore). The proteins were purified from the filtered supernatants by nickel affinity chromatography on HisTrap™ HP columns (GE Life Sciences) and eluted using a linear gradient of imidazole (0.02-0.5 M). Fractions containing pure protein(s) of interest were pooled, concentrated using centrifugal filter devices (Sartorius Stedim Biotech), and further purified on a Superdex™ 200 30/100 gel filtration column (GE Life Sciences) using 25 mM TRIS pH 8.0, 150 mM NaCl, 1 mM DTT as running buffer. Gel filtration fractions containing pure protein in the desired assembly state were pooled, concentrated, and stored at room temperature or 4° C. for subsequent use in analytical size exclusion chromatography, in vitro mixing, electron microscopy, and X-ray crystallography.

Analytical Size Exclusion Chromatography.

Analytical SEC was performed on a Superdex™ 200 30/100 gel filtration column (GE Life Sciences) using 25 mM TRIS pH 8.0, 150 mM NaCl, 1 mM DTT as the running buffer. The designed materials were loaded onto the column with each component present at a subunit concentration of 50 µM. Individual designed components and wild-type proteins were loaded at a concentration of 50 µM. The apparent molecular weights of the designed proteins were estimated by comparison to the corresponding wild-type proteins and a set of globular protein standards.

In Vitro Mixing.

Individual components of the five successful designs were expressed from pET29b vectors encoding C-terminally His-tagged versions of each component (under the same induction conditions outlined above). Lysates containing corresponding pairs of designed components were mixed either immediately following lysis (crude lysates) or after clearance by centrifugation (cleared lysates). Each was mixed with either a one-to-one volumetric ratio or with adjusted volumetric ratios intended to account for observed differences in expression levels of the two components in each designed pair. After incubating for two hours at room temperature, insoluble material was cleared by centrifugation and the samples were subjected to native PAGE analysis. For comparison, these samples were analyzed together with cleared lysates of unmixed component A and B, and cleared lysates from co-expressed A1-tagged designs, co-expressed His-tagged designs, and corresponding His-tagged wild-types. Bands corresponding to the assembled state were clearly visible in the crude lysate mixtures of T32-28 and T33-15. Corresponding bands for T32-28 and T33-15 were also visible in the cleared lysate mixtures, although noticeably less intense in the case of T32-28. It is also noteworthy that while the A1-tagged co-expression construct of T33-09 yielded a visible band for the assembled material, the His-tagged co-expression construct did not.

While the His-tagged construct also provided low yield from purification, it did clearly express and assemble (as shown by size exclusion chromatography and electron microscopy). Thus the concentration of the His-tagged assembly appears to be below the detection limit of our native PAGE analysis.

Based on the results from the mixed lysates experiments, T32-28 and T33-15 were additionally subjected to in vitro mixing experiments from purified components. Each of the C-terminally His-tagged components was purified by nickel affinity and gel filtration chromatography, and the purified components were mixed in a 1:1 molar ratio with each component present at a subunit concentration of 50 µM. Following incubation for two hours at room temperature, the mixtures were subjected to analytical size exclusion chromatography. The purifications and size exclusion chromatography were carried out as described above with the exception that 5% (v/v) glycerol was added to all buffers. While T33-15 assembled efficiently from the independently purified components, T32-28 yielded only a small peak for the assembly product. The purified T32-28A component eluted significantly earlier than 3lzl-wt, indicating that lack of assembly in this case may be due to aggregation of the T32-28A component in the absence of T32-28B.

For T32-28A and 3lzl-wt containing samples, DTT was excluded from all buffers and 1 mM $CuSO_4$ added to the lysis buffer. This was done in accordance with previous work on the 3lzl-wt protein, which revealed copper binding sites at the dimeric interface and putative copper-dependent dimerization. While T32-28 did yield a native PAGE band and a size exclusion peak corresponding to the 24mer assembly without these modifications to the buffers, the purified assemblies were found to partially dissociate upon dilution (as assessed by size exclusion chromatography). In contrast, lysis and purification with the modified buffers yielded stable assemblies with no detectable disassembly upon dilution.

Negative Stain Electron Microscopy.

2-3 µl of purified T32-28, T33-09, T33-15, T33-21 and T33-28 samples at concentrations ranging from 0.01 mg/mL to 5 mg/mL were applied to negatively glow discharged, carbon coated 200-mesh copper grids (Ted Pella, Inc.), washed with Milli-Q™ water and stained with 0.075% uranyl formate. Grids were visualized for oligomer validation and optimized for data collection. Screening and data collection was performed on a 120 kV Tecnai Spirit™ T12 transmission electron microscope (FEI, Hillsboro, Oreg.). All images were recorded using a Teitz CMOS 4 k camera at either 49,000× (T33-21 and T33-28) or 60,000× (T32-28, T33-09 and T33-15) magnification.

Coordinates for 3,910 (T32-28), 29,153 (T33-09), 18,197 (T33-15), 5,478 (T33-21) and 13,715 (T33-28) unique particles were obtained for averaging using either Ximdisp™ or EMAN™. Extracted frames of these particles were used to obtain class averages by refinement in either SPIDER™ or IMAGIC™ using multiple rounds of MSA (multivariate statistical analysis) and MRA (multi-reference alignment). A low-resolution (17-30 Å) volume from the design .pdb files outputted from Rosetta3 was obtained using SPIDER™ and validated using UCSF Chimera. Back-projection images were obtained by calculation using SPIDER™ on the low-resolution volumes and visualized using WEB.

Separated, purified components (T33-15A and T33-15B) were screened as above, T33-15A and T33-15B were then mixed in a 1:1 ratio and grids prepared of the mixture after 5 minutes, 1 hour and 2 hours at room temperature and screened as above.

Crystallization of T32-28.

T32-28 was crystallized with hanging drop vapor diffusion at room temperature. Crystals were formed within four days by mixing 1 uL of 11.7 mg mL$^{-1}$ protein and 1 uL of a 500 uL well solution containing only 1.675 M D,L-malic acid at pH 7.0. The crystals were cryo-protected in 2.0 M lithium sulfate and soaked for 20 seconds. The crystals diffracted to at least 4.5 Å and the asymmetric unit contained 12 molecules of T32-28A and 12 molecules of T32-28B in space group P3$_1$21.

Crystallization of T33-15.

As described above, crystals of T33-15 were grown within one week by mixing 1 uL of 7.6 mg mL$^{-1}$ protein and 1 uL of a 500 uL well solution containing 100 mM sodium cacodylate at pH 6.5, 200 mM calcium acetate, and 28% (v/v) PEG 300. Crystals were cryo-protected by successive 30-second soaking in 10 uL solutions of mother liquor with glycerol added at final concentrations of 5%, 10%, 15%, and 20%. The crystals diffracted to at least 2.8 Å and the asymmetric unit contained one molecule each of T33-15A and T33-15B molecules in space group F432.

Crystallization of T33-21 in space groups R32 and F4$_1$32.

T33-21 was crystallized similarly as described above. Crystals grew within three weeks following the mixing of 1 uL of 8.6 mg mL$^{-1}$ protein and 0.5 uL of a 200 uL well solution containing 100 mM citric acid pH at 5.0 and 800 mM ammonium sulfate. Crystals were cryo-protected with 2.0 M lithium sulfate as described above. The crystals diffracted to at least 2.0 Å and the asymmetric unit contained 4 molecules each of T33-21A and T33-21B in space group R32.

Alternatively, crystals also grew within one week by mixing 0.5 uL of 8.6 mg mL$^{-1}$ protein and 1 uL of a 200 uL well solution containing 100 mM Bis-Tris at pH 5.5 and 2.12 M ammonium sulfate. Cryo-protection was performed with 2.0 M lithium sulfate as described above. These crystals diffracted to at least 2.6 Å and the asymmetric unit contained one molecule each of T33-21A and T33-21B in space group F4$_1$32.

Crystallization of T33-28.

T33-28 was crystallized as described above. Crystals grew within three days in hanging drops containing 0.5 uL of 15.8 mL$^{-1}$ protein and 0.5 uL of a 200 uL well solution containing 100 mM sodium citrate tribasic dihydrate pH at 5.6, 200 mM ammonium acetate, and 24% (v/v) (+/−)-2-methyl-2,4-pentanediol. Cryo-protection involved passage of the crystal through drops of paratone-N oil until no more mother liquor appeared present around the crystal. The crystals diffracted to at least 3.5 Å and the asymmetric unit contained 48 molecules each of T33-28A and T33-28B in space group P2$_1$.

Crystallographic data collection and structure determination. Diffraction data sets were collected at the Advanced Photon Source (APS) beamline 24-ID-C equipped with a Pilatus™-6M detector. All data were collected at 100 K. Data were collected for T32-28, T33-15, T33-21 (space group R32), T33-21 (space group F4$_1$32), and T33-28 at detector distances of 650 mm, 450 mm, 300 mm, 300 mm, and 575 mm; with 0.5°, 0.5°, 0.2°, 0.5°, and 0.5° degree oscillations; and at wavelengths of 0.9793 Å, 0.9792 Å, 1.0393 Å, 0.9716 Å, and 0.9793 Å, respectively.

Data reduction, integration, and scaling were performed with XDS/XSCALE™. The program PHASER™ was used to determine all crystal structures by molecular replacement (MR). For T33-15 and T33-21 structures, the MR search models were the original PDB scaffolds for each computationally-designed component. The MR search models for the structures of T33-28 and T32-28 were models of the tetrahedral assemblies with and without side-chain atoms beyond β-carbons, respectively.

The X-ray diffraction data collected for T32-28 underwent additional processing in XSCALE™ to visualize anomalous scattering from copper ions anticipated in the T32-28A subunits. The data was scaled with unmerged Friedel mates and the resultant electron density map was used to calculate an anomalous Fourier map with the refined model in PHENIX™. The anomalous peaks in the calculated map were not used to model copper ions in the final structure due to unmodeled, coordinating side chains. All deposited structure factors used for refinement were scaled with merged Friedel mates.

Crystallographic Refinement.

All refinement steps were run using the phenix.refine module of PHENIX™. Molecular replacement solutions were first refined with rigid body refinement, and then underwent individual coordinate refinement in addition to other strategies. Refinement strategies were tested comparing grouped and individual atomic displacement parameter (ADP) refinement, translation libration screw-motion (TLS) group definitions, and simulated annealing. Each refinement protocol was iteratively run while the quality of the model between runs was assessed in COOT™ using the 2mF$_o$–DF$_c$ with unfilled F$_{obs}$ map and the mF$_o$–DF$_c$ difference map. Subsequent cycles of alternating refinement and model adjustment in COOT were performed to obtain the final refined models.

T32-28, T33-15, T33-21 (space group F4$_1$32), and T33-28 were refined with individual isotropic ADP parameterization with 1 TLS group per polypeptide chain. T32-28 was refined as a model comprised of glycine, alanine, proline, and all other side chains truncated to the β-carbon due to poor electron density visibility in regions occupied by side chains. T33-15 was refined with reference model restraints assigned to T33-15B from chain A of PDB entry 1UFY. T33-21 (space group R32) was refined with individual isotropic ADP parameterization and 3-8 TLS group definitions per chain determined near residual minimization from the TLSMD server.

Model quality was assessed during and after refinement using geometric validation and MolProbity™ tools as a part of the PHENIX™ suite. Structures of T33-15, T33-21, and T33-28 contain 97-100% of the residues within the most favored regions of the Ramachandran plot. Residues in the disallowed regions of the Ramachandran plot are found in T32-28 at positions where the phi and psi angles of the scaffold protein are also disallowed. T32-28, T33-15, and both T33-21 structures have ERRAT scores of 97.0%, 96.6%, 99.4%, and 98.2%, respectively. ERRAT scores indicate the percentage of residues that fall below the 95% confidence limit for erroneous modeling. The large asymmetric unit of the T33-28 structure was inspected with VERIFY3D due to incompatibility with ERRAT, and resulted in a passing score of greater than 80% of residues scored greater than or equal to 0.2 in the 3D/1D profile. The coordinates of the final models and the merged structure factors have been deposited in the Protein Data Bank with PDB codes 4NWN, 4NWO, 4NWR, 4NWP, and 4NWQ.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The above definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3$^{rd}$ Edition or a dictionary known to those of skill in the art, such as the Oxford Dictionary of Biochemistry and Molecular Biology (Ed. Anthony Smith, Oxford University Press, Oxford, 2004).

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural or singular number, respectively. Additionally, the words "herein," "above" and "below" and words of similar import, when used in this application, shall refer to this application as a whole and not to any particular portions of this application.

The above description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure. The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The above detailed description describes various features and functions of the disclosed systems, devices, and methods with reference to the accompanying figures. In the figures, similar symbols typically identify similar components, unless context dictates otherwise. The illustrative embodiments described in the detailed description, figures, and claims are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, or a tangible storage device.

Moreover, a block that represents one or more information transmissions may correspond to information transmissions between software and/or hardware modules in the same physical device. However, other information transmissions may be between software modules and/or hardware modules in different physical devices.

Numerous modifications and variations of the present disclosure are possible in light of the above teachings.

The invention claimed is:

1. An isolated nanostructure, comprising
   (a) a plurality of first proteins that self-interact to form a first multimeric substructure comprising at least one axis of rotational symmetry; and
   (b) a plurality of second proteins that self-interact to form a second multimeric substructure comprising at least one axis of rotational symmetry;
   wherein multiple copies of the first multimeric substructure and the second multimeric substructure interact with each other at one or more symmetrically repeated, non-natural, non-covalent protein-protein interfaces that orient the first multimeric substructures and the second multimeric substructures such that their symmetry axes are aligned with symmetry axes of the same kind in a designated mathematical symmetry group;
   wherein the first protein and the second protein comprise proteins selected from the following pairs of first and second proteins:
   (a) T32-28A (SEQ ID NO: 11) and T32-28B (SEQ ID NO: 12);
   (b) T33-09A (SEQ ID NO: 13) and T33-09B (SEQ ID NO: 14);
   (c) T33-15A (SEQ ID NO: 15) and T33-15B (SEQ ID NO: 16);
   (d) T33-21A (SEQ ID NO: 17) and T33-21B (SEQ ID NO: 18);
   (e) T33-28A (SEQ ID NO: 19) and T33-28B (SEQ ID NO: 20);
   (f) T32-28A (SEQ ID NO: 21) and T32-28B (SEQ ID NO: 22);
   (g) T33-09A (SEQ ID NO: 23) and T33-09B (SEQ ID NO: 24);
   (h) T33-15A (SEQ ID NO: 25) and T33-15B (SEQ ID NO: 26);
   (i) T33-21A (SEQ ID NO: 27) and T33-21B (SEQ ID NO: 28);
   (j) T33-28A (SEQ ID NO: 29) and T33-28B (SEQ ID NO: 30);
   (k) T32-28A (SEQ ID NO: 31) and T32-28B (SEQ ID NO: 32);
   (l) T33-09A (SEQ ID NO: 33) and T33-09B (SEQ ID NO: 34);
   (m) T33-15A (SEQ ID NO: 35) and T33-15B (SEQ ID NO: 36);
   (n) T33-21A (SEQ ID NO: 37) and T33-21B (SEQ ID NO: 38); and
   (o) T33-28A (SEQ ID NO: 39) and T33-28B (SEQ ID NO: 40).

2. The isolated nanostructure of claim 1, wherein the first protein and the second protein comprise T32-28A (SEQ ID NO: 11) and T32-28B (SEQ ID NO: 12).

3. The isolated nanostructure of claim 1, wherein the first protein and the second protein comprise T33-09A (SEQ ID NO: 13) and T33-09B (SEQ ID NO: 14).

4. The isolated nanostructure of claim 1, wherein the first protein and the second protein comprise T33-15A (SEQ ID NO: 15) and T33-15B (SEQ ID NO: 16).

5. The isolated nanostructure of claim 1, wherein the first protein and the second protein comprise T33-21A (SEQ ID NO: 17) and T33-21B (SEQ ID NO: 18).

6. The isolated nanostructure of claim 1, wherein the first protein and the second protein comprise T33-28A (SEQ ID NO: 19) and T33-28B (SEQ ID NO: 20).

7. The isolated nanostructure of claim 1, wherein the first protein and the second protein comprise T32-28A (SEQ ID NO: 21) and T32-28B (SEQ ID NO: 22).

8. The isolated nanostructure of claim 1, wherein the first protein and the second protein comprise T33-09A (SEQ ID NO: 23) and T33-09B (SEQ ID NO: 24).

9. The isolated nanostructure of claim 1, wherein the first protein and the second protein comprise T33-15A (SEQ ID NO: 25) and T33-15B (SEQ ID NO: 26).

10. The isolated nanostructure of claim 1, wherein the first protein and the second protein comprise T33-21A (SEQ ID NO: 27) and T33-21B (SEQ ID NO: 28).

11. The isolated nanostructure of claim 1, wherein the first protein and the second protein comprise T33-28A (SEQ ID NO: 29) and T33-28B (SEQ ID NO: 30).

12. The isolated nanostructure of claim 1, wherein the first protein and the second protein comprise T32-28A (SEQ ID NO: 31) and T32-28B (SEQ ID NO: 32).

13. The isolated nanostructure of claim 1, wherein the first protein and the second protein comprise T33-09A (SEQ ID NO: 33) and T33-09B (SEQ ID NO: 34).

14. The isolated nanostructure of claim 1, wherein the first protein and the second protein comprise T33-15A (SEQ ID NO: 35) and T33-15B (SEQ ID NO: 36).

15. The isolated nanostructure of claim 1, wherein the first protein and the second protein comprise T33-21A (SEQ ID NO: 37) and T33-21B (SEQ ID NO: 38).

16. The isolated nanostructure of claim 1, wherein the first protein and the second protein comprise T33-28A (SEQ ID NO: 39) and T33-28B (SEQ ID NO: 40).

17. An isolated nanostructure, comprising
   (a) a plurality of first proteins that self-interact to form a first multimeric substructure comprising at least one axis of rotational symmetry; and (b) a plurality of second proteins that self-interact to form a second multimeric substructure comprising at least one axis of rotational symmetry;

wherein multiple copies of the first multimeric substructure and the second multimeric substructure interact with each other at one or more symmetrically repeated, non-natural, non-covalent protein-protein interferences that orient the first multimeric substructures and the second multimeric substructures such that their symmetry axes are aligned with symmetry axes of the same kind in a designated mathematical symmetry group;

wherein the first protein and the second protein comprise proteins selected from the following pairs of first and second proteins:

(a) SEQ ID NOs: 1 and 2;
(b) SEQ ID NOs: 3 and 4;
(c) SEQ ID NOs: 5 and 6;
(d) SEQ ID NOs: 7 and 8; and
(e) SEQ ID NOs: 9 and 10.

18. The isolated nanostructure of claim 17, wherein the first protein and the second protein comprise SEQ ID NOS: 1-2.

19. The isolated nanostructure of claim 17, wherein the first protein and the second protein comprise SEQ ID NOS: 3-4.

20. The isolated nanostructure of claim 17, wherein the first protein and the second protein comprise SEQ ID NOS: 5-6.

21. The isolated nanostructure of claim 17, wherein the first protein and the second protein comprise SEQ ID NOS: 7-8.

22. The isolated nanostructure of claim 17, wherein the first protein and the second protein comprise SEQ ID NOS: 9-10.

* * * * *